United States Patent
Mogi et al.

(10) Patent No.: US 8,198,271 B2
(45) Date of Patent: Jun. 12, 2012

(54) THIOPHENEDIAMINE DERIVATIVE HAVING UREA STRUCTURE

(75) Inventors: Hiroyuki Mogi, Ikoma (JP); Hisashi Tajima, Ikoma (JP); Noriko Mishina, Ikoma (JP); Yusuke Yamazaki, Ikoma (JP); Shinji Yoneda, Ikoma (JP); Katsuhiko Watanabe, Ikoma (JP); Junko Fujikawa, Ikoma (JP); Minoru Yamamoto, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 19 days.

(21) Appl. No.: 12/993,452

(22) PCT Filed: May 25, 2009

(86) PCT No.: PCT/JP2009/059494
§ 371 (c)(1),
(2), (4) Date: Nov. 18, 2010

(87) PCT Pub. No.: WO2009/142321
PCT Pub. Date: Nov. 26, 2009

(65) Prior Publication Data
US 2011/0077244 A1    Mar. 31, 2011

(30) Foreign Application Priority Data
May 23, 2008   (JP) ................ 2008-134902

(51) Int. Cl.
| A61K 31/444 | (2006.01) |
| A61K 31/5377 | (2006.01) |
| A61K 31/4436 | (2006.01) |
| A61K 31/381 | (2006.01) |
| A61K 31/496 | (2006.01) |
| A61K 31/4439 | (2006.01) |
| C07D 409/14 | (2006.01) |
| C07D 409/12 | (2006.01) |
| C07D 413/12 | (2006.01) |
| C07D 333/36 | (2006.01) |
| C07D 417/14 | (2006.01) |

(52) U.S. Cl. ............. 514/231.5; 514/233.5; 514/233.8; 514/237.2; 514/253.11; 514/333; 514/336; 514/338; 514/342; 514/343; 514/444; 514/447; 544/131; 544/146; 544/364; 546/256; 546/270.7; 546/276.4; 546/281.4; 549/59; 549/60; 549/69

(58) Field of Classification Search ............... None
See application file for complete search history.

(56) References Cited

U.S. PATENT DOCUMENTS

| 6,673,812 B1 | 1/2004 | Azuma et al. |
| 2006/0058282 A1 | 3/2006 | Finn et al. |
| 2009/0069250 A1 | 3/2009 | Grimm et al. |
| 2009/0306077 A1 | 12/2009 | Mogi et al. |
| 2010/0056522 A1 | 3/2010 | Yoneda et al. |
| 2010/0063045 A1 | 3/2010 | Mogi et al. |

FOREIGN PATENT DOCUMENTS

| JP | 2005-272419 A | 10/2005 |
| WO | WO 97/30701 A2 | 8/1997 |
| WO | WO 00/09162 A1 | 2/2000 |
| WO | WO 03/024448 A2 | 3/2003 |
| WO | WO 2004/043348 A2 | 5/2004 |
| WO | WO 2004/052838 A1 | 6/2004 |
| WO | WO 2004/065354 A1 | 8/2004 |
| WO | WO 2005/030704 A1 | 4/2005 |
| WO | WO 2005/030705 A1 | 4/2005 |

OTHER PUBLICATIONS

Glaucoma, 2012, http://www.mayoclinic.com/health/glaucoma/DS00283/DSECTION=treatments-and-drugs.* Protein, Nucleic Acid and Enzyme, vol. 51, No. 14, (2006), pp. 2069-2075.
Lawrence S. Cousens et al., "Different Accessibilities in Chromatin to Histone Acetylase," The Journal of Biological Chemistry, vol. 254, No. 5, (1979), pp. 1716-1723.
Minoru Yoshida et al., "Effects of Trichostatins on Differentiation of Murine Erythroleukemia Cells," Cancer Research, 47, 3688-3695, Jul. 15, 1987.
Minoru Yoshida et al., "Reversible Arrest of Proliferation of Rat 3Y1 Fibroblasts in Both the G1 and G2 Phases by Trichostatin A," Experimental Cell Research, 177, (1988), 122-131.

(Continued)

Primary Examiner — Sun Jae Loewe
(74) Attorney, Agent, or Firm — Holtz, Holtz, Goodman & Chick, P.C.

(57) ABSTRACT

A compound having the following formula (1) or a salt thereof:

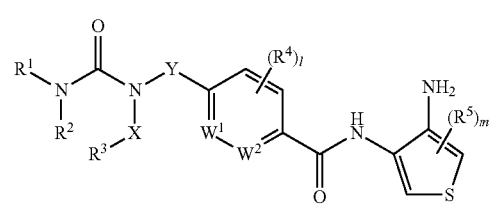

(1)

wherein $R^1$ and $R^2$ represent hydrogen, a lower alkyl, a lower alkenyl, a lower alkynyl or a group having the following formula (2):

$$(R^6)_n\text{—}\textcircled{A}\text{—}Z\text{—} \quad (2),$$

$R^3$ represents hydroxy, a lower alkoxy, a lower cycloalkyloxy, an aryloxy, carboxy, a lower alkoxycarbonyl, or —$NR^aR^b$ having the following formula (3):

$$(R^7)_o\text{—}\textcircled{B}\text{—} \quad (3),$$

$R^4$ and $R^5$ represent halogen, a lower alkyl, hydroxy, or a lower alkoxy; $R^6$ represents halogen, a lower alkyl, an aryl group, a heterocyclic, a hydroxy, a lower alkoxy, mercapto, a lower alkylthio, a lower alkylcarbonyl, amino, nitro or cyano; $R^7$ represents a lower alkyl, hydroxy or a lower alkoxy; $R^a$ and $R^b$ represent hydrogen or a lower alkyl; the ring A represents a cyclic hydrocarbon or a heterocyclic ring; the ring B represents a heterocyclic ring having one or more heteroatoms selected from the group consisting of nitrogen and oxygen; X represents a lower alkylene; Y represents a lower alkylene; Z represents a single bond or a lower alkylene; $W^1$-$W^2$ represents N—CH or C—N and l, m, n and o represent 0, 1, 2, or 3.

14 Claims, No Drawings

OTHER PUBLICATIONS

Minoru Yoshida et al., "Potent and Specific Inhibition of Mammalian Histone Deacetylase Both in Vivo and in Vitro by Trichostatin A," *The Journal of Biological Chemistry*, vol. 265, No. 28, 17174-17179, (1990).

Hiroshi Itazaki et al., "Isolation and Structural Elucidation of New Cyclotetrapeptides, Trapoxins A and B, Having Detransofrmation Activities As Antitumor Agents," *The Journal of Antibiotics*, vol. 43, No. 12, 1524-1534, (1990).

Masako Kijima et al., "Trapoxin, an Antitumor Cyclic Tetrapeptide, Is an Irreversible Inhibitor of Mammalian Histone Deacetylase," *The Journal of Biological Chemistry*, vol. 268, No. 30, 22429-22435, (1993).

Supplementary European Search Report dated May 16, 2011 for EP 09750683.

* cited by examiner

THIOPHENEDIAMINE DERIVATIVE HAVING UREA STRUCTURE

This application is the United States national phase application of International Application PCT/JP2009/059494 filed May 25, 2009.

TECHNICAL FIELD

The present invention relates to a novel thiophenediamine derivative having a urea structure or a salt thereof which is useful as a pharmaceutical. The derivative has a histone deacetylase inhibitory activity and is therefore expected as a preventive and/or therapeutic agent for a disease against which a histone deacetylase inhibitor is considered to be effective. In addition, the derivative has an effect of morphological change on trabecular meshwork cells and an effect of intraocular pressure reduction, and is useful as a preventive and/or therapeutic agent for a disease considered to be associated with circulation of aqueous humor and/or intraocular pressure.

BACKGROUND ART

Eukaryotic chromosomal DNA wraps around core histone proteins, histones H2A, H2B, H3 and H4, etc. to form a basic structure called nucleosome. Further, the nucleosome structures assemble to form a chromatin structure. Post-translational modifications of histones are closely related to the constitution of the chromatin structure, and as the post-translational modification, acetylation, methylation, phosphorylation, ubiquitination and the like are known.

For example, it is thought that histone acetylation is related to gene transcriptional induction, replication, repair and the like.

The histone acetylation is reversibly regulated by a histone acetyltransferase (hereinafter referred to as "HAT") and a histone deacetylase (hereinafter referred to as "HDAC").

It is thought that if HDAC is inhibited, histone acetylation by HAT is enhanced and subsequent gene transcriptional induction, replication, repair and the like are activated, and therefore, various diseases considered to be associated with cell proliferation, senescence and the like. Such as cancer, autoimmune diseases, neurodegenerative diseases and infectious diseases can be prevented and/or treated (Protein, Nucleic Acid and Enzyme, Vol. 51. No. 14 (2006), JP-A-2005-272419 and JP-T-2006-517532).

As typical examples of an HDAC inhibitor, butyric acid which has an effect of cell cycle arrest, an effect of normalization and differentiation of transformed cells and the like (J. Biol. Chem., 254, 1716-1723 (1979)), trichostatin A which is a microbial metabolite and has an effect of cell cycle arrest, an effect of induction of differentiation and the like (Cancer Res., 47, 3688-3691 (1987), Exp. Cell Res., 177, 122-131 (1988) and J. Biol. Chem., 265, 17174-17179 (1990)), trapoxin which is a microbial metabolite and has an inhibitory effect of cell proliferation (J. Antibiotics, 43, 1524-1534 (1990) and J. Biol. Chem., 268, 22429-22435 (1993)) and the like are known.

Moreover, the aqueous humor circulation in the eye is closely related to intraocular pressure, and the hindrance of the aqueous humor circulation effect on the intraocular pressure. In particular, when the aqueous humor circulation is hindered, the intraocular pressure is increased to cause a disease considered to be associated with aqueous humor circulation or intraocular pressure such as glaucoma or ocular hypertension.

In general, aqueous humor is produced by filtration or active transport of plasma components and most aqueous humor flows out of the eyeball through the trabecular outflow pathway. That is, it becomes possible to prevent and/or treat a disease considered to be associated with aqueous humor circulation or intraocular pressure by changing the morphology of trabecular meshwork cells with a medicinal agent or the like to reduce the resistance to aqueous humor outflow thereby enhancing aqueous humor outflow.

For example, as a medicinal agent for changing the morphology of trabecular meshwork cells to enhance aqueous humor outflow, latrunculin A (an actin polymerization inhibitor), H-7 (a myosin light chain kinase (MLCK) inhibitor), Y-39983 (a Rho kinase inhibitor) (WO 1997/030701 and WO 2000/009162) and the like are known.

On the other hand, a compound having a thiophenediamine structure is disclosed as an inhibitor of tumor cell proliferation in WO 2005/030704 and 2005/030705. However, there is no specific description regarding a novel thiophenediamine derivative having a urea structure.

DISCLOSURE OF THE INVENTION

Problems to be Solved

It is a very interesting subject to study the synthesis of a novel thiophenediamine derivative having a urea structure or a salt thereof and to study its pharmacological effects.

Means for Solving the Problems

The present inventors conducted studies of the synthesis of a novel chemical structure, that is, a novel thiophenediamine derivative having a urea structure or a salt thereof and succeeded in creating a large number of novel compounds.

Further, as a result of studies of a pharmacological effect of the derivative or a salt thereof, the present inventors found that the derivative or a salt thereof has an HDAC inhibitory activity and therefore is useful as a preventive and/or therapeutic agent for a disease against which an HDAC inhibitor is considered to be effective. As a result of further studies, they found that the derivative or salt thereof has an effect of morphological change on trabecular meshwork cells and an effect of intraocular pressure reduction and therefore is useful as a preventive and/or therapeutic agent for a disease considered to be associated with circulation of aqueous humor and/or intraocular pressure, and thus, the present invention has been completed.

That is, the invention relates to a compound represented by the following general formula (1) or a salt thereof (hereinafter referred to as "the present compound"), and a pharmaceutical composition containing the same.

Further, a preferred invention of the medical use thereof is an invention relating to a preventive and/or therapeutic agent for a diseases against which an HDAC inhibitor is considered to be useful in treating, such as cancer, autoimmune diseases, inflammatory diseases, neurodegenerative diseases, infectious diseases, hematopoietic disorders, fibrosis, cardiovascular disorders, diseases associated with angiogenesis, further, since the present compound has an effect of morphological change on trabecular meshwork cells and an effect of intraocular pressure reduction, it is an invention relating to a preventive and/or therapeutic agent for a disease considered to be associated with circulation of aqueous humor and/or intraocular pressure such as glaucoma or ocular hypertension.

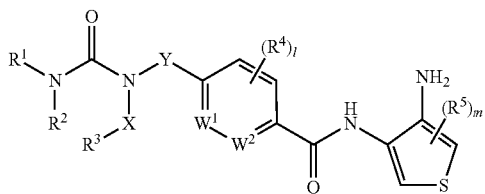
(1)

[R$^1$ and R$^2$ are the same or different and represent a hydrogen atom, a lower alkyl group which may have a substituent, a lower alkenyl group which may have a substituent, a lower alkynyl group which may have a substituent or a group represented by the following general formula (2);

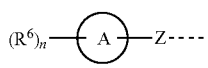
(2)

R$^3$ represents a hydroxy group, a lower alkoxy group which may have a substituent, a lower cycloalkyloxy group which may have a substituent, an aryloxy group which may have a substituent, a carboxy group, a lower alkoxycarbonyl group which may have a substituent, —NR$^a$R$^b$ or a group represented by the following general formula (3);

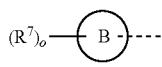
(3)

R$^4$ and R$^5$ are the same or different and represent a halogen atom, a lower alkyl group, a hydroxy group or a lower alkoxy group;
R$^6$ represents a halogen atom, a lower alkyl group which may have a substituent, an aryl group which may have a substituent, a heterocyclic group which may have a substituent, a hydroxy group, a lower alkoxy group which may have a substituent, a mercapto group, a lower alkylthio group which may have a substituent, a lower alkylcarbonyl group which may have a substituent, an amino group, a nitro group or a cyano group;
R$^7$ represents a lower alkyl group which may have a substituent, a hydroxy group or a lower alkoxy group which may have a substituent;
R$^a$ and R$^b$ are the same or different and represent a hydrogen atom or a lower alkyl group which may have a substituent;
the ring A represents a cyclic hydrocarbon or a heterocyclic ring;
the ring B represents a heterocyclic ring having one or plural heteroatoms selected from the group consisting of a nitrogen atom and an oxygen atom in the ring;
X represents a lower alkylene group which may have a substituent;
Y and Z are the same or different and represent a single bond or a lower alkylene group which may have a substituent;
W$^1$-W$^2$ represents N—CH, CH—N or CH—CH; and
l, m, n and o are the same or different and represent 0, 1, 2 or 3. The same shall apply hereinafter.]

Advantageous Effects of the Invention

The invention provides a novel thiophenediamine derivative having a urea structure or a salt thereof which is useful as a pharmaceutical. The present compound has an HDAC inhibitory activity, and is therefore useful as a preventive and/or therapeutic agent for a disease against which an HDAC inhibitor is considered to be effective, and is particularly expected as a preventive and/or therapeutic agent for cancer, autoimmune diseases, inflammatory diseases, neurodegenerative diseases, infectious diseases, hematopoietic disorders, fibrosis, cardiovascular diseases or diseases considered to be associated with angiogenesis. Further since the present compound has an effect of morphological change on trabecular meshwork cells and an effect of intraocular pressure reduction, is expected as a preventive and/or therapeutic agent for a disease considered to be associated with circulation of aqueous humor and/or intraocular pressure such as glaucoma or ocular hypertension.

BEST MODE FOR CARRYING OUT THE INVENTION

Hereinafter, definitions of terms and phrases (atoms, groups, rings and the like) used in this specification will be described in detail.

The "halogen atom" refers to a fluorine, chlorine, bromine or iodine atom.

The "lower alkyl group" refers to a straight chain or branched alkyl group having 1 to 8 carbon atoms, preferably 1 to 6. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower alkenyl group" refers to a straight chain or branched alkenyl group having 2 to 8 carbon atoms, preferably 2 to 6. Specific examples thereof include vinyl, propenyl, butenyl, pentenyl, hexenyl, heptenyl, octenyl, isopropenyl, 2-methyl-1-propenyl and 2-methyl-2-butenyl groups and the like.

The "lower alkynyl group" refers to a straight chain or branched alkynyl group having 2 to 8 carbon atoms, preferably 2 to 6. Specific examples thereof include ethynyl, propynyl, butynyl, pentynyl, hexynyl, heptynyl, octynyl, isobutynyl and isopentynyl groups and the like.

The "lower cycloalkyl group" refers to a cycloalkyl group having 3 to 8 carbon atoms, preferably 3 to 6. Specific examples thereof include cyclopropyl, cyclobutyl, cyclopentyl, cyclohexyl, cycloheptyl and cyclooctyl groups.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Specific examples thereof include phenyl, naphthyl, anthryl and phenanthryl groups and the like.

The "lower alkoxy group" refers to a group formed by replacing the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentoxy groups and the like.

The "lower cycloalkyloxy group" refers to a group formed by replacing the hydrogen atom of a hydroxy group with a lower cycloalkyl group. Specific examples thereof include cyclopropyloxy, cyclobutyloxy, cyclopentyloxy, cyclohexyloxy, cycloheptyloxy, cyclooctyloxy groups.

The "aryloxy group" refers to a group formed by replacing the hydrogen atom of a hydroxy group with an aryl group. Specific examples thereof include phenoxy, naphthoxy, anthryloxy, phenanthryloxy and the like.

The "lower alkylthio group" refers to a group formed by replacing the hydrogen atom of a mercapto group with a lower alkyl group. Specific examples thereof include methylthio, ethylthio, n-propylthio, n-butylthio, n-pentylthio, n-hexylthio, n-heptylthio, n-octylthio, isopropylthio, isobutylthio, sec-butylthio, tert-butylthio and isopentylthio groups and the like.

The "lower alkylcarbonyl group" refers to a group formed by replacing the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl and isopentylcarbonyl groups and the like.

The "lower alkoxycarbonyl group" refers to a group formed by replacing the hydrogen atom of a formyl group with a lower alkoxy group. Specific examples thereof include methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl and isopentoxycarbonyl groups and the like.

The "heterocyclic ring" refers to a saturated or unsaturated monocyclic heterocyclic ring having one or a plurality of heteroatoms selected from a nitrogen atom, an oxygen atom and a sulfur atom in the ring, or a bicyclic or tricyclic condensed polycyclic heterocyclic ring.

Specific examples of the "saturated monocyclic heterocyclic ring" include aziridine, azetidine, pyrrolidine, pyrazolidine, imidazolidine, triazolidine, piperidine, hexahydropyridazine, hexahydropyrimidine, piperazine, homopiperidine and homopiperazine rings and the like having at least a nitrogen atom in the ring, tetrahydrofuran and tetrahydropyran, [1,4]dioxane, [1,2]dioxirane rings and the like having at least an oxygen atom in the ring, tetrahydrothiophene and tetrahydrothiopyran rings and the like having at least a sulfur atom in the ring, oxazolidine, isoxazolidine and morpholine rings and the like having at least a nitrogen atom and an oxygen atom in the ring, and thiazolidine, isothiazolidine and thiomorpholine rings and the like having at least a nitrogen atom and a sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, 2,3-dihydro-1-benzofuran, 1,3-dihydro-2-benzofuran, chromane, isochromane, benzo[1,3]dioxole, 2,3-dihydrobenzo[1,4]dioxine, dihydrobenzothiophene, dihydroisobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzothiazine, xanthene, 4a-carbazole, or perimidine rings and the like.

Specific examples of the "unsaturated monocyclic heterocyclic ring" include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine rings and the like having at least a nitrogen atom in the ring, dihydrofuran, furan, dihydropyran and pyran rings and the like having at least an oxygen atom in the ring, dihydrothiophene, thiophene, dihydrothiopyran and thiopyran rings and the like having at least a sulfur atom in the ring, dihydrooxazole, oxazole, dihydroisoxazole, isoxazole, dihydrooxazine and oxazine rings and the like having at least a nitrogen atom and an oxygen atom in the ring, dihydrothiazole, thiazole, dihydroisothiazole, isothiazole, dihydrothiazine and thiazine rings and the like having at least a nitrogen atom and a sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, tetrahydrobenzothiazole, benzisothiazole, benzothiazine, phenoxanthin, carbazole, β-carboline, phenanthridine, acridine, phenanthroline, phenazine, phenothiazine or phenoxazine rings and the like.

Further, among these heterocyclic rings, in the case of a heterocyclic ring having two hydrogen atoms on the same carbon atom, these hydrogen atoms may be substituted with an oxo group to form a heterocyclic ketone such as 2-pyrrolidone, 4-piperidone, 4-thiazolidone, pyran-4-(4H)-one or pyrazin-2-(3H)-one, and these heterocyclic ketones are also included in the scope of the heterocyclic ring of this invention.

The "heterocyclic ring having one or plural heteroatoms selected from the group consisting of a nitrogen atom and an oxygen atom in the ring" refers to a heterocyclic ring having one or plural nitrogen atoms and/or oxygen atoms in the ring among the above-mentioned heterocyclic rings.

The "heterocyclic group" refers to a residue formed by removing one hydrogen atom from a heterocyclic ring.

The "cyclic hydrocarbon" refers to a saturated or unsaturated monocyclic hydrocarbon, or bicyclic or tricyclic hydrocarbon having 3 to 10 carbon atoms.

Specific examples of the saturated monocyclic hydrocarbon include cyclopropane, cyclobutane, cyclopentane, cyclohexane, cycloheptane, cyclooctane and the like.

Specific examples of the saturated bicyclic hydrocarbon include octahydropentalene, octahydroindene, decahydronaphthalene and the like.

Specific examples of the saturated tricyclic hydrocarbon include bicyclo[2.2.1]heptane and the like.

Specific examples of the unsaturated monocyclic hydrocarbon include cyclopentene, cyclohexene, cyclopentadiene, cyclohexadiene, benzene and the like.

Specific examples of the unsaturated bicyclic hydrocarbon include indan, 1,2,3,4-tetrahydronaphthalene, naphthalene and the like.

The "lower alkylene group" refers to a straight or branched alkylene group having 1 to 8, preferably 1 to 6 carbon atoms. Specific examples thereof include methylene, ethylene, trimethylene, tetramethylene, pentamethylene, hexamethylene, heptamethylene, octamethylene, methylmethylene, ethylmethylene and the like.

The "lower alkyl group which may have a substituent", "lower alkenyl group which may have a substituent", "lower alkynyl group which may have a substituent", "lower alkoxy group which may have a substituent", "lower alkylthio group which may have a substituent", "lower alkylcarbonyl group which may have a substituent", "lower alkoxycarbonyl group which may have a substituent" and/or "lower alkylene group which may have a substituent" refers to a "lower alkyl group", a "lower alkenyl group", a "lower alkynyl group", a "lower alkoxy group", a "lower alkylthio group", a "lower alkylcarbonyl group", a "lower alkoxycarbonyl group" and/or a "lower alkylene group" which may have one or plural substituents selected from the group consisting of a halogen atom, a lower cycloalkyl group, an aryl group, a heterocyclic group, a nitro group, a cyano group, an oxo group, —$OR^p$, —$SR^q$, —$COR^r$, —$COOR^s$, —$CONR^tR^u$ and —$NR^vR^w$.

The "aryl group which may have a substituent", "heterocyclic group which may have a substituent", "lower cycloalkyloxy group which may have a substituent" and/or "aryloxy group which may have a substituent" refers to an "aryl group", a "heterocyclic group", a "lower cycloalkyloxy group" and/or an "aryloxy group" which may have one or plural substituents selected from the group consisting of a halogen atom, a lower alkyl group, a lower alkenyl group, a lower alkynyl group, a lower cycloalkyl group, an aryl group, a heterocyclic group, a nitro group, a cyano group, an oxo group, —$OR^p$, —$SR^q$, —$COR^r$, —$COOR^s$, —$CONR^tR^u$ and —$NR^vR^w$.

Here, $R^p$, $R^q$, $R^r$, $R^s$, $R^t$, $R^u$, $R^v$ and $R^w$ are the same or different and represent a group selected from the group consisting of a hydrogen atom, a lower alkyl group, a lower alkenyl group, a lower alkynyl group, a lower cycloalkyl group, an aryl group and a heterocyclic group.

The "lower alkyl group having a hydroxy group as a substituent" refers to a "lower alkyl group" substituted with one or plural hydroxy groups.

The "lower alkyl group having a lower alkoxy group as a substituent" refers to a "lower alkyl group" substituted with one or plural lower alkoxy groups.

The "lower alkyl group having a lower alkoxycarbonyl group as a substituent" refers to a "lower alkyl group" substituted with one or plural lower alkoxycarbonyl groups.

With regard to the term "plural groups" as used in this invention, the respective groups may be the same or different, and the number of the groups is preferably 2 or 3, particularly preferably 2. Further, a hydrogen atom and a halogen atom are also included in the concept of the "group".

In the invention, when "l", "m", "n" and/or "o" represent 2 or 3, the respective plural groups represented by $R^4$, $R^5$, $R^6$ or $R^7$ may be the same or different. Incidentally, when "l", "m", "n" and/or "o" represent 0, the respective groups represented by $R^4$, $R^5$, $R^6$ and/or $R^7$ do not exist. That is, it shows that the compound does not have the substituents.

The "HDAC inhibitor" as used in this invention refers to a pharmaceutical composition which inhibits HDAC thereby enhancing acetylation of histones and the like to exhibit a pharmaceutical effect.

The "disease against which an HDAC inhibitor is considered to be effective" as used in this invention refers to a disease on which it is known that an HDAC inhibitor is expected to have a therapeutic effect and/or a preventive effect. Specific examples thereof include cancer, autoimmune diseases, inflammatory diseases, neurodegenerative diseases, infectious diseases, hematopoietic disorder, fibrosis and cardiovascular diseases and the like.

More specific examples thereof include cancer such as acute leukemia, chronic leukemia, malignant lymphoma, multiple myeloma, colon cancer, brain tumor, head and neck cancer, breast cancer, lung cancer, esophageal cancer, stomach cancer, liver cancer, gallbladder cancer, bile duct cancer, pancreatic cancer, islet cell carcinoma, renal cell carcinoma, adrenal cortical carcinoma, bladder cancer, prostate cancer, testicular tumor, ovarian cancer, uterine cancer, choriocarcinoma, thyroid cancer, malignant carcinoid tumor, skin cancer, malignant melanoma, osteosarcoma, soft tissue sarcoma, neuroblastoma, Wilms' tumor and retinoblastoma; autoimmune diseases and/or inflammatory diseases such as rheumatoid arthritis, nephritis, diabetes, systemic lupus erythematosus, human autoimmune lymphoproliferative lymphadenopathy, immunoblastic lymphadenopathy, Crohn's disease, ulcerative colitis, multiple sclerosis, inflammatory bowel diseases, psoriasis, osteoarthropathy, juvenile chronic arthritis, graft-versus-host rejection, asthma, alcoholic hepatitis, Sjogren's syndrome, ankylosing spondylitis, membranous glomerulonephritis, intervertebral disk pain, atopic dermatitis, allergic rhinitis, allergic conjunctivitis, keratitis, conjunctivitis, uveitis, age-related macular degeneration, diabetic retinopathy and diabetic macular edema; neurodegenerative diseases such as Alzheimer's disease, Parkinson's disease, Huntington's disease, amyotrophic lateral sclerosis, spinocerebellar degeneration, polyglutamine diseases, striatonigral degeneration, progressive supranuclear palsy, torsion dystonia, cervical dystonia, familial tremor, Gilles de la Tourette syndrome, diffuse Lewy body disease, Pick's disease, intracerebral hemorrhage, primary lateral sclerosis, spinal muscular atrophy, amyotrophic lateral sclerosis, hypertrophic interstitial neuropathy, retinitis pigmentosa, hereditary optic atrophy, hereditary spastic paraplegia, progressive ataxia and Shy-Drager syndrome; infectious diseases such as fungal infection (such as candidal fungus), bacterial infection, viral infection (including herpes simplex), protozoan infection (such as malaria), toxoplasmosis and coccidiosis; hematopoietic disorder such as anemia, sickle cell anemia and thalassemia; fibrosis such as hepatic fibrosis, cystic fibrosis, and vascular fibrosis; cardiovascular diseases such as heart failure, restenosis, arteriosclerosis and cardiac hypertrophy; and diseases considered to be associated with angiogenesis such as the above-mentioned cancer, rheumatoid arthritis, psoriasis, age-related macular degeneration and diabetic retinopathy.

Incidentally, the above-mentioned specific diseases are described for the purpose of understanding the invention better and are not meant to limit the scope of the invention, and there is no particular limitation as long as it is a disease against which an HDAC inhibitor is considered to be effective.

Further, in the case where there are families and/or subtypes in HDAC in the invention, these families and/or subtypes are also included in the scope of HDAC of the invention.

The "disease considered to be associated with aqueous humor circulation and/or intraocular pressure" as used herein is not particularly limited as long as it is a disease considered to be associated with aqueous humor circulation and/or intraocular pressure, preferred examples thereof include glaucoma and ocular hypertension.

The "salt" of the present compound is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, sulfosalicylic acid or the like; quaternary ammonium salts with methyl bromide, methyl iodide or the like; salts with a halogen ion such as a bromine ion, a chlorine ion, an iodine ion or the like; salts with an alkali metal such as lithium, sodium, potassium or the like; salts with an alkaline earth metal such as calcium, magnesium or the like; salts with a metal such as iron, zinc or the like; salts with ammonia; and salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis(phenylmethyl)-1,2-ethanediamine or the like.

In the case where there are geometric isomers or optical isomers in the present compound, these isomers are also included in the scope of the invention.

Further, the present compound may be in the form of a hydrate or a solvate.

Further, in the case where there is proton tautomerism in the present compound, the tautomeric isomers thereof are also included in the invention.

In the case where there are crystalline polymorphisms and crystalline polymorphism groups (crystalline polymorphism systems) in the present compound, these crystalline polymorphisms and crystalline polymorphism groups (crystalline polymorphism systems) are also included in the invention. Here, the crystalline polymorphism groups (crystalline polymorphism systems) mean individual crystal forms in respective stages when the crystal forms are changed by the conditions for the production, crystallization, storage or the like of these crystals and the states thereof (the states also include a formulated state), and all the processes thereof.

(a) Examples of the present compound include compounds in which the respective groups are as defined below and salts thereof in the compounds represented by the general formula (1) and salts thereof:

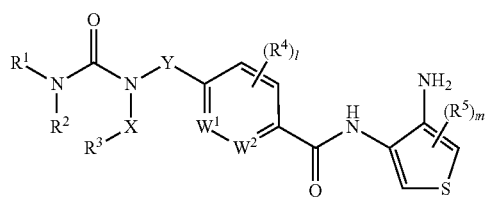
(1)

(a1) $R^1$ and $R^2$ are the same or different and represent a hydrogen atom, a lower alkyl group which may have a substituent, a lower alkenyl group which may have a substituent, a lower alkynyl group which may have a substituent or a group represented by the following general formula (2); and/or

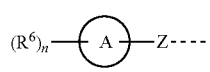
(2)

(a2) $R^3$ represents a hydroxy group, a lower alkoxy group which may have a substituent, a lower cycloalkyloxy group which may have a substituent, an aryloxy group which may have a substituent, a carboxy group, a lower alkoxycarbonyl group which may have a substituent, $-NR^aR^b$ or a group represented by the following general formula (3); and/or

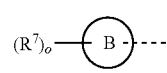
(3)

(a3) $R^4$ and $R^5$ are the same or different and represent a halogen atom, a lower alkyl group, a hydroxy group or a lower alkoxy group; and/or (a4) $R^6$ represents a halogen atom, a lower alkyl group which may have a substituent, an aryl group which may have a substituent, a heterocyclic group which may have a substituent, a hydroxy group, a lower alkoxy group which may have a substituent, a mercapto group, a lower alkylthio group which may have a substituent, a lower alkylcarbonyl group which may have a substituent, an amino group, a nitro group or a cyano group; and/or (a5) $R^7$ represents a lower alkyl group which may have a substituent, a hydroxy group or a lower alkoxy group which may have a substituent; and/or (a6) $R^a$ and $R^b$ are the same or different and represent a hydrogen atom or a lower alkyl group which may have a substituent; and/or (a7) the ring A represents a cyclic hydrocarbon or a heterocyclic ring; and/or (a8) the ring B represents a heterocyclic ring having one or plural heteroatoms selected from the group consisting of a nitrogen atom and an oxygen atom in the ring;

(a9) X represents a lower alkylene group which may have a substituent; and/or (a10) Y and Z are the same or different and represent a single bond or a lower alkylene group which may have a substituent; and/or (a11) $W^1$-$W^2$ represents N—CH, CH—N or CH—CH; and/or (a12) l, m, n and o are the same or different and represent 0, 1, 2 or 3.

That is, examples of the present compound include, in the compounds represented by the general formula (1), compounds which comprise one or a combination of two or more selected from the group consisting of the above-mentioned (a1), (a2), (a3), (a4), (a5), (a6), (a7), (a8), (a9), (a10), (a11) and (a12) and salts thereof.

(b) Preferred examples of the present compound include compounds in which the respective groups are as defined below and salts thereof in the compounds represented by the general formula (1) and salts thereof:

(b1) $R^1$ and $R^2$ are the same or different and represent a hydrogen atom, a lower alkyl group, a lower alkyl group having a lower alkoxy group (preferably an isopropoxy group) as a substituent, a lower alkyl group having a lower alkoxycarbonyl group (preferably an ethoxycarbonyl group) as a substituent, a lower alkenyl group, a lower alkynyl group or a group represented by the following general formula (2); and/or

(2)

(b2) $R^3$ represents a hydroxy group, a lower alkoxy group, a lower cycloalkyloxy group, an aryloxy group, a carboxy group, a lower alkoxycarbonyl group, —NR$^a$R$^b$ or a group represented by the following general formula (3); and/or

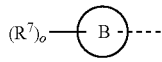
(3)

(b3) R$^6$ represents a halogen atom, a lower alkyl group, a lower alkyl group having a hydroxy group as a substituent, a lower alkyl group having a lower alkoxy group as a substituent, an aryl group, a heterocyclic group, a hydroxy group, a lower alkoxy group, a mercapto group, a lower alkylthio group, a lower alkylcarbonyl group, an amino group, a nitro group or a cyano group; and/or (b4) R$^7$ represents a lower alkyl group or a lower alkoxy group; and/or (b5) R$^a$ and R$^b$ are the same or different and represent a hydrogen atom or a lower alkyl group; and/or (b6) the ring A represents a cyclic hydrocarbon or a heterocyclic ring; and/or (b7) the ring B represents a heterocyclic ring having one or plural heteroatoms selected from the group consisting of a nitrogen atom and an oxygen atom in the ring; and/or (b8) X represents a lower alkylene group; and/or (b9) Y and Z are the same or different and represent a single bond or a lower alkylene group; and/or (b10) W$^1$-W$^2$ represents CH—N or CH—CH; and/or (b11) l and m represent 0; and/or (b12) n and o are the same or different and represent 0, 1, 2 or 3.

That is, preferred examples of the present compound include, in the compounds represented by the general formula (1), compounds which comprise one or a combination of two or more selected from the group consisting of the above-mentioned (b1), (b2), (b3), (b4), (b5), (b6), (b7), (b8), (b9), (b10), (b11) and (b12) and salts thereof. The selected conditions can be also combined with the condition (a).

(c) More preferred examples of the present compound include compounds in which the respective groups are as defined below and salts thereof in the compounds represented by the general formula (1) and salts thereof:

(c1) R$^1$ represents a hydrogen atom, a lower alkyl group, a lower alkyl group having a lower alkoxy group (preferably an isopropoxy group) as a substituent, a lower alkyl group having a lower alkoxycarbonyl group (preferably an ethoxycarbonyl group) as a substituent or a group represented by the following general formula (2); and/or

(2)

(c2) R$^2$ represents a hydrogen atom; and/or (c3) R$^3$ represents —NR$^a$R$^b$ or a group represented by the following general formula (3); and/or

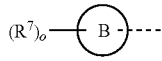
(3)

(c4) R$^6$ represents a halogen atom, a lower alkyl group, a lower alkyl group having a hydroxy group as a substituent, an aryl group, a lower alkoxy group or a lower alkylcarbonyl group; and/or (c5) R$^7$ represents a lower alkyl group; and/or (c6) R$^a$ and R$^b$ represent a lower alkyl group; and/or (c7) the ring A represents a cyclic hydrocarbon or a heterocyclic ring; and/or (c8) the ring B represents a heterocyclic ring having one or plural heteroatoms selected from the group consisting of a nitrogen atom and an oxygen atom in the ring; and/or (c9) X and Y represent a lower alkylene group; and/or (c10) Z represents a single bond or a lower alkylene group; and/or (c11) W$^1$-W$^2$ represents CH—N or CH—CH; and/or (c12) l and m represent 0; and/or (c13) n represents 0, 1 or 2; and/or (c14) o represents 0 or 1.

That is, preferred examples of the present compound include, in the compounds represented by the general formula (1), compounds which comprise one or a combination of two or more selected from the group consisting of the above-mentioned (c1), (c2), (c3), (c4), (c5), (c6), (c7), (c8), (c9), (c10), (c11), (c12), (c13) and (c14) and salts thereof. The selected conditions can be also combined with the condition (a) and/or (b).

(d) Preferred examples of the ring A include the following rings.

The ring A represents cyclopentane, cyclohexane, benzene, indan, thiophene, furan, benzo[1,3]dioxole, 2,3-dihydro-1-benzofuran, thiazole, 2,3-dihydrobenzo[1,4]dioxine or pyridine.

Further, compounds which have the condition (d) and satisfy the requirements of the above-mentioned (a), (b), (c) and/or the following (e) or salts thereof are more preferred.

(e) Preferred examples of the ring B include the following rings.

The ring B represents pyrrolidine, piperazine or morpholine

Further, compounds which have the condition (e) and satisfy the requirements of the above-mentioned (a), (b), (c) and/or (d) or salts thereof are more preferred.

(f) Particularly preferred specific examples of the present compound include the following compounds or salts thereof.

N-(4-Aminothiophen-3-yl)-5-[3-(2,3-dihydrobenzo[1,4]dioxin-6-yl)-1-(2-dimethylaminoethyl)ureidomethyl]pyridine-2-carboxylic acid amide, N-(4-Aminothiophen-3-yl)-4-[3-(2,3-dihydro-1-benzofuran-5-yl)-1-[3-(morpholin-4-yl)propyl]ureidomethyl] benzamide, N-(4-Aminothiophen-3-yl)-5-[1-(2-dimethylaminoethyl)-3-(thiophen-3-yl)ureidomethyl]pyridine-2-carboxylic acid amide, N-(4-Aminothiophen-3-yl)-5-[1-(2-dimethylaminoethyl)-3-phenethylureidomethyl]pyridine-2-carboxylic acid amide, N-(4-Aminothiophen-3-yl)-5-[1-(3-dimethylaminopropyl)-3-(thiophen-3-yl)ureidomethyl]pyridine-2-carboxylic acid amide, N-(4-Aminothiophen-3-yl)-5-[3-cyclopentyl-1-[3-(morpholin-4-yl)propyl]ureidomethyl]pyridine-2-carboxylic acid amide, N-(4-Aminothiophen-3-yl)-5-[1-(2-dimethylaminoethyl)-3-isopropylureidomethyl]pyridine-2-carboxylic acid amide, N-(4-Aminothiophen-3-yl)-5-[3-isopropyl-1-[3-(4-methylpiperazin-1-yl)propyl]ureidomethyl]pyridine-2-carboxylic acid amide, N-(4-Aminothiophen-3-yl)-5-[1-[4-(morpholin-4-yl) butyl]-3-phenethylureidomethyl]pyridine-2-carboxylic acid amide, N-(4-Aminothiophen-3-yl)-5-[3-cyclopentyl-1-[2-(pyrrolidin-1-yl)ethyl]ureidomethyl]pyridine-2-carboxylic acid amide, N-(4-Aminothiophen-3-yl)-5-[2-[3-(benzo[1,3]dioxol-5-yl)]ethyl-1-[2-(4-methylpiperazin-1-yl)ethyl]ureidomethyl]pyridine-2-carboxylic acid amide, N-(4-Aminothiophen-3-yl)-5-[1-[4-(morpholin-4-yl) butyl]-3-propylureidomethyl]pyridine-2-carboxylic acid amide, N-(4-Aminothiophen-3-yl)-5-[3-ethoxycarbonylmethyl-1-[3-(morpholin-4-yl)propyl]ureidomethyl]pyridine-2-carboxylic acid amide, N-(4-Aminothiophen-3-yl)-5-[1-(2-dimethylaminoethyl)-3-(thiazol-2-yl)ureidomethyl]pyridine-2-carboxylic acid amide, and N-(4-Aminothiophen-3-yl)-5-[1-(2-dimethylaminoethyl) ureidomethyl]pyridine-2-carboxylic acid amide.

The present compounds can be prepared according to the following methods. Each specific process for preparing the present compounds are described in detail in the following examples (section of Production Examples). Additionally, the term "Boc" used in the following synthetic routes represents a tert-butoxycarbonyl group. In the case that an oxygen atom, a nitrogen atom, a sulfur atom, and so on are contained in $R^1$, $R^2$, $R^3$, $R^4$, $R^5$ of the following scheme, they will be able to be protected or deprotected by generally used methods.

The processes for preparing the present compounds are divided roughly into the methods described below, and the suitable method can be chosen according to the kind of substituents.

1) The present compound (I) can be synthesized according to the synthetic route 1. Namely, the compound (I) can be given by the treatment of the compound (II) in an organic solvent such as methanol in the presence of an acid such as hydrogen chloride-ethyl acetate solution at 0° C. to room temperature for 30 minutes to 24 hours.

Synthetic Route 1

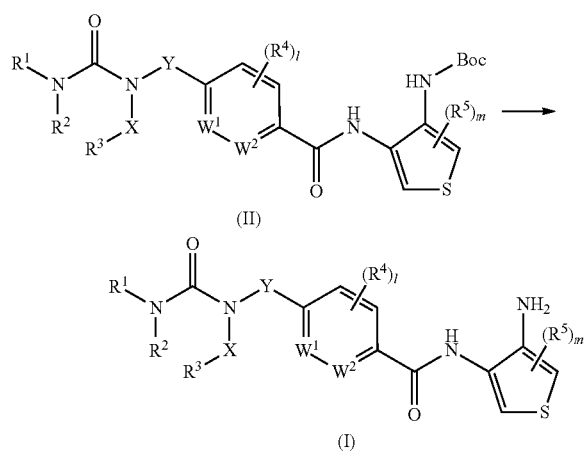

The compound (IIa, $R^2$=H) can be synthesized according to the synthetic route 1-1. Namely, it can be given by the reaction of the compound (III) with an isocyanate (IV) in an organic solvent such as dichloromethane at 0° C. to room temperature for 30 minutes to 24 hours.

Synthetic Route 1-1

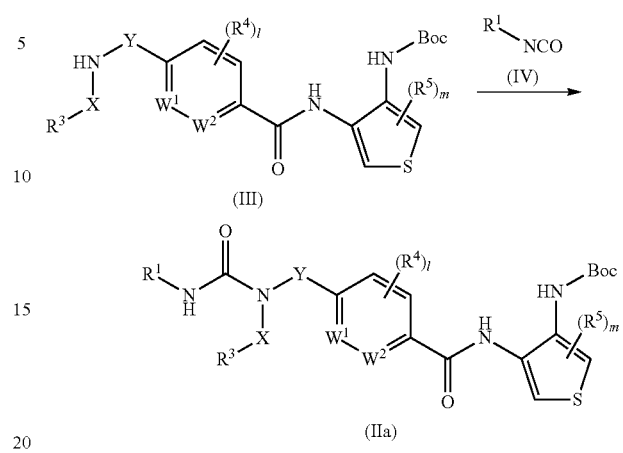

The compound (III) can be synthesized according to the synthetic route 1-2. Namely, it can be given by the reaction of the sulfonate (V) with an amine (VI) in an organic solvent such as acetonitrile at 0° C. to room temperature for 30 minutes to 24 hours.

Synthetic Route 1-2

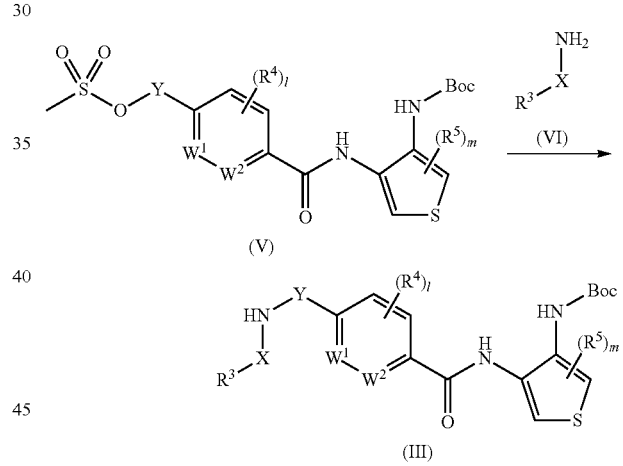

The compound (V) can be synthesized according to the synthetic route 1-3. Namely, it can be given by the reaction of the compound (VII) with methanesulfonyl chloride (VIII) in an organic solvent such as dichloromethane in the presence of a base such as triethylamine at 0° C. to room temperature for 30 minutes to 3 hours.

Synthetic Route 1-3

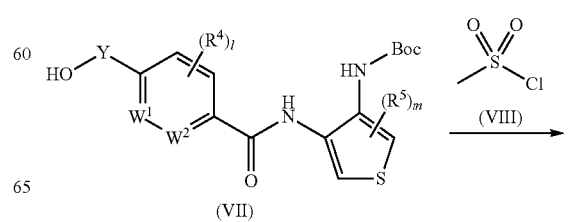

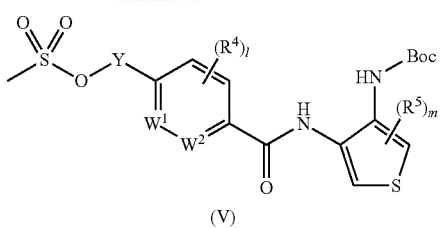

(V)

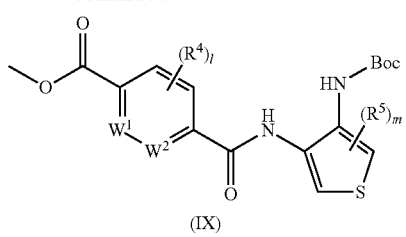

(IX)

The compound (VIIa, Y=CH₂) can be synthesized according to the synthetic route 1-4. Namely, it can be given by the treatment of the compound (IX) in an organic solvent such as tetrahydrofuran (hereinafter referred to as "THF") in the presence of a reducing reagent such as lithium borohydride at 0° C. to room temperature for 30 minutes to 24 hours.

Synthetic Route 1-4

The compound (X) can be synthesized according to the synthetic route 1-6. Namely, it can be given by the reaction of the compound (XII) with di-tert-butyl dicarbonate (XIII) in an organic solvent such as THF in the presence of a base such as triethylamine at −20° C. to room temperature for 1 hour to 24 hours.

Synthetic Route 1-6

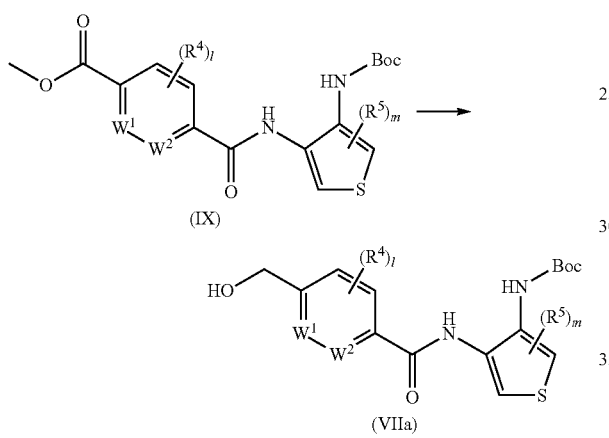

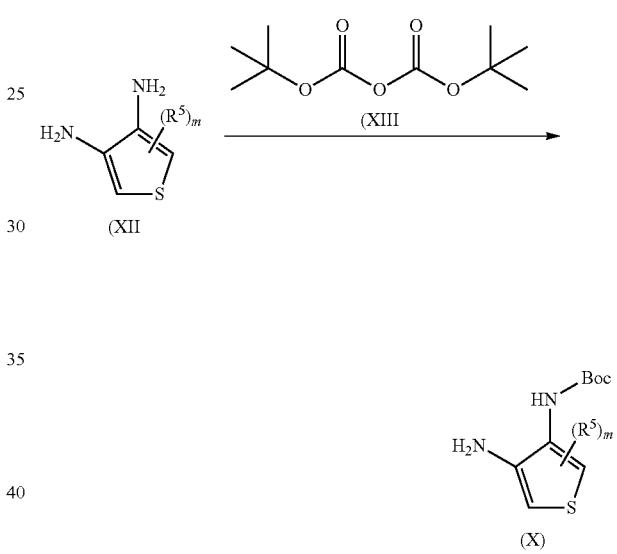

The compound (IX) can be synthesized according to the synthetic route 1-5. Namely, it can be given by the reaction of the compound (X) with the compound (XI) in an organic solvent such as N,N-dimethylformamide (hereinafter referred to as "DMF") in the presence of a condensing reagent such as O-(7-azabenzotriazol-1-yl)-1,1,3,3-tetramethyluronium hexafluorophosphate (hereinafter referred to as "HATU") and a base such as N-methylmorpholine at room temperature for 1 hour to 24 hours.

Synthetic Route 1-5

2) The compound (II) can be synthesized according to the synthetic route 2. Namely, it can be given by the reaction of the compound (III) with an amine (XIV) in an organic solvent such as THF in the presence of a reagent for urea formation such as 1,1'-carbonyldiimidazole at 0° C. to 60° C. for 30 minutes to 24 hours.

Synthetic Route 2

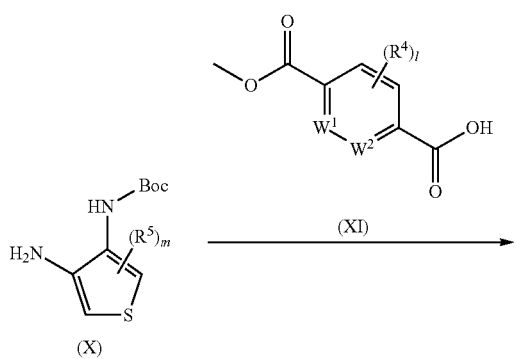

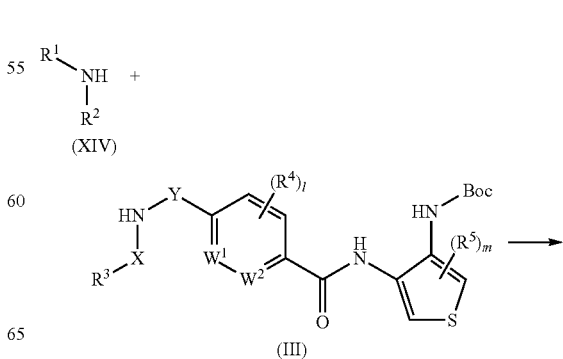

-continued

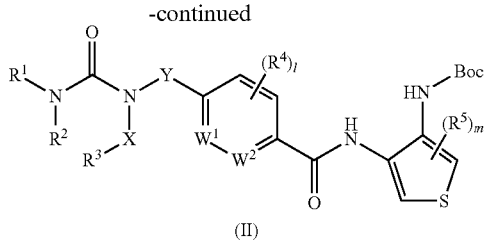

(II)

A pharmacological activity of the present compound will be described in detail in the following Examples under the item of "Pharmacological Tests", as a result of studying an HDAC inhibitory activity of the present compound using HDAC Fluorimetric Assay/Drug Discovery Kit (manufactured by BIOMOL, Inc.) according to the protocol of the kit, it was found that the present compound has an excellent HDAC inhibitory activity. That is, the present compound is useful as a preventive and/or therapeutic agent for a disease against which an HDAC inhibitor is considered to be effective, and is particularly expected as a preventive and/or therapeutic agent for cancer, autoimmune disease S, inflammatory disease S, neurodegenerative disease S, infectious disease S, hematopoietic disorders, fibrosis, cardiovascular diseases, diseases considered to be associated with angiogenesis or the like.

Further, as a result of studying an effect of morphological change of the present compound on trabecular meshwork cells, i.e., an effect of morphological change of the present compound on trabecular meshwork cells in an evaluation system using the cell shape index (hereinafter referred to as "CSI") reported in The Journal of Clinical Investigation, 103, 1141-1150 (1999) as an index, it was found the present compound has an excellent effect of morphological change on trabecular meshwork cells.

Further, as a result of studying an effect of intraocular pressure reduction of the present compound through intracameral administration using male Japanese white rabbits in order to confirm an actual effect of intraocular pressure reduction of the present compound, it was confirmed that the present compound has an effect of intraocular pressure reduction. That is, the present compound has an effect of morphological change on trabecular meshwork cells and an effect of intraocular pressure reduction and therefore is expected as a preventive and/or therapeutic agent for a disease considered to be associated with aqueous humor circulation and/or intraocular pressure such as glaucoma or ocular hypertension.

The present compound can be administered either orally or parenterally. Examples of the dosage form include a tablet, a capsule, a granule, a powder, an injection and an eye drop, and such a preparation can be prepared by a widely used technique.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl para-hydroxybenzoate or benzyl alcohol; a corrigent such as a sweetener, a sour agent or a flavor; or the like.

Further, a parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polysorbate 80, polyoxy 40 stearate or polyoxyethylene hydrogenated castor oil 60; a stabilizer such as sodium citrate or sodium edetate; a preservative such as benzalkonium chloride, paraben, benzethonium chloride, para-hydroxybenzoate ester, sodium benzoate, chlorobutanol or sorbic acid; a pH adjusting agent such as hydrochloric acid, citric acid, phosphoric acid, glacial acetic acid, sodium hydroxide, sodium carbonate or sodium hydrogen carbonate; a soothing agent such as benzyl alcohol; or the like.

The dose of the present compound can be properly selected depending on the symptoms, age, dosage form or the like. For example, in the case of an oral preparation, it can be administered in an amount of generally from 0.01 to 1000 mg, preferably from 1 to 100 mg per day in a single dose or several divided doses. Further, in the case of an eye drop, a preparation containing the present compound at a concentration of generally from 0.0001 to 10% (w/v), preferably from 0.01 to 5% (w/v) can be administered in a single dose or several divided doses.

Hereinafter, Production Examples, Preparation Examples and results of Pharmacological Tests of the present compound will be described. However, these examples are described for the purpose of understanding the invention better and are not meant to limit the scope of the invention.

PRODUCTION EXAMPLES

Reference Example 1

3-Amino-4-t-butoxycarbonylaminothiophene
(Reference Compound No. 1-1)

Under ice cooling, di-t-butyl dicarbonate (0.16 g, 0.72 mmol) was added to a solution of 3,4-diaminothiophene dihydrochloride (0.13 g, 0.71 mmol) and triethylamine (0.29 mL, 2.1 mmol) in THF (4.0 mL) and then the mixture was stirred at room temperature overnight. Water (40 mL) was added to the reaction solution and the whole was extracted with ethyl acetate (30 mL) twice. The organic layer was washed with water (30 mL) and brine (30 mL), dried over anhydrous sodium sulfate, and then the solvent was removed under reduced pressure. The obtained residue was purified by silica gel column chromatography (hexane-ethyl acetate) to give 87 mg of the title reference compound as a brown solid. (Yield 58%)

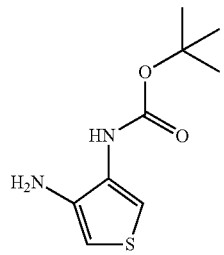

¹H-NMR (500 MHz, CDCl₃)
δ 1.52 (s, 9H), 3.33 (br s, 2H), 6.33 (d, J = 3.7 Hz, 1H), 6.52 (br s, 1H), 7.13 (br s, 1H)

Reference Example 2

N-(4-t-Butoxycarbonylaminothiophen-3-yl)-5-methoxycarbonylpyridine-2-carboxylic acid amide (Reference Compound No. 2-1)

HATU (1.3 g, 3.5 mmol) was added to a solution of 3-amino-4-t-butoxycarbonylaminothiophene (Reference Compound No. 1-1, 0.68 g, 3.2 mmol), 5-methoxycarbonylpyridine-2-carboxylic acid (0.64 g, 3.5 mmol), and N-methylmorpholine (0.70 mL, 6.4 mmol) in DMF (20 mL), and then the reaction mixture was stirred at room temperature overnight. Water (0.30 L) and ethyl acetate (0.40 L) were added thereto, and the insoluble materials were filtered off to give 0.50 g of the title reference compound as a pale yellow solid. The filtrate was partitioned and the organic layer was dried over anhydrous sodium sulfate. The solvent was evaporated under reduced pressure, and then the obtained solid was collected by filtration with ethylacetate (30 mL) to give 0.30 g of the title reference compound as a pale brown solid. (Yield 67%)

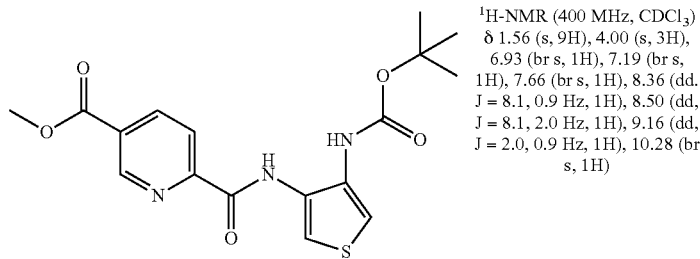

¹H-NMR (400 MHz, CDCl₃)
δ 1.56 (s, 9H), 4.00 (s, 3H), 6.93 (br s, 1H), 7.19 (br s, 1H), 7.66 (br s, 1H), 8.36 (dd, J = 8.1, 0.9 Hz, 1H), 8.50 (dd, J = 8.1, 2.0 Hz, 1H), 9.16 (dd, J = 2.0, 0.9 Hz, 1H), 10.28 (br s, 1H)

By using any compounds selected from Reference Compound No. 1-1 and commercially available compounds, the following Reference Compound No. 2-2 was obtained by a method similar to that of Reference Compound No. 2-1.

N-(4-t-Butoxycarbonylaminothiophen-3-yl)-4-methoxycarbonylbenzamide (Reference Compound No. 2-2)

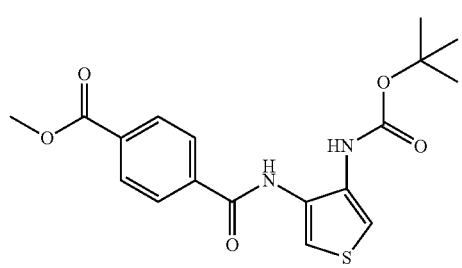

¹H-NMR (400 MHz, CDCl₃)
δ 1.55 (s, 9H), 3.96 (s, 3H), 6.71 (s, 1H), 6.88 (d, J = 3.8 Hz, 1H), 7.83 (d, J = 3.8 Hz, 1H), 8.00 (d, J = 8.7 Hz, 2H), 8.13 (d, J = 8.7 Hz, 2H), 9.79 (br s, 1H)

Reference Example 3

N-(4-t-Butoxycarbonylaminothiophen-3-yl)-5-hydroxymethylpyridine-2-carboxylic acid amide (Reference Compound No. 3-1)

Under ice cooling, lithium tetrahydroborate (1.5 g, 70 mmol) was added to a mixed solution of N-(4-t-butoxycarbonylaminothiophen-3-yl)-5-methoxycarbonylpyridine-2-carboxylic acid amide (Reference Compound No. 2-1, 24 g, 64 mmol) in THF (1.3 L)-1,4-dioxane (1.3 L), and then the reaction mixture was stirred at same temperature overnight. Lithium tetrahydroborate (0.30 g, 14 mmol) was added thereto and the mixture was stirred at room temperature for 2 hours. Under ice cooling, water (0.40 L) and 10% aqueous citric acid solution (25 mL) were added thereto. The precipitates were filtered off and the filtrate was evaporated under reduced pressure. Water (0.30 L) was added thereto and the precipitates were filtered and dried under reduced pressure to give 21 g of the title reference compound as a pale yellow solid. (Yield 95%)

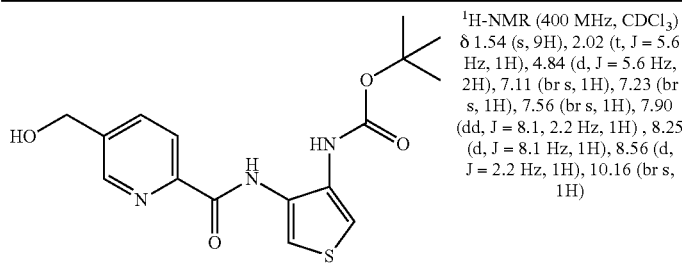

$^1$H-NMR (400 MHz, CDCl$_3$)
δ 1.54 (s, 9H), 2.02 (t, J = 5.6 Hz, 1H), 4.84 (d, J = 5.6 Hz, 2H), 7.11 (br s, 1H), 7.23 (br s, 1H), 7.56 (br s, 1H), 7.90 (dd, J = 8.1, 2.2 Hz, 1H), 8.25 (d, J = 8.1 Hz, 1H), 8.56 (d, J = 2.2 Hz, 1H), 10.16 (br s, 1H)

By using any compounds selected from Reference Compound No. 2-2 and commercially available compounds, the following Reference Compound No. 3-2 was obtained by a method similar to that of Reference Compound No. 3-1.

N-(4-t-Butoxycarbonylaminothiophen-3-yl)-4-hydroxymethylbenzamide (Reference Compound No. 3-2)

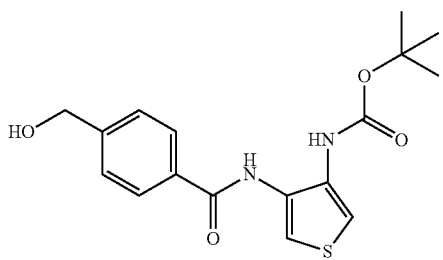

$^1$H-NMR (400 MHz, CDCl$_3$)
δ 1.54 (s, 9H), 1.99 (br s, 1H), 4.77 (d, J = 4.6 Hz, 2H), 6.87 (s, 1H), 6.93 (d, J = 3.8 Hz, 1H), 7.44 (d, J = 8.4 Hz, 2H), 7.71 (d, J = 3.8 Hz, 1H), 7.90 (d, J = 8.4 Hz, 2H), 9.47 (br s, 1H)

Reference Example 4

N-(4-t-Butoxycarbonylaminothiophen-3-yl)-5-methanesulfonyloxymethylpyridine-2-carboxylic acid amide (Reference Compound No. 4-1)

Under ice cooling, methanesulfonyl chloride (71 μL, 0.92 mmol) was added to a solution of N-(4-t-butoxycarbonylaminothiophen-3-yl)-5-hydroxymethylpyridine-2-carboxylic acid amide (Reference Compound No. 3-1, 0.32 g, 0.93 mmol) and triethylamine (0.32 mL, 2.3 mmol) in anhydrous dichloromethane (20 mL), and then the reaction mixture was stirred for 2 hour. Water (0.15 L) and ethyl acetate (0.15 L) were added thereto and the whole was partitioned. The organic layer was washed with brine (0.15 L), dried over anhydrous sodium sulfate, and then the solvent was evaporated under reduced pressure to give 0.36 g of the title reference compound as a yellow solid. (Yield 91%)

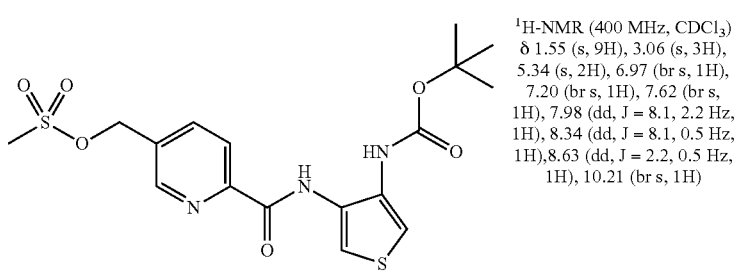

$^1$H-NMR (400 MHz, CDCl$_3$)
δ 1.55 (s, 9H), 3.06 (s, 3H), 5.34 (s, 2H), 6.97 (br s, 1H), 7.20 (br s, 1H), 7.62 (br s, 1H), 7.98 (dd, J = 8.1, 2.2 Hz, 1H), 8.34 (dd, J = 8.1, 0.5 Hz, 1H), 8.63 (dd, J = 2.2, 0.5 Hz, 1H), 10.21 (br s, 1H)

Reference Example 5

N-(4-t-Butoxycarbonylaminothiophen-3-yl)-5-(2-dimethylamino ethylaminomethyl)pyridine-2-carboxylic acid amide (Reference Compound No. 5-1)

N-(4-t-Butoxycarbonylaminothiophen-3-yl)-5-methanesulfonyloxymethylpyridine-2-carboxylic acid amide (Reference Compound No. 4-1, 0.36 g, 0.83 mmol) and N,N-dimethylethylenediamine (0.46 mL, 4.2 mmol) were dissolved in anhydrous dichloromethane (5.0 mL)-anhydrous acetonitrile (5.0 mL), and then the reaction mixture was stirred at room temperature for 1.5 hours. Ethyl acetate (0.10 L) and water (0.10 L) were added to the reaction solution, and then the mixture was partitioned. The organic layer was washed with brine (0.10 L), dried over anhydrous sodium sulfate, and then the solvent was evaporated under reduced pressure. The obtained residue was purified by silica gel column chromatography (chloroform-methanol) to give 98 mg of the title reference compound as a brown amorphous product. (Yield 28%)

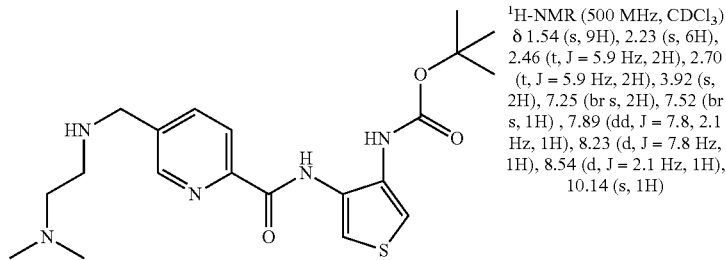

$^1$H-NMR (500 MHz, CDCl$_3$)
δ 1.54 (s, 9H), 2.23 (s, 6H), 2.46 (t, J = 5.9 Hz, 2H), 2.70 (t, J = 5.9 Hz, 2H), 3.92 (s, 2H), 7.25 (br s, 2H), 7.52 (br s, 1H), 7.89 (dd, J = 7.8, 2.1 Hz, 1H), 8.23 (d, J = 7.8 Hz, 1H), 8.54 (d, J = 2.1 Hz, 1H), 10.14 (s, 1H)

N-(4-t-Butoxycarbonylaminothiophen-3-yl)-4-[3-(morpholin-4-yl)propylaminomethyl]benzamide (Reference Compound No. 5-2)

Under ice cooling, methanesulfonyl chloride (0.37 mL, 4.8 mmol) was added to a solution of N-(4-t-butoxycarbonylaminothiophen-3-yl)-4-hydroxymethylbenzamide (Reference Compound No. 3-2, 1.51 g, 4.3 mmol) and triethylamine (1.5 mL, 11 mmol) in anhydrous dichloromethane (70 mL), and the reaction mixture was stirred for 1.5 hours. Acetonitrile (50 mL) and N-(3-aminopropyl)morpholin (3.1 mL, 21 mmol) were added to the reaction solution and the mixture was stirred at room temperature overnight. Water (0.20 L) and ethyl acetate (0.20 L) were added to the reaction solution, and then the mixture was partitioned. The organic layer was washed with brine (0.20 L), dried over anhydrous sodium sulfate, and then the solvent was evaporated under reduced pressure. The obtained residue was purified by silica gel column chromatography (chloroform-methanol) to give 0.81 g of the title reference compound as yellow oil. (Yield 39%)

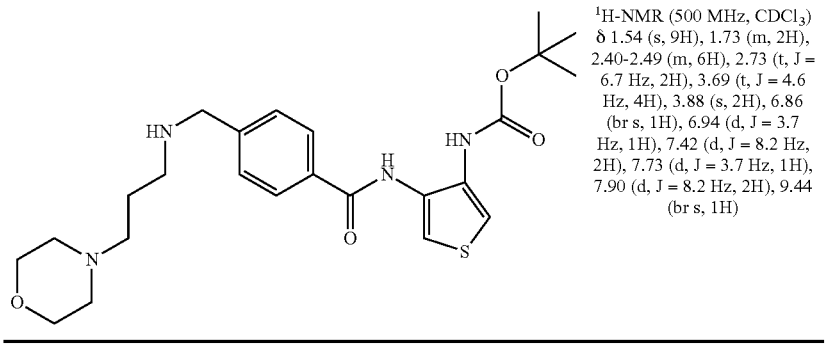

$^1$H-NMR (500 MHz, CDCl$_3$) δ 1.54 (s, 9H), 1.73 (m, 2H), 2.40-2.49 (m, 6H), 2.73 (t, J = 6.7 Hz, 2H), 3.69 (t, J = 4.6 Hz, 4H), 3.88 (s, 2H), 6.86 (br s, 1H), 6.94 (d, J = 3.7 Hz, 1H), 7.42 (d, J = 8.2 Hz, 2H), 7.73 (d, J = 3.7 Hz, 1H), 7.90 (d, J = 8.2 Hz, 2H), 9.44 (br s, 1H)

By using any compounds selected from Reference Compound No. 3-2, 4-1 and commercially available compounds, the following Reference Compounds (No. 5-3~5-12) were obtained by a method similar to that of Reference Compound No. 5-1 or 5-2.

N-(4-t-Butoxycarbonylaminothiophen-3-yl)-5-(3-dimethylaminopropylaminomethyl)pyridine-2-carboxylic acid amide (Reference Compound No. 5-3)

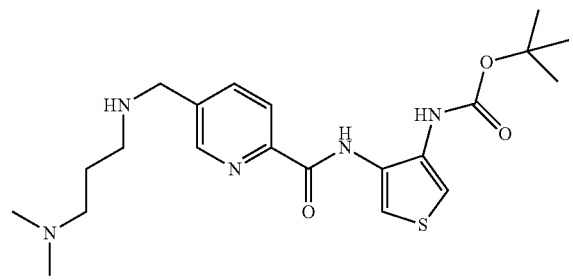

$^1$H-NMR (400 MHz, DMSO-d$_6$) δ 1.51 (s, 9H), 1.51-1.58 (m, 2H), 2.09 (s, 6H), 2.22 (t, J = 7.2 Hz, 2H), 2.49-2.51 (m, 2H), 3.80 (s, 2H), 7.22 (d, J = 3.6 Hz, 1H), 7.81 (d, J = 3.6 Hz, 1H), 7.99 (dd, J = 7.9, 1.5 Hz, 1H), 8.10 (d, J = 7.9 Hz, 1H), 8.58 (d, J = 1.5 Hz, 1H), 9.30 (br s, 1H), 10.48 (br s, 1H)

N-(4-t-Butoxycarbonylaminothiophen-3-yl)-5-[3-(4-methylpiperazin-1-yl)propylaminomethyl]pyridine-2-carboxylic acid amide (Reference Compound No. 5-4)

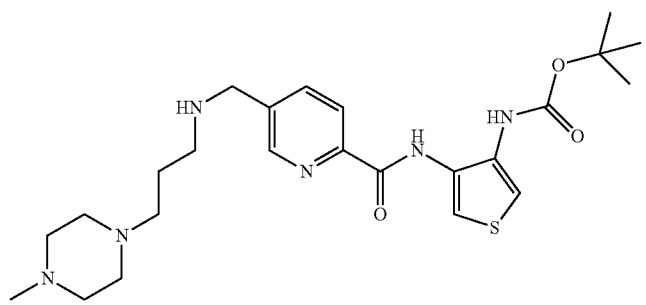

$^1$H-NMR (400 MHz, CDCl$_3$) δ 1.54 (s, 9H), 1.74 (m, 2H), 1.92 (br s, 4H), 2.30 (s, 3H), 2.46 (t, J = 7.1 Hz, 2H), 2.50 (br s, 4H), 2.71 (t, J = 6.7 Hz, 2H), 3.90 (s, 2H), 7.18-7.28 (m, 2H), 7.52 (br s, 1H), 7.89 (dd, J = 8.1, 2.2 Hz, 1H), 8.24 (d, J = 8.1 Hz, 1H), 8.54 (d, J = 2.2 Hz, 1H), 10.15 (s, 1H)

| Compound | NMR |
|---|---|
| N-(4-t-Butoxycarbonylaminothiophen-3-yl)-5-[2-(4-methylpiperazin-1-yl)ethylaminomethyl]pyridine-2-carboxylic acid amide (Reference Compound No. 5-5) 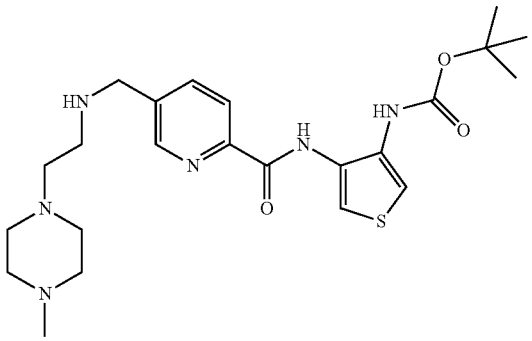 | $^1$H-NMR (500 MHz, CDCl$_3$) δ 1.54 (s, 9H), 2.28 (s, 3H), 2.46 (br s, 8H), 2.52 (t, J = 6.0 Hz, 2H), 2.70 (t, J = 6.0 Hz, 2H), 3.91 (s, 2H), 7.20 (br s, 1H), 7.26 (m, 1H), 7.52 (br s, 1H), 7.88 (dd, J = 7.9, 2.1 Hz, 1H), 8.24 (d, J = 7.9 Hz, 1H), 8.53 (d, J = 2.1 Hz, 1H), 10.14 (s, 1H) |
| N-(4-t-Butoxycarbonylaminothiophen-3-yl)-5-(1-ethylpyrrolidin-2-ylmethylaminomethyl)pyridine-2-carboxylic acid amide (Reference Compound No. 5-6) 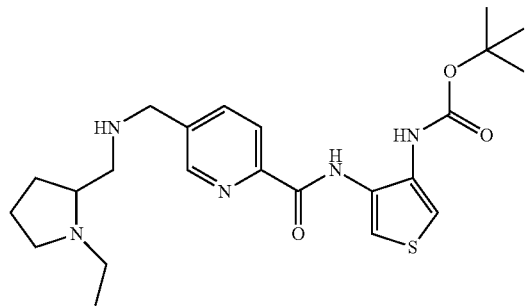 | $^1$H-NMR (500 MHz, CDCl$_3$) δ 1.09 (t, J = 7.2 Hz, 3H), 1.54 (s, 9H), 1.66-1.79 (m, 3H), 1.90 (m, 1H), 2.11-2.25 (m, 2H), 2.50 (m, 1H), 2.59 (dd, J = 11.3, 5.8 Hz, 1H), 2.66 (dd, J = 11.3, 4.0 Hz, 1H), 2.79 (m, 1H), 3.15 (m, 1H), 3.90 (d, J = 14.4 Hz, 1H), 3.93 (d, J = 14.4 Hz, 1H), 7.18 (br s, 2H), 7.51 (br s, 1H), 7.88 (dd, J = 7.9, 2.0 Hz, 1H), 8.23 (d, J = 7.9 Hz, 1H), 8.54 (d, J = 2.0 Hz, 1H), 10.14 (s, 1H) |
| N-(4-t-Butoxycarbonylaminothiophen-3-yl)-5-[2-(morpholin-4-yl)ethylaminomethyl]pyridine-2-carboxylic acid amide (Reference Compound No. 5-7) 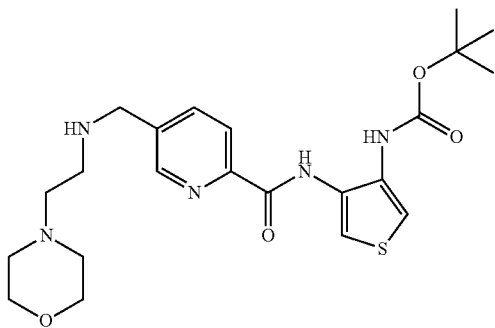 | $^1$H-NMR (500 MHz, CDCl$_3$) δ 1.54 (s, 9H), 2.43 (t, J = 4.5 Hz, 4H), 2.52 (t, J = 5.9 Hz, 2H), 2.71 (t, J = 5.9 Hz, 2H), 3.70 (t, J = 4.5Hz, 4H), 3.92 (s, 2H), 7.25 (br s, 1H), 7.26 (br s, 1H), 7.53 (br s, 1H), 7.88 (dd, J = 7.9, 2.0 Hz, 1H), 8.24 (d, J = 7.9 Hz, 1H), 8.54 (d, J = 2.0 Hz, 1H), 10.14 (br s, 1H) |

| | |
|---|---|
| N-(4-t-Butoxycarbonylaminothiophen-3-yl)-5-[4-(morpholin-4-yl)butylaminomethyl]pyridine-2-carboxylic acid amide (Reference Compound No. 5-8) 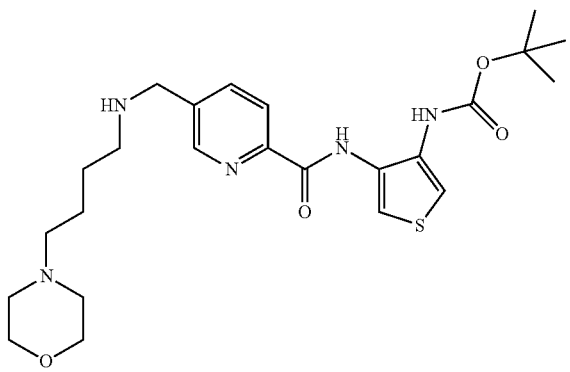 | $^1$H-NMR (400 MHz, CDCl$_3$) δ 1.53-1.58 (m, 4H), 1.54 (s, 9H), 2.34 (m, 2H), 2.43 (m, 4H), 2.65 (t, J = 6.6 Hz, 2H), 3.71 (t, J = 4.6 Hz, 4H), 3.90 (s, 2H), 7.19 (br s, 1H), 7.25 (m, 1H), 7.52 (br s, 1H), 7.88 (dd, J = 8.1, 2.2 Hz, 1H), 8.23 (d, J = 8.1 Hz, 1H), 8.53 (d, J = 2.2 Hz, 1H), 10.14 (s, 1H) |
| N-(4-t-Butoxycarbonylaminiothiophen-3-yl)-5-[2-(pyrrolidin-1-yl)ethylaminomethyl]pyridine-2-carboxylic acid amide (Reference Compound No. 5-9) 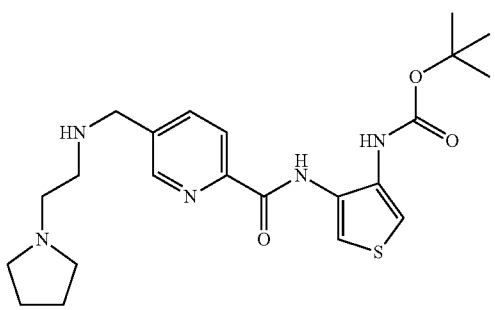 | $^1$H-NMR (500 MHz, CDCl$_3$) δ 1.54 (s, 9H), 1.80 (br s, 4H), 2.55 (br s, 4H), 2.67 (t, J = 5.9 Hz, 2H), 2.76 (t, J = 5.9 Hz, 2H), 3.92 (s, 2H), 7.20 (br s, 2H), 7.51 (br s, 1H), 7.89 (dd, J = 7.9, 2.1 Hz, 1H), 8.23 (dd, J = 7.9, 0.6 Hz, 1H), 8.54 (dd, J = 2.1, 0.6 Hz, 1H), 10.14 (s, 1H) |
| N-(4-t-Butoxycarbonylaminothiophen-3-yl)-5-[3-(pyrrolidin-1-yl)propylaminomethyl]pyridine-2-carboxylic acid amide (Reference Compound No. 5-10) 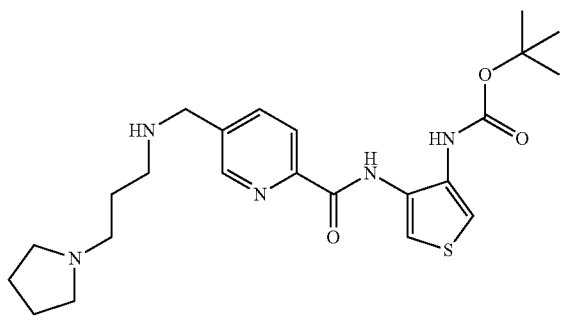 | $^1$H-NMR (500 MHz, CDCl$_3$) δ 1.54 (s, 9H), 1.71-1.79 (m, 6H), 2.48-2.54 (m, 6H), 2.70 (t, J = 6.9 Hz, 2H), 3.89 (s, 2H), 7.19 (br s, 2H), 7.52 (br s, 1H), 7.87 (dd, J = 7.9, 2.1 Hz, 1H), 8.23 (d, J = 7.9 Hz, 1H), 8.53 (d, J = 2.1 Hz, 1H), 10.14 (s, 1H) |

-continued

| Compound | NMR |
|---|---|
| N-(4-t-Butoxycarbonylaminothiophen-3-yl)-4-(2-dimethylaminoethylaminomethyl) benzamide (Reference Compound No. 5-11) 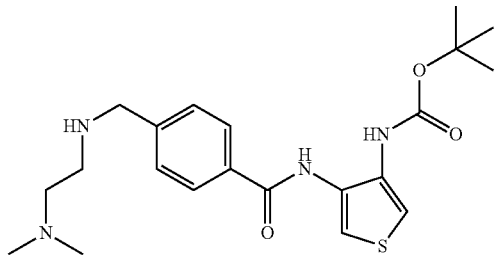 | $^1$H-NMR (400 MHz, CDCl$_3$) δ 1.54 (s, 9H), 2.24 (s, 6H), 2.48 (t, J = 6.0 Hz, 2H), 2.71 (t, J = 6.0 Hz, 2H), 3.88 (s, 2H), 6.95 (d, J = 3.7 Hz, 1H), 6.99 (s, 1H), 7.42 (d, J = 8.4 Hz, 2H), 7.72 (d, J = 3.7 Hz, 1H), 7.88 (d, J = 8.4 Hz, 2H), 9.41 (br s, 1H) |
| N-(4-t-Butoxycarbonylaminothiophen-3-yl)-5-[3-(morpholin-4-yl) propylaminomethyl]pyridine-2-carboxylic acid amide (Reference Compound No. 5-12) 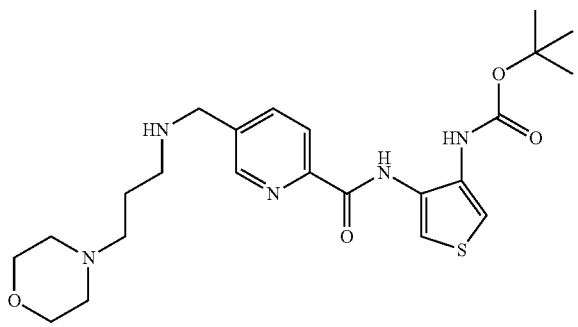 | $^1$H-NMR (400 MHz, CDCl$_3$) δ 1.54 (s, 9H), 1.72 (m, 2H), 2.39-2.48 (m, 6H), 2.70 (t, J = 6.7 Hz, 2H), 3.70 (t, J = 4.6 Hz, 4H), 3.90 (s, 2H), 7.18 (br s, 1H), 7.24 (br s, 1H), 7.53 (br s, 1H), 7.88 (dd, J = 1.9, 2.1 Hz, 1H), 8.24 (dd, J = 7.9, 0.7 Hz, 1H), 8.54 (dd, J = 2.1, 0.7 Hz, 1H), 10.14 (br s, 1H) |

Reference Example 6

N-(4-t-Butoxycarbonylaminothiophen-3-yl)-5-[3-(3,4-difluoro phenyl)-1-[3-(morpholin-4-yl)propyl]ureidomethyl]pyridine-2-carboxylic acid amide (Reference Compound No. 6-1)

3,4-Difluorophenyl isocyanate (15 μL, 0.13 mmol) was added to a solution of N-(4-t-butoxycarbonylaminothiophen-3-yl)-5-[3-(morpholin-4-yl)propylaminomethyl]pyridine-2-carboxylic acid amide (Reference Compound No. 5-12, 43 mg, 0.091 mmol) in dichloromethane (2.0 mL), and then the reaction mixture was stirred at room temperature for 1.5 hours. The reaction solution was purified by silica gel column chromatography (chloroform-methanol) to give 53 mg of the title reference compound as a colorless solid. (Yield 92%)

N-(4-t-Butoxycarbonylaminothiophen-3-yl)-5-[1-(2-dimethylaminoethyl)-3-(thiazol-2-yl)ureidomethyl] pyridine-2-carboxylic acid amide (Reference Compound No. 6-2)

Under ice cooling, N,N'-carbonyldiimidazole (0.10 g, 0.64 mmol) and 2-aminothiazol (63 mg, 0.63 mmol) were dissolved in THF (2.0 mL), and then the reaction mixture was stirred for 30 minutes. N-(4-t-Butoxycarbonylaminothiophen-3-yl)-5-(2-dimethylamino ethylaminomethyl) pyridine-2-carboxylic acid amide (Reference Compound No. 5-1, 79 mg, 0.19 mmol) was added to the reaction solution, and then the reaction mixture was stirred at 50° C. overnight. Water (30 mL) was added to the reaction solution, the whole was extracted with ethyl acetate (30 mL) twice. The organic layer was washed with water (30 mL), dried over anhydrous

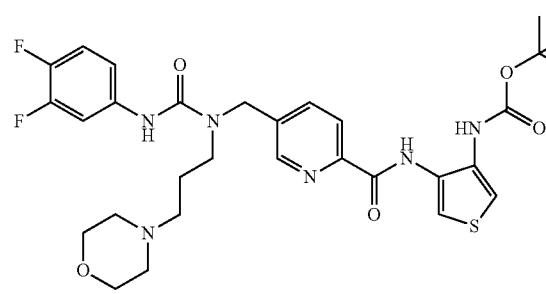

$^1$H-NMR (500 MHz, CDCl$_3$) δ 1.53 (s, 9H), 1.79 (m, 2H), 2.43-2.51 (m, 6H), 3.37 (m, 2H), 3.67 (m, 4H), 4.63 (s, 2H), 7.00-7.13 (m, 3H), 7.24 (br s, 1H), 7.46-7.57 (m, 2H), 7.90 (dd, J = 7.9, 2.0 Hz, 1H), 8.23 (d, J = 7.9 Hz, 1H), 8.55 (d, J = 2.0 Hz, 1H), 9.15 (s, 1H), 10.14 (s, 1H)

magnesium sulfate, and then the solvent was evaporated under reduced pressure. The obtained residue was purified by silica gel column chromatography (chloroform-methanol) to give 91 mg of the title reference compound as a colorless amorphous product. (Yield 84%)

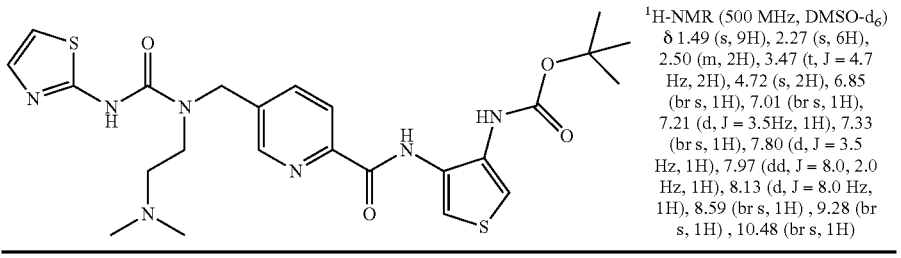

$^1$H-NMR (500 MHz, DMSO-$d_6$) δ 1.49 (s, 9H), 2.27 (s, 6H), 2.50 (m, 2H), 3.47 (t, J = 4.7 Hz, 2H), 4.72 (s, 2H), 6.85 (br s, 1H), 7.01 (br s, 1H), 7.21 (d, J = 3.5Hz, 1H), 7.33 (br s, 1H), 7.80 (d, J = 3.5 Hz, 1H), 7.97 (dd, J = 8.0, 2.0 Hz, 1H), 8.13 (d, J = 8.0 Hz, 1H), 8.59 (br s, 1H), 9.28 (br s, 1H), 10.48 (br s, 1H)

By using any compounds selected from Reference Compound No. 5-1~5-12 and commercially available compounds, the following Reference Compounds (No. 6-3~6-120) were obtained by a method similar to that of Reference Compound No. 6-1 or 6-2.

N-(4-t-Butoxycarbonylaminothiophen-3-yl)-5-[3-(2,3-dihydrobenzo[1,4]dioxini-6-yl)-1-[3-(morpholin-4-yl)propyl]ureidomethyl]pyridine-2-carboxylic acid amide (Reference Compound No. 6-3)

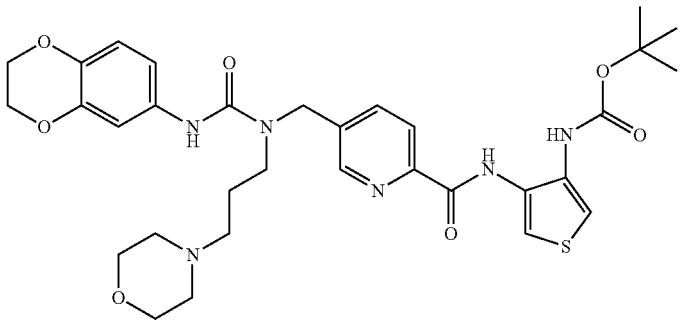

$^1$H-NMR (500 MHz, CDCl$_3$) δ 1.53 (s, 9H), 1.76 (m, 2H), 2.41-2.50 (m, 6H), 3.35 (t, J = 5.5 Hz, 2H), 3.65 (t, J = 4.3 Hz, 4H), 4.23-4.25 (m, 4H), 4.62 (s, 2H), 6.79-6.83 (m, 2H), 6.98 (m, 1H), 7.15 (br s, 1H), 7.27 (br s, 1H), 7.51 (br s, 1H), 7.92 (dd, J = 7.9, 2.0 Hz, 1H), 8.22 (d, J = 7.9 Hz, 1H), 8.55 (d, J = 2.0 Hz, 1H), 8.95 (s, 1H), 10.12 (s, 1H)

N-(4-t-Butoxycarbonylaminothiophen-3-yl)-5-[3-(2,3-dihydrobenzo[1,4]dioxin-6-yl)-1-(2-dimethylaminoethyl)ureidomethyl]pyridine-2-carboxylic acid amide (Reference Compound No. 6-4)

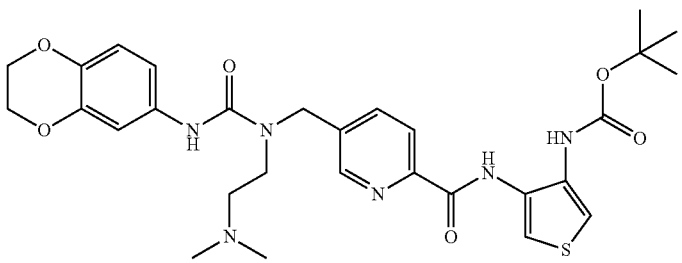

$^1$H-NMR (400 MHz, CDCl$_3$) δ 1.54 (s, 9H), 2.38 (s, 6H), 2.50 (t, J = 4.2 Hz, 2H), 3.30 (t, J = 4.2 Hz, 2H), 4.20-4.26 (m, 4H), 4.64 (s, 2H), 6.78 (d, J = 8.8 Hz, 1H), 6.81 (dd, J = 8.8, 2.2 Hz, 1H), 6.93 (d, J = 2.2 Hz, 1H), 7.12 (br s, 1H), 7.25 (br s, 1H), 7.53 (br s, 1H), 7.90 (dd, J = 8.1, 2.2 Hz, 1H), 8.24 (dd, J = 8.1, 0.7 Hz, 1H), 8.54 (dd, J = 2.2, 0.7 Hz, 1H), 10.14 (br s, 1H), 10.85 (br s, 1H)

N-(4-t-Butoxycarbonylaminothiophen-
3-yl)-5-[1-(2-dimethylaminoethyl)-
3-(3-fluorophenyl)ureidomethyl]
pyridine-2-carboxylic acid amide
(Reference Compound No. 6-5)

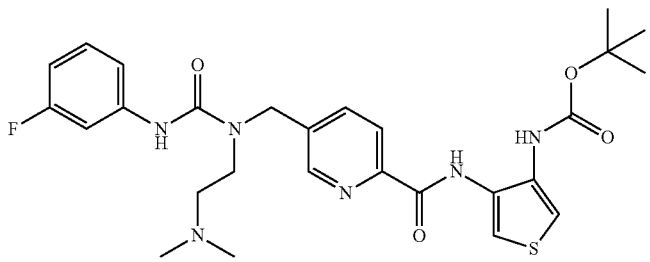

$^1$H-NMR (400 MHz, CDCl$_3$)
δ 1.54 (s, 9H), 2.41 (s, 6H),
2.54 (t, J = 4.3Hz, 2H), 3.32
(t, J = 4.3Hz, 2H), 4.65 (s,
2H), 6.68 (tdd, J = 8.4, 2.6,
0.9 Hz, 1H), 7.00 (m, 1H),
7.10 (br s, 1H), 7.17-7.30
(m, 3H), 7.54 (br s, 1H),
7.90 (dd, J = 8.0, 2.1 Hz,
1H), 8.25 (dd, J = 8.0, 0.7
Hz, 1H), 8.55 (dd, J = 2.1,
0.7 Hz, 1H), 10.15 (br s,
1H), 11.32 (br s, 1H)

N-(4-t-Butoxycarbonylaminothiophen-
3-yl)-5-[1-(2-dimethylaminoethyl)-
3-(thiophen-3-yl)ureidomethyl]
pyridine-2-carboxylic acid amide
(Reference Compound No. 6-6)

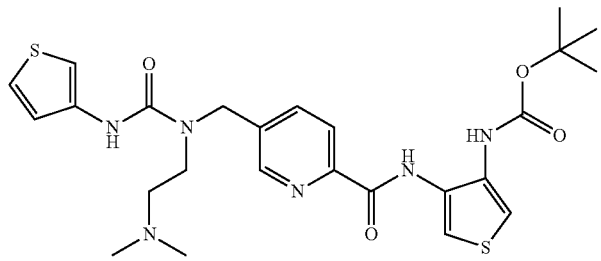

$^1$H-NMR (400 MHz, CDCl$_3$)
δ 1.54 (s, 9H), 2.39 (s, 6H),
2.52 (t, J = 4.3 Hz, 2H), 3.31
(t, J = 4.3 Hz, 2H), 4.67 (s,
2H), 6.87 (dd, J = 5.1, 1.3
Hz, 1H), 7.12 (br s, 1H),
7.21 (dd, J = 5.1, 3.4 Hz,
1H), 7.25 (m, 1H), 7.30 (dd,
J = 3.4, 1.3 Hz, 1H), 7.53
(br s, 1H), 7.90 (dd, J = 8.1,
2.2 Hz, 1H), 8.24 (dd, J =
8.1, 0.6 Hz, 1H), 8.54 (dd,
J = 2.2, 0.6 Hz, 1H), 10.14
(s, 1H), 11.51 (s, 1H)

N-(4-t-Butoxycarbonylaminothiophen-
3-yl)-5-[1-(2-dimethylaminoethyl)-
3-phenethylureidomethyl]pyridine-
2-carboxylic acid amide
(Reference Compound No. 6-7)

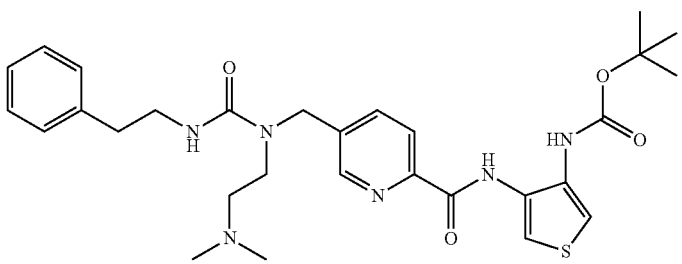

$^1$H-NMR (400 MHz, CDCl$_3$)
δ 1.54 (s, 9H), 2.04 (s,
6H), 2.30 (t, J = 4.7 Hz, 2H),
2.84 (t, J = 7.0Hz, 2H), 3.11
(t, J = 4.7 Hz, 2H), 3.52 (m,
2H), 4.58 (s, 2H), 7.14 (br
s, 1H), 7.21 (m, 1H), 7.22
(m, 2H), 7.27-7.32 (m, 3H),
7.52 (br s, 1H), 7.74 (br s,
1H), 7.81 (dd, J = 8.0, 1.8
Hz, 1H), 8.22 (d, J = 8.0 Hz,
1H), 8.48 (d, J = 1.8 Hz, 1H),
10.13 (s, 1H)

N-(4-t-Butoxycarbonylaminothiophen-
3-yl)-5-[3-cyclopentyl-1-(2-
dimethylaminoethyl)ureidomethyl]
pyridine-2-carboxylic acid amide
(Reference Compound No. 6-8)

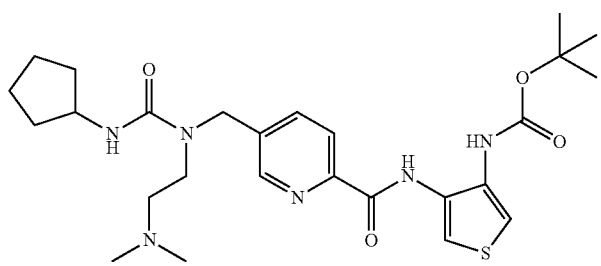

1H-NMR (500 MHz, CDCl$_3$)
δ 1.37 (m, 2H), 1.53 (s, 9H),
1.56-1.68 (m, 4H), 1.94 (m,
2H), 2.24 (s, 6H), 2.38 (t,
J = 4.4 Hz, 2H), 3.16 (t, J=
4.4 Hz, 2H), 4.06 (m, 1H),
4.57 (s, 2H), 7.11 (br s,
1H), 7.24 (m, 1H), 7.51 (br
s, 1H), 7.84 (dd, J = 7.9,
2.0 Hz, 1H), 8.04 (d, J = 6.4
Hz, 1H), 8.21 (d, J = 7.9 Hz,
1H), 8.48 (d, J = 2.0 Hz, 1H),
10.12 (s, 1H)

| | |
|---|---|
| 5-[3-(Benzo[1,3]dioxol-5-yl)-1-(2-dimethylaminoethyl)ureidomethyl]-N-(4-t-butoxycarbonylaminothiophen-3-yl)pyridine-2-carboxylic acid amide (Reference Compound No. 6-9)<br>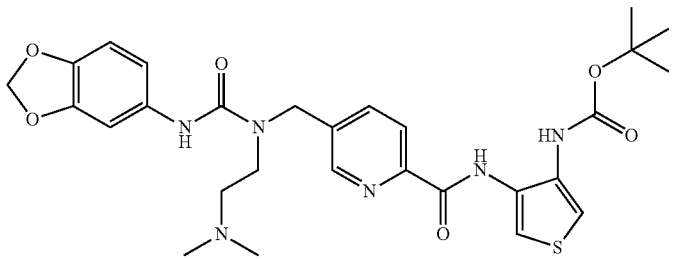 | $^1$H-NMR (400 MHz, CDCl$_3$) δ 1.54 (s, 9H), 2.38 (s, 6H), 2.51 (t, J= 4.3 Hz, 2H), 3.31 (t, J = 4.3 Hz, 2H), 4.64 (s, 2H), 5.92 (s, 2H), 6.65 (dd, J = 8.3, 2.1 Hz, 1H), 6.73 (d, J = 8.3 Hz, 1H), 7.08 (d, J = 2.1 Hz, 1H), 7.13 (br s, 1H), 7.24 (m, 1H), 7.54 (br s, 1H), 7.90 (dd, J = 8.0, 2.1 Hz, 1H), 8.24 (dd, J = 8.0, 0.7 Hz, 1H), 8.54 (dd, J = 2.1, 0.7 Hz, 1H), 10.14 (s, 1H), 10.94 (s, 1H) |
| N-(4-t-Butoxycarbonylaminothiophen-3-yl)-5-[1-(2-dimethylaminoethyl)-3-(4-fluoro-3-methylphenyl)ureidomethyl]pyridine-2-carboxylic acid amide (Reference Compound No. 6-10)<br>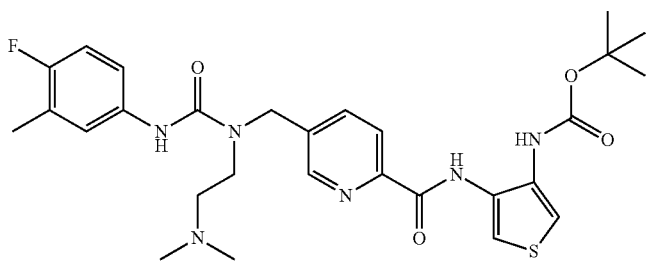 | $^1$H-NMR (400 MHz, CDCl$_3$) δ 1.54 (s, 9H), 2.26 (d, J = 2.0 Hz, 3H), 2.39 (s, 6H), 2.53 (t, J = 4.3 Hz, 2H), 3.32 (t, J = 4.3 Hz, 2H), 4.65 (s, 2H), 6.91 (t, J = 9.0 Hz, 1H), 7.00 (m, 1H), 7.11 (br s, 1H), 7.24 (m, 1H), 7.28 (m, 1H), 7.54 (br s, 1H), 7.91 (dd, J = 7.9, 2.2 Hz, 1H), 8.25 (dd, J = 7.9, 0.7 Hz, 1H), 8.55 (dd, J = 2.2, 0.7 Hz, 1H), 10.14 (s, 1H), 10.96 (s, 1H) |
| N-(4-t-Butoxycarbonylaminothiophen-3-yl)-5-[1-(2-dimethylaminoethyl)-3-(3-methylphenyl)ureidomethyl]pyridine-2-carboxylic acid amide (Reference Compound No. 6-11)<br>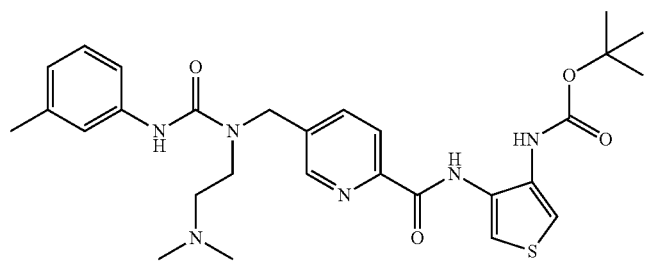 | $^1$H-NMR (400 MHz, CDCl$_3$) δ 1.54 (s, 9H), 2.34 (s, 3H), 2.40 (s, 6H), 2.53 (t, J = 4.4 Hz, 2H), 3.33 (t, J = 4.4 Hz, 2H), 4.66 (s, 2H), 6.82 (d, J = 7.9 Hz, 1H), 7.05 (d, J = 7.9 Hz, 1H), 7.15 (br s, 1H), 7.17 (t, J = 7.9Hz, 1H), 7.24 (br s, 1H), 7.29 (br s, 1H), 7.53 (br s, 1H), 7.92 (dd, J = 7.9, 2.1 Hz, 1H), 8.25 (d, J = 7.9Hz, 1H), 8.56 (d, J = 2.1 Hz, 1H), 10.14 (s, 1H), 10.97 (s, 1H) |
| N-(4-t-Butoxycarbonylaminothiophen-3-yl)-5-[1-(2-dimethylaminoethyl)-3-(3-methoxyphenyl)ureidomethyl]pyridine-2-carboxylic acid amide (Reference Compound No. 6-12)<br>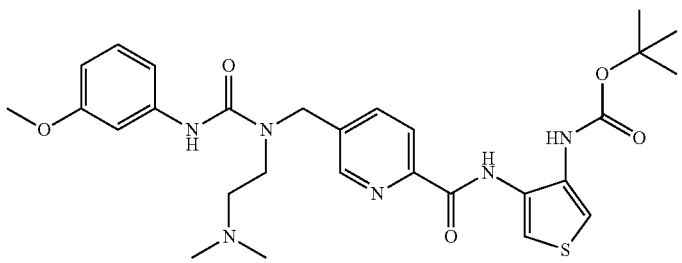 | $^1$H-NMR (400 MHz, CDCl$_3$) δ 1.54 (s, 9H), 2.40 (s, 6H), 2.52 (t, J = 4.4 Hz, 2H), 3.33 (t, J = 4.4 Hz, 2H), 3.82 (s, 3H), 4.66 (s, 2H), 6.56 (ddd, J = 8.2, 2.3, 0.9 Hz, 1H), 6.84 (ddd, J = 8.2, 2.3, 0.9 Hz, 1H), 7.14 (t, J = 2.3 Hz, 1H), 7.15 (br s, 1H), 7.18 (t, J = 8.2 Hz, 1H), 7.26 (m, 1H), 7.53 (br s, 1H), 7.91 (dd, J = 8.0, 2.2 Hz, 1H), 8.25 (dd, J = 8.0, 0.7 Hz, 1H), 8.55 (dd, J = 2.2, 0.7 Hz, 1H), 10.15 (s, 1H), 11.13 (s, 1H) |

N-(4-t-butoxycarbonylaminothiophen-
3-yl)-5-[1-[3-(morpholin-4-yl)
propyl]-3-(thiophen-3-yl)ureidomethyl]
pyridine-2-carboxylic acid amide
(Reference Compound No. 6-13)

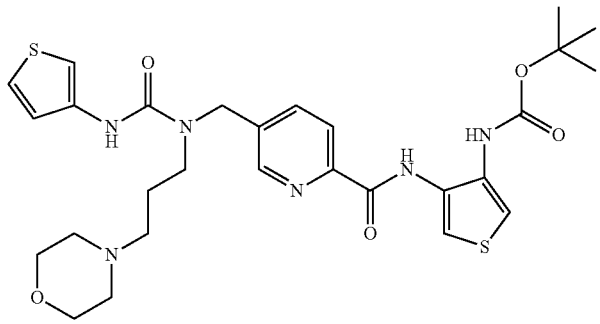

$^1$H-NMR (500 MHz, CDCl$_3$)
δ 1.53 (s, 9H), 1.77 (m, 2H),
2.42-2.50 (m, 6H), 3.36 (t,
J = 5.7 Hz, 2H), 3.72 (t, J =
4.6 Hz, 4H), 4.64 (s, 2H),
7.10 (dd, J = 5.2, 1.5 Hz,
1H), 7.22-7.27 (m, 3H), 7.30
(m, 1H), 7.52 (br s, 1H),
7.91 (dd, J = 8.0, 1.9 Hz,
1H), 8.23 (d, J = 8.0 Hz, 1H),
8.55 (d, J = 1.9 Hz, 1H), 9.22
(br s, 1H), 10.12 (br s, 1H)

N-(4-t-Butoxycarbonylaminothiophen-
3-yl)-5-[3-(3-fluorophenyl)-1-
[3-(morpholin-4-yl)propyl]ureidomethyl]
pyridine-2-carboxylic acid amide
(Reference Compound No. 6-14)

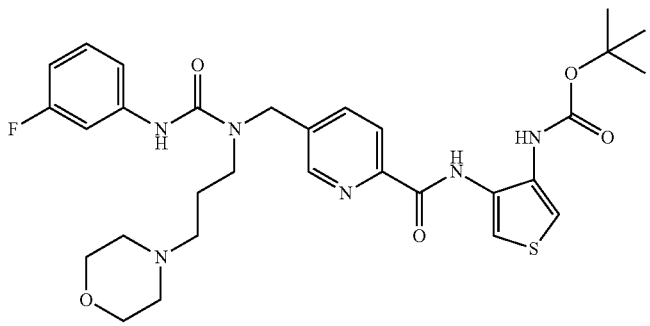

$^1$H-NMR (500 MHz, CDCl$_3$)
δ 1.53 (s, 9H), 1.79 (m, 2H),
2.44-2.51 (m, 6H), 3.38 (t,
J = 5.7 Hz, 2H), 3.71 (t, J =
4.6 Hz, 4H), 4.64 (s, 2H),
6.78 (tdd, J = 8.3, 2.5, 0.8
Hz, 1H), 7.01-7.15 (m, 2H),
7.20-7.30 (m, 2H), 7.41 (dt,
J = 11.1, 2.2 Hz, 1H), 7.53
(br s, 1H), 7.91 (dd, J = 8.0,
1.9 Hz, 1H), 8.23 (d, J = 8.0
Hz, 1H), 8.56 (d, J = 1.9 Hz,
1H), 9.03 (s, 1H), 10.14 (br
s, 1H)

N-(4-t-Butoxycarbonylaminothiophen-
3-yl)-5-[3-(4-fluoro-3-methylphenyl)-
1-[3-(morpholin-4-yl)propyl]ureidomethyl]
pyridine-2-carboxylic acid amide
(Reference Compound No. 6-15)

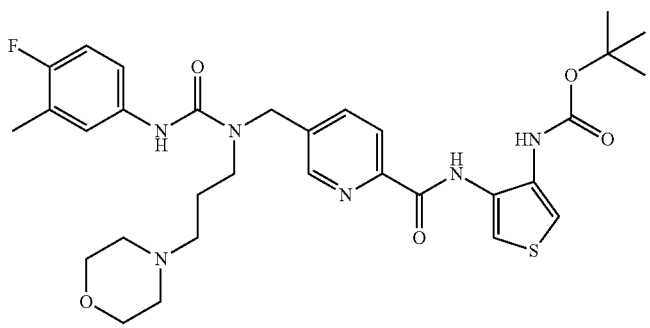

$^1$H-NMR (400 MHz, CDCl$_3$)
δ 1.53 (s, 9H), 1.78 (m, 2H),
2.27 (d, J = 2.0 Hz, 3H),
2.41-2.51 (m, 6H), 3.37 (t,
J = 5.6 Hz, 2H), 3.64 (t, J =
4.6 Hz, 4H), 4.63 (s, 2H),
6.95 (t, J = 8.9 Hz, 1H), 7.12
(m, 1H), 7.21-7.31 (m, 3H),
7.53 (br s, 1H), 7.91 (dd,
J = 7.9, 2.1 Hz, 1H), 8.22
(dd, J = 7.9, 0.5 Hz, 1H),
8.55 (dd, J = 2.1, 0.5 Hz,
1H), 8.98 (s, 1H), 10.12 (br
s, 1H)

N-(4-t-Butoxycarbonylaminothiophen-
3-yl)-5-[3-(2,3-dihydro-1-
benzofuran-5-yl)-1-[3-(morpholin-4-
yl)propyl]ureidomethyl]pyridine-
2-carboxylic acid amide
(Reference Compound No. 6-16)

$^1$H-NMR (500 MHz, CDCl$_3$)
δ 1.53 (s, 9H), 1.77 (m, 2H),
2.44 (br s, 4H), 2.48 (t, J =
6.0 Hz, 2H), 3.21 (t, J =
8.6 Hz, 2H), 3.37 (t, J = 5.5
Hz, 2H), 3.61 (t, J = 4.6 Hz,
4H), 4.57 (t, J = 8.6 Hz, 2H),
4.63 (s, 2H), 6.72 (d, J =
8.3 Hz, 1H), 6.95 (dd, J =
8.3, 2.2 Hz, 1H), 7.14 (br
s, 1H), 7.21-7.29 (m, 1H),
7.33 (d, J = 2.2 Hz, 1H), 7.51
(br s, 1H), 7.93 (dd, J= 7.9,
2.1 Hz, 1H), 8.22 (dd, J =
7.9, 0.5 Hz, 1H), 8.55 (dd,
J = 2.1, 0.5 Hz, 1H), 8.99
(br s, 1H), 10.12 (br s, 1H)

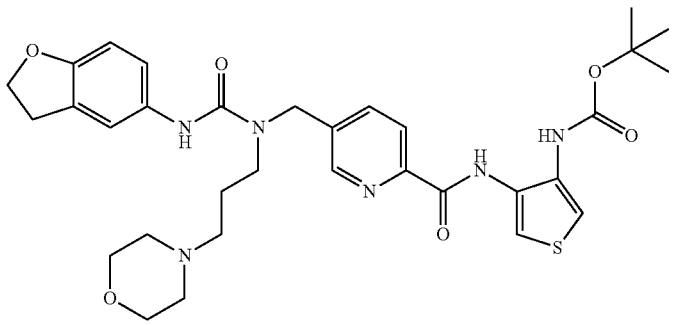

N-(4-t-Butoxycarbonylaminothiophen-
3-yl)-5-[3-(3,4-difluorophenyl)-
1-(2-dimethylaminoethyl)ureidomethyl]
pyridine-2-carboxylic acid amide
(Reference Compound No. 6-17)

$^1$H-NMR (500 MHz, CDCl$_3$)
δ 1.54 (s, 9H), 2.40 (s, 6H),
2.54 (m, 2H), 3.32 (t, J =
4.3 Hz, 2H), 4.64 (s, 2H),
6.90 (m, 1H), 6.98-7.17 (m,
2H), 7.24 (br s, 1H), 7.39
(m, 1H), 7.55 (br s, 1H),
7.89 (dd, J = 8.0, 1.9 Hz,
1H), 8.25 (d, J = 8.0 Hz, 1H),
8.55 (d, J = 1.9 Hz, 1H),
10.15 (s, 1H), 11.30 (s, 1H)

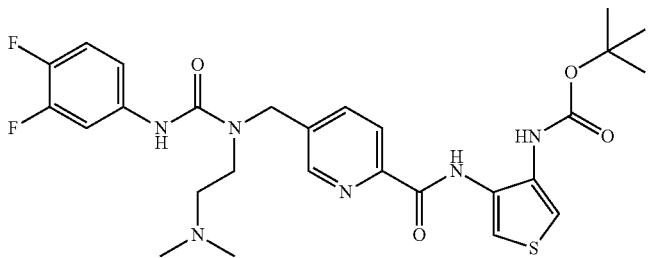

N-(4-t-Butoxycarbonylaminothiophen-
3-yl)-5-5-[1-(2-dimethylaminoethyl)-
3-(4-fluorophenyl)ureidomethyl]
pyridine-2-carboxylic acid amide
(Reference Compound No. 6-18)

$^1$H-NMR (500 MHz, CDCl$_3$)
δ 1.54 (s, 9H), 2.40 (s, 6H),
2.53 (t, J = 4.2 Hz, 2H), 3.33
(t, J = 4.2 Hz, 2H),4.65 (s,
2H), 6.98 (t, J = 8.9 Hz, 2H),
7.12 (br s, 1H), 7.25 (br s,
1H), 7.30 (dd, J = 8.9, 4.7
Hz, 2H), 7.53 (br s, 1H),
7.91 (dd, J = 7.9, 2.0 Hz,
1H), 8.25 (d, J = 7.9 Hz, 1H),
8.55 (d, J = 2.0 Hz, 1H),
10.14 (s, 1H), 11.06 (s, 1H)

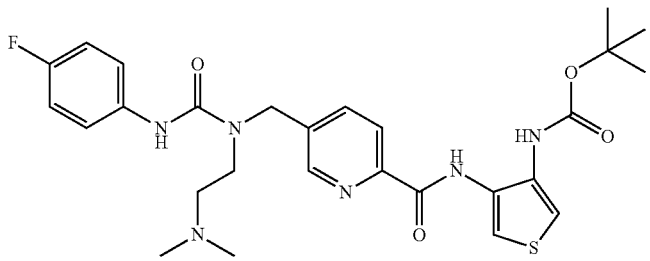

5-[3-(3-Acetylphenyl)-1-(2-
dimethylaminoethyl)ureidomethyl]-N-(4-
t-butoxycarbonylaminothiophen-3-
yl)pyridine-2-carboxylic acid amide
(Reference Compound No. 6-19)

$^1$H-NMR (500 MHz, CDCl$_3$)
δ 1.54 (s, 9H), 2.43 (s, 6H),
2.56 (t, J = 4.1 Hz, 2H), 2.61
(s, 3H), 3.35 (t, J = 4.1 Hz,
2H), 4.67 (s, 2H), 7.10 (br
s, 1H), 7.25 (br s, 1H),7.39
(t, J = 8.0 Hz, 1H), 7.54 (br
s, 1H), 7.58 (d, J = 8.0 Hz,
1H), 7.66 (ddd, J = 8.0, 1.0,
0.5 Hz, 1H), 7.89-7.93 (m,
2H), 8.26 (d, J = 8.2Hz, 1H),
8.56 (d, J = 2.1 Hz, 1H),
10.15 (s, 1H), 11.43 (s, 1H)

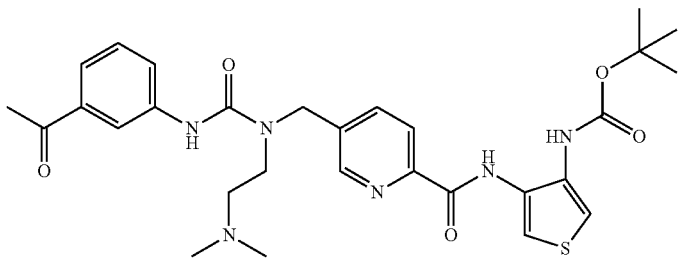

| Compound | NMR |
|---|---|
| 5-[3-(Benzo[1,3]dioxol-5-yl)-1-(2-dimethylaminoethyl)ureidomethyl]-N-(4-t-butoxycarbonylaminothiophen-3-yl)pyridine-2-carboxylic acid amide (Reference Compound No. 6-20) 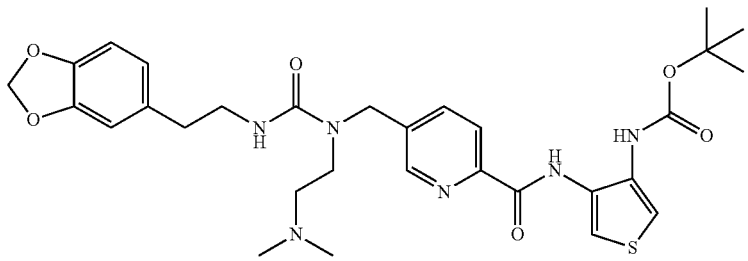 | $^1$H-NMR (500 MHz, CDCl$_3$) δ 1.54 (s, 9H), 2.11 (s, 6H), 2.33 (t, J = 4.5 Hz, 2H), 2.75 (t, J = 6.9 Hz, 2H), 3.14 (t, J = 4.5 Hz, 2H), 3.46 (m, 2H), 4.58 (s, 2H), 5.92 (s, 2H), 6.66 (dd, J = 7.7 1.6 Hz, 1H), 6.72 (d, J = 1.6 Hz, 1H), 6.75 (d, J = 7.7 Hz, 1H), 7.17 (br s, 2H), 7.52 (br s, 1H), 7.61 (br s, 1H), 7.81 (dd, J = 8.1, 2.1 Hz, 1H), 8.22 (dd, J = 8.1, 0.6 Hz, 1H), 8.44 (dd, J = 2.1, 0.6 Hz, 1H), 10.13 (s, 1H) |
| N-(4-t-Butoxycarbonylaminothiophen-3-yl)-5-[1-(3-dimethylaminopropyl)-3-(3-methylphenyl)ureidomethyl]pyridine-2-carboxylic acid amide (Reference Compound No. 6-21) 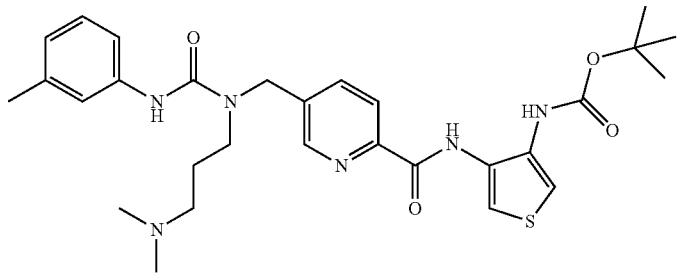 | $^1$H-NMR (400 MHz, DMSO-d$_6$) δ 1.49 (s, 9H), 1.70 (m, 2H), 2.20 (s, 6H), 2.26 (s, 3H), 2.27 (m, 2H), 3.34 (m, 2H), 4.62 (s, 2H), 6.76 (d, J = 7.7 Hz, 1H), 7.12 (t, J = 7.7 Hz, 1H), 7.19 (d, J = 7.7 Hz, 1H), 7.21 (d, J = 3.7 Hz, 1H), 7.27 (s, 1H), 7.81 (d, J = 3.7 Hz, 1H), 7.98 (dd, J = 8.1, 1.6 Hz, 1H), 8.13 (d, J = 8.1 Hz, 1H), 8.60 (d, J = 1.6 Hz, 1H), 9.30 (br s, 1H), 9.61 (br s, 1H), 10.49 (br s, 1H). |
| N-(4-t-Butoxycarbonylaminothiophen-3-yl)-5-[3-(3,4-difluorophenyl)-1-(3-dimethylaminopropyl)ureidomethyl]pyridine-2-carboxylic acid amide (Reference Compound No. 6-22) 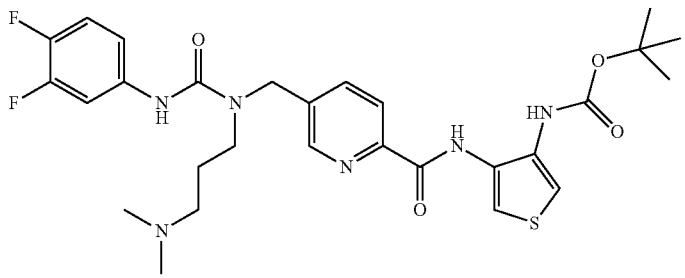 | $^1$H-NMR (400 MHz, DMSO-d$_6$) δ 1.49 (s, 9H), 1.70 (m, 2H), 2.19 (s, 6H), 2.26 (t, J = 6.2 Hz, 2H), 3.35 (m, 2H), 4.63 (s, 2H), 7.08 (m, 1H), 7.21 (d, J = 3.7 Hz, 1H), 7.31 (m, 1H), 7.67 (ddd, J = 13.8, 7.4, 2.7 Hz, 1H), 7.81 (d, J = 3.7 Hz, 1H), 7.97 (dd, J = 7.9, 1.7 Hz, 1H), 8.13 (d, J = 7.9 Hz, 1H), 8.59 (d, J = 1.7 Hz, 1H), 9.30 (br s, 1H), 9.95 (br s, 1H), 10.48 (br s, 1H). |
| N-(4-t-Butoxycarbonylaminothiophen-3-yl)-5-[1-(3-dimethylaminopropyl)-3-(thiophen-3-yl)ureidomethyl]pyridine-2-carboxylic acid amide (Reference Compound No. 6-23) 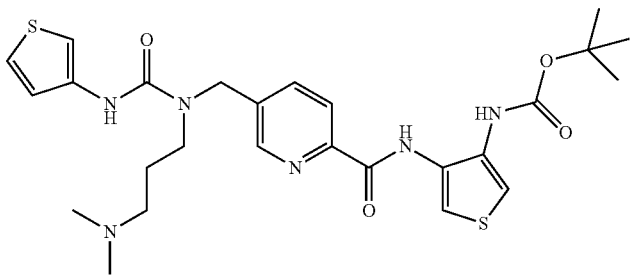 | $^1$H-NMR (400 MHz, DMSO-d$_6$) δ 1.49 (s, 9H), 1.68 (m, 2H), 2.19 (s, 6H), 2.25 (t, J = 6.1 Hz, 2H), 3.33 (m, 2H), 4.62 (s, 2H), 7.04 (dd, J = 5.1, 1.5 Hz, 1H), 7.22 (d, J = 3.7 Hz, 1H), 7.27 (dd, J = 3.2, 1.5 Hz, 1H), 7.39 (dd, J = 5.1, 3.2 Hz, 1H), 7.81 (d, J = 3.7 Hz, 1H), 7.96 (dd, J = 8.1, 1.6 Hz, 1H), 8.13 (d, J = 8.1 Hz, 1H), 8.59 (d, J = 1.6 Hz, 1H), 9.29 (br s, 1H), 10.06 (br s, 1H), 10.48 (br s, 1H). |

N-(4-t-Butoxycarbonylaminothiophen-3-yl)-5-[3-(2,3-dihydrobenzo[1,4]dioxin-6-yl)-1-(3-dimethylaminopropyl)ureidomethyl]pyridine-2-carboxylic acid amide
(Reference Compound No. 6-24)

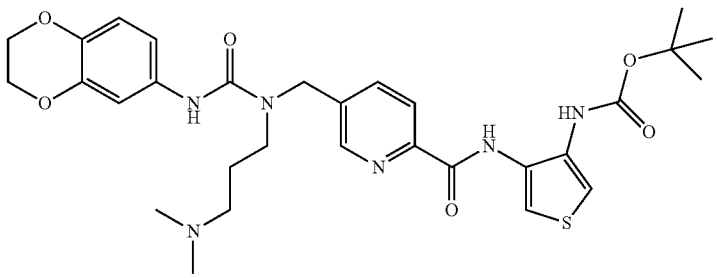

$^1$H-NMR (500 MHz, DMSO-$d_6$) δ 1.50 (s, 9H), 1.67 (m, 2H), 2.17 (s, 6H), 2.25 (t, J = 6.3 Hz, 2H), 3.30 (m, 2H), 4.17-4.21 (m, 4H), 4.60 (s, 2H), 6.73 (d, J = 8.9 Hz, 1H), 6.77 (dd, J = 8.9, 2.4 Hz, 1H), 7.07 (d, J = 2.4Hz, 1H), 7.21 (d, J = 3.7 Hz, 1H), 7.81 (d, J = 3.7 Hz, 1H), 7.95 (dd, J = 7.9, 2.1 Hz, 1H), 8.13 (d, J = 7.9 Hz, 1H), 8.58 (s, 1H), 9.30 (br s, 1H), 9.43 (s, 1H), 10.49 (br s, 1H).

N-(4-t-Butoxycarbonylaminothiophen-3-yl)-5-[1-(3-dimethylaminopropyl)-3-(3-fluorophenyl)ureidomethyl]pyridine-2-carboxylic acid amide
(Reference Compound No. 6-25)

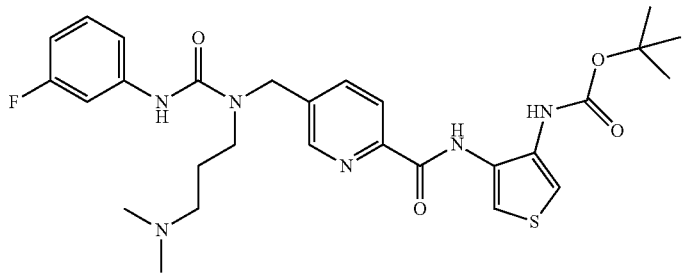

$^1$H-NMR (500 MHz, DMSO-$d_6$) δ 1.49 (s, 9H), 1.71 (m, 2H), 2.20 (s, 6H), 2.27 (t, J = 6.3 Hz, 2H), 3.35 (m, 2H), 4.63 (s, 2H), 6.75 (td, J = 8.3, 2.4 Hz, 1H), 7.07 (d, J = 8.3 Hz, 1H), 7.21 (d, J = 3.7 Hz, 1H), 7.28 (m, 1H), 7.48 (dt, J = 12.4, 2.4 Hz, 1H), 7.81 (d, J = 3.7 Hz, 1H), 7.98 (dd, J = 8.0, 1.6 Hz, 1H), 8.13 (d, J = 8.0 Hz, 1H), 8.60 (d, J = 1.6 Hz, 1H), 9.29 (br s, 1H), 10.00 (br s, 1H), 10.49 (br s, 1H).

N-(4-t-Butoxycarbonylaminothiophen-3-yl)-5-[1-[3-(4-methylpiperazin-1-yl)propyl]-3-(thiophen-3-yl)ureidomethyl]pyridine-2-carboxylic acid amide
(Reference Compound No. 6-26)

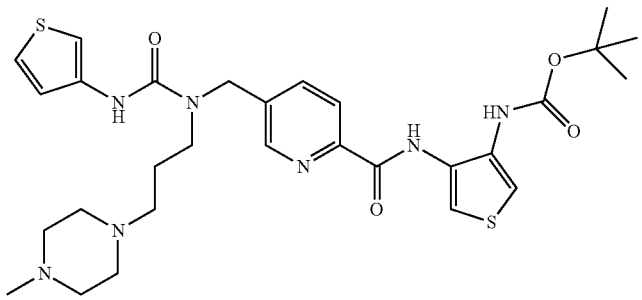

$^1$H-NMR (400 MHz, CDCl$_3$) δ 1.53 (s, 9H), 1.76 (m, 2H), 2.29 (s, 3H), 2.46 (t, J = 5.9 Hz, 2H), 2.49 (br s, 8H), 3.34 (t, J = 5.5 Hz, 2H), 4.63 (s, 2H), 7.13 (dd, J = 5.1, 1.5 Hz, 1H), 7.22-7.27 (m, 2H), 7.23 (dd, J = 5.1, 3.4 Hz, 1H), 7.30 (dd, J = 3.4, 1.5 Hz, 1H), 7.52 (br s, 1H), 7.91 (dd, J = 8.1, 2.2 Hz, 1H), 8.22 (d, J = 8.1 Hz, 1H), 8.54 (d, J = 2.2 Hz, 1H), 9.34 (s, 1H), 10.12 (s, 1H)

| | |
|---|---|
| N-(4-t-Butoxycarbonylaminothiophen-3-yl)-5-[3-(3-methylphenyl)-1-3-(4-methylpiperazin-1-yl)propyl]ureidomethyl]pyridine-2-carboxylic acid amide (Reference Compound No. 6-27)<br>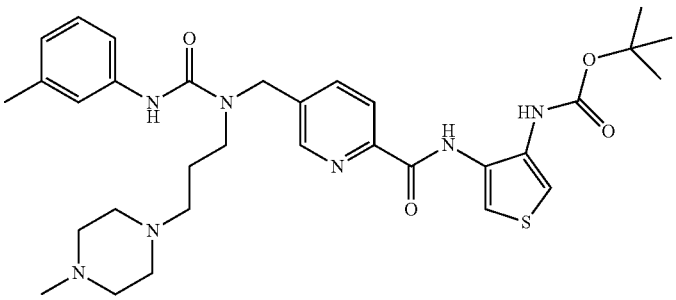 | $^1$H-NMR (400 MHz, CDCl$_3$) δ 1.53 (s, 9H), 1.77 (m, 2H), 2.27 (s, 3H), 2.35 (s, 3H), 2.46 (br s, 8H), 2.47 (t, J = 5.9 Hz, 2H), 3.36 (t, J = 5.5 Hz, 2H), 4.63 (s, 2H), 6.90 (d, J = 7.7 Hz, 1H), 7.11-7.31 (m, 4H), 7.20 (t, J = 7.7 Hz, 1H), 7.51 (br s, 1H), 7.92 (dd, J = 8.1, 2.2 Hz, 1H), 8.22 (d, J = 8.1 Hz, 1H), 8.55 (d, J = 2.2 Hz, 1H), 9.02 (s, 1H), 10.13 (s, 1H) |
| N-(4-t-Butoxycarbonylaminothiophen-3-yl)-5-[3-(2,3-dihydrobenzo[1,4]dioxin-6-yl)-1-[3-(4-methylpiperazin-1-yl)propyl]ureidomethyl]pyridine-2-carboxylic acid amide (Reference Compound No. 6-28)<br>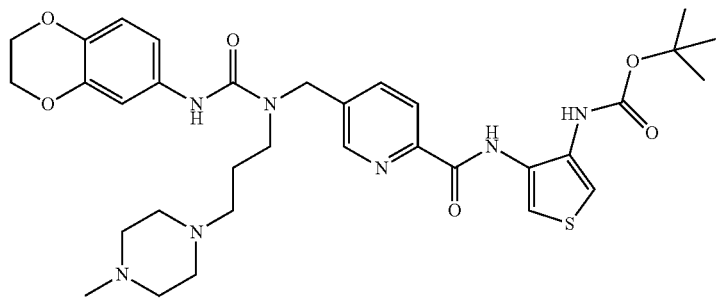 | $^1$H-NMR (400 MHz, CDCl$_3$) δ 1.53 (s, 9H), 1.75 (m, 2H), 2.24 (s, 3H), 2.40 (br s, 4H), 2.46 (t, J = 6.0 Hz, 2H), 2.48 (br s, 4H), 3.33 (t, J = 5.5 Hz, 2H), 4.23-4.25 (m, 4H), 4.61 (s, 2H), 6.80 (d, J = 8.5 Hz, 1H), 6.83 (dd, J = 8.5, 2.4 Hz, 1H), 7.01 (d, J = 2.4 Hz, 1H), 7.15-7.29 (m, 2H), 7.51 (br s, 1H), 7.92 (dd, J = 8.1, 2.1 Hz, 1H), 8.21 (d, J = 8.1 Hz, 1H), 8.54 (d, J = 2.1 Hz, 1H), 9.07 (s, 1H), 10.12 (s, 1H) |
| 5-[3-(Benzo[1,3]dioxol-5-yl)-1-(3-dimethylaminopropyl)ureidomethyl]-N-(4-t-butoxycarbonylaminothiophen-3-yl)pyridine-2-carboxylic acid amide (Reference Compound No. 6-29)<br>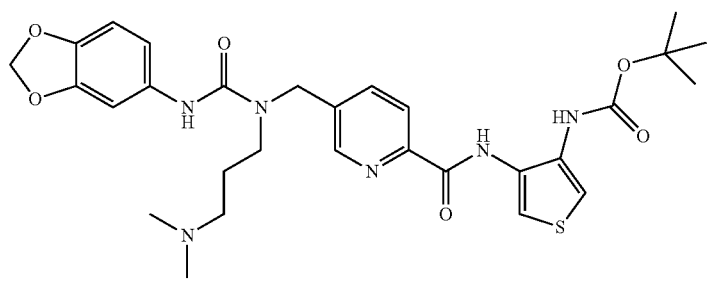 | $^1$H-NMR (500 MHz, DMSO-d$_6$) δ 1.50 (s, 9H), 1.68 (m, 2H), 2.17 (s, 6H), 2.25 (t, J = 6.4 Hz, 2H), 3.34 (m, 2H), 4.61 (s, 2H), 5.95 (s, 2H), 6.72 (dd, J = 8.4, 2.1 Hz, 1H), 6.80 (d, J = 8.4 Hz, 1H), 7.17 (d, J = 2.1 Hz, 1H), 7.21 (d, J = 3.5 Hz, 1H), 7.81 (d, J = 3.5 Hz, 1H), 7.96 (dd, J = 7.9, 1.7 Hz, 1H), 8.13 (d, J = 7.9 Hz, 1H), 8.58 (d, J = 1.7 Hz, 1H), 9.29 (br s, 1H), 9.50 (br s, 1H), 10.48 (br s, 1H) |

| Compound | NMR |
|---|---|
| N-(4-t-Butoxycarbonylaminothiophen-3-yl)-5-[1-(3-dimethylaminopropyl)-3-phenethylureidomethyl]pyridine-2-carboxylic acid amide (Reference Compound No. 6-30) 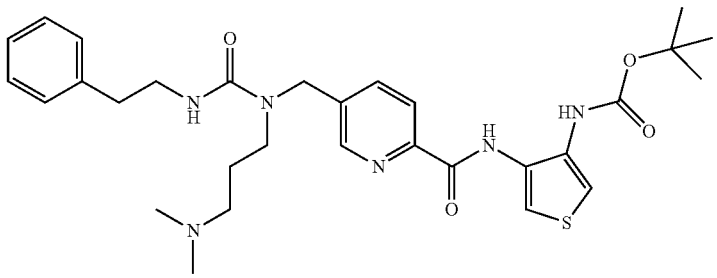 | $^1$H-NMR (500 MHz, DMSO-$d_6$) δ 1.50 (s, 9H), 1.53 (m, 2H), 2.04 (s, 6H), 2.13 (t, J = 6.6 Hz, 2H), 2.73 (t, J = 7.3 Hz, 2H), 3.13 (t, J = 6.6 Hz, 2H), 3.30 (m, 2H), 4.53 (s, 2H), 7.11 (t, J = 5.2 Hz, 1H), 7.18-7.22 (m, 4H), 7.29 (t, J = 7.5 Hz, 2H), 7.81 (d, J = 3.7 Hz, 1H), 7.83 (dd, J = 7.9, 1.7 Hz, 1H), 8.10 (d, J = 7.9 Hz, 1H), 8.50 (d, J = 1.7 Hz, 1H), 9.29 (br s, 1H), 10.48 (br s, 1H). |
| N-(4-t-Butoxycarbonylaminothiophen-3-yl)-5-[3-cyclopentyl-1-(3-dimethylaminopropyl)ureidomethyl]pyridine-2-carboxylic acid amide (Reference Compound No. 6-31) 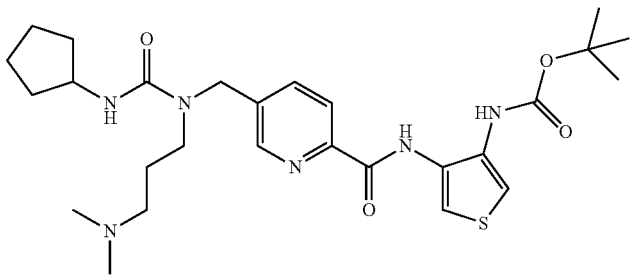 | $^1$H-NMR (500 MHz, DMSO-$d_6$) δ 1.34 (m, 2H), 1.49 (s, 9H), 1.57 (m, 2H), 1.59-1.64 (m, 4H), 1.84 (m, 2H), 2.11 (s, 6H), 2.16 (t, J = 6.6 Hz, 2H), 3.17 (t, J = 6.4 Hz, 2H), 3.89 (m, 1H), 4.52 (s, 2H), 6.89 (d, J = 6.4 Hz, 1H), 7.21 (d, J = 3.7 Hz, 1H), 7.81 (d, J = 3.7 Hz, 1H), 7.88 (dd, J = 7.9, 1.5 Hz, 1H), 8.11 (d, J = 7.9 Hz, 1H), 8.50 (d, J = 1.5 Hz, 1H), 9.29 (br s, 1H), 10.48 (br s, 1H). |
| 5-[3-(2-Benzo[1,3]dioxol-5-ylethyl)-1-[3-(morpholin-3-yl)propyl]ureidomethyl]-N-(4-t-butoxycarbonylaminothiophen-3-yl)pyridine-2-carboxylic acid amide (Reference Compound No. 6-32) 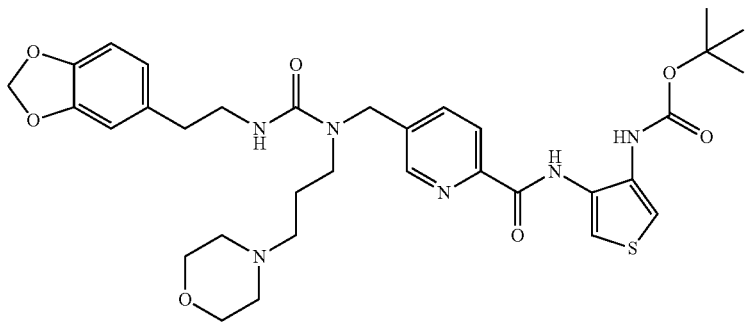 | $^1$H-NMR (400 MHz, CDCl$_3$) δ 1.53 (s, 9H), 1.63 (m, 2H), 2.27-2.37 (m, 6H), 2.77 (t, J = 6.7 Hz, 2H), 3.16 (t, J = 5.7 Hz, 2H), 3.44 (q, J = 6.7 Hz, 2H), 3.60 (br s, 4H), 4.56 (s, 2H), 5.92 (s, 2H), 6.64 (dd, J = 7.8, 1.7 Hz, 1H), 6.70 (d, J = 1.7 Hz, 1H), 6.76 (d, J = 7.8 Hz, 1H), 7.09 (br s , 1H), 7.23 (br s, 2H), 7.52 (s, 1H), 7.79 (dd, J = 8.0, 2.2 Hz, 1H), 8.22 (dd, J = 8.0, 0.5 Hz, 1H), 8.43 (dd, J = 2.2, 0.5 Hz, 1H), 10.13 (s, 1H) |

N-(4-t-Butoxycarbonylaminothiophen-
3-yl)-5-[3-cyclopentyl-1-[3-
(morpholin-4-yl)propyl]ureidomethyl]
pyridine-2-carboxylic acid amide
(Reference Compound No. 6-33)

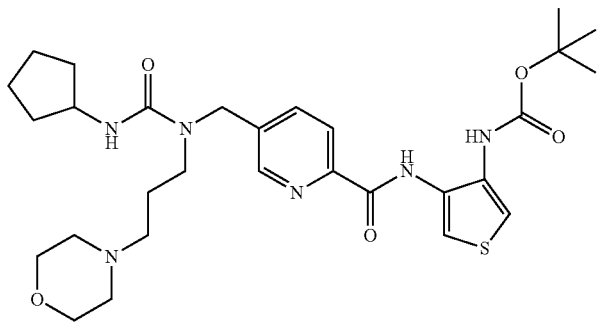

$^1$H-NMR (500 MHz, CDCl$_3$)
δ 1.35 (m, 2H), 1.54 (s, 9H),
1.61 (m, 2H), 1.69 (m, 4H),
2.06 (m, 2H), 2.37 (t, J =
6.1 Hz, 2H), 2.44 (br s, 4H),
3.20 (t, J = 6.1 Hz, 2H), 3.74
(t, J = 4.6 Hz, 4H), 4.11 (m,
1H), 4.57 (s, 2H), 5.91 (d,
J = 7.0 Hz, 1H), 7.12 (br s,
1H), 7.24 (br s, 1H), 7.52
(br s, 1H), 7.84 (dd, J = 7.9,
2.0 Hz, 1H), 8.22 (d, J = 7.9
Hz, 1H), 8.50 (d, J = 2.0 Hz,
1H), 10.12 (s, 1H)

N-(4-t-Butoxycarbonylaminothiophen-
3-yl)-5-[3-cyclohexyl-1-[3-
(morpholin-3-yl)propyl]ureidomethyl]
pyridine-3-carboxylic acid amide
(Reference Compound No. 6-34)

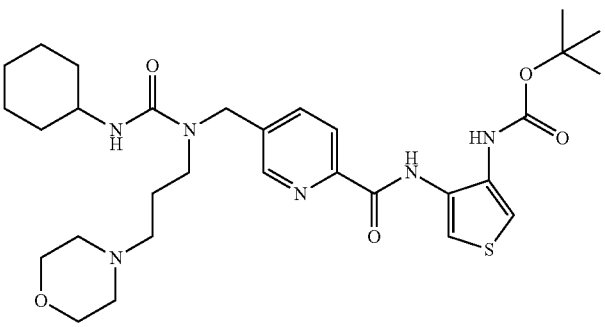

$^1$H-NMR (400 MHz, CDCl$_3$)
δ 1.12 (m, 2H), 1.38 (m, 2H),
1.54 (s, 9H), 1.60-1.79 (m,
6H), 1.99 (m, 2H), 2.37 (t,
J = 6.1 Hz, 2H), 2.44 (br s,
4H), 3.21 (t, J = 6.2 Hz, 2H),
3.65 (m, 1H), 3.76 (t, J =
4.6 Hz, 4H), 4.56 (s, 2H),
5.89 (d, J = 8.3Hz, 1H), 7.27
(br s, 2H) ,7.52 (br s, 1H),
7.84 (dd, J = 8.1, 2.2 Hz,
1H), 8.22 (d, J = 8.1 Hz, 1H),
8.50 (d, J = 2.2 Hz, 1H),
10.12 (s, 1H)

N-(4-t-Butoxycarbonylaminothiophen-
3-yl)-5-[1-[2-(4-methylpiperazin-
1-yl)ethyl]-3-(thiophen-3-yl)
ureidomethyl]pyridine-2-
carboxylic acid amide
(Reference Compound No. 6-35)

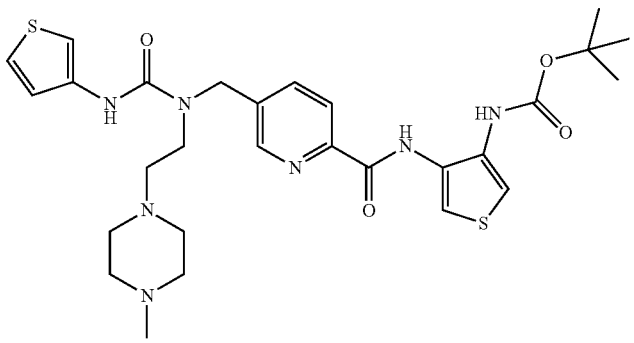

$^1$H-NMR (400 MHz, CDCl$_3$)
δ 1.54 (s, 9H), 2.32 (s, 3H),
2.53 (br s, 4H), 2.56 (t, J =
4.2 Hz, 2H), 2.65 (br s,
4H), 3.34 (t, J = 4.2 Hz, 2H),
4.66 (s, 2H), 7.12 (br s,
1H), 7.15 (dd, J = 5.1, 1.5
Hz, 1H), 7.24 (m, 1H), 7.25
(dd, J = 5.1, 3.2 Hz, 1H),
7.31 (dd, J = 3.2, 1.5 Hz,
1H), 7.54 (br s, 1H), 7.90
(dd, J = 8.1, 2.2 Hz, 1H),
8.24 (d, J = 8.1 Hz, 1H), 8.53
(d, J = 2.2 Hz, 1H), 10.13
(s, 1H), 10.36 (s, 1H)

| | |
|---|---|
| N-(4-t-Butoxycarbonylaminothiophen-3-yl)-5-[3-(2,3-dihydrobenzo[1,4]dioxin-6-yl)-1-[2-(4-methylpiperazin-1-yl)ethyl]ureidomethyl]pyridine-2-carboxylic acid amide (Reference Compound No. 6-36)<br>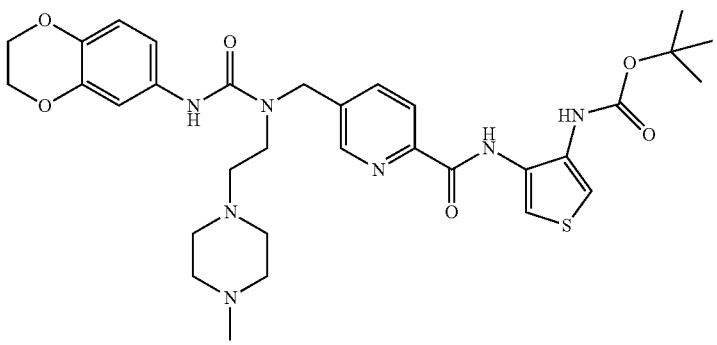 | $^1$H-NMR (500 MHz, CDCl$_3$) δ 1.54 (s, 9H), 2.31 (s, 3H), 2.51 (br s, 4H), 2.55 (t, J = 4.3 Hz, 2H), 2.63 (br s, 4H), 3.34 (t, J = 4.3 Hz, 2H), 4.22-4.26 (m, 4H), 4.63 (s, 2H), 6.80 (d, J = 8.6 Hz, 1H), 6.87 (dd, J = 8.6, 2.4 Hz, 1H), 7.03 (d, J = 2.4 Hz, 1H), 7.14 (br s, 1H), 7.24 (m, 1H), 7.53 (br s, 1H), 7.91 (dd, J = 8.1, 2.0 Hz, 1H), 8.23 (d, J = 8.1 Hz, 1H), 8.54 (d, J = 2.0 Hz, 1H), 0.85 (s, 1H), 10.13 (s, 1H) |
| N-(4-t-Butoxycarbonylaminothiophen-3-yl)-5-[3-cyclopentyl-1-[2-(4-methylpiperazin-1-yl)ethyl]ureidomethyl]pyridine-2-carboxylic acid amide (Reference Compound No. 6-37)<br>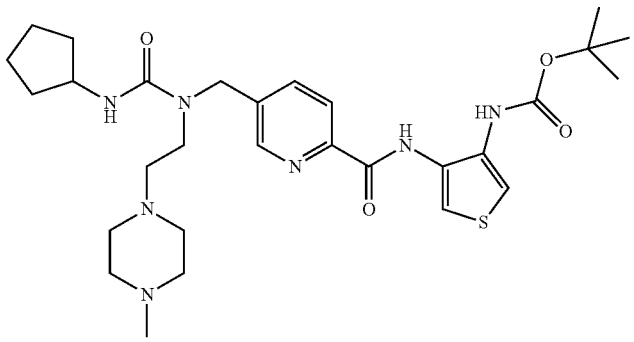 | $^1$H-NMR (400 MHz, CDCl$_3$) δ 1.43 (m, 2H), 1.54 (s, 9H), 1.61 (m, 2H), 1.70 (m, 2H), 2.04 (m, 2H), 2.29 (s, 3H), 2.44 (br s, 4H), 2.45 (t, J = 4.5 Hz, 2H), 2.54 (br s, 4H), 3.20 (t, J = 4.5 Hz, 2H), 4.11 (m, 1H), 4.58 (s, 2H), 7.06 (d, J= 7.1 Hz, 1H), 7.16 (br s, 1H), 7.24 (m, 1H), 7.52 (br s, 1H), 7.84 (dd, J = 7.9, 2.1 Hz, 1H), 8.22 (d, J = 7.9 Hz, 1H), 8.48 (d, J = 2.1 Hz, 1H), 10.12 (s, 1H) |
| N-(4-t-Butoxycarbonylaminothiophen-3-yl)-5-[1-(1-ethylpyrrolidin-2-ylmethyl)-3-(thiophen-3-yl)ureidomethyl]pyridine-2-carboxylic acid amide (Reference Compound No. 6-38)<br>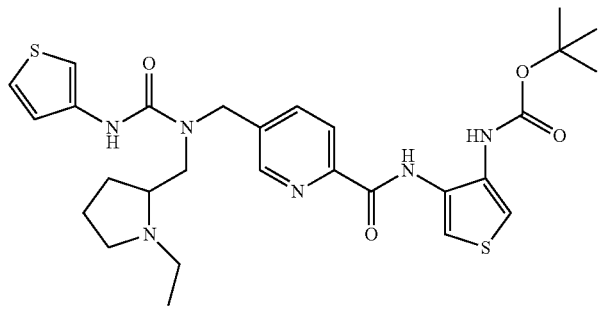 | $^1$H-NMR (500 MHz, CDCl$_3$) δ 1.12 (t, J = 7.2 Hz, 3H), 1.54 (m, 1H), 1.54 (s, 9H), 1.75-1.94 (m, 3H), 2.49 (m, 2H), 2.83 (m, 2H), 3.18-3.34 (m, 3H), 4.51 (d, J = 15.6 Hz, 1H), 4.82 (d, J = 15.6 Hz, 1H), 6.93 (dd, J = 5.1, 1.4 Hz, 1H), 7.13 (br s, 2H), 7.21 (dd, J = 5.1, 3.4 Hz, 1H), 7.27 (m, 1H), 7.52 (br s, 1H), 7.91 (dd, J = 8.1, 2.0 Hz, 1H), 8.24 (d, J = 8.1 Hz, 1H), 8.55 (d, J = 2.0 Hz, 1H), 10.13 (s, 1H), 11.77 (s, 1H) |

| | |
|---|---|
| N-(4-t-Butoxycarbonylaminothiophen-3-yl)-5-[3-(2,3-dihydrobenzo[1,4]dioxin-6-yl)-1-(1-ethylpyrrolidin-2-ylmethyl)ureidomethyl]pyridine-2-carboxylic acid amide (Reference Compound No. 6-39) 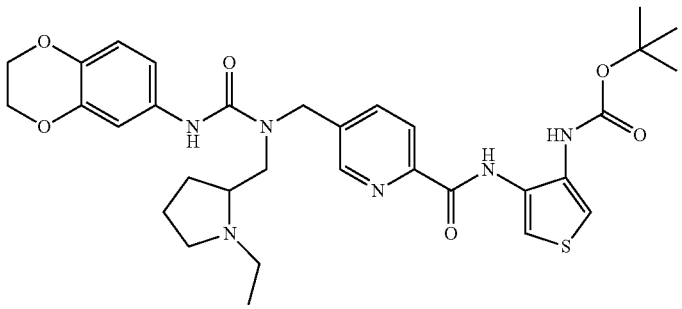 | $^1$H-NMR (400 MHz, CDCl$_3$) δ 1.10 (t, J = 7.2 Hz, 3H), 1.54 (s, 9H), 1.61 (m, 1H), 1.73-1.96 (m, 3H), 2.47 (m, 2H), 2.83 (m, 2H), 3.18-3.34 (m, 3H), 4.20-4.28 (m, 4H), 4.51 (d, J = 15.6 Hz, 1H), 4.76 (d, J = 15.6 Hz, 1H), 6.77 (d, J = 8.8 Hz, 1H), 6.82 (dd, J = 8.8, 2.3 Hz, 1H), 6.95 (d, J = 2.3 Hz, 1H), 7.15 (br s, 1H), 7.25 (br s, 1H), 7.53 (br s, 1H), 7.91 (dd, J = 8.1, 2.1 Hz, 1H), 8.23 (dd, J = 8.1, 0.7 Hz, 1H), 8.55 (dd, J = 2.1, 0.7 Hz, 1H), 10.13 (s, 1H), 11.18 (s, 1H) |
| N-(4-t-Butoxycarbonylaminothiophen-3-yl)-5-[1-(1-ethylpyrrolidin-2-ylmethyl)-3-phenethylureidomethyl]pyridine-2-carboxylic acid amide (Reference Compound No. 6-40) 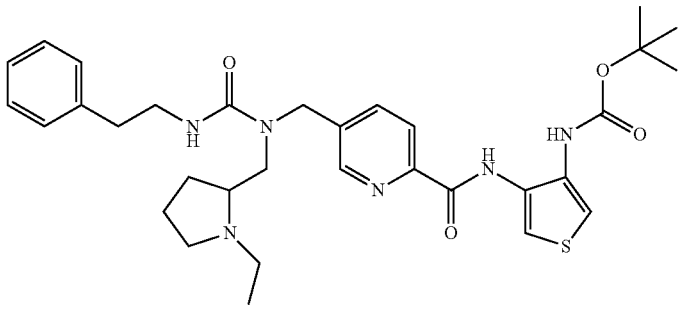 | $^1$H-NMR (400 MHz, CDCl$_3$) 0.93 (t, J = 7.2 Hz, 3H), 1.39-1.80 (m, 4H), 1.53 (s, 9H), 2.07-2.25 (m, 2H), 2.62 (m, 2H), 2.77-2.90 (m, 3H), 3.08 (m, 2H), 3.38 (m, 1H), 3.59 (m, 1H), 4.43 (d, J = 15.6 Hz, 1H), 4.72 (d, J = 15.6 Hz, 1H), 7.11-7.32 (m, 7H), 7.51 (br s, 1H), 7.81 (dd, J = 8.1, 2.2 Hz, 1H), 8.21 (dd, J = 8.1, 0.7 Hz, 1H), 8.48 (dd, J = 2.2, 0.7 Hz, 1H), 8.50 (br s, 1H), 10.12 (s, 1H) |
| N-(4-t-Butoxycarbonylaminothiophen-3-yl)-5-[3-cyclopentyl-1-(1-ethylpyrrolidin-2-ylmethyl)ureidomethyl]pyridine-2-carboxylic acid amide (Reference Compound No. 6-41) 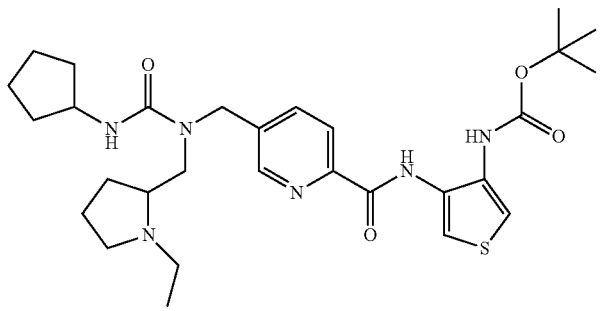 | $^1$H-NMR (400 MHz, CDCl$_3$) δ 1.08 (t, J = 7.2 Hz, 3H), 1.39 (m, 2H), 1.46-1.87 (m, 8H), 1.54 (s, 9H), 1.98 (m, 2H), 2.29-2.45 (m, 2H), 2.70-2.80 (m, 2H), 3.06 (m, 1H), 3.13 (d, J = 5.4 Hz, 2H), 4.04 (m, 1H), 4.41 (d, J = 15.6 Hz, 1H), 4.75 (d, J = 15.6 Hz, 1H), 7.14 (br s, 2H), 7.51 (br s, 1H), 7.86 (dd, J = 8.0, 2.1 Hz, 1H), 8.21 (dd, J = 8.0, 0.6 Hz, 1H), 8.38 (d, J = 6.3 Hz, 1H), 8.49 (dd, J = 2.1, 0.6 Hz, 1H), 10.12 (s, 1H) |

| | |
|---|---|
| N-(4-t-Butoxycarbonylaminothiophen-3-yl)-5-[1-(2-dimethylaminoethyl)-3-isopropylureidomethyl]pyridine-2-carboxylic acid amide (Reference Compound No. 6-42) 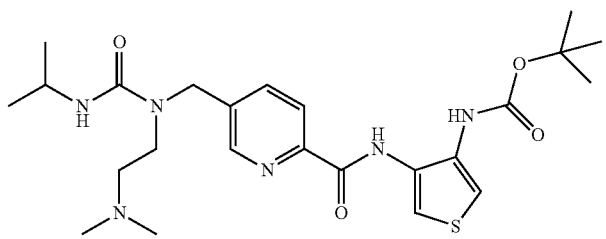 | $^1$H-NMR (400 MHz, DMSO-d$_6$) δ 1.05 (d, J = 6.7 Hz, 6H), 1.50 (s, 9H), 2.14 (s, 6H), 2.32 (t, J = 5.7 Hz, 2H), 3.24 (t, J = 5.7 Hz, 2H), 3.74 (m, 1H), 4.56 (s, 2H), 7.06 (d, J = 7.1 Hz, 1H), 7.21 (d, J = 3.7 Hz, 1H), 7.81 (d, J = 3.7 Hz, 1H), 7.88 (dd, J = 8.1, 1.7 Hz, 1H), 8.11 (d, J = 8.1 Hz, 1H), 8.50 (d, J = 1.7 Hz, 1H), 9.29 (br s, 1H), 10.48 (br s, 1H). |
| N-(4-t-Butoxycarbonylaminothiophen-3-yl)-5-[1-(2-dimethylaminoethyl)-3-propylureidomethyl]pyridine-2-carboxylic acid amide (Reference Compound No. 6-43) 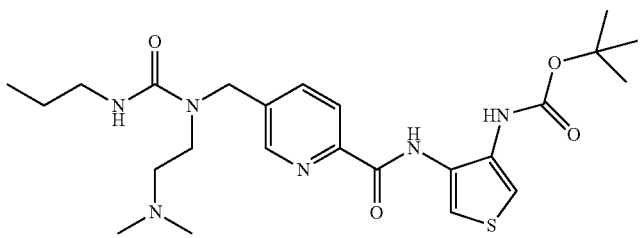 | $^1$H-NMR (400 MHz, DMSO-d$_6$) δ 0.83 (t, J = 7.4 Hz, 3H), 1.41, (m, 2H), 1.50 (s, 9H), 2.13 (s, 6H), 2.31 (t, J = 6.0 Hz, 2H), 3.00 (m, 2H), 3.26 (t, J = 6.0 Hz, 2H), 4.57 (s, 2H), 6.95 (t, J = 5.2 Hz, 1H), 7.21 (d, J = 3.7Hz, 1H), 7.81 (d, J = 3.7 Hz, 1H),7.87 (dd, J = 8.1, 1.7 Hz, 1H), 8.11 (d, J = 8.1Hz, 1H), 8.49 (d, J = 1.7 Hz, 1H), 9.30 (br s, 1H), 10.48 (br s, 1H). |
| N-(4-t-Butoxycarbonylaminothiophen-3-yl)-5-[1-(2-dimethylaminoethyl)-3-(4-fluorophenethyl)ureidomethyl]pyridine-2-carboxylic acid amide (Reference Compound No. 6-44) 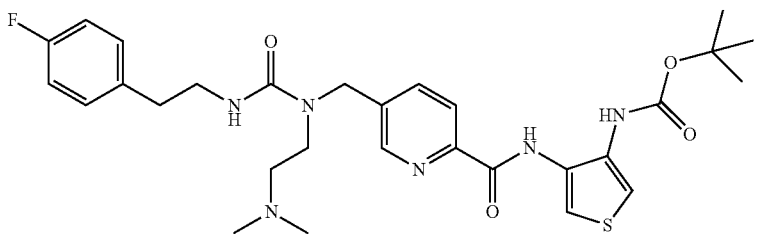 | 1H-NMR (400 MHz, DMSO-d$_6$) δ 1.49 (s, 9H), 2.07 (s, 6H), 2.25 (t, J = 6.3 Hz, 2H), 2.72 (t, J = 7.1 Hz, 2H), 3.23 (t, J = 6.3Hz, 2H), 3.27 (m, 2H), 4.56 (s, 2H), 6.95 (t, J = 5.4 Hz, 1H), 7.07 (t, J = 8.9 Hz, 2H), 7.19-7.22 (m, 3H), 7.81 (dd, J = 8.0, 1.9 Hz, 1H), 7.81 (d, J = 3.7 Hz, 1H), 8.11 (d, J= 8.0 Hz, 1H), 8.49 (d, J = 1.9 Hz, 1H), 9.29 (br s, 1H), 10.48 (br s, 1H). |
| N-(4-t-Butoxycarbonylaminothiophen-3-yl)-5-[3-t-butyl-1-(2-dimethylaminoethyl)ureidomethyl]pyridine-2-carboxylic acid amide (Reference Compound No. 6-45) 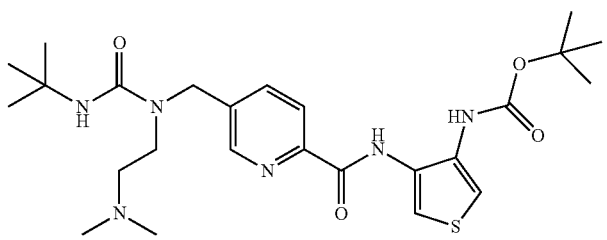 | $^1$H-NMR (500 MHz, DMSO-d$_6$) δ 1.26 (s, 9H), 1.50 (s, 9H), 2.17 (s, 6H), 2.34 (t, J = 5.0 Hz, 2H), 3.20 (t, J = 5.0 Hz, 2H), 4.52 (s, 2H), 7.21 (d, J = 3.7 Hz, 1H), 7.44 (s, 1H), 7.81 (d, J = 3.7 Hz, 1H), 7.88 (dd, J = 8.0, 1.6 Hz, 1H), 8.11 (d, J = 8.0 Hz, 1H), 8.51 (d, J = 1.6 Hz, 1H), 9.29 (br s, 1H), 10.49 (br s, 1H). |

| | |
|---|---|
| N-(4-t-Butoxycarbonylaminothiophen-3-yl)-5-[1-(2-dimethylaminoethyl)-3-(pyridin-3-yl)ureidomethyl]pyridine-2-carboxylic acid amide (Reference Compound No. 6-46)<br>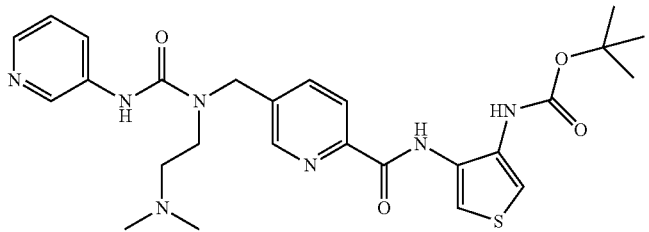 | $^1$H-NMR (400 MHz, DMSO-d$_6$) δ 1.49 (s, 9H), 2.27 (s, 6H), 2.48 (m, 2H), 3.45 (t, J = 5.1 Hz, 2H), 4.69 (s, 2H), 7.22 (d, J = 3.7 Hz, 2H), 7.28 (ddd, J = 8.3, 4.6, 0.7 Hz, 1H), 7.81 (d, J = 3.7Hz, 1H), 7.85 (ddd, J = 8.3, 2.6, 1.5 Hz, 1H), 7.99 (dd, J = 7.9, 1.6 Hz, 1H), 8.14 (d, J = 7.9 Hz, 1H), 8.15 (dd, J = 4.6, 1.5 Hz, 1H), 8.52 (dd, J = 2.6, 0.7 Hz, 1H), 8.59 (d, J = 1.6 Hz, 1H), 0.20 (br s, 1H), 10.49 (br s, 1H). |
| N-(4-t-Butoxycarbonylaminothiophen-3-yl)-5-[3-(2,3-dihydro-1-benzofuran-5-yl)-1-(2-dimethylaminoethyl)ureidomethyl]pyridine-2-carboxylic acid amide (Reference Compound No. 6-47)<br>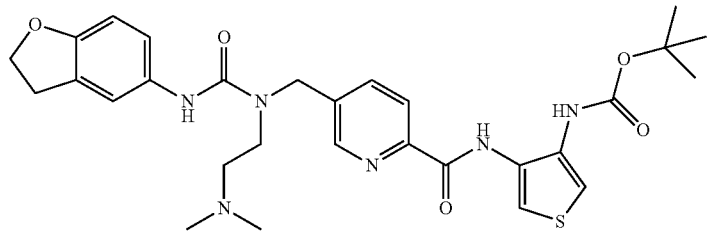 | $^1$H-NMR (400 MHz, DMSO-d$_6$) δ 1.50 (s, 9H), 2.24 (s, 6H), 2.45 (t, J = 5.2 Hz, 2H), 3.13 (m, 2H), 3.39 (t, J = 5.2 Hz, 2H), 4.47 (t, J = 8.7 Hz, 2H), 4.65 (s, 2H), 6.64 (d, J = 8.4 Hz, 1H), 6.97 (dd, J = 8.4, 2.1 Hz, 1H), 7.22 (d, J = 3.7 Hz, 1H), 7.28 (d, J = 2.1 Hz, 1H), 7.81 (d, J = 3.7 Hz, 1H), 7.96 (dd, J = 7.9, 1.6 Hz, 1H), 8.13 (d, J = 7.9 Hz, 1H), 8.58 (d, J = 1.6 Hz, 1H), 9.30 (br s, 1H), 9.76 (br s, 1H), 10.49 (br s, 1H). |
| N-(4-t-Butoxycarbonylaminothiophen-3-yl)-5-[1-(2-dimethylaminoethyl)-3-hexylureidomethyl]pyridine-2-carboxylic acid amide (Reference Compound No. 6-48)<br>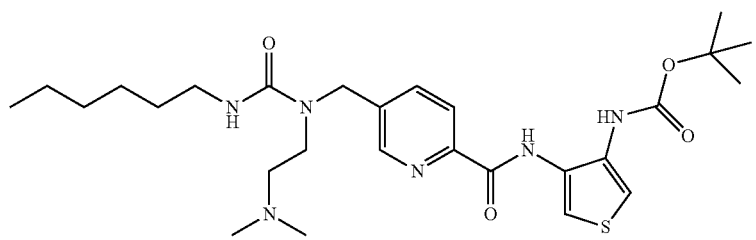 | $^1$H-NMR (400 MHz, DMSO-d$_6$) δ 0.85 (t, J = 7.0 Hz, 3H), 1.21-1.26 (m, 6H), 1.39 (m, 2H), 1.51 (s, 9H), 2.13 (s, 6H), 2.31 (t, J = 6.1 Hz, 2H), 3.02 (m, 2H), 3.27 (t, J = 6.1 Hz, 2H), 4.57 (s, 2H), 6.90 (t, J = 5.2 Hz, 1H), 7.21 (d, J = 3.7 Hz, 1H), 7.81 (d, J = 3.7 Hz, 1H), 7.87 (dd, J = 8.1, 1.7 Hz, 1H), 8.11 (d, J = 8.1 Hz, 1H), 8.49 (d, J = 1.7 Hz, 1H), 9.29 (br s, 1H), 10.48 (br s, 1H). |
| N-(4-t-Butoxycarbonylaminothiophen-3-yl)-5-[3-cyclopropyl-1-(2-dimethylaminoethyl)ureidomethyl]pyridine-2-carboxylic acid amide (Reference Compound No. 6-49)<br>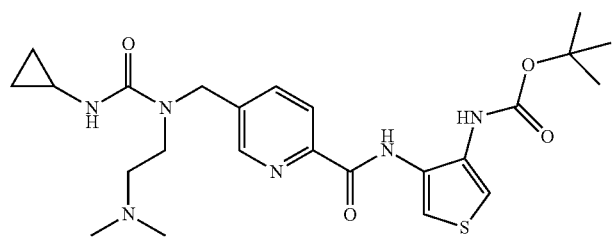 | $^1$HNMR (500 MHz, DMSO-d$_6$) δ 0.30-0.35 (m, 2H), 0.52-0.58 (m, 2H), 1.51 (s, 9H), 2.12 (s, 6H), 2.29 (t, J = 6.0 Hz, 2H), 2.39 (m, 1H), 3.22 (t, J = 6.0 Hz, 2H), 4.55 (s, 2H), 7.20 (m, 1H), 7.22 (d, J = 3.7 Hz, 1H), 7.81 (d, J = 3.7 Hz, 1H), 7.87 (dd, J = 8.1, 1.5 Hz, 1H), 8.11 (d, J = 8.1 Hz, 1H), 8.49 (d, J = 1.5 Hz, 1H), 9.29 (br s, 1H), 10.48 (br s, 1H). |

N-(4-t-Butoxycarbonylaminothiophen-3-yl)-5-[1-[2-(morpholin-4-yl)ethyl]-3-(thiophen-3-yl-ureidomethyl]pyridine-2-carboxylic acid amide
(Reference Compound No. 6-50)

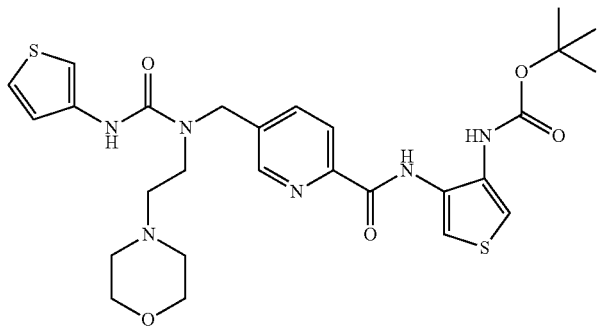

$^1$H-NMR (400 MHz, CDCl$_3$) δ 1.54 (s, 9H), 2.57 (t, J = 4.3 Hz, 2H), 2.62 (t, J = 4.5 Hz, 4H), 3.36 (t, J = 4.3 Hz, 2H), 3.78 (t, J = 4.5 Hz, 4H), 4.66 (s, 2H), 7.11 (dd, J = 5.1, 1.4 Hz, 1H), 7.15 (br s, 1H), 7.24 (br s, 1H), 7.26 (dd, J = 5.1, 3.2 Hz, 1H), 7.31 (dd, J = 3.2, 1.4 Hz, 1H), 7.54 (br s, 1H), 7.90 (dd, J = 8.1, 2.2 Hz, 1H), 8.24 (dd, J = 8.1, 0.7 Hz, 1H), 8.54 (dd, J = 2.2, 0.7 Hz, 1H), 10.14 (br s, 1H), 10.22 (br s, 1H)

N-(4-t-Butoxycarbonylaminothiophen-3-yl)-5-[3-(2,3-dihydrobenzo[1,4]dioxin-6-yl)-1-[2-(morpholin-4-yl)ethyl]ureidomethyl]pyridine-2-carboxylic acid amide
(Reference Compound No. 6-51)

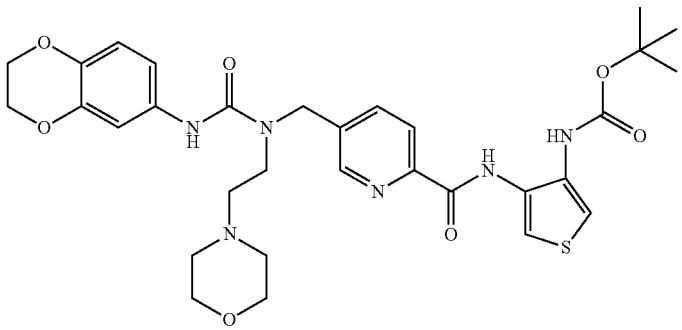

$^1$H-NMR (500 MHz, CDCl$_3$) δ 1.54 (s, 9H), 2.56 (t, J = 4.3 Hz, 2H), 2.60 (br s, 4H), 3.35 (t, J= 4.3 Hz, 2H), 3.76 (t, J = 4.6 Hz, 4H), 4.22-4.26 (m, 4H), 4.64 (s, 2H), 6.81 (d, J = 8.7 Hz, 1H), 6.85 (dd, J = 8.7, 2.3 Hz, 1H), 6.99 (d, J = 2.3 Hz, 1H), 7.12 (br s, 1H), 7.24 (br s, 1H), 7.53 (br s, 1H), 7.91 (dd, J = 7.9, 1.8 Hz, 1H), 8.24 (d, J = 7.9 Hz, 1H), 8.55 (d, J = 1.8 Hz, 1H), 9.68 (br s, 1H), 10.14 (br s, 1H)

N-(4-t-Butoxycarbonylaminothiophen-3-yl)-5-[1-[2-(morpholin-4-yl)ethyl]-3-phenethylureidomethyl]pyridine-2-carboxylic acid amide
(Reference Compound No. 6-52)

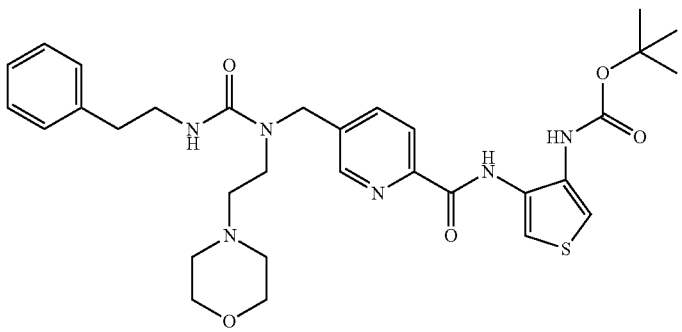

$^1$H-NMR (500 MHz, CDCl$_3$) δ 1.54 (s, 9H), 2.30 (t, J = 4.4 Hz, 4H), 2.36 (t, J = 4.7 Hz, 2H), 2.86 (t, J = 6.7 Hz, 2H), 3.16 (t, J = 4.7 Hz, 2H), 3.45 (br s, 4H), 3.50 (q, J = 6.7 Hz, 2H), 4.59 (s, 2H), 7.12 (br s, 1H), 7.19-7.31 (m, 6H), 7.47 (br s, 1H), 7.53 (br s, 1H), 7.82 (dd, J = 8.1, 2.1 Hz, 1H), 8.23 (d, J = 8.1 Hz, 1H), 8.49 (d, J = 2.1 Hz, 1H), 10.13 (br s, 1H)

| | |
|---|---|
| N-(4-t-Butoxycarbonylaminothiophen-3-yl)-5-[3-cyclopentyl-1-[2-(morpholin-4-yl)ethyl]ureidomethyl]pyridine-2-carboxylic acid amide (Reference Compound No. 6-53)<br>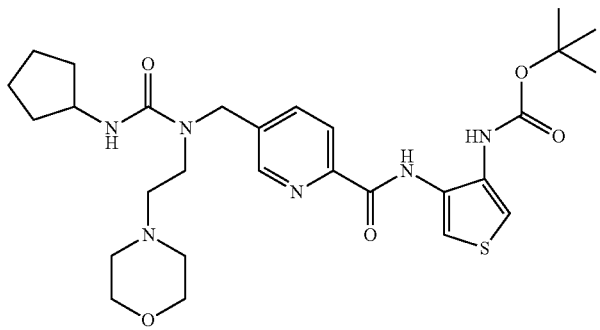 | $^1$H-NMR (400 MHz, CDCl$_3$) δ 1.40 (m, 2H), 1.54 (s, 9H), 1.58-1.73 (m, 4H), 2.05 (m, 2H), 2.46 (t, J = 4.7 Hz, 2H), 2.51 (t, J = 4.5 Hz, 4H), 3.23 (t, J = 4.7 Hz, 2H), 3.72 (t, J = 4.5Hz, 4H) , 4.11 (m, 1H), 4.59 (s, 2H), 6.85 (d, J = 6.3 Hz, 1H), 7.11 (br s, 1H), 7.25 (br s, 1H), 7.53 (br s, 1H), 7.85 (dd, J = 7.9, 2.1 Hz, 1H), 8.23 (dd, J = 7.9, 0.6 Hz, 1H), 8.49 (dd, J = 2.1, 0.6 Hz, 1H), 10.13 (br s, 1H) |
| N-(4-t-Butoxycarbonylaminothiophen-3-yl)-5-[1-[3-(4-methylpiperazin-1-yl)propyl]-3-phenethylureidomethyl]pyridine-2-carboxylic acid amide (Reference Compound No. 6-54)<br>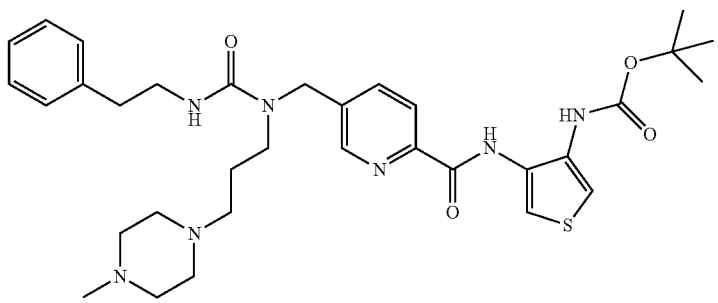 | $^1$H-NMR (500 MHz, CDCl$_3$) δ 1.53 (s, 9H), 1.61 (m, 2H), 2.26 (s, 3H), 2.31 (t, J = 6.1 Hz, 2H), 2.32 (br s, 8H), 2.87 (t, J = 6.7 Hz, 2H), 3.13 (t, J = 5.7 Hz, 2H), 3.48 (q, J = 6.7 Hz, 2H), 4.57 (s, 2H), 7.17 (br s, 1H), 7.20-7.24 (m, 3H), 7.26-7.31 (m, 3H), 7.35 (m, 1H), 7.52 (br s, 1H), 7.78 (dd, J = 7.9, 2.1 Hz, 1H), 8.22 (d, J = 7.9 Hz, 1H), 8.49 (d, J = 2.1 Hz, 1H), 10.13 (s, 1H) |
| N-(4-t-Butoxycarbonylaminothiophen-3-yl)-5-[3-isopropyl-1-[3-(4-methylpiperazin-1-yl)propyl]ureidomethyl]pyridine-2-carboxylic acid amide (Reference Compound No. 6-55)<br>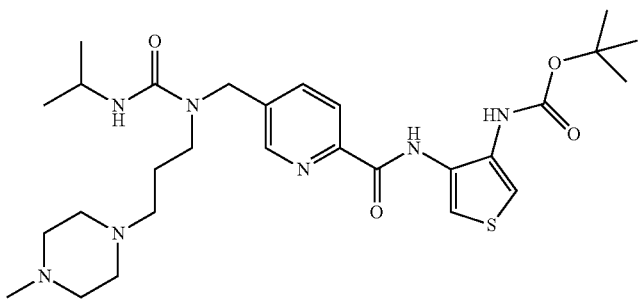 | $^1$H-NMR (500 MHz, CDCl$_3$) δ 1.21 (d, J = 6.7 Hz, 6H), 1.54 (s, 9H), 1.67 (m, 2H), 2.31 (s, 3H), 2.36 (t, J = 6.1 Hz, 2H), 2.49 (br s, 8H), 3.18 (t, J = 6.0 Hz, 2H), 4.01 (m, 1H), 4.56 (s, 2H), 6.04 (d, J = 8.2 Hz, 1H), 7.16 (br s, 1H), 7.26 (m, 1H), 7.51 (br s, 1H), 7.84 (dd, J = 7.9, 2.1 Hz, 1H), 8.22 (d, J = 7.9 Hz, 1H), 8.50 (d, J = 2.1 Hz, 1H), 10.12 (s, 1H) |

| Compound | NMR |
|---|---|
| N-(4-t-Butoxycarbonylaminothiophen-3-yl)-5-[3-cyclopentyl-1-[3-(4-methylpiperazin-1-yl)propyl]ureidomethyl]pyridine-2-carboxylic acid amide (Reference Compound No. 6-56) 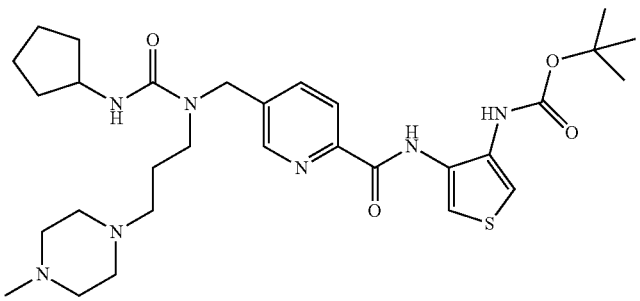 | $^1$H-NMR (500 MHz, CDCl$_3$) δ 1.39 (m, 2H), 1.54 (s, 9H), 1.60 (m, 2H), 1.64-1.74 (m, 4H), 2.05 (m, 2H), 2.30 (s, 3H), 2.36 (t, J = 6.0 Hz, 2H), 2.47 (br s, 8H), 3.19 (t, J = 6.0 Hz, 2H), 4.10 (m, 1H), 4.56 (s, 2H), 6.05 (d, J = 7.6 Hz, 1H), 7.15 (br s, 1H), 7.25 (m, 1H), 7.51 (br s, 1H), 7.84 (dd, J = 8.1, 2.0 Hz, 1H), 8.22 (d, J = 8.1 Hz, 1H), 8.50 (d, J = 2.0 Hz, 1H), 10.12 (s, 1H) |
| N-(4-t-Butoxycarbonylaminothiophen-3-yl)-5-[3-(2,3-dihydrobenzo[1,4]dioxin-6-yl)-1-[4-(morpholin-4-yl)butyl]ureidomethyl]pyridine-2-carboxylic acid amide (Reference Compound No. 6-57) 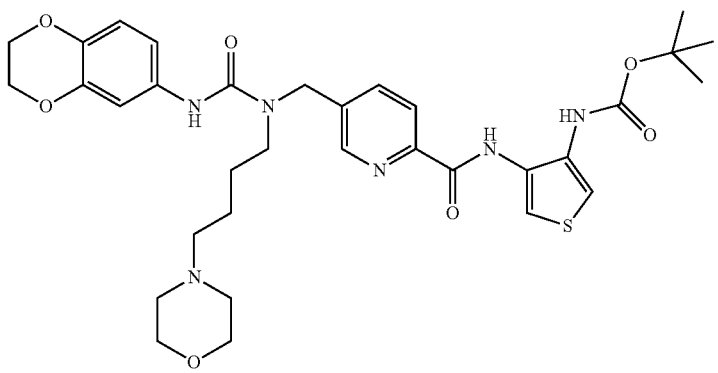 | $^1$H-NMR (400 MHz, CDCl$_3$) δ 1.52 (m, 2H), 1.54 (s, 9H), 1.69 (m, 2H), 2.38 (t, J = 7.0 Hz, 2H), 2.41 (m, 4H), 3.28 (t, J = 7.9 Hz, 2H), 3.63 (t, J = 4.6 Hz, 4H), 4.22-4.25 (m, 4H), 4.66 (s, 2H), 6.61 (m, 1H), 6.75 (dd, J = 8.7, 2.4 Hz, 1H), 6.80 (d, J = 8.7 Hz, 1H), 6.91 (d, J = 2.4 Hz, 1H), 7.11 (br s, 1H), 7.24 (m, 1H), 7.54 (br s, 1H), 7.88 (dd, J = 8.1, 2.2 Hz, 1H), 8.24 (d, J = 8.1 Hz, 1H), 8.53 (d, J = 2.2 Hz, 1H), 10.13 (s, 1H) |
| N-(4-t-Butoxycarbonylaminothiophen-3-yl)-5-[1-[4-(morpholin-4-yl)butyl]-3-phenethylureidomethyl]pyridine-2-carboxylic acid amide (Reference Compound No. 6-58) 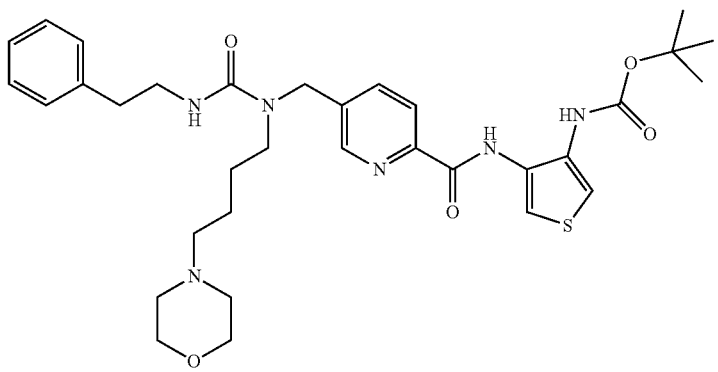 | $^1$H-NMR (500 MHz, CDCl$_3$) δ 1.39 (m, 2H), 1.48 (m, 2H), 1.54 (s, 9H), 2.24 (t, J = 7.0 Hz, 2H), 2.32 (m, 4H), 2.85 (t, J = 6.5 Hz, 2H), 3.08 (t, J = 7.9 Hz, 2H), 3.54 (q, J = 6.5 Hz, 2H), 3.64 (t, J = 4.6 Hz, 4H), 4.57 (s, 2H), 4.75 (t, J = 6.5 Hz, 1H), 7.14 (br s, 1H), 7.17 (d, J = 7.0 Hz, 2H), 7.22 (m, 1H), 7.26-7.30 (m, 3H), 7.54 (br s, 1H), 7.75 (dd, J = 8.1, 1.8 Hz, 1H), 8.21 (d, J = 8.1 Hz, 1H), 8.45 (d, J = 1.8 Hz, 1H), 10.13 (s, 1H) |

| | |
|---|---|
| N-(4-t-Butoxycarbonylaminothiophen-3-yl)-5-[3-cyclopentyl-1-[4-(morpholin-4-yl)butyl]ureidomethyl]pyridine-2-carboxylic acid amide (Reference Compound No. 6-59)<br>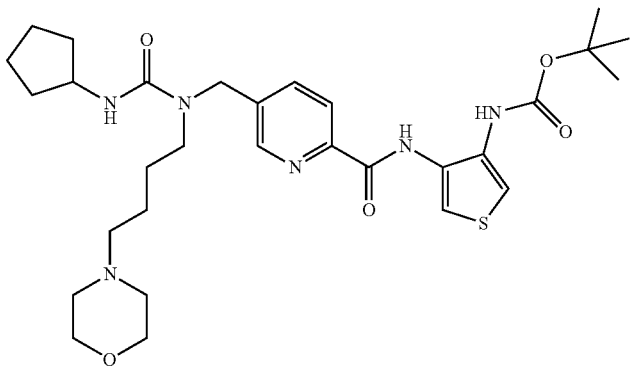 | $^1$H-NMR (400 MHz, CDCl$_3$) δ 1.33 (m, 2H), 1.47 (m, 2H), 1.54 (s, 9H), 1.54-1.65 (m, 6H), 2.00 (m, 2H), 2.32 (t, J = 7.1 Hz, 2H), 2.40 (m, 4H), 3.16 (t, J = 7.6 Hz, 2H), 3.70 (t, J = 4.6 Hz, 4H), 4.14 (m, 1H), 4.35 (d, J = 6.9 Hz, 1H), 4.58 (s, 2H), 7.11 (br s, 1H), 7.24 (m, 1H), 7.54 (br s, 1H), 7.80 (dd, J = 8.1, 2.2 Hz, 1H), 8.23 (d, J = 8.1 Hz, 1H), 8.48 (d, J = 2.2 Hz, 1H), 10.13 (s, 1H) |
| N-(4-t-Butoxycarbonylaminothiophen-3-yl)-5-[3-sec-butyl-1-(2-dimethylaminoethyl)ureidomethyl]pyridine-2-carboxylic acid amide (Reference Compound No. 6-60)<br>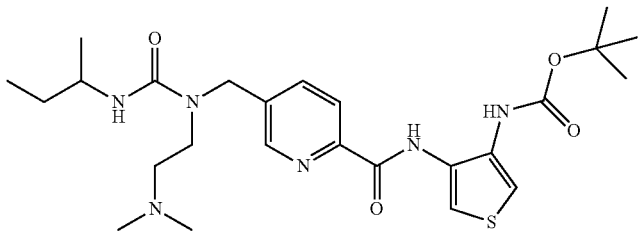 | $^1$H-NMR (500 MHz, DMSO-d$_6$) δ 0.83 (t, J = 7.5 Hz, 3H), 1.03 (d, J = 6.4 Hz, 3H), 1.39 (m, 2H), 1.50 (s, 9H), 2.14 (s, 6H), 2.32 (t, J = 5.8 Hz, 2H), 3.25 (m, 2H), 3.57 (m, 1H), 4.57 (s, 2H), 6.98 (d, J = 7.6 Hz, 1H), 7.21 (d, J = 3.7 Hz, 1H), 7.81 (d, J = 3.7 Hz, 1H), 7.88 (dd, J = 7.9, 2.1 Hz, 1H), 8.11 (d, J = 7.9 Hz, 1H), 8.49 (br s, 1H), 9.29 (br s, 1H), 10.48 (br s, 1H). |
| N-(4-t-Butoxycarbonylaminothiophen-3-yl)-5-[1-[3-(morpholin-4-yl)propyl]-3-(3-phenylpropyl)ureidomethyl]pyridine-2-carboxylic acid amide (Reference Compound No. 6-61)<br>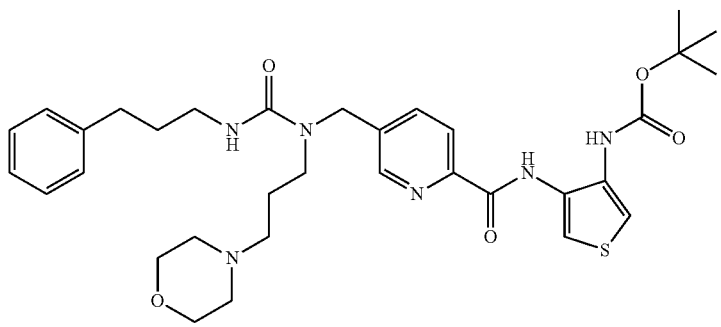 | $^1$H-NMR (400 MHz, CDCl$_3$) δ 1.53 (s, 9H), 1.64 (m, 2H), 1.89 (m, 2H), 2.35 (t, J = 6.0 Hz, 2H), 2.41 (br s, 4H), 2.68 (t, J = 7.5 Hz, 2H), 3.17 (t, J = 5.7 Hz, 2H), 3.27 (td, J = 7.5, 5.6 Hz, 2H), 3.66 (t, J = 4.4 Hz, 4H), 4.56 (s, 2H), 7.07 (t, J = 5.6 Hz, 1H), 7.17 (m, 1H), 7.19 (d, J = 7.1 Hz, 2H), 7.25 (m, 1H), 7.27 (t, J = 7.1 Hz, 2H), 7.28 (m, 1H), 7.52 (s, 1H), 7.84 (dd, J = 7.9, 2.1 Hz, 1H), 8.22 (dd, J = 7.9, 0.6 Hz, 1H), 8.50 (dd, J = 2.1, 0.6 Hz, 1H), 10.12 (s, 1H) |

| Compound | NMR |
|---|---|
| 5-[3-Benzyl-1-[3-(morpholin-4-yl)propyl]ureidomethyl[-N-(4-t-butoxycarbonylaminothiophen-3-yl)pyridine-2-carboxylic acid amide (Reference Compound No. 6-62) 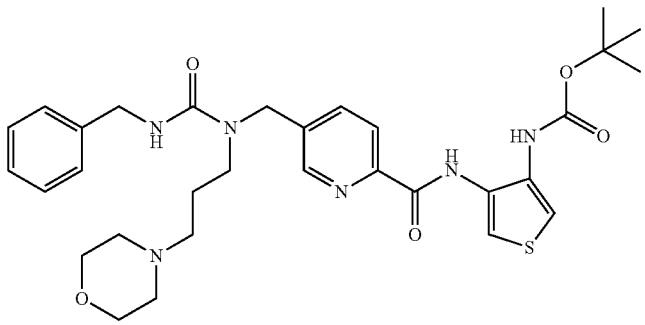 | $^1$H-NMR (500 MHz, CDCl$_3$) δ 1.54 (s, 9H), 1.67 (m, 2H), 2.25 (br s, 4H), 2.34 (t, J = 5.9 Hz, 2H), 3.29 (t, J = 5.9 Hz, 2H), 3.40 (br s, 4H), 4.49 (d, J = 5.5 Hz, 2H), 4.63 (s, 2H), 7.12 (br s, 1H), 7.15 (d, J = 7.1 Hz, 1H), 7.24 (m, 1H), 7.28-7.36 (m, 4H), 7.52 (br s, 1H), 7.57 (t, J = 5.5 Hz, 1H), 7.88 (dd, J = 7.9, 2.1Hz, 1H), 8.23 (dd, J = 7.9, 0.6 Hz, 1H), 8.54 (dd, J = 2.1, 0.6 Hz, 1H), 10.13 (s, 1H) |
| N-(4-t-Butoxycarbonylamino-thiophene-3-yl)-5-[3-hexyl-1-[3-(morpholin-4-yl)propyl]ureidomethyl]pyridine-2-carboxylic acid amide (Reference Compound No. 6-63) 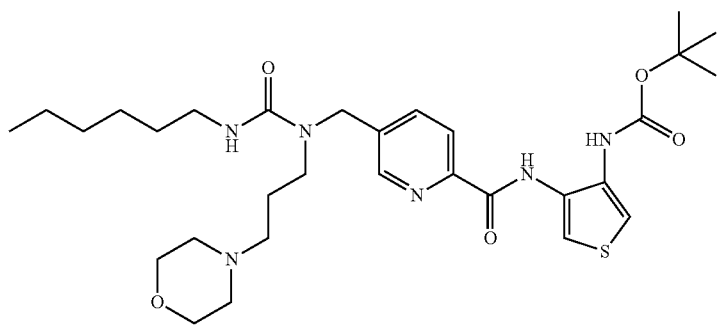 | $^1$H-NMR (500 MHz, CDCl$_3$) δ 0.89 (t, J = 6.9 Hz, 3H), 1.29-1.36 (m, 6H), 1.51 (m, 2H), 1.54 (s, 9H), 1.66 (m, 2H), 2.38 (t, J = 6.1 Hz, 2H), 2.44 (br s, 4H), 3.19-3.24 (m, 4H), 3.73 (t, J = 4.4 Hz, 4H), 4.57 (s, 2H), 6.99 (t, J = 5.5 Hz, 1H), 7.15 (br s, 1H), 7.26 (m, 1H), 7.52 (br s, 1H), 7.84 (dd, J = 7.9, 1.8 Hz, 1H), 8.22 (d, J = 7.9 Hz, 1H), 8.50 (d, J = 1.8 Hz, 1H), 10.12 (s, 1H) |
| N-(4-t-Butoxycarbonylaminothiophen-3-yl)-5-[3-(3,4-dimethoxyphenethyl)-1-[3-morpholin-4-yl)propyl]ureidomethyl]pyridine-2-carboxylic acid amide (Reference Compound No. 6-64) 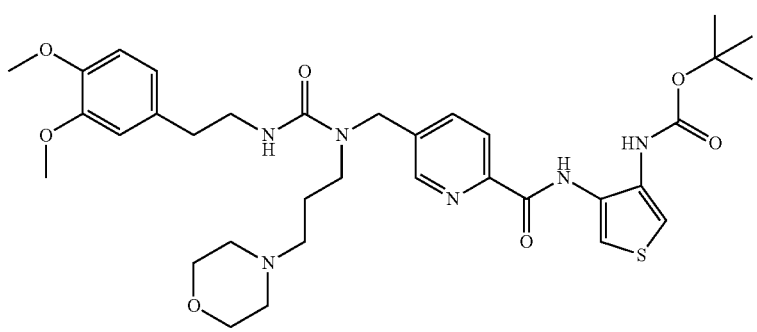 | $^1$H-NMR (400 MHz, CDCl$_3$) δ 1.52 (s, 9H), 1.63 (m, 2H), 2.34 (t, J = 5.6 Hz, 2H), 2.34 (m, 4H), 2.81 (t, J = 6.8 Hz, 2H), 3.15 (t, J = 5.7 Hz, 2H), 3.48 (m, 2H), 3.61 (br s, 4H), 3.82 (s, 3H), 3.82 (s, 3H), 4.55 (s, 2H), 6.72-6.76 (m, 2H), 6.80 (d, J = 8.5 Hz, 1H), 7.11 (br s, 1H), 7.27-7.31 (m, 2H), 7.57 (br s, 1H), 7.79 (d, J = 8.0 Hz, 1H), 8.21 (d, J = 8.0 Hz, 1H), 8.32 (s, 1H), 10.19 (s, 1H) |

N-(4-t-Butoxycarbonylaminothiophen-3-yl)-5-[1-(2-dimethylaminoethyl)-3-(4-phenylphenethyl)ureidomethyl]pyridine-2-carboxylic acid amide (Reference Compound No. 6-65)

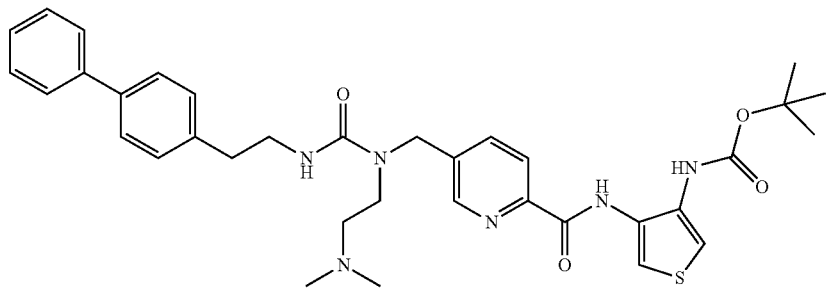

$^1$H-NMR (400 MHz, DMSO-$d_6$) δ 1.49 (s, 9H), 2.07 (s, 6H), 2.27 (t, J = 6.2 Hz, 2H), 2.50 (m, 2H), 2.78 (t, J = 7.1 Hz, 2H), 3.25 (t, J = 6.2 Hz, 2H), 4.58 (s, 2H), 6.98 (t, J = 5.4 Hz, 1H), 7.22 (d, J = 3.7 Hz, 1H), 7.27 (d, J = 8.3 Hz, 2H), 7.33 (dt, J = 7.4, 1.6 Hz, 1H), 7.42 (t, J = 7.4 Hz, 2H), 7.56 (d, J = 8.3 Hz, 2H), 7.61 (m, 2H), 7.82 (d, J = 3.7 Hz, 1H), 7.86 (dd, J = 8.2, 1.7 Hz, 1H), 8.11 (d, J = 8.2 Hz, 1H), 8.51 (d, J = 1.7 Hz, 1H), 9.30 (br s, 1H), 10.50 (br s, 1H).

N-(4-t-butoxycarbonylaminothiophen-3-yl)-5-[1-(2-dimethylaminoethyl)-3-(4-methoxyphenethyl)ureidomethyl]pyridine-2-carboxylic acid amide (Reference Compound No. 6-66)

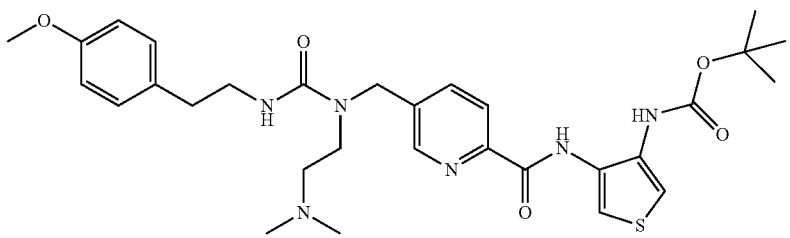

$^1$H-NMR (400 MHz, DMSO-$d_6$) δ 1.50 (s, 9H), 2.08 (s, 6H), 2.27 (t, J = 6.3 Hz, 2H), 2.50 (m, 2H), 2.66 (t, J = 7.3 Hz, 2H), 3.23 (m, 2H), 3.70 (s, 3H), 4.56 (s, 2H), 6.83 (d, J = 8.7 Hz, 2H), 6.92 (t, J = 5.0 Hz, 1H), 7.08 (d, J = 8.7 Hz, 2H), 7.21 (d, J = 3.7 Hz, 1H), 7.80-7.83 (m, 2H), 8.10 (d, J = 7.8 Hz, 1H), 8.50 (d, J = 1.5 Hz, 1H), 9.29 (br s, 1H), 10.49 (br s, 1H).

N-(4-t-Butoxycarbonylaminothiophen-3-yl)-5-[1-[2-(pyrrolidin-1-yl)ethyl]-3-(thiophen-3-yl)ureidomethyl]pyridine-2-carboxylic acid amide (Reference Compound No. 6-67)

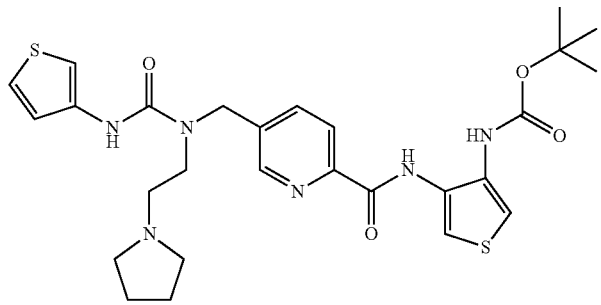

$^1$H-NMR (400 MHz, CDCl$_3$) δ 1.54 (s, 9H), 1.90 (m, 4H), 2.65-2.76 (m, 6H), 3.34 (t, J = 4.3 Hz, 2H), 4.67 (s, 2H), 6.91 (dd, J = 5.1, 1.5 Hz, 1H), 7.11 (br s, 1H), 7.21 (dd, J = 5.1, 3.3 Hz, 1H), 7.24 (br s, 1H), 7.28 (dd, J = 3.3, 1.5 Hz, 1H), 7.53 (s, 1H), 7.90 (dd, J = 8.1, 2.2 Hz, 1H), 8.24 (dd, J = 8.1, 0.6 Hz, 1H), 8.54 (dd, J = 2.2, 0.6 Hz, 1H), 10.13 (s, 1H), 11.28 (s, 1H)

| | |
|---|---|
| N-(4-t-Butoxycarbonylaminothiophen-3-yl)-5-[3-(2,3-dihydrobenzo[1,4]dioxin-6-yl)-1-[2-(pyrrolidin-1-yl)ethyl]ureidomethyl]pyridine-2-carboxylic acid amide (Reference Compound No. 6-68)<br>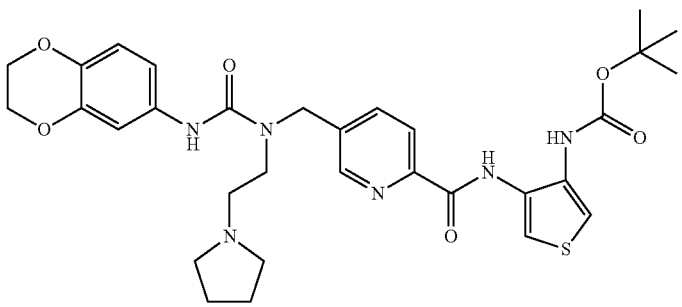 | $^1$H-NMR (400 MHz, CDCl$_3$) δ 1.54 (s, 9H), 1.89 (br s, 4H), 2.63-2.75 (m, 6H), 3.34 (t, J = 4.2 Hz, 2H), 4.20-4.27 (m, 4H), 4.64 (s, 2H), 6.77 (dd, J = 8.8, 0.5 Hz, 1H), 6.80 (dd, J = 8.8, 2.1 Hz, 1H), 6.92 (dd, J = 2.1, 0.5 Hz, 1H), 7.13 (br s, 1H), 7.25 (br s, 1H), 7.53 (s, 1H), 7.91 (dd, J = 8.0, 2.1 Hz, 1H), 8.23 (dd, J = 8.0, 0.6 Hz, 1H), 8.54 (dd, J = 2.1, 0.6 Hz, 1H), 10.14 (s, 1H), 10.63 (s, 1H) |
| N-(4-t-Butoxycarbonylaminothiophen-3-yl)-5-[3-phenethyl-1-[2-(pyrrolidin-1-yl)ethyl]ureidomethyl]pyridine-2-carboxylic acid amide (Reference Compound No. 6-69)<br>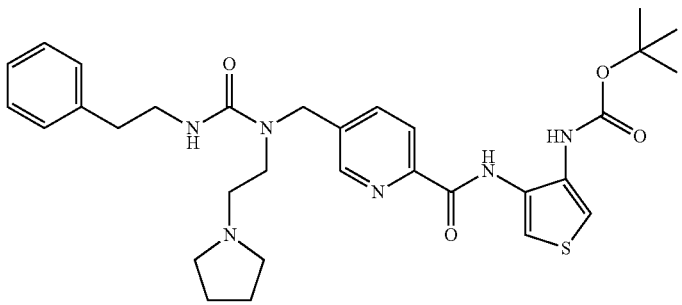 | $^1$H-NMR (400 MHz, CDCl$_3$) δ 1.54 (s, 9H), 1.65 (br s, 4H), 2.40 (br s, 4H), 2.53 (t, J = 4.8 Hz, 2H), 2.83 (t, J = 7.0 Hz, 2H), 3.17 (t, J = 4.8 Hz, 2H), 3.46 (q, J = 7.0 Hz, 2H), 4.59 (s, 2H), 7.04-7.32 (m, 7H), 7.52 (br s, 1H), 7.81 (dd, J = 8.1, 2.2 Hz, 1H), 7.83 (br s, 1H), 8.22 (dd, J = 8.1, 0.6 Hz, 1H), 8.48 (dd, J = 2.2, 0.6 Hz, 1H), 10.13 (s, 1H) |
| N-(4-t-Butoxycarbonylaminothiophen-3-yl)-5-[3-cyclopentyl-1-[2-(pyrrolidin-1-yl)ethyl]ureidomethyl]pyridine-2-carboxylic acid amide (Reference Compound No. 6-70)<br>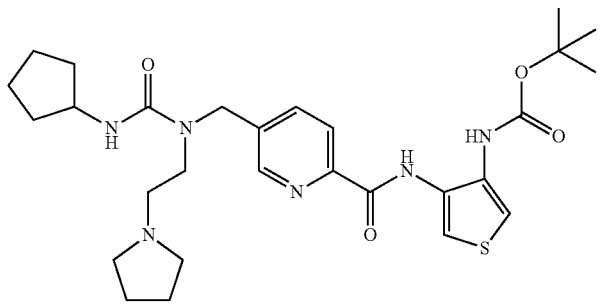 | $^1$H-NMR (400 MHz, CDCl$_3$) δ 1.33 (m, 2H), 1.54 (s, 9H), 1.56-1.70 (m, 4H), 1.79 (br s, 4H), 1.99 (m, 2H), 2.53-2.62 (m, 6H), 3.21 (t, J = 4.5 Hz, 2H), 4.09 (m, 1H), 4.59 (s, 2H), 7.15 (br s, 1H), 7.25 (br s, 1H), 7.52 (br s, 1H), 7.80 (d, J = 6.1 Hz, 1H), 7.85 (dd, J = 7.9, 2.0 Hz, 1H), 8.22 (dd, J = 7.9, 0.5 Hz, 1H), 8.49 (dd, J = 2.0, 0.5 Hz, 1H), 10.13 (s, 1H) |

| | |
|---|---|
| N-(4-t-Butoxycarbonylaminothiophen-3-yl)-5-[1-[3-(pyrrolidin-1-yl)propyl]-3-(thiophen-3-yl)ureidomethyl]pyridine-2-carboxylic acid amide (Reference Compound No. 6-71) 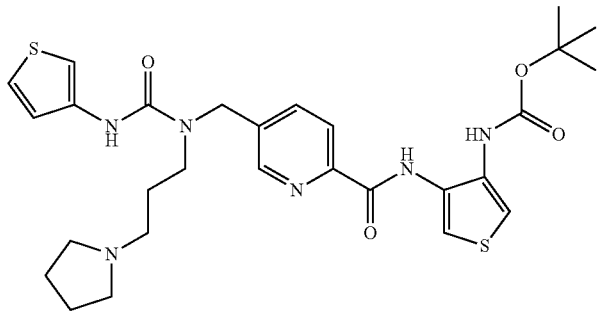 | $^1$H-NMR (400 MHz, CDCl$_3$) δ 1.53 (s, 9H), 1.73 (m, 2H), 1.89 (m, 4H), 2.52-2.61 (m, 6H), 3.38 (t, J = 5.6 Hz, 2H), 4.63 (s, 2H), 6.96 (dd, J = 5.1, 1.3 Hz, 1H), 7.14 (br s, 1H), 7.20 (dd, J = 5.1, 3.2 Hz, 1H), 7.27 (br s, 1H), 7.30 (dd, J = 3.2, 1.3 Hz, 1H), 7.51 (br s, 1H), 7.91 (dd, J = 8.1, 2.1 Hz, 1H), 8.23 (dd, J = 8.1, 0.5 Hz, 1H), 8.55 (dd, J = 2.1, 0.5 Hz, 1H), 10.12 (s, 1H), 10.25 (s, 1H) |
| N-(4-t-Butoxycarbonylaminothiophen-3-yl)-5-[3-(2,3-dihydrobenzo[1,4]dioxin-6-yl)-1-[3-(pyrrolidin-1-yl)propyl]ureidomethyl]pyridine-2-carboxylic acid amide (Reference Compound No. 6-72) 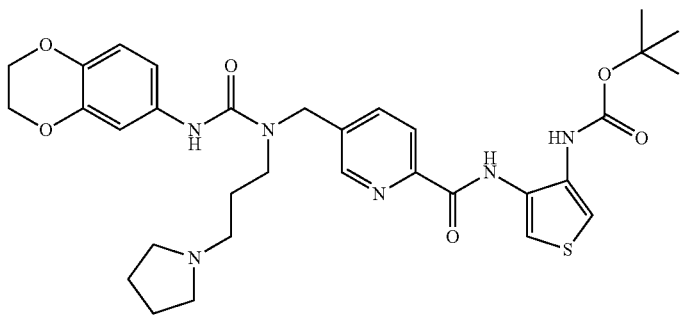 | $^1$H-NMR (500 MHz, CDCl$_3$) δ 1.53 (s, 9H), 1.72 (m, 2H), 1.84 (br s, 4H), 2.50-2.59 (m, 6H), 3.38 (t, J = 5.3 Hz, 2H), 4.20-4.26 (m, 4H), 4.61 (s, 2H), 6.77 (d, J = 8.7 Hz, 1H), 6.85 (dd, J = 8.7, 2.4 Hz, 1H), 6.99 (d, J = 2.4 Hz, 1H), 7.16 (br s, 1H), 7.24 (br s, 1H), 7.51 (br s, 1H), 7.92 (dd, J = 8.0, 2.1 Hz, 1H), 8.22 (d, J = 8.0 Hz, 1H), 8.55 (d, J = 2.1 Hz, 1H), 9.73 (s, 1H), 10.12 (s, 1H) |
| N-(4-t-Butoxycarbonylaminothiophen-3-yl)-5-[3-phenethyl-1-[3-(pyrrolidin-1-yl)propyl]ureidomethyl]pyridine-2-carboxylic acid amide (Reference Compound No. 6-73) 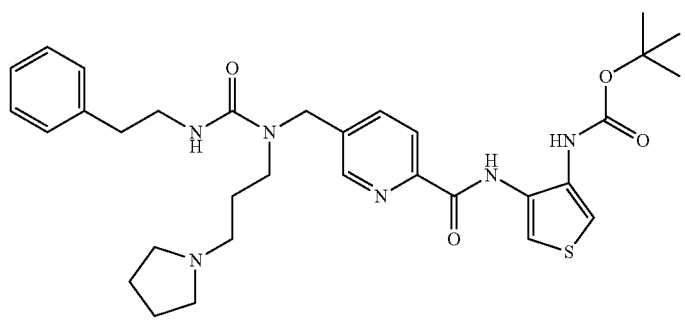 | $^1$H-NMR (400 MHz, CDCl$_3$) δ 1.53 (s, 9H), 1.58 (m, 2H), 1.69 (br s, 4H), 2.34-2.46 (m, 6H), 2.82 (t, J = 7.1 Hz, 2H), 3.19 (t, J = 5.6 Hz, 2H), 3.44 (q, J = 7.1 Hz, 2H), 4.57 (s, 2H), 7.15 (br s, 1H), 7.18-7.24 (m, 3H), 7.25-7.32 (m, 3H), 7.51 (br s, 1H), 7.80 (dd, J = 8.0, 2.1 Hz, 1H), 7.88 (br s, 1H), 8.22 (dd, J = 8.0, 0.7 Hz, 1H), 8.49 (dd, J = 2.1, 0.7 Hz, 1H), 10.12 (s, 1H) |

| | |
|---|---|
| N-(4-t-Butoxycarbonylaminothiophen-3-yl)-5-[3-cyclopentyl-1-[3-(pyrrolidin-1-yl)propyl]ureidomethyl]pyridine-2-carboxylic acid amide (Reference Compound No. 6-74) 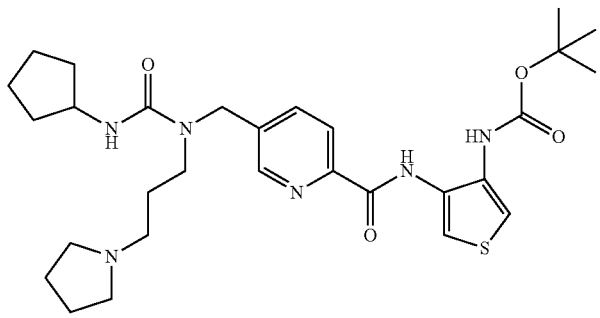 | $^1$H-NMR (400 MHz, CDCl$_3$) δ 1.29 (m, 2H), 1.54 (s, 9H), 1.56-1.71 (m, 6H), 1.80 (br s, 4H), 2.05 (m, 2H), 2.45 (t, J = 6.0 Hz, 2H), 2.49 (br s, 4H), 3.23 (t, J = 5.7 Hz, 2H), 4.03 (m, 1H), 4.55 (s, 2H), 7.07 (d, J = 6.1 Hz, 1H), 7.17 (br s, 1H), 7.24 (br s, 1H), 7.51 (br s, 1H), 7.86 (dd, J = 8.0, 2.1 Hz, 1H), 8.21 (dd, J = 8.0, 0.6 Hz, 1H), 8.50 (dd, J = 2.1, 0.6 Hz, 1H), 10.12 (s, 1H) |
| N-(4-t-Butoxycarbonylaminothiophen-3-yl)-5-[1-[2-(4-methylpiperazin-1-yl)ethyl]-3-phenethylureidomethyl]pyridine-2-carboxylic acid amide (Reference Compound No. 6-75) 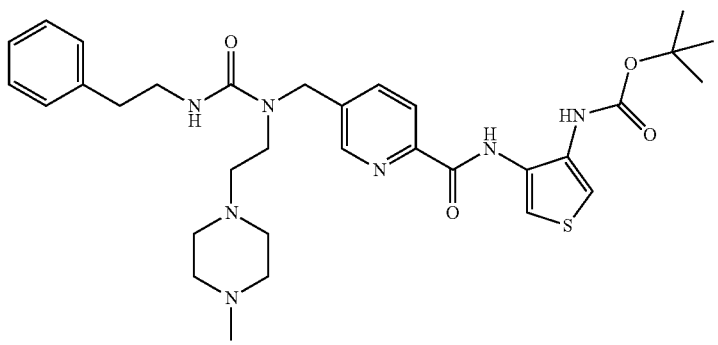 | $^1$H-NMR (500 MHz, CDCl$_3$) δ 1.54 (s, 9H), 2.22 (br s, 4H), 2.23 (s, 3H), 2.38 (t, J = 4.6 Hz, 2H), 2.39 (br s, 4H), 2.87 (t, J = 6.7 Hz, 2H), 3.15 (t, J = 4.6 Hz, 2H), 3.48 (q, J = 6.7 Hz, 2H), 4.59 (s, 2H), 7.14 (br s, 1H), 7.20-7.23 (m, 3H), 7.26 (m, 1H), 7.30 (t, J = 7.5 Hz, 2H), 7.53 (br s, 1H), 7.74 (br s, 1H), 7.81 (dd, J = 8.2, 2.1 Hz, 1H), 8.22 (d, J = 8.2 Hz, 1H), 8.48 (d, J = 2.1 Hz, 1H), 10.13 (s, 1H) |
| 5-[3-(Benzo[1,3]dioxol-5-yl-1-[2-(4-methylpiperazin-1-yl)ethyl]ureidomethyl]-N-(4-t-butoxycarbonylaminothiophen-3-yl)pyridine-2-carboxylic acid amide (Reference Compound No. 6-76) 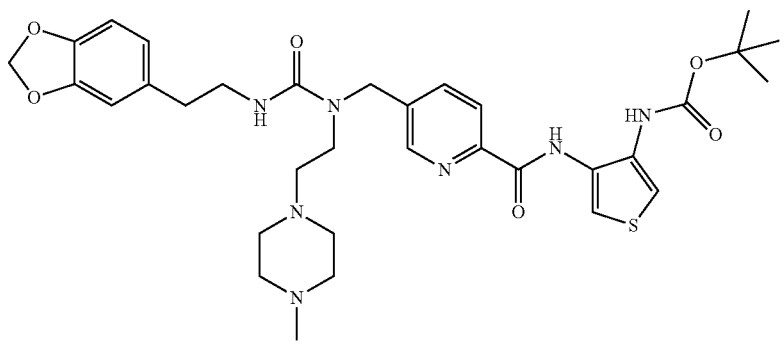 | $^1$H-NMR (400 MHz, CDCl$_3$) δ 1.53 (s, 9H), 2.25 (s, 3H), 2.26 (br s, 4H), 2.41 (t, J = 4.5 Hz, 2H), 2.42 (br s, 4H), 2.78 (t, J = 6.8 Hz, 2H), 3.17 (t, J = 4.5 Hz, 2H), 3.44 (q, J = 6.8 Hz, 2H), 4.58 (s, 2H), 5.92 (s, 2H), 6.65 (dd, J = 8.0, 1.7 Hz, 1H), 6.71 (d, J = 1.7 Hz, 1H), 6.75 (d, J = 8.0 Hz, 1H), 7.17 (br s, 1H), 7.25 (m, 1H), 7.52 (br s, 1H), 7.69 (br s, 1H), 7.81 (dd, J = 8.1, 2.2 Hz, 1H), 8.22 (d, J = 8.1 Hz, 1H), 8.44 (d, J = 2.2 Hz, 1H), 10.13 (S, 1H) |

| | |
|---|---|
| N-(4-t-Butoxycarbonylaminothiophen-3-yl)-5-[3-isopropyl-1-[2-(4-methylpiperazin-1-yl)ethyl]ureidomethyl]pyridine-2-carboxylic acid amide (Reference Compound No. 6-77)<br>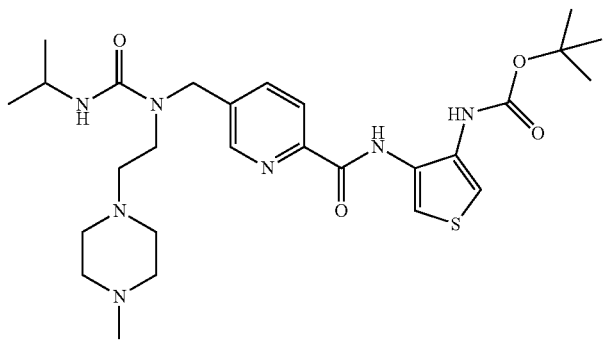 | $^1$H-NMR (500 MHz, CDCl$_3$) δ 1.22 (d, J = 6.4 Hz, 6H), 1.54 (s, 9H), 2.30 (s, 3H), 2.45 (t, J = 4.6 Hz, 2H), 2.47 (br s, 4H), 2.54 (br s, 4H), 3.20 (t, J = 4.6 Hz, 2H), 3.99 (m, 1H), 4.58 (s, 2H), 7.04 (d, J = 7.3 Hz, 1H), 7.15 (br s, 1H), 7.25 (m, 1H), 7.52 (br s, 1H), 7.84 (dd, J = 8.1, 2.0 Hz, 1H), 8.22 (d, J = 8.1 Hz, 1H), 8.48 (d, J = 2.0 Hz, 1H), 10.12 (s, 1H) |
| N-(4-t-Butoxycarbonylaminothiophen-3-yl)-5-[1-(2-dimethylaminoethyl)-3-(2-isopropyloxyethyl)ureidomethyl]pyridine-2-carboxylic acid amide (Reference Compound No. 6-78)<br>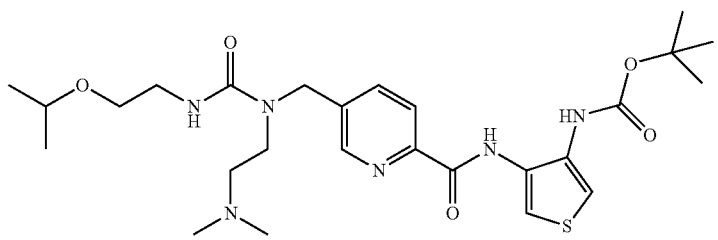 | $^1$H-NMR (500 MHz, DMSO-d$_6$) δ 1.08 (d, J = 6.1 Hz, 6H), 1.51 (s, 9H), 2.13 (s, 6H), 2.32 (t, J = 6.1 Hz, 2H), 3.16 (m, 2H), 3.26 (t, J = 6.1 Hz, 2H), 3.36 (m, 2H), 3.52 (m, 1H), 4.58 (s, 2H), 6.97 (t, J = 5.2 Hz, 1H), 7.21 (d, J = 3.7 Hz, 1H), 7.81 (d, J = 3.7 Hz, 1H), 7.88 (dd, J = 7.9, 2.1 Hz, 1H), 8.10 (d, J = 7.9 Hz, 1H), 8.50 (br s, 1H), 10.48 (br s, 1H). |
| N-(4-t-Butoxycarbonylaminothiophen-3-yl)-5-[1-(2-dimethylaminoethyl)-3-[2-(thiophen-2-yl)ethyl]ureidomethyl]pyridine-2-carboxylic acid amide (Reference Compound No. 6-79)<br>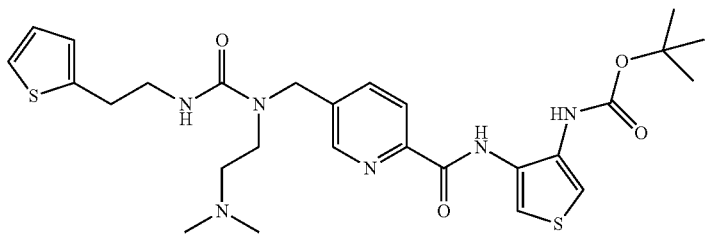 | $^1$H-NMR (500 MHz, DMSO-d$_6$) δ 1.50 (s, 9H), 2.09 (s, 6H), 2.29 (t, J = 6.2 Hz, 2H), 2.95 (t, J = 7.0 Hz, 2H), 3.25 (t, J = 6.2 Hz, 2H), 3.30 (m, 2H), 4.58 (s, 2H), 6.86 (m, 1H), 6.94 (dd, J = 5.2, 3.7 Hz, 1H), 7.08 (t, J = 5.0 Hz, 1H), 7.22 (d, J = 3.7 Hz, 1H), 7.32 (dd, J = 5.2, 1.2 Hz, 1H), 7.81 (d, J = 3.7 Hz, 1H), 7.86 (dd, J = 8.1, 1.7 Hz, 1H), 8.10 (d, J = 8.1 Hz, 1H), 8.50 (d, J = 1.7 Hz, 1H), 9.28 (br s, 1H), 10.48 (br s, 1H). |
| N-(4-t-Butoxycarbonylaminothiophen-3-yl-5-[3-(3-chlorophenethyl)-1-(2-dimethylaminoethyl)ureidomethyl]pyridine-2-carboxylic acid amide (Reference Compound No. 6-80)<br>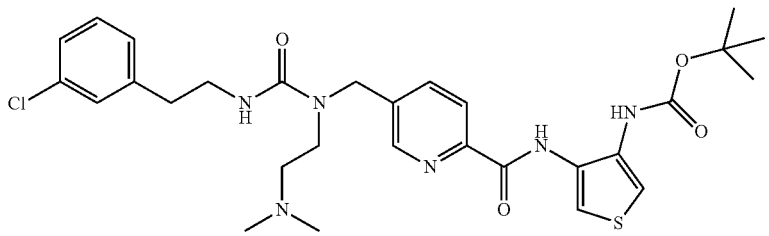 | $^1$H-NMR (400 MHz, DMSO-d$_6$) δ 1.50 (s, 9H), 2.06 (s, 6H), 2.25 (t, J = 6.2 Hz, 2H), 2.75 (t, J = 6.8 Hz, 2H), 3.22 (t, J = 6.2 Hz, 2H), 3.29 (m, 2H), 4.56 (s, 2H), 6.96 (t, J = 5.4 Hz, 1H), 7.14 (d, J = 7.6 Hz, 1H), 7.22 (d, J = 3.7 Hz, 1H), 7.23-7.33 (m, 3H), 7.81 (m, 1H), 7.82 (d, J = 3.7 Hz, 1H), 8.09 (d, J = 8.1 Hz, 1H), 8.49 (d, J = 1.5 Hz, 1H), 9.29 (br s, 1H), 10.48 (br s, 1H). |

N-(4-t-Butoxycarbonylaminothiophen-3-yl)-5-[1-[4-(morpholin-4-yl)butyl]-3-propylureidomethyl]pyridine-2-carboxylic acid amide
(Reference Compound No. 6-81)

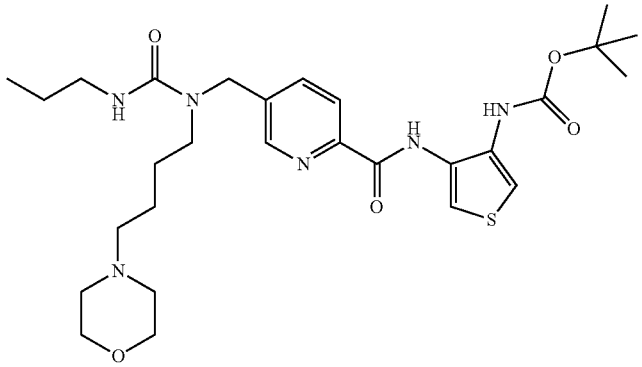

1H-NMR (500 MHz, CDCl$_3$) δ 0.92 (t, J = 7.5 Hz, 3H), 1.49 (m, 2H), 1.51-1.63 (m, 4H), 1.54 (s, 9H), 2.35 (t, J = 7.0 Hz, 2H), 2.41 (m, 4H), 3.17 (t, J = 7.8 Hz, 2H), 3.25 (td, J = 7.0, 5.9 Hz, 2H), 3.71 (t, J = 4.6 Hz, 4H), 4.61 (s, 2H), 4.78 (t, J = 5.9 Hz, 1H), 7.11 (br s, 1H), 7.24 (m, 1H), 7.54 (br s, 1H), 7.82 (dd, J = 7.9, 2.1 Hz, 1H), 8.23 (d, J = 7.9 Hz, 1H), 8.49 (d, J = 2.1 Hz, 1H), 10.13 (s, 1H)

N-(4-t-Butoxycarbonylaminothiophen-3-yl)-5-[3-isopropyl-1-[4-(morpholin-4-yl)butyl]ureidomethyl]pyridine-2-carboxylic acid amide
(Reference Compound No. 6-82)

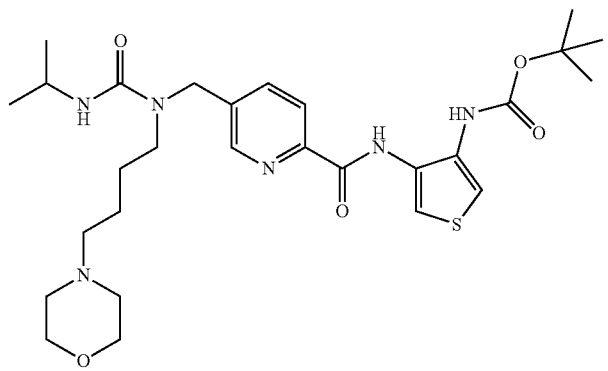

$^1$H-NMR (400 MHz, CDCl$_3$) δ 1.17 (d, J = 6.6 Hz, 6H), 1.49 (m, 2H), 1.54 (s, 9H), 1.58 (m, 2H), 2.33 (t, J = 7.1 Hz, 2H), 2.41 (m, 4H), 3.16 (t, J = 7.7 Hz, 2H), 3.71 (t, J = 4.6 Hz, 4H), 4.03 (m, 1H), 4.23 (d, J = 7.6 Hz, 1H), 4.59 (s, 2H), 7.11 (br s, 1H), 7.24 (m, 1H), 7.54 (br s, 1H), 7.80 (dd, J = 8.1, 2.2 Hz, 1H), 8.23 (d, J = 8.1 Hz, 1H), 8.48 (d, J = 2.2 Hz, 1H), 10.14 (s, 1H)

N-(4-t-Butoxycarbonylaminothiophen-3-yl)-5-[3-sec-butyl-1-[4-(morpholin-4-yl)butyl]ureidomethyl]pyridine-2-carboxylic acid amide
(Reference Compound No. 6-83)

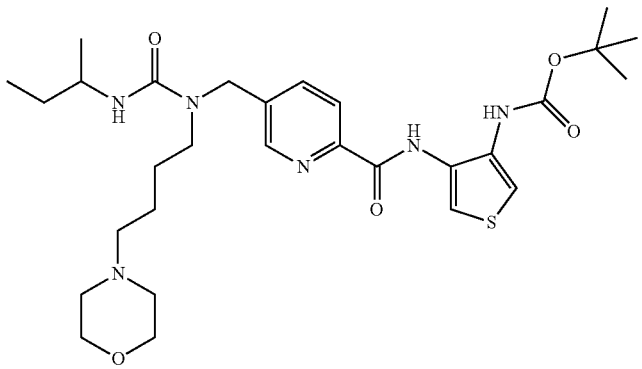

$^1$H-NMR (500 MHz, CDCl$_3$) δ 0.91 (t, J = 7.3 Hz, 3H), 1.14 (d, J = 6.4 Hz, 3H), 1.43-1.52 (m, 4H), 1.54 (s, 9H), 1.59 (m, 2H), 2.33 (t, J = 7.2 Hz, 2H), 2.40 (m, 4H), 3.17 (m, 2H), 3.70 (t, J = 4.7 Hz, 4H), 3.85 (m, 1H), 4.21 (d, J = 7.9 Hz, 1H), 4.60 (s, 2H), 7.11 (br s, 1H), 7.24 (m, 1H), 7.54 (br s, 1H), 7.80 (dd, J = 7.9, 2.1 Hz, 1H), 8.23 (d, J = 7.9 Hz, 1H), 8.48 (d, J = 2.1 Hz, 1H), 10.13 (s, 1H)

| | |
|---|---|
| N-(4-t-Butoxycarbonylaminothiophen-3-yl)-5-[1-[3-(morpholin-4-yl)propyl]-3-propylureidomethyl]pyridine-2-carboxylic acid amide (Reference Compound No. 6-84) 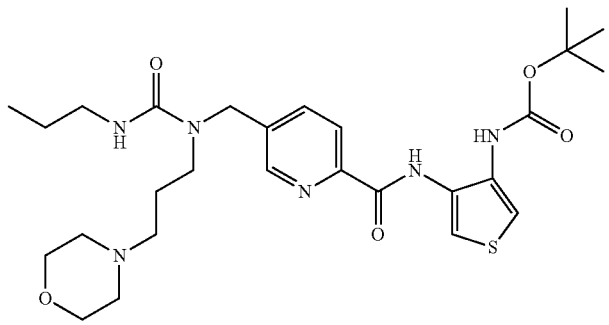 | $^1$H-NMR (400 MHz, CDCl$_3$) δ 0.94 (t, J = 7.4 Hz, 3H), 1.54 (s, 9H), 1.55 (m, 2H), 1.67 (m, 2H), 2.38 (t, J = 6.1 Hz, 2H), 2.44 (br s, 4H), 3.16-3.24 (m, 4H), 3.73 (t, J = 4.5 Hz, 4H), 4.57 (s, 2H), 7.04 (t, J= 5.6 Hz, 1H), 7.12 (br s, 1H), 7.24 (m, 1H), 7.52 (s, 1H), 7.84 (dd, J = 7.9, 2.1 Hz, 1H), 8.22 (d, J = 7.9, 0.6 Hz, 1H), 8.50 (dd, J = 2.1, 0.6 Hz, 1H), 10.12 (s, 1H) |
| N-(4-t-Butoxycarbonylaminothiophen-3-yl)-5-[3-isopropyl-1-[3-(morpholin-4-yl)propyl]ureidomethyl]pyridine-2-carboxylic acid amide (Reference Compound No. 6-85) 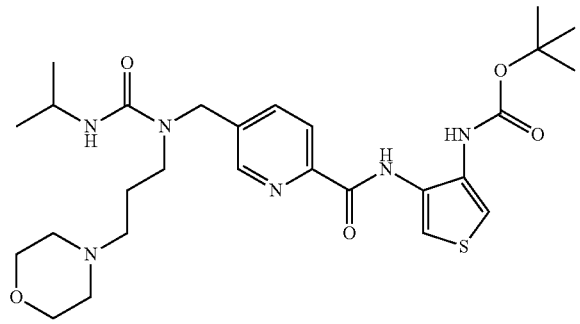 | $^1$H-NMR (400 MHz, CDCl$_3$) δ 1.20 (d, J = 6.6 Hz, 6H), 1.54 (s, 9H), 1.68 (m, 2H), 2.37 (t, J = 6.1 Hz, 2H), 2.45 (t, J = 4.4 Hz, 4H), 3.20 (t, J = 6.1 Hz, 2H), 3.76 (t, J = 4.4 Hz, 4H), 4.02 (m, 1H), 4.57 (s, 2H), 5.89 (d, J = 8.1 Hz, 1H), 7.12 (br s, 1H), 7.24 (m, 1H), 7.52 (br s, 1H), 7.84 (dd, J = 8.1, 2.2 Hz, 1H), 8.22 (dd, J = 8.1, 0.7 Hz, 1H), 8.50 (dd, J = 2.2, 0.7 Hz, 1H), 10.13 (s, 1H) |
| N-(4-t-Butoxycarbonylaminothiophen-3-yl)-5-[3-sec-butyl-1-[3-(morpholin-4-yl)propyl]ureidomethyl]pyridine-2-carboxylic acid amide (Reference Compound No. 6-86) 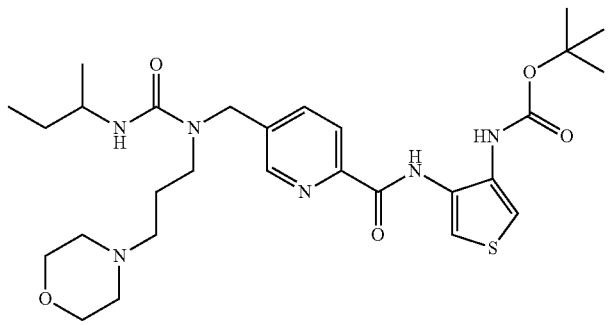 | $^1$H-NMR (500 MHz, CDCl$_3$) δ δ 0.94 (t, J = 7.5 Hz, 3H), 1.17 (d, J = 6.4 Hz, 3H), 1.48 (m, 2H), 1.54 (s, 9H), 1.68 (m, 2H), 2.35 (m, 1H), 2.40 (m, 1H), 2.42 (m, 4H), 3.18 (m, 1H), 3.26 (m, 1H), 3.74 (m, 4H), 3.81 (m, 1H), 4.52 (d, J = 15.9 Hz, 1H), 4.63 (d, J = 15.9 Hz, 1H), 5.83 (d, J = 8.2 Hz, 1H), 7.12 (br s, 1H), 7.25 (m, 1H), 7.52 (br s, 1H), 7.84 (dd, J = 8.1, 2.0 Hz, 1H), 8.22 (d, J = 8.1 Hz, 1H), 8.50 (d, J = 2.0 Hz, 1H), 10.12 (s, 1H) |

| | |
|---|---|
| N-(4-t-Butoxycarbonylaminothiophen-3-yl)-5-[3-ethoxycarbonylmethyl-1-[3-(morpholin-4-yl)propyl]ureidomethyl]pyridine-2-carboxylic acid amide (Reference Compound No. 6-87)<br>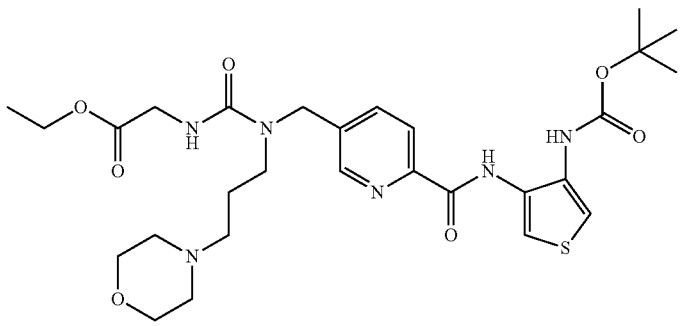 | $^1$H-NMR (500 MHz, CDCl$_3$) δ 1.29 (t, J = 7.2 Hz, 3H), 1.54 (s, 9H), 1.70 (m, 2H), 2.47 (t, J = 6.0 Hz, 2H) ,2.48 (br s, 4H), 3.30 (t, J = 5.7 Hz, 2H), 3.68 (br s, 4H), 3.93 (d, J = 5.9 Hz, 2H), 4.21 (q, J = 7.2 Hz, 2H), 4.59 (s, 2H), 7.16 (br s, 1H), 7.26 (m, 1H), 7.50 (br s, 1H), 7.85 (dd, J = 7.9, 2.0 Hz, 1H), 7.90 (t, J = 5.9 Hz, 1H), 8.22 (d, J = 7.9 Hz, 1H), 8.50 (d, J = 2.0 Hz, 1H), 10.10 (s, 1H) |
| N-(4-t-Butoxycarbonylaminothiophen-3-yl)-5-[3-(3-t-butyldimethylsilyloxymethylphenyl)-1-(2-dimethylaminoethyl)ureidomethyl]pyridine-2-carboxylic acid amide (Reference Compound No. 6-88)<br>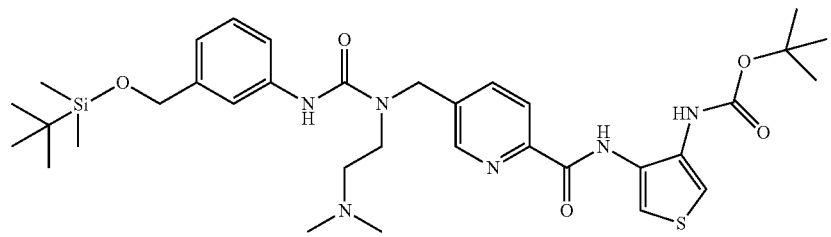 | 1H-NMR (500 MHz, DMSO-d6) δ 0.08 (s, 6H), 0.90 (s, 9H), 1.49 (s, 9H), 2.28 (s, 6H), 2.47 (m, 2H), 3.41 (t, J = 4.9 Hz, 2H), 4.66 (br s, 4H), 6.87 (d, J = 7.3 Hz, 1H), 7.19-7.22 (m, 2H), 7.27-7.30 (m, 2H), 7.81 (d, J = 3.7 Hz, 1H), 7.98 (dd, J = 7.9, 2.1 Hz, 1H), 8.13 (d, J = 7.9 Hz, 1H), 8.59 (br s, 1H), 9.29 (br s, 1H), 10.29 (br s, 1H), 10.48 (br s, 1H). |
| N-(4-t-Butoxycarbonylaminothiophen-3-yl)-5-[1-(2-dimethylaminoethyl)-3-(3-methylphenethyl)ureidomethyl]pyridine-2-carboxylic acid amide (Reference Compound No. 6-89)<br>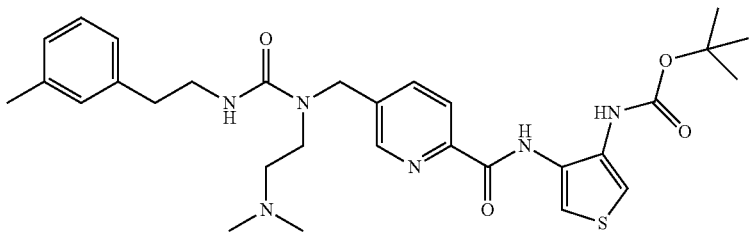 | $^1$H-NMR (400 MHz, DMSO-d$_6$) δ 1.49 (s, 9H), 2.07 (s, 6H), 2.25-2.27 (m, 5H), 2.69 (t, J = 7.1 Hz, 2H), 3.23 (t, J = 6.2 Hz, 2H), 3.28 (m, 2H), 4.57 (s, 2H), 6.98-7.06 (m, 4H), 7.14-7.22 (m, 2H), 7.81-7.84 (m, 2H), 8.10 (d, J = 7.8 Hz, 1H), 8.50 (d, J = 1.5 Hz, 1H), 9.29 (br s, 1H), 10.48 (br s, 1H). |
| 5-[3-Benzyl-1-(2-dimethylaminoethyl)ureidomethyl]-N-(4-t-butoxycarbonylaminothiophen-3-yl)pyridine-2-carboxylic acid amide (Reference Compound No. 6-90)<br>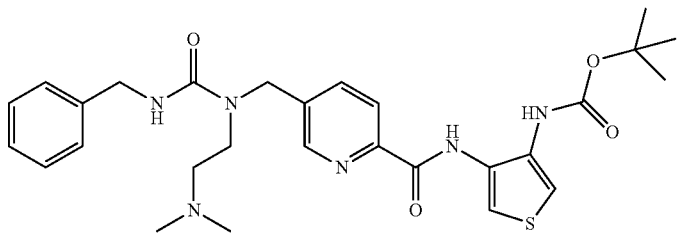 | $^1$H-NMR (400 MHz, DMSO-d$_6$) δ 1.50 (s, 9H), 2.09 (s, 6H), 2.34 (t, J = 6.0 Hz, 2H), 4.22-4.27 (m, 4H), 4.62 (s, 2H), 6.42 (t, J = 6.0 Hz, 1H), 7.13-7.34 (m, 6H), 7.81 (d, J = 3.7 Hz, 1H), 7.89 (dd, J = 8.0, 2.0 Hz, 1H), 8.11 (d, J = 8.0 Hz, 1H), 8.52 (d, J = 2.0 Hz, 1H), 9.29 (br s, 1H), 10.48 (br s, 1H). |

| Compound | NMR |
|---|---|
| N-(4-t-Butoxycarbonylaminothiophen-3-yl)-5-[1-(2-dimethylaminoethyl)-3-(3-phenylpropyl)ureidomethyl]pyridine-2-carboxylic acid amide (Reference Compound No. 6-91)<br>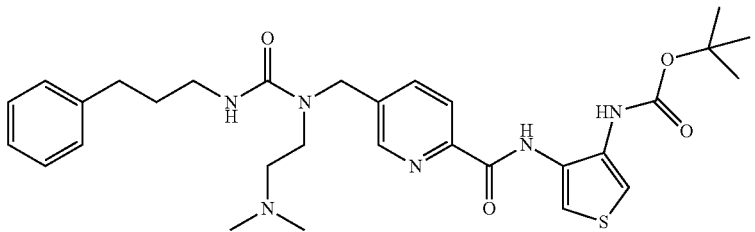 | ¹H-NMR (400 MHz, DMSO-d₆) δ 1.48 (s, 9H), 1.68 (m, 2H), 2.13 (s, 6H), 2.32 (t, J = 6.0 Hz, 2H), 2.56 (m, 2H), 2.98 (m, 2H), 3.28 (m, 2H), 4.58 (s, 2H), 6.94 (t, J = 5.1 Hz, 1H), 7.15-7.21 (m, 4H), 7.25-7.29 (m, 2H), 7.81 (d, J = 3.7 Hz, 1H), 7.88 (dd, J = 8.1, 1.9 Hz, 1H), 8.11 (d, J = 8.1 Hz, 1H), 8.50 (d, J = 1.9 Hz, 1H), 9.29 (br s, 1H), 10.48 (br s, 1H). |
| N-(4-t-Butoxycarbonylaminothiophen-3-yl)-5-[1-(2-dimethylaminoethyl)-3-(furan-2-ylmethyl)ureidomethyl]pyridine-2-carboxylic acid amide (Reference Compound No. 6-92)<br>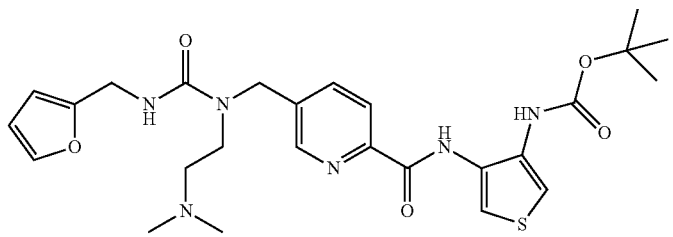 | ¹H-NMR (400 MHz, DMSO-d₆) δ 1.50 (s, 9H), 2.10 (s, 6H), 2.32 (t, J = 6.0 Hz, 2H), 3.29 (m, 2H), 4.24 (d, J = 5.1 Hz, 2H), 4.60 (s, 2H), 6.17 (m, 1H), 6.36-6.38 (m, 2H), 7.22 (d, J = 3.7 Hz, 1H), 7.55 (m, 1H), 7.81 (d, J = 3.7 Hz, 1H), 7.88 (dd, J = 7.8, 1.6 Hz, 1H), 8.11 (d, J = 7.8 Hz, 1H), 8.51 (d, J = 1.6 Hz, 1H), 9.30 (br s, 1H), 10.48 (br s, 1H). |
| N-(4-t-Butoxycarbonylaminothiophen-3-yl)-4-[1-(2-dimethylaminoethyl)-3-(thiophen-3-yl)ureidomethyl]benzamide (Reference Compound No. 6-93)<br>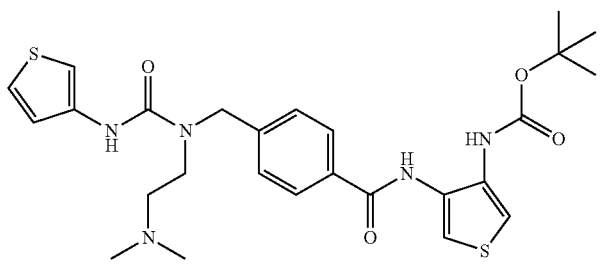 | ¹H-NMR (400 MHz, CDCl₃) δ 1.52 (s, 9H), 2.36 (s, 6H), 2.45 (t, J = 4.3Hz, 2H), 3.29 (t, J = 4.3 Hz, 2H), 4.63 (s, 2H), 6.88 (dd, J = 5.1, 1.4 Hz, 1H), 6.98 (d, J = 3.7 Hz, 1H), 7.10 (s, 1H), 7.20 (dd, J = 5.1, 3.2 Hz, 1H), 7.31 (dd, J = 3.2, 1.4 Hz, 1H), 7.35 (d, J = 8.2 Hz, 2H), 7.71 (d, J = 3.7 Hz, 1H), 7.86 (d, J = 8.2 Hz, 2H), 9.48 (br s, 1H), 11.41 (s, 1H) |
| N-(4-t-Butoxycarbonylaminothiophen-3-yl)-4-[3-(2,3-dihydrobenzo[1,4]dioxin-6-yl)-1-(2-dimethylaminoethyl)ureidomethyl]benzamide (Reference Compound No. 6-94)<br>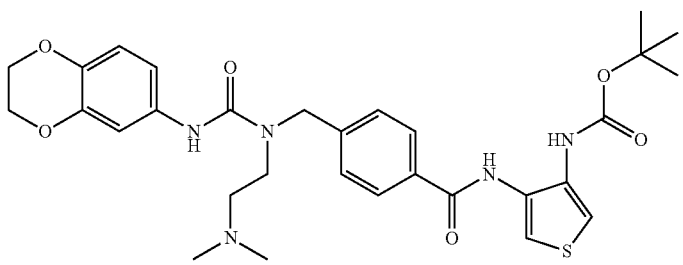 | 1H-NMR (500 MHz, CDCl₃) δ 1.53 (s, 9H), 2.35 (s, 6H), 2.43 (t, J = 4.1 Hz, 2H), 3.30 (t, J = 4.1 Hz, 2H), 4.20-4.25 (m, 4H), 4.62 (s, 2H), 6.77 (d, J = 8.6 Hz, 1H), 6.82 (dd, J = 8.6, 2.4 Hz, 1H), 6.93 (d, J = 2.4 Hz, 1H), 6.96 (s, 1H), 6.98 (d, J = 3.7 Hz, 1H), 7.39 (d, J = 8.2 Hz, 2H), 7.71 (d, J = 3.7 Hz, 1H), 7.88 (d, J = 8.2 Hz, 2H), 9.44 (br s, 1H), 10.76 (s, 1H) |

| | |
|---|---|
| 4-[3-Benzyl-1-(2-dimethylaminoethyl)ureidomethyl]-N-(4-t-butoxycarbonylaminothiophen-3-yl)benzamide (Reference Compound No. 6-95) 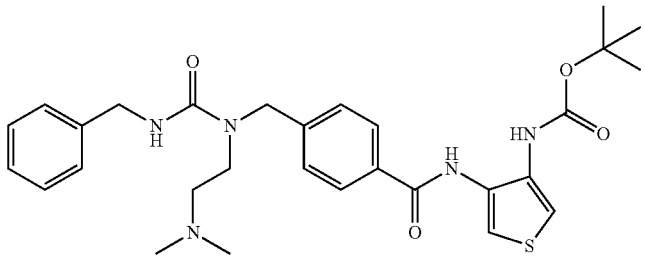 | $^1$H-NMR (500 MHz, CDCl$_3$) δ 1.54 (s, 9H), 2.03 (s, 6H), 2.32 (t, J = 4.4 Hz, 2H), 3.21 (t, J = 4.4 Hz, 2H), 4.39 (d, J = 4.9Hz, 2H), 4.60 (s, 2H), 6.80 (br s, 1H), 6.96 (d, J = 3.8 Hz, 1H), 7.26 (m, 1H), 7.31-7.33 (m, 4H), 7.38 (d, J = 8.2 Hz, 2H), 7.73 (d, J = 3.8 Hz, 1H), 7.88 (d, J = 8.2 Hz, 2H), 8.22 (br s, 1H), 9.39 (br s, 1H) |
| N-(4-t-Butoxycarbonylaminothiophen-3-yl)-4-[1-(2-dimethylaminoethyl)-3-phenethylureidomethyl]benzamide (Reference Compound No. 6-96) 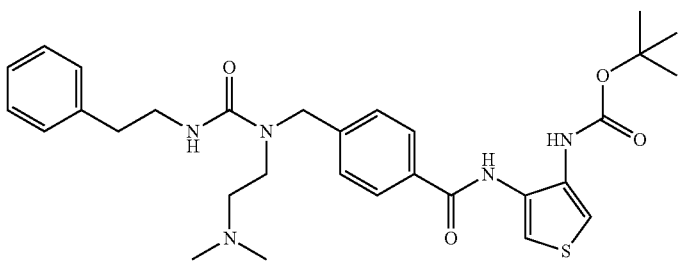 | $^1$H-NMR (500 MHz, CDCl$_3$) δ 1.52 (s, 9H), 2.04 (s, 6H), 2.27 (t, J = 5.0 Hz, 2H), 2.82 (t, J = 6.8 Hz, 2H), 3.14 (t, J = 5.0 Hz, 2H), 3.51 (q, J = 6.8 Hz, 2H), 4.54 (s, 2H), 7.00 (d, J = 3.7 Hz, 1H), 7.10 (br s, 1H), 7.18-7.21 (m, 3H), 7.26-7.32 (m, 4H), 7.42 (br s, 1H), 7.72 (d, J = 3.7 Hz, 1H), 7.87 (d, J = 8.2 Hz, 2H), 9.50 (br s, 1H) |
| N-(4-t-Butoxycarbonylaminothiophen-3-yl)-4-[1-(2-dimethylaminoethyl)-3-isopropylureidomethyl]benzamide (Reference Compound No. 6-97) 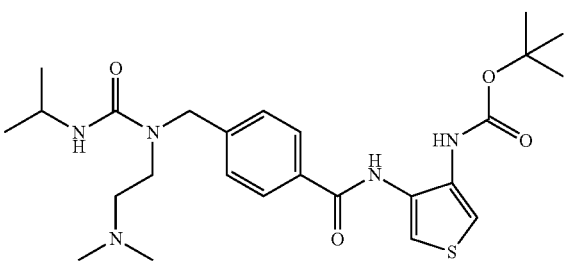 | $^1$H-NMR (400 MHz, CDCl$_3$) δ 1.12 (d, J = 6.6 Hz, 6H), 1.52 (s, 9H), 2.23 (s, 6H), 2.34 (t, J = 4.6 Hz, 2H), 3.17 (t, J = 4.6 Hz, 2H), 3.89 (m, 1H), 4.54 (s, 2H), 7.03 (d, J = 3.7 Hz, 1H), 7.25 (br s, 1H), 7.31 (d, J = 8.3 Hz, 2H), 7.70 (d, J = 3.7 Hz, 1H), 7.72 (br s, 1H), 7.87 (d, J = 8.3 Hz, 2H), 9.52 (br s, 1H) |
| N-(4-t-Butoxycarbonylaminothiophen-3-yl)-4-[3-cyclopentyl-1-(2-dimethylaminoethyl)ureidomethyl]benzamide (Reference Compound No. 6-98) 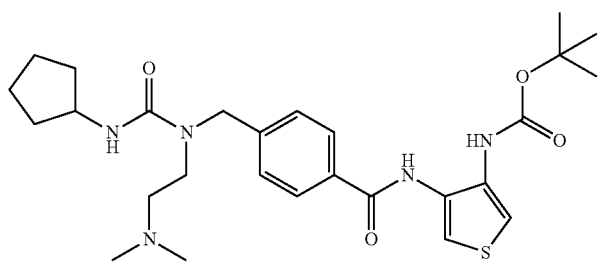 | $^1$H-NMR (400 MHz, CDCl$_3$) δ 1.36 (m, 2H), 1.52 (s, 9H), 1.55-1.68 (m, 4H), 1.92 (m, 2H), 2.22 (s, 6H), 2.34 (t, J = 4.5 Hz, 2H), 3.17 (t, J = 4.5 Hz, 2H), 4.06 (m, 1H), 4.54 (s, 2H), 7.04 (d, J = 3.8 Hz, 1H), 7.25 (br s, 1H), 7.32 (d, J = 8.3 Hz, 2H), 7.70 (d, J = 3.8Hz, 1H), 7.85 (br s, 1H), 7.88 (d, J = 8.3 Hz, 2H), 9.53 (br s, 1H) |

N-(4-t-Butoxycarbonylaminothiophen-3-yl)-5-[1-[3-(4-methylpiperazin-1-yl)propyl]-3-propylureidomethyl]pyridine-2-carboxylic acid amide (Reference Compound No. 6-99)

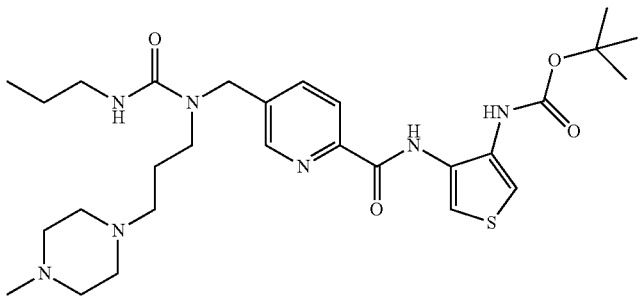

¹H-NMR (500 MHz, CDCl₃) δ 0.95 (t, J = 7.5 Hz, 3H), 1.54 (s, 9H), 1.56 (m, 2H), 1.65 (m, 2H), 2.31 (s, 3H), 2.37 (t, J = 6.0 Hz, 2H), 2.46 (br s, 8H), 3.18-3.22 (m, 4H), 4.57 (s, 2H), 7.14 (br s, 1H), 7.21 (t, J = 5.8 Hz, 1H), 7.26 (m, 1H), 7.51 (br s, 1H), 7.84 (dd, J = 7.9, 2.1 Hz, 1H), 8.21 (d, J = 7.9 Hz, 1H), 8.50 (d, J = 2.1 Hz, 1H), 10.11 (s, 1H)

N-(4-t-Butoxycarbonylaminothiophen-3-yl)-5-[3-sec-butyl-1-[3-(4-methylpiperazin-1-yl)propyl]ureidomethyl]pyridine-2-carboxylic acid amide (Reference Compound No. 6-100)

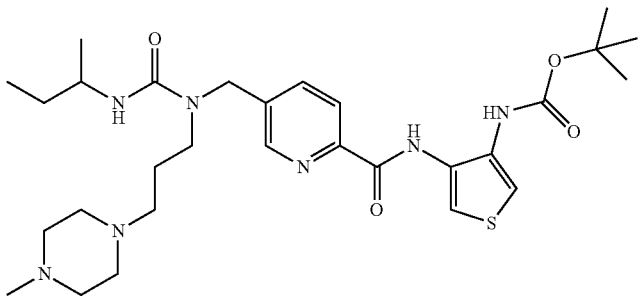

¹H-NMR (500 MHz, CDCl₃) δ 0.95 (t, J = 7.5 Hz, 3H), 1.18 (d, J = 6.7 Hz, 3H), 1.50 (m, 2H), 1.54 (s, 9H), 1.67 (m, 2H), 2.31 (s, 3H), 2.34 (m, 1H), 2.38 (m, 1H), 2.46 (br s, 8H), 3.16 (m, 1H), 3.24 (m, 1H), 3.80 (m, 1H), 4.52 (d, J = 15.9 Hz, 1H), 4.62 (d, J = 15.9 Hz, 1H), 5.96 (d, J = 7.9 Hz, 1H), 7.14 (br s, 1H), 7.26 (m, 1H), 7.51 (br s, 1H), 7.84 (dd, J = 7.9, 2.1 Hz, 1H), 8.22 (d, J = 7.9 Hz, 1H), 8.50 (d, J = 2.1 Hz, 1H), 10.12 (s, 1H)

5-[3-Benzyl-1-[3-(4-methylpiperazin-1-yl)propyl]ureidomethyl]-N-(4-t-butoxycarbonylaminothiophen-3-yl)pyridine-2-carboxylic acid amide (Reference Compound No. 6-101)

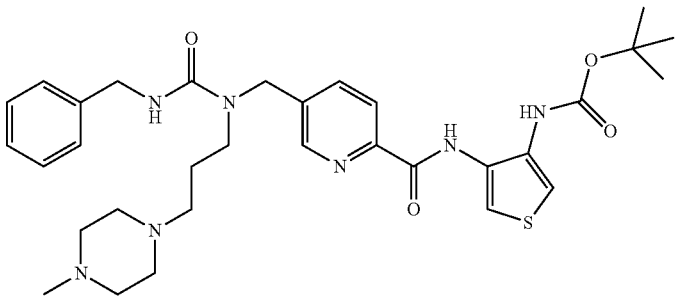

¹H-NMR (500 MHz, CDCl₃) δ 1.53 (s, 9H), 1.67 (m, 2H), 2.09 (s, 3H), 2.29 (br s, 8H), 2.35 (t, J = 6.0 Hz, 2H), 3.28 (t, J = 5.5 Hz, 2H), 4.50 (d, J = 5.7 Hz, 2H), 4.62 (s, 2H), 7.08-7.19 (m, 2H), 7.25 (m, 1H), 7.28-7.35 (m, 4H), 7.51 (br s, 1H), 7.79 (t, J = 5.7 Hz, 1H), 7.87 (dd, J = 7.9, 2.1 Hz, 1H), 8.23 (d, J = 7.9 Hz, 1H), 8.53 (d, J = 2.1 Hz, 1H), 10.12 (s, 1H)

N-(4-t-Butoxycarbonylaminothiophen-
3-yl)-5-[1-[3-(morpholin-4-yl)
propyl]-3-phenethylureidomethyl]
pyridine-2-carboxylic acid amide
(Reference Compound No. 6-102)

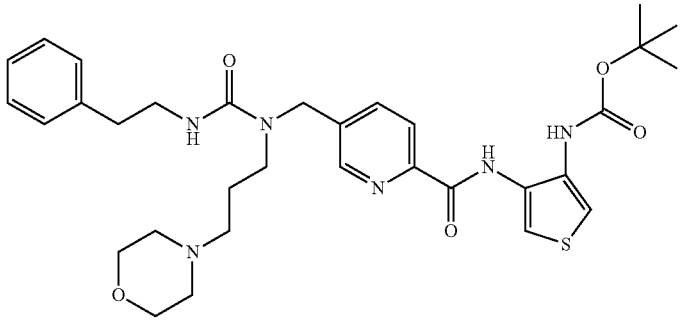

$^1$H-NMR (500 MHz, CDCl$_3$)
δ 1.54 (s, 9H), 1.61 (m, 2H),
2.24-2.32 (m, 6H), 2.86 (t,
J = 6.7 Hz, 2H), 3.14 (t, J =
5.8 Hz, 2H), 3.47 (m, 2H),
3.52 (br s, 4H), 4.58 (s,
2H), 7.15 (t, J = 5.8 Hz, 1H),
7.18-7.24 (m, 5H),
7.28-7.32 (m, 2H), 7.52 (br
s, 1H), 7.80 (dd, J = 7.9,
2.0 Hz, 1H), 8.23 (d, J = 7.9
Hz, 1H), 8.50 (d, J = 2.0 Hz,
1H), 10.14 (s, 1H)

N-(4-t-Butoxycarbonylaminothiophen-
3-yl)-5-[1-(2-dimethylaminoethyl)
ureidomethyl]pyridine-2-
carboxylic acid amide
(Reference Compound No. 6-103)

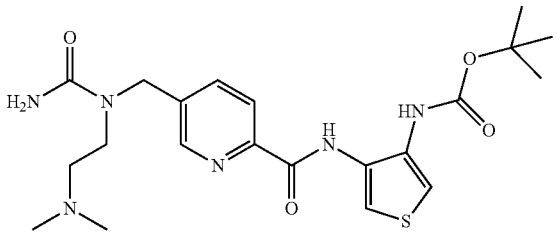

$^1$H-NMR (400 MHz, DMSO-d$_6$)
δ 1.51 (s, 9H), 2.12 (s, 6H),
2.32 (t, J = 6.4 Hz, 2H), 3.26
(t, J = 6.4 Hz, 2H), 4.57 (s,
2H), 6.12 (s, 2H), 7.22 (d,
J = 3.7 Hz, 1H), 7.81 (d, J =
3.7 Hz, 1H), 7.89 (dd, J =
8.0, 1.9 Hz, 1H), 8.12 (d,
J = 8.0 Hz, 1H), 8.52 (d, J =
1.9 Hz, 1H), 9.29 (br s,
1H), 10.48 (br s, 1H).

N-(4-t-Butoxycarbonylaminothiophen-
3-yl)-5-[1-(2-dimethylaminoethyl)-3-
ethylureidomethyl]pyridine-
2-carboxylic acid amide
(Reference Compound No. 6-104)

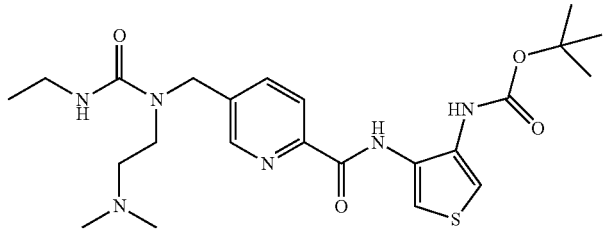

$^1$H-NMR (400 MHz, DMSO-d$_6$)
δ 1.02 (t, J = 7.2 Hz, 3H),
1.51 (s, 9H), 2.13 (s, 6H),
2.31 (t, J = 6.2 Hz, 2H), 3.07
(m, 2H), 3.27 (m, 2H), 4.57
(s, 2H), 6.92 (t, J = 5.1 Hz,
1H), 7.22 (d, J = 3.7 Hz, 1H),
7.81 (d, J = 3.7 Hz, 1H), 7.87
(dd, J = 7.9, 1.7 Hz, 1H),
8.11 (d, J = 7.9 Hz, 1H), 8.50
(d, J = 1.7 Hz, 1H), 9.29 (br
s, 1H), 10.48 (br s, 1H).

N-(4-t-Butoxycarbonylaminothiophen-
3-yl)-4-[1-[3-(morpholin-4-yl)
propyl]-3-(thiophen-3-yl)ureidomethyl]benzamide
(Reference Compound No. 6-105)

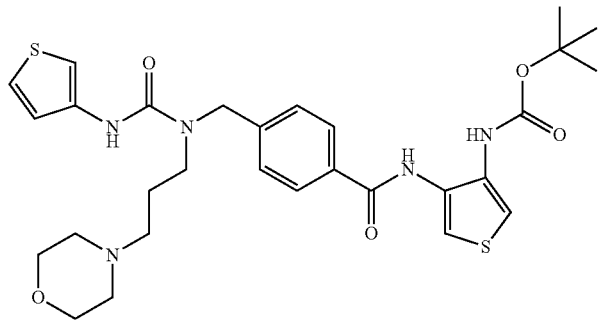

$^1$H-NMR (500 MHz, CDCl$_6$)
δ 1.52 (s, 9H), 1.72 (m, 2H),
2.39-2.49 (m, 6H), 3.34 (t,
J = 5.8 Hz, 2H), 3.71 (t, J =
4.6 Hz, 4H), 4.62 (s, 2H),
6.93 (br s, 1H), 6.97 (d, J =
3.8 Hz, 1H), 7.10 (dd, J =
5.2, 1.5 Hz, 1H), 7.23 (dd,
J = 5.2, 3.1 Hz, 1H), 7.31
(dd, J = 3.1, 1.5 Hz, 1H),
7.38 (d, J = 8.2 Hz, 2H), 7.71
(d, J = 3.8 Hz, 1H), 7.86 (d,
J = 8.2 Hz, 2H), 9.08 (br s,
1H), 9.41 (br s, 1H)

N-(4-t-Butoxycarbonylaminothiophen-
3-yl)-4-[3-(2,3-dihydrobenzo
[1,4]dioxin-6-yl)-1-[3-(morpholin-
4-yl)propyl]ureidomethyl]benzamide
(Reference Compound No. 6-106)

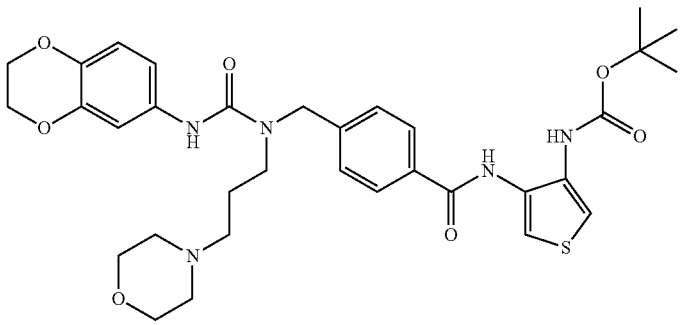

¹H-NMR (500 MHz, CDCl₆)
δ 1.52 (s, 9H), 1.71 (m, 2H),
2.38-2.47 (m, 6H), 3.34 (t,
J = 5.7 Hz, 2H), 3.64 (t, J =
4.6 Hz, 4H), 4.19-4.27 (m,
4H), 4.61 (s, 2H), 6.77 (d,
J = 8.7 Hz, 1H), 6.80 (dd,
J = 8.7, 2.4 Hz, 1H), 6.97
(d, J = 2.4 Hz, 1H), 6.98 (br
s, 1H), 6.99 (d, J = 4.0 Hz,
1H), 7.40 (d, J = 8.2 Hz, 2H),
7.70 (d, J = 4.0 Hz, 1H), 7.87
(d, J = 8.2 Hz, 2H), 8.77 (br
s, 1H), 9.41 (br s, 1H)

4-[3-Benzyl-1-[3-(morpholin-4-yl-
propyl]ureidomethyl]-N-(4-t-
butoxycarbonylaminothiophen-3-yl)
benzamide
(Reference Compound No. 6-107)

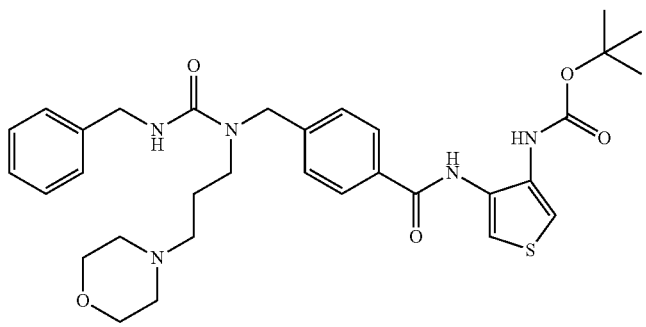

¹H-NMR (500 MHz, CDCl₆)
δ 1.53 (s, 9H), 1.62 (m, 2H),
2.24 (br s, 4H), 2.31 (t, J =
6.0 Hz, 2H), 3.28 (t, J =
5.8 Hz, 2H), 3.41 (br s, 4H),
4.49 (d, J = 5.5 Hz, 2H), 4.61
(s, 2H), 6.91 (br s, 1H),
6.97 (d, J = 3.7 Hz, 1H),
7.23-7.34 (m, 5H), 7.38 (br
s, 1H), 7.38 (d, J = 8.2 Hz,
2H), 7.71 (d, J = 3.7 Hz, 1H),
7.88 (d, J = 8.2 Hz, 2H), 9.41
(br s, 1H)

N-(4-t-Butoxycarbonylaminothiophen-
3-yl)-5-[1-(2-dimethylaminoethyl)-
3-(pyridin-2-ylmethyl)ureidomethyl]
pyridine-2-carboxylic acid amide
(Reference Compound No. 6-108)

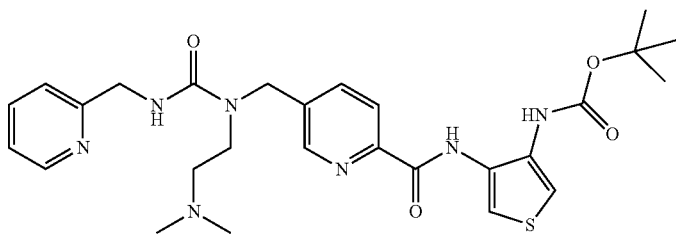

¹H-NMR (500 MHz, DMSO-d₆)
δ 1.50 (s, 9H), 2.13 (s, 6H),
2.38 (t, J = 6.3 Hz, 2H), 3.35
(t, J = 6.3 Hz, 2H), 4.35 (d,
J = 5.4 Hz, 2H), 4.64 (s, 2H),
7.21-7.26 (m, 3H), 7.54 (t,
J = 5.4 Hz, 1H), 7.74 (td,
J = 7.7, 1.7 Hz, 1H), 7.81
(d, J = 3.7 Hz, 1H), 7.93 (dd,
J = 7.9, 1.7 Hz, 1H), 8.13
(d, J = 7.9 Hz, 1H), 8.48 (m,
1H), 8.54 (d, J = 1.7 Hz, 1H),
9.28 (br s, 1H), 10.48 (br
s, 1H).

N-(4-t-Butoxycarbonylaminothiophen-
3-yl)-5-[1-(2-dimethylaminoethyl)-
3-(pyridin-3-ylmethyl)ureidomethyl]
pyridine-2-carboxylic acid amide
(Reference Compound No. 6-109)

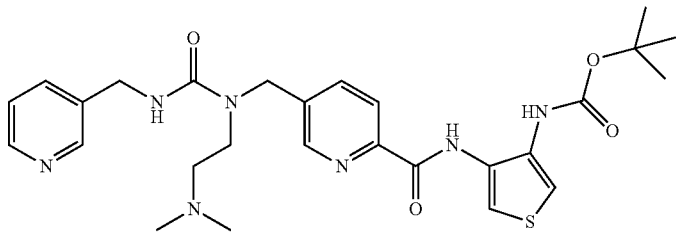

¹H-NMR (500 MHz, DMSO-d₆)
δ 1.50 (s, 9H), 2.09 (s, 6H),
2.33 (t, J = 6.3 Hz, 2H), 3.33
(m, 2H), 4.27 (d, J = 5.3 Hz,
2H), 4.61 (s, 2H), 7.22 (d,
J = 3.7 Hz, 1H), 7.33 (dd,
J = 7.6, 4.9 Hz, 1H), 7.53
(t, J = 5.3 Hz, 1H), 7.64 (dd,
J = 7.6, 1.7 Hz, 1H), 7.81
(d, J = 3.7 Hz, 1H), 7.87 (dd,
J = 8.1, 2.1 Hz, 1H), 8.11
(d, J = 8.1 Hz, 1H), 8.43 (dd,
J = 4.9, 1.7 Hz, 1H), 8.47
(m, 1H), 8.51 (br s, 1H),
9.29 (br s, 1H), 10.48 (br
s, 1H).

| | | |
|---|---|---|
| N-(4-t-Butoxycarbonylaminothiophen-3-yl)-5-[1-(2-dimethylaminoethyl)-3-(pyridin-4-ylmethyl)ureidomethyl]pyridine-2-carboxylic acid amide (Reference Compound No. 6-110) | 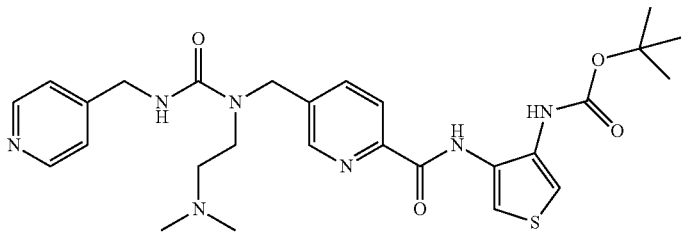 | $^1$H-NMR (400 MHz, DMSO-d$_6$) δ 1.50 (s, 9H), 2.13 (s, 6H), 2.36 (t, J = 6.3 Hz, 2H), 3.35 (t, J = 6.3 Hz, 2H), 4.27 (d, J = 5.6 Hz, 2H), 4.63 (s, 2H), 7.21-7.23 (m, 3H), 7.53 (br s, 1H), 7.81 (d, J = 3.7 Hz, 1H), 7.90 (dd, J = 8.2, 2.0 Hz, 1H), 8.13 (d, J = 8.2 Hz, 1H), 8.47 (d, J = 6.1 Hz, 2H), 8.52 (d, J = 2.0 Hz, 1H), 9.30 (br s, 1H), 10.48 (br s, 1H). |
| N-(4-t-butoxycarbonylaminothiophen-3-yl)-5-[1-(2-dimethylaminoethyl)-3-methylureidomethyl]pyridine-2-carboxylic acid amide (Reference Compound No. 6-111) | 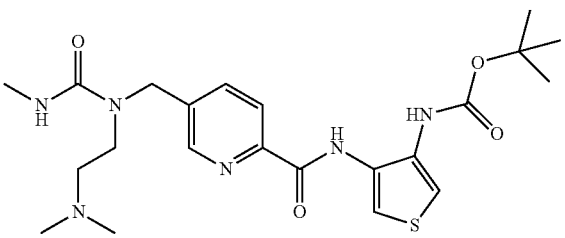 | $^1$H-NMR (500 MHz, DMSO-d$_6$) δ 1.51 (s, 9H), 2.12 (s, 6H), 2.30 (t, J = 6.5 Hz, 2H), 2.60 (d, J = 4.3 Hz, 3H), 3.26 (t, J = 6.5 Hz, 2H), 4.57 (s, 2H), 6.66 (m, 1H), 7.22 (d, J = 3.7 Hz, 1H), 7.81 (d, J = 3.7 Hz, 1H), 7.87 (dd, J = 8.0, 1.7 Hz, 1H), 8.11 (d, J = 8.0 Hz, 1H), 8.50 (d, J = 1.7 Hz, 1H), 9.28 (br s, 1H), 10.47 (br s, 1H). |
| N-(4-t-Butoxycarbonylaminothiophen-3-yl)-5-[1-(2-dimethylaminoethyl)-3-(2-methoxybenzyl)ureidomethyl]pyridine-2-carboxylic acid amide (Reference Compound No. 6-112) | 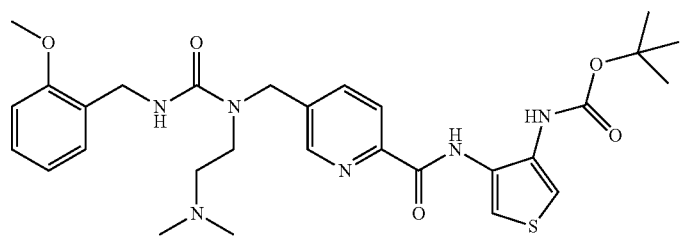 | $^1$H-NMR (500 MHz, DMSO-d$_6$) δ 1.50 (s, 9H), 2.10 (s, 6H), 2.35 (t, J = 6.0 Hz, 2H), 3.32 (m, 2H), 3.78 (s, 3H), 4.23 (d, J = 5.5 Hz, 2H), 4.62 (s, 2H), 6.89 (t, J = 7.5 Hz, 1H), 6.95 (d, J= 7.5 Hz, 1H), 7.12 (dd, J = 7.5, 0.9 Hz, 1H), 7.20 (m, 1H), 7.22 (d, J = 3.5 Hz, 1H), 7.33 (br s, 1H), 7.81 (d, J = 3.5 Hz, 1H), 7.90 (dd, J = 8.1, 1.7 Hz, 1H), 8.11 (d, J = 8.1 Hz, 1H), 8.53 (d, J = 1.7 Hz, 1H), 9.29 (br s, 1H), 10.48 (br s, 1H). |
| N-(4-t-Butoxycarbonylaminothiophen-3-yl)-5-[1-(2-dimethylaminoethyl)-3-(3-methoxybenzyl)ureidomethyl]pyridine-2-carboxylic acid amide (Reference Compound No. 6-113) | 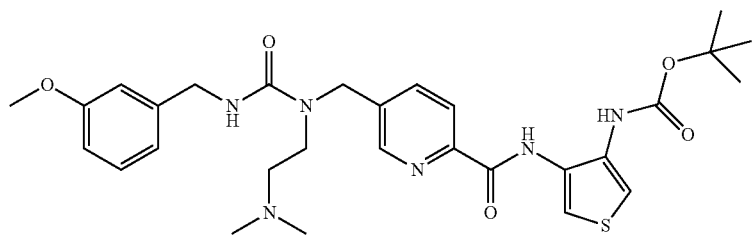 | 1H-NMR (500 MHz, DMSO-d6) δ 1.50 (s, 9H), 2.10 (s, 6H), 2.35 (t, J = 6.1 Hz, 2H), 3.33 (m, 2H), 3.71 (s, 3H), 4.24 (d, J = 5.3 Hz, 2H), 4.62 (s, 2H), 6.76-6.81 (m, 3H), 7.20 (m, 1H), 7.22 (d, J = 3.7 Hz, 1H), 7.45 (t, J = 5.3 Hz, 1H), 7.82 (d, J = 3.7 Hz, 1H), 7.89 (dd, J = 8.1, 1.7 Hz, 1H), 8.11 (d, J= 8.1 Hz, 1H), 8.52 (d, J = 1.7 Hz, 1H), 9.29 (br s, 1H), 10.47 (br s, 1H). |

| | |
|---|---|
| N-(4-t-Butoxycarbonylaminothiophen-3-yl)-5-[1-(2-dimethylaminoethyl)-3-(4-methoxybenzyl)ureidomethyl]pyridine-2-carboxylic acid amide (Reference Compound No. 6-114)<br/>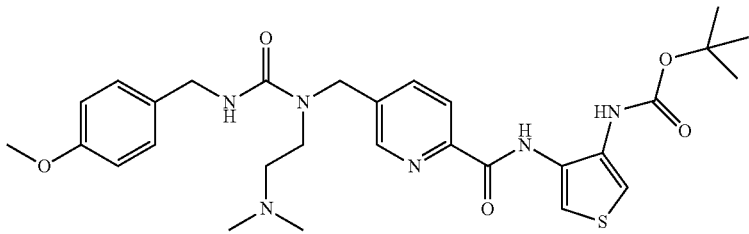 | ¹H-NMR (500 MHz, DMSO-d₆) δ 1.50 (s, 9H), 2.09 (s, 6H), 2.33 (t, J = 6.2 Hz, 2H), 3.29 (t, J = 6.2 Hz, 2H), 3.72 (s, 3H), 4.18 (d, J = 5.3 Hz, 2H), 4.61 (s, 2H), 6.85 (d, J = 8.6 Hz, 2H), 7.16 (d, J = 8.6 Hz, 2H), 7.22 (d, J = 3.7 Hz, 1H), 7.43 (t, J = 5.3 Hz, 1H), 7.81 (d, J = 3.7 Hz, 1H), 7.88 (dd, J = 8.0, 2.0 Hz, 1H), 8.11 (d, J = 8.0 Hz, 1H), 8.51 (br s, 1H), 9.29 (br s, 1H), 10.48 (br s, 1H). |
| N-(4-t-Butoxycarbonylaminothiophen-3-yl)-4-[1-[3-(morpholin-4-yl)propyl]-3-phenethylureidomethyl]benzamide (Reference Compound No. 6-115)<br/>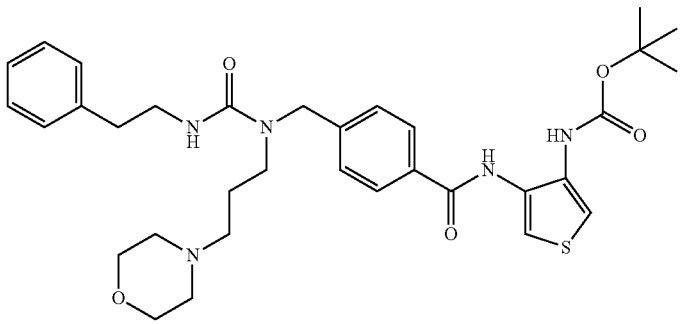 | ¹H-NMR (500 MHz, CDCl₃) δ 1.53 (s, 9H), 1.56 (m, 2H), 2.24-2.30 (m, 6H), 2.85 (t, J = 6.6 Hz, 2H), 3.15 (t, J = 6.0 Hz, 2H), 3.47 (q, J = 6.6 Hz, 2H), 3.53 (br s, 4H), 4.55 (s, 2H), 6.86 (br s, 1H), 6.88 (br s, 1H), 6.97 (d, J = 3.7 Hz, 1H), 7.17-7.23 (m, 3H), 7.27-7.31 (m, 2H), 7.34 (d, J = 8.2 Hz, 2H), 7.73 (d, J = 3.7 Hz, 1H), 7.88 (d, J = 8.2 Hz, 2H), 9.43 (br s, 1H) |
| N-(4-t-Butoxycarbonylaminothiophen-3-yl)-4-[3-isopropyl-1-[3-(morpholin-4-yl)propyl]ureidomethyl]benzamide (Reference Compound No. 6-116)<br/>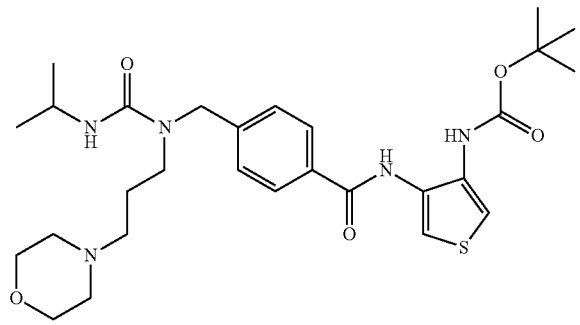 | ¹H-NMR (500 MHz, CDCl₃) δ 1.17 (d, J = 6.4 Hz, 6H), 1.53 (s, 9H), 1.65 (m, 2H), 2.34 (t, J = 6.4 Hz, 2H), 2.43 (br s, 4H), 3.22 (t, J = 6.3 Hz, 2H), 3.74 (t, J = 4.7 Hz, 4H), 4.01 (m, 1H), 4.54 (s, 2H), 5.54 (d, J = 7.6 Hz, 1H), 6.96 (br s, 1H), 6.98 (d, J = 3.7 Hz, 1H), 7.34 (d, J = 8.4 Hz, 2H), 7.71 (d, J = 3.7 Hz, 1H), 7.87 (d, J = 8.4 Hz, 2H), 9.44 (br s, 1H) |

| | |
|---|---|
| N-(4-t-Butoxycarbonylaminothiophen-3-yl)-4-[3-cyclopentyl-1-[3-(morpholin-4-yl)propyl]ureidomethyl]benzamide (Reference Compound No. 6-117) 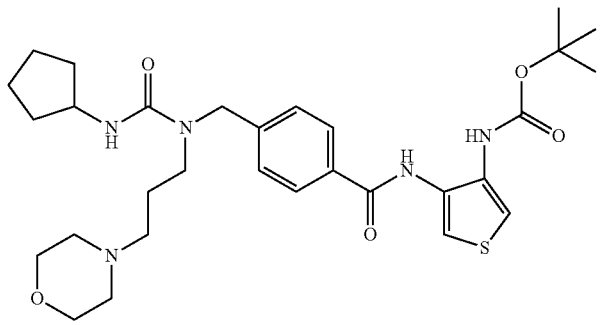 | $^1$H-NMR (500 MHz, CDCl$_3$) δ 1.32 (m, 2H), 1.53 (s, 9H), 1.55-1.69 (m, 6H), 2.02 (m, 2H), 2.34 (t, J = 6.4 Hz, 2H), 2.42 (br s, 4H), 3.23 (t, J = 6.3 Hz, 2H), 3.72 (t, J = 4.6 Hz, 4H), 4.11 (m, 1H), 4.54 (s, 2H), 5.55 (d, J = 6.1 Hz, 1H), 6.90 (br s, 1H), 6.97 (d, J = 3.7 Hz, 1H), 7.35 (d, J = 8.4 Hz, 2H), 7.72 (d, J = 3.7 Hz, 1H), 7.88 (d, J = 8.4 Hz, 2H), 9.44 (br s, 1H) |
| N-(4-t-Butoxycarbonylaminothiophen-3-yl)-5-[1-(2-dimethylaminoethyl)-3-(2-fluorophenethyl)ureidomethyl]pyridine-2-carboxylic acid amide (Reference Compound No. 6-118) 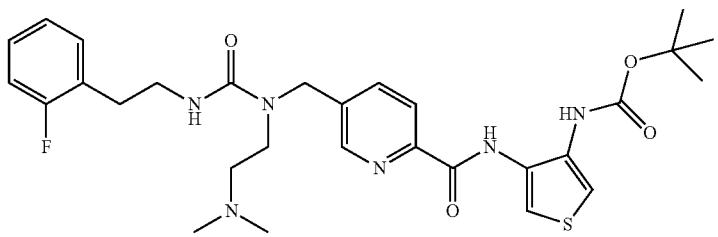 | $^1$H-NMR (400 MHz, DMSO-d$_6$) δ 1.49 (s, 9H), 2.07 (s, 6H), 2.26 (t, J = 6.3 Hz, 2H), 2.77 (t, J = 7.1 Hz, 2H), 3.23 (t, J = 6.3 Hz, 2H), 3.30 (m, 2H), 4.56 (s, 2H), 7.00 (t, J = 5.4 Hz, 1H), 7.09-7.15 (m, 2H), 7.22 (d, J = 3.7 Hz, 1H), 7.22-7.27 (m, 2H), 7.82 (d, J = 3.7 Hz, 1H), 7.82 (m, 1H), 8.10 (d, J = 8.0 Hz, 1H), 8.48 (d, J = 1.2 Hz, 1H), 9.28 (br s, 1H), 10.48 (br s, 1H). |
| N-(4-t-Butoxycarbonylaminothiophen-3-yl)-5-[1-(2-dimethylaminoethyl)-3-(3-fluorobenzyl)ureidomethyl]pyridine-2-carboxylic acid amide (Reference Compound No. 6-119) 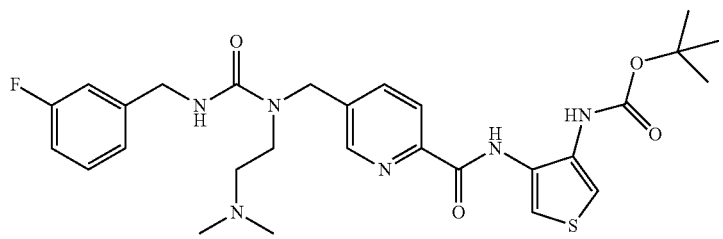 | $^1$H-NMR (500 MHz, DMSO-d$_6$) δ 1.50 (s, 9H), 2.11 (s, 6H), 2.35 (t, J = 6.3 Hz, 2H), 3.34 (t, J = 6.3 Hz, 2H), 4.27 (d, J = 5.4 Hz, 2H), 4.62 (s, 2H), 7.01-7.08 (m, 3H), 7.21 (d, J = 3.7 Hz, 1H), 7.33 (m, 1H), 7.49 (t, J = 5.4 Hz, 1H), 7.81 (d, J = 3.7 Hz, 1H), 7.89 (dd, J = 8.0, 1.9 Hz, 1H), 8.11 (d, J = 7.9 Hz, 1H), 8.51 (br s, 1H), 9.28 (br s, 1H), 10.48 (br s, 1H). |

N-(4-t-Butoxycarbonylaminothiophen-3-yl)-5-[1-(2-dimethylaminoethyl)-3-(4-fluorobenzyl)ureidomethyl]pyridine-2-carboxylic acid amide (Reference Compound No. 6-120)

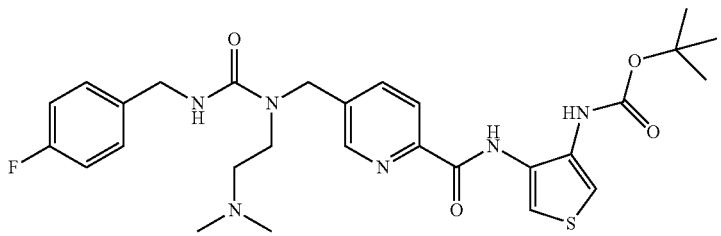

$^1$H-NMR (500 MHz, DMSO-$d_6$) δ 1.50 (s, 9H), 2.09 (s, 6H), 2.33 (t, J = 6.1 Hz, 2H), 3.29 (m, 2H), 4.23 (d, J = 5.5 Hz, 2H), 4.61 (s, 2H), 7.12 (t, J = 8.9 Hz, 2H), 7.21 (d, J = 3.7 Hz, 1H), 7.28 (m, 2H), 7.50 (t, J = 5.5 Hz, 1H), 7.81 (d, J = 3.7 Hz, 1H), 7.88 (dd, J = 7.9, 1.7 Hz, 1H), 8.11 (d, J = 7.9 Hz, 1H), 8.51 (d, J = 1.7 Hz, 1H), 9.29 (br s, 1H), 10.48 (br s, 1H).

Reference Example 7

4-Hydroxymethylbenzoic acid benzyl ester (Reference Compound No. 7-1)

Benzy bromide (7.8 mL, 66 mmol) was added to a suspension of 4-hydroxymethylbenzoic acid (10 g, 66 mmol) and cesium carbonate (11 g, 34 mmol) in mixed solvent (DMF 0.10 L-methanol 30 mL-water 30 mL), and then the reaction mixture was stirred at room temperature for 2 hours. Water (0.50 L) and ethyl acetate (0.50 L) were added to the reaction solution, and the mixture was partitioned. The organic layer was washed with saturated aqueous sodium hydrogen carbonate solution (0.30 L) and water (0.30 L) twice, respectively. The organic layer was dried over anhydrous magnesium sulfate, and then the solvent was evaporated under reduced pressure. The obtained solid was filtered and dried at 35° C. under reduced pressure to give 13 g of the title reference compound as a white solid. (Yield 81%)

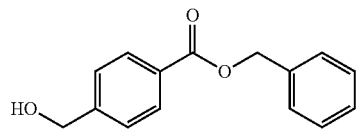

$^1$H-NMR (400 MHz, DMSO-$d_6$) δ 4.58 (d, J = 5.8 Hz, 2 H), 5.35 (s, 2 H), 5.38 (t, J = 5.8 Hz, 1 H), 7.33-7.44 (m, 4 H), 7.46 (m, 1 H), 7.47 (d, J = 8.2 Hz, 2 H), 7.96 (d, J = 8.2 Hz, 2 H)

Reference Example 8

4-Methanesulfonyloxymethylbenzoic acid benzyl ester (Reference Compound No. 8-1)

Under ice cooling, methanesulfonyl chloride (2.1 mL, 27 mmol) was added to a solution of 4-hydroxymethylbenzoic acid benzyl ester (Reference Compound No. 7-1, 6.0 g, 24.8 mmol) and triethylamine (7.6 mL, 54 mmol) in dichloromethane (60 mL), and then the reaction mixture was stirred at room temperature for 50 minutes. Brine (0.30 L) was added to the reaction solution, and the mixture was extracted with chloroform (0.15 L) four times. The organic layer was dried over anhydrous magnesium sulfate, and the solvent was evaporated under reduced pressure to give 5.8 g of the title reference compound as yellow oil. (Yield 73%)

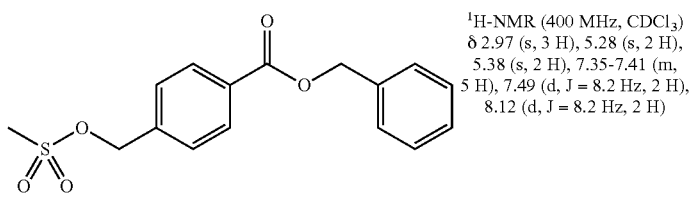

$^1$H-NMR (400 MHz, CDCl$_3$) δ 2.97 (s, 3 H), 5.28 (s, 2 H), 5.38 (s, 2 H), 7.35-7.41 (m, 5 H), 7.49 (d, J = 8.2 Hz, 2 H), 8.12 (d, J = 8.2 Hz, 2 H)

Reference Example 9

4-(2-Dimethylaminoethylaminomethyl) benzoic acid benzyl ester (Reference Compound No. 9-1)

N,N-Dimethylethylenediamine (0.90 mL, 8.2 mmol) was added to a solution of 4-methanesulfonyloxymethylbenzoic acid benzyl ester (Reference Compound No. 8-1, 2.3 g, 7.2 mmol) and triethylamine (3.0 mL, 22 mmol) in DMF (10 mL), and then the reaction mixture was stirred at room temperature for 2 hours. Saturated aqueous sodium hydrogen carbonate solution (0.15 L) was added to the reaction solution, and the whole was extracted with chloroform (0.10 L) three times. The organic layer was dried over anhydrous magnesium sulfate, and then the solvent was evaporated under reduced pressure to give 1.2 g of mixture including the title reference compound as yellow oil.

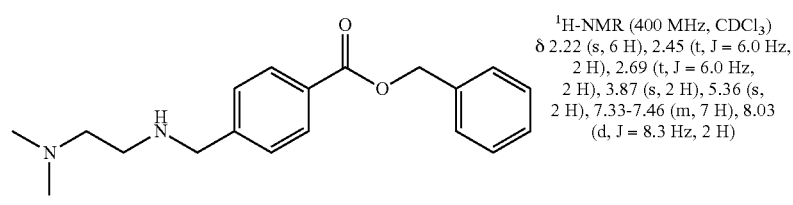

$^1$H-NMR (400 MHz, CDCl$_3$)
δ 2.22 (s, 6 H), 2.45 (t, J = 6.0 Hz, 2 H), 2.69 (t, J = 6.0 Hz, 2 H), 3.87 (s, 2 H), 5.36 (s, 2 H), 7.33-7.46 (m, 7 H), 8.03 (d, J = 8.3 Hz, 2 H)

By using Reference Compound No. 8-1 and commercially available compounds, the following Reference Compound No. 9-2 was obtained by a method similar to that of Reference Compound No. 9-1.

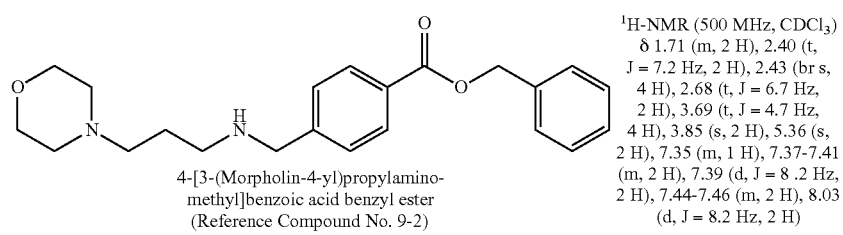

4-[3-(Morpholin-4-yl)propylaminomethyl]benzoic acid benzyl ester (Reference Compound No. 9-2)

$^1$H-NMR (500 MHz, CDCl$_3$)
δ 1.71 (m, 2 H), 2.40 (t, J = 7.2 Hz, 2 H), 2.43 (br s, 4 H), 2.68 (t, J = 6.7 Hz, 2 H), 3.69 (t, J = 4.7 Hz, 4 H), 3.85 (s, 2 H), 5.36 (s, 2 H), 7.35 (m, 1 H), 7.37-7.41 (m, 2 H), 7.39 (d, J = 8 .2 Hz, 2 H), 7.44-7.46 (m, 2 H), 8.03 (d, J = 8.2 Hz, 2 H)

Reference Example 10

4-[1-(2-Dimethylaminoethyl)-3-(indan-5-yl)ureidomethyl]benzoic acid benzyl ester (Reference Compound No. 10-1)

Indan-5-ylisocyanate (0.62 mL, 4.3 mmol) was added to a solution of a mixture including 4-(2-dimethylaminoethylaminomethyl) benzoic acid benzyl ester (Reference Compound No. 9-1, 1.2 g, 3.8 mmol) in dichloromethane (10 mL), and the reaction mixture was stirred at room temperature for 15 hours. The reaction solution was evaporated under reduced pressure and the obtained residue was purified by silica gel column chromatography (chloroform-methanol) to give 0.98 g of the title reference compound as colorless oil. (Yield 29% in 2 steps)

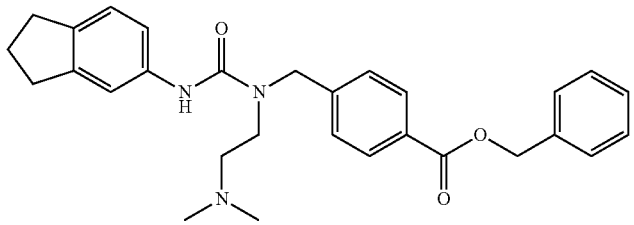

| | $^1$H-NMR (500 MHz, CDCl$_3$) δ 2.04 (m, 2 H), 2.35 (s, 6 H), 2.43 (t, J = 4.3 Hz, 2 H), 2.82-2.89 (m, 4 H), 3.30 (t, J = 4.3 Hz, 2 H), 4.62 (s, 2 H), 5.36 (s, 2 H), 6.97 (dd, J = 8.2, 1.6 Hz, 1 H), 7.10 (d, J = 8.2 Hz, 1 H), 7.34-7.37 (m, 4 H), 7.39 (d, J = 8.3 Hz, 2 H), 7.44 (d, J = 7.0 Hz, 2 H), 8.03 (d, J = 8.3 Hz, 2 H), 10.72 (s, 1 H) |
|---|---|

By using Reference Compound No. 9-2 and commercially available compounds, the following Reference Compound No. 10-2 was obtained by a method similar to that of Reference Compound No. 10-1.

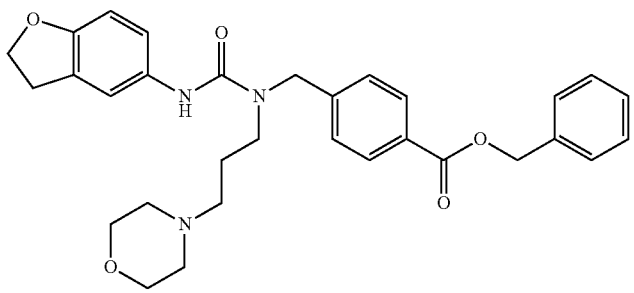

4-[3-(2,3-Dihydro-1-benzofuran-5-yl)-1-[3-(morpholin-4-yl)propyl] ureidomethyl]benzoic acid benzyl ester (Reference Compound No. 10-2)

$^1$H-NMR (400 MHz, CDCl$_3$) δ 1.70 (m, 2 H), 2.40 (t, J = 7.2 Hz, 2 H), 2.44 (m, 4 H), 3.19 (t, J = 8.7 Hz, 2 H), 3.35 (t, J = 5.7 Hz, 2 H), 3.61 (t, J = 4.5 Hz, 4 H), 4.55 (t, J = 8.7 Hz, 2 H), 4.61 (s, 2 H), 5.36 (s, 2 H), 6.71 (d, J = 8.4 Hz, 1 H), 6.94 (dd, J = 8.4, 2.2 Hz, 1 H), 7.32-7.41 (m, 5 H), 7.43-7.48 (m, 3 H), 8.02 (d, J = 8.5 Hz, 2 H), 8.78 (s, 1 H)

Reference Example 11

4-[1-(2-Dimethylaminoethyl)-3-(indan-5-yl)ureidomethyl]benzoic acid (Reference Compound No. 11-1)

10% Palladium-carbon (0.10 g) was added to a solution of 4-[1-(2-dimethylaminoethyl)-3-(indan-5-yl)ureidomethyl] benzoic acid benzyl ester (Reference Compound No. 12-1, 0.97 g, 2.1 mmol) in methanol (20 mL), and then the reaction mixture was stirred at room temperature for 29 hours under hydrogen atmosphere. The insoluble materials were filtered out and the filtrate was evaporated under reduced pressure. The obtained solid was filtered with ethyl acetate to give 0.78 g of the title reference compound as a white solid quantitatively.

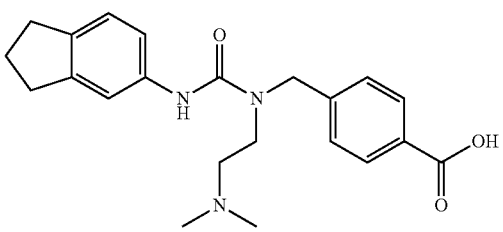

$^1$H-NMR (500 MHz, DMSO-d$_6$) δ 1.99 (m, 2 H), 2.34 (s, 6 H), 1.57 (br s, 2 H), 2.75-2.82 (m, 4 H), 3.39 (t, J = 5.2 Hz, 2 H), 4.62 (s, 2 H), 7.07-7.09 (m, 2 H), 7.31 (s, 1 H), 7.38 (d, J = 8.2 Hz, 2 H), 7.92 (d, J = 8.2 Hz, 2 H), 9.68 (s, 1 H)

By using Reference Compound No. 10-2 and commercially available compounds, the following Reference Compound No. 11-2 was obtained by a method similar to that of Reference Compound No. 11-1.

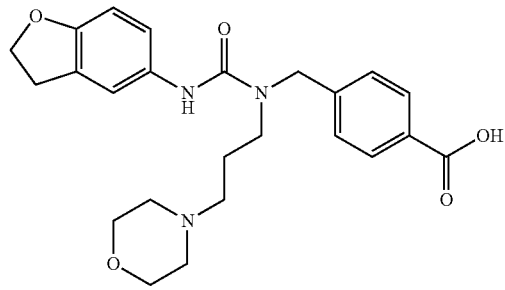

4-[3-(2,3-Dihydro-1-benzofuran-5-yl)-1-[3-(morpholin-4-yl)propyl]ureidomethyl]benzoic acid (Reference Compound No. 11-2)

$^1$H-NMR (400 MHz, CDCl$_3$)
δ 1.66 (m, 2 H), 2.26 (t, J = 7.0 Hz, 2 H), 2.32 (m, 4 H), 3.13 (t, J = 8.7 Hz, 2 H), 3.29 (t, J = 6.8 Hz, 2 H), 3.52 (t, J = 6.8 Hz, 4 H), 4.48 (t, J = 8.7 Hz, 2 H), 4.59 (s, 2 H), 6.64 (d, J = 8.5 Hz, 1 H), 7.05 (dd, J = 8.5, 2.3 Hz, 1 H), 7.33 (d, J = 8.3 Hz, 2 H), 7.34 (m, 1 H), 7.89 (d, J = 8.3 Hz, 2 H), 8.42 (s, 1 H)

Example 1

N-(4-Aminothiophen-3-yl)-5-[3-(2,3-dihydrobenzo[1,4]dioxin-6-yl)-1-(2-dimethylaminoethyl)ureidomethyl]pyridine-2-carboxylic acid amide (Compound No. 1-1)

4.0 M Hydrogen chloride-ethyl acetate solution (5.0 mL) was added to a solution of N-(4-t-butoxycarbonylaminothiophen-3-yl)-5-[3-(2,3-dihydrobenzo[1,4]dioxin-6-yl)-1-(2-dimethylaminoethyl)ureidomethyl]pyridine-2-carboxylic acid amide (Reference Compound No. 6-4, 60 mg, 0.10 mmol) in a mixed solvent of ethyl acetate (2.0 mL)-methanol (3.0 mL), and then the reaction mixture was stirred at room temperature for 2 hours. Chloroform (0.10 L) and saturated aqueous sodium hydrogen carbonate solution (0.15 L) were added to a reaction solution, and then the whole was partitioned. The organic layer was washed with brine (0.10 L). The organic layer was dried over anhydrous magnesium sulfate and the solvent was evaporated under reduced pressure. The obtained residue was purified by silica gel column chromatography (chloroform-methanol) to give 38 mg of the title compound as an orange amorphous product. (Yield 77%)

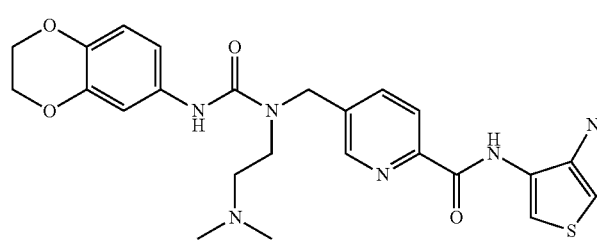

$^1$H-NMR (400 MHz, CDCl$_3$)
δ 2.38 (s, 6 H), 2.50 (t, J = 4.2 Hz, 2 H), 3.31 (t, J = 4.2 Hz, 2 H), 3.54 (br s, 2 H), 4.20-4.27 (m, 4 H), 4.64 (s, 2 H), 6.40 (d, J = 3.4 Hz, 1 H), 6.78 (d, J = 8.7 Hz, 1 H), 6.82 (dd, J = 8.7, 2.4 Hz, 1 H), 6.93 (d, J = 2.4 Hz, 1 H), 7.62 (d, J = 3.4 Hz, 1 H), 7.90 (dd, J = 8.0, 2.2 Hz, 1 H), 8.23 (dd, J = 8.0, 0.7 Hz, 1 H), 8.57 (dd, J = 2.2, 0.7 Hz, 1 H), 10.05 (br s, 1 H), 10.84 (br s, 1 H)

By using any compounds selected from Reference Compound No. 6-1~6-3, 6-5~6-120, the following Compounds (No. 1-2~1-120) were obtained by a method similar to that of Compound No. 1-1.

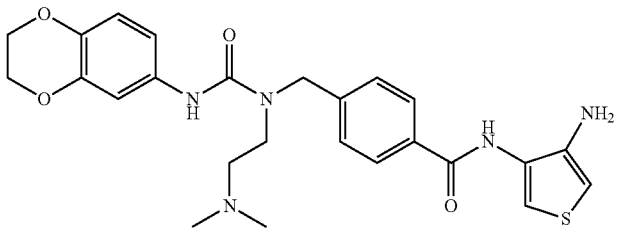

N-(4-Aminothiophen-3-yl)-4-[3-(2,3-dihydrobenzo[1,4]dioxin-6-yl)-1-(2-dimethylaminoethyl)ureidomethyl]benzamide (Compound No. 1-2)

$^1$H-NMR (400 MHz, CDCl$_3$)
δ 2.35 (s, 6 H), 2.45 (t, J = 4.3 Hz, 2 H), 3.30 (t, J = 4.3 Hz, 2 H), 3.43 (s, 2 H), 4.20-4.26 (m, 4 H), 4.60 (s, 2 H), 6.45 (d, J = 3.4 Hz, 1 H), 6.77 (t, J = 8.7 Hz, 1 H), 6.81 (dd, J = 8.7, 2.3 Hz, 1 H), 6.93 (d, J = 2.3 Hz, 1 H), 7.41 (d, J = 8.3 Hz, 2 H), 7.55 (d, J = 3.4 Hz, 1 H), 7.84 (d, J = 8.3 Hz, 2 H), 8.26 (s, 1 H), 10.79 (s, 1 H)

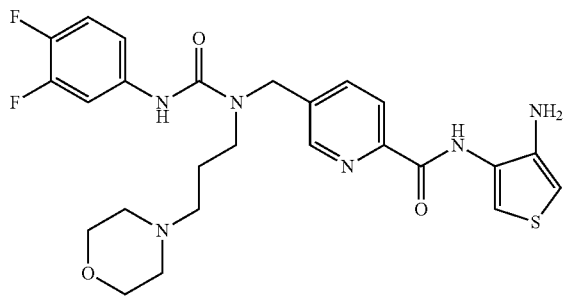

N-(4-Aminothiophen-3-yl)-5-[3-(3,4-difluorophenyl)-1-[3-(morpholin-4-yl)propyl]ureidomethyl]pyridine-2-carboxylic acid amide (Compound No. 1-3)

$^1$H-NMR (400 MHz, CDCl$_3$)
δ 1.79 (m, 2 H), 2.40-2.53 (m, 6 H), 3.37 (t, J = 5.4 Hz, 2 H), 3.54 (br s, 2 H), 3.67 (t, J = 4.5 Hz, 4 H), 4.63 (s, 2 H), 6.40 (d, J = 3.4 Hz, 1 H), 7.01-7.15 (m, 2 H), 7.50 (m, 1 H), 7.62 (d, J = 3.4 Hz, 1 H), 7.90 (dd, J = 8.1, 2.0 Hz, 1 H), 8.23 (d, J = 8.1 Hz, 1 H), 8.58 (d, J = 2.0 Hz, 1 H), 9.15 (s, 1 H), 10.04 (s, 1 H)

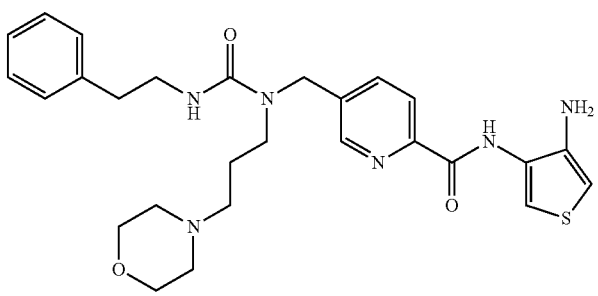

N-(4-Aminothiophen-3-yl)-5-[1-[3-(morpholin-4-yl)propyl]-3-phenethylureidomethyl]pyridine-2-carboxylic acid amide (Compound No. 1-4)

$^1$H-NMR (400 MHz, CDCl$_3$)
δ 1.60 (m, 2 H), 2.24-2.33 (m, 6 H), 2.87 (t, J = 6.8 Hz, 2 H), 3.14 (t, J = 5.7 Hz, 2 H), 3.45-3.56 (m, 8 H), 4.58 (s, 2 H), 6.40 (d, J = 3.3 Hz, 1 H), 7.15 (t, J = 5.7 Hz, 1 H), 7.18-7.25 (m, 3 H), 7.28-7.33 (m, 2 H), 7.62 (d, J = 3.3 Hz, 1 H), 7.79 (dd, J = 8.1, 2.1 Hz, 1 H), 8.22 (dd, J = 8.1, 0.5 Hz, 1 H), 8.51 (dd, J = 2.1, 0.5 Hz, 1 H), 10.05 (s, 1 H)

-continued

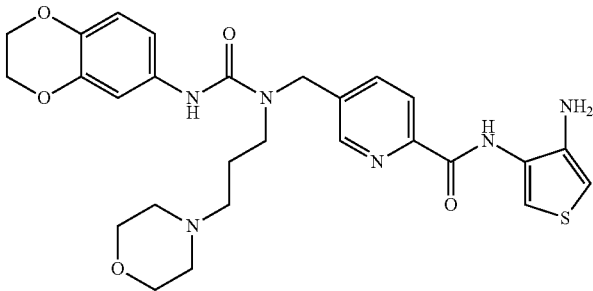

N-(4-Aminothiophen-3-yl)-5-[3-(2,3-dihydrobenzo[1,4]dioxin-6-yl)-1-[3-(morpholin-4-yl)propyl]ureidomethyl]pyridine-2-carboxylic acid amide (Compound No. 1-5)

$^1$H-NMR (400 MHz, CDCl$_3$)
δ 1.76 (m, 2 H), 2.42-2.50 (m, 6 H), 3.36 (t, J = 5.4 Hz, 2 H), 3.54 (br s, 2 H), 3.65 (t, J = 4.6 Hz, 4 H), 4.23-4.25 (m, 4 H), 4.62 (s, 2 H), 6.39 (d, J = 3.4 Hz, 1 H), 6.79-6.84 (m, 2 H), 6.99 (m, 1 H), 7.61 (d, J = 3.4 Hz, 1 H), 7.91 (dd, J = 7.9, 2.2 Hz, 1 H), 8.21 (dd, J = 7.9, 0.7 Hz, 1 H), 8.57 (dd, J = 2.2, 0.7 Hz, 1 H), 8.96 (s, 1 H), 10.04 (s, 1 H)

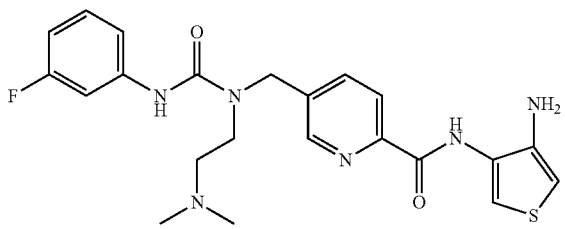

N-(4-Aminothiophen-3-yl)-5-[1-(2-dimethylaminoethyl)-3-(3-fluoro-phenyl)ureidomethyl]pyridine-2-carboxylic acid amide (Compound No. 1-6)

$^1$H-NMR (400 MHz, CDCl$_3$)
δ 2.41 (s, 6 H), 2.54 (t, J = 4.2 Hz, 2 H), 3.33 (t, J = 4.2 Hz, 2 H), 3.54 (br s, 2 H), 4.66 (s, 2 H), 6.40 (d, J = 3.6 Hz, 1 H), 6.68 (tdd, J = 8.4, 2.5, 0.9 Hz, 1 H), 7.00 (m, 1 H), 7.18-7.31 (m, 2 H), 7.63 (d, J = 3.6 Hz, 1 H), 7.90 (dd, J = 8.0, 2.1 Hz, 1 H), 8.25 (dd, J = 8.0, 0.7 Hz, 1 H), 8.58 (dd, J = 2.1, 0.7 Hz, 1 H), 10.05 (s, 1 H), 11.32 (s, 1 H)

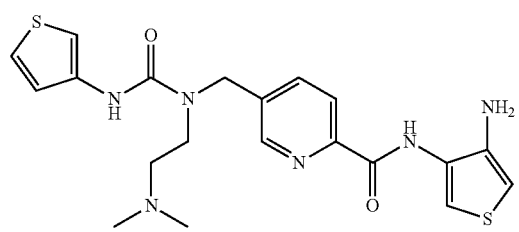

N-(4-Aminothiophen-3-yl)-5-[1-(2-dimethylaminoethyl)-3-(thiophen-3-yl)ureidomethyl]pyridine-2-carboxylic acid amide (Compound No. 1-7)

$^1$H-NMR (400 MHz, CDCl$_3$)
δ 2.39 (s, 6 H), 2.52 (t, J = 4.3 Hz, 2 H), 3.31 (t, J = 4.3 Hz, 2 H), 3.54 (s, 2 H), 4.67 (s, 2 H), 6.40 (d, J = 3.4 Hz, 1 H), 6.87 (dd, J = 5.1, 1.4 Hz, 1 H), 7.21 (dd, J = 5.1, 3.4 Hz, 1 H), 7.30 (dd, J = 3.4, 1.4 Hz, 1 H), 7.62 (d, J = 3.4 Hz, 1 H), 7.89 (dd, J = 8.1, 2.2 Hz, 1 H), 8.23 (dd, J = 8.1, 0.6 Hz, 1 H), 8.57 (dd, J = 2.2, 0.6 Hz, 1 H), 10.04 (s, 1 H), 11.49 (s, 1 H)

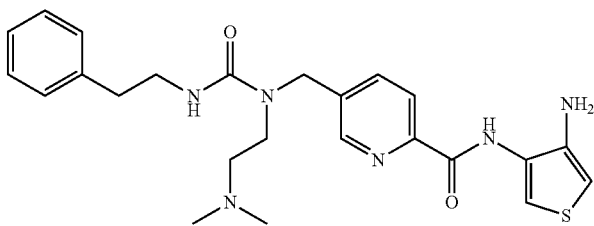

N-(4-Aminothiophen-3-yl)-5-[1-(2-dimethylaminoethyl)-3-phenethyl-ureidomethyl]pyridine-2-carboxylic acid amide (Compound No. 1-8)

$^1$H-NMR (400 MHz, CDCl$_3$)
δ 2.04 (s, 6 H), 2.30 (t, J = 4.8 Hz, 2 H), 2.84 (t, J = 7.0 Hz, 2 H), 3.12 (t, J = 4.8 Hz, 2 H), 3.52 (td, J = 7.0, 5.5 Hz, 2 H), 3.53 (br s, 2 H), 4.58 (s, 2 H), 6.40 (d, J = 3.3 Hz, 1 H), 7.19-7.24 (m, 3 H), 7.30 (m, 2 H), 7.62 (d, J = 3.3 Hz, 1 H), 7.72 (br s, 1 H), 7.80 (dd, J = 8.1, 2.2 Hz, 1 H), 8.21 (dd, J = 8.1, 0.7 Hz, 1 H), 8.50 (dd, J = 2.2, 0.7 Hz, 1 H), 10.05 (s, 1 H)

-continued

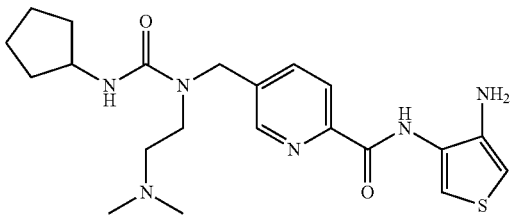

N-(4-Aminothiophen-3-yl)-5-[3-cyclopentyl-1-(2-dimethylaminoethyl)ureidomethyl]pyridine-2-carboxylic acid amide (Compound No. 1-9)

¹H-NMR (400 MHz, CDCl₃) δ 1.39 (m, 2 H), 1.58-1.68 (m, 4 H), 1.96 (m, 2 H), 2.25 (s, 6 H), 2.39 (t, J = 4.4 Hz, 2 H), 3.17 (t, J = 4.4 Hz, 2 H), 3.54 (s, 2 H), 4.07 (m, 1 H), 4.59 (s, 2 H), 6.40 (d, J = 3.3 Hz, 1 H), 7.62 (d, J = 3.3 Hz, 1 H), 7.85 (dd, J = 8.0, 2.1 Hz, 1 H), 8.06 (d, J = 5.6 Hz, 1 H), 8.21 (dd, J = 8.0, 0.7 Hz, 1 H), 8.52 (dd, J = 2.1, 0.7 Hz, 1 H), 10.04 (s, 1 H)

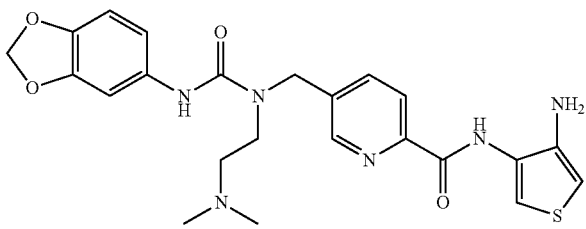

N-(4-Aminothiophen-3-yl)-5-[3-(benzo[1,3]dioxol-5-yl)-1-(2-dimethylaminoethyl)ureidomethyl]pyridine-2-carboxylic acid amide (Compound No. 1-10)

¹H-NMR (400 MHz, CDCl₃) δ 2.38 (s, 6 H), 2.51 (t, J = 4.3 Hz, 2 H), 3.32 (t, J = 4.3 Hz, 2 H), 3.54 (s, 2 H), 4.65 (s, 2 H), 5.92 (s, 2 H), 6.40 (d, J = 3.3 Hz, 1 H), 6.65 (dd, J = 8.3, 2.1 Hz, 1 H), 6.73 (d, J = 8.3 Hz, 1 H), 7.08 (d, J = 2.1 Hz, 1 H), 7.62 (d, J = 3.3 Hz, 1 H), 7.90 (dd, J = 8.1, 2.2 Hz, 1 H), 8.24 (dd, J = 8.1, 0.7 Hz, 1 H), 8.57 (dd, J = 2.2, 0.7 Hz, 1 H), 10.05 (s, 1 H), 10.95 (s, 1 H)

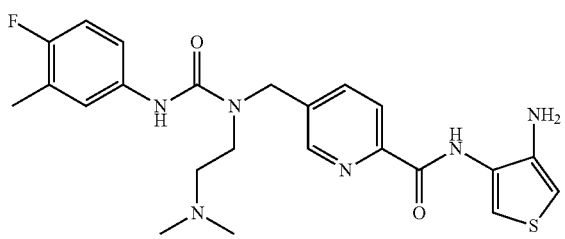

N-(4-Aminothiophen-3-yl)-5-[1-(2-dimethylaminoethyl)-3-(4-fluoro-3-methylphenyl)ureidomethyl]pyridine-2-carboxylic acid amide (Compound No. 1-11)

¹H-NMR (400 MHz, CDCl₃) δ 2.26 (d, J = 1.7 Hz, 3 H), 2.39 (s, 6 H), 2.53 (t, J = 4.3 Hz, 2 H), 3.33 (t, J = 4.3 Hz, 2 H), 3.54 (s, 2 H), 4.65 (s, 2 H), 6.40 (d, J = 3.6 Hz, 1 H), 6.91 (t, J = 8.9 Hz, 1 H), 7.00 (m, 1 H), 7.28 (m, 1 H), 7.62 (d, J = 3.6 Hz, 1 H), 7.90 (dd, J = 8.1, 2.2 Hz, 1 H), 8.24 (dd, J = 8.1, 0.7 Hz, 1 H), 8.58 (dd, J = 2.2, 0.7 Hz, 1 H), 10.05 (s, 1 H), 10.95 (s, 1 H)

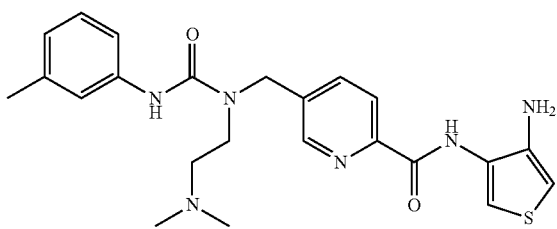

N-(4-Aminothiophen-3-yl)-5-[1-(2-dimethylaminoethyl)-3-(3-methylphenyl)ureidomethyl]pyridine-2-carboxylic acid amide (Compound No. 1-12)

¹H-NMR (400 MHz, CDCl₃) δ 2.34 (s, 3 H), 2.40 (s, 6 H), 2.52 (t, J = 4.3 Hz, 2 H), 3.33 (t, J = 4.3 Hz, 2 H), 3.54 (s, 2 H), 4.66 (s, 2 H), 6.40 (d, J = 3.4 Hz, 1 H), 6.82 (d, J = 7.7 Hz, 1 H), 7.05 (d, J = 7.7 Hz, 1 H), 7.17 (t, J = 7.7 Hz, 1 H), 7.29 (br s, 1 H), 7.62 (d, J = 3.4 Hz, 1 H), 7.91 (dd, J = 8.1, 2.2 Hz, 1 H), 8.24 (dd, J = 8.1, 0.7 Hz, 1 H), 8.58 (dd, J = 2.2, 0.7 Hz, 1 H), 10.05 (s, 1 H), 10.97 (s, 1 H)

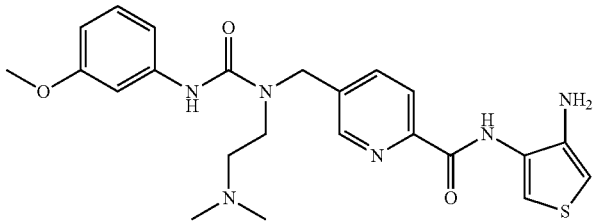

N-(4-Aminothiophen-3-yl)-5-[1-
(2-dimethylaminoethyl)-3-(3-methoxy-
phenyl)ureidomethyl]pyridine-2-
carboxylic acid amide
(Compound No. 1-13)

$^1$H-NMR (400 MHz, CDCl$_3$)
δ 2.40 (s, 6 H), 2.52 (t,
J = 4.3 Hz, 2 H), 3.33 (t,
J = 4.3 Hz, 2 H), 3.54 (s, 2 H),
3.82 (s, 3 H), 4.66 (s, 2 H),
6.40 (d, J = 3.4 Hz, 1 H),
6.56 (ddd, J = 8.2, 2.3, 1.0 Hz,
1 H), 6.84 (ddd, J = 8.2,
2.3, 1.0 Hz, 1 H), 7.15 (t,
J = 2.3 Hz, 1 H), 7.18 (t,
J = 8.2 Hz, 1 H), 7.62 (d,
J = 3.4 Hz, 1 H), 7.90 (dd,
J = 8.0, 2.2 Hz, 1 H), 8.24 (dd,
J = 8.0, 0.7 Hz, 1 H), 8.58
(dd, J = 2.2, 0.7 Hz, 1 H),
10.05 (s, 1 H), 11.12 (s, 1 H)

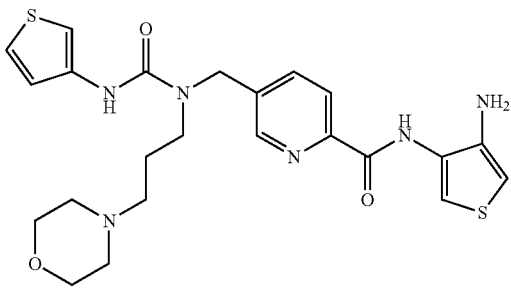

N-(4-Aminothiophen-3-yl)-5-[1-
[3-(morpholin-4-yl)propyl]-3-
thiophen-3-yl)ureidomethyl]
pyridine-2-carboxylic acid
amide (Compound No. 1-14)

$^1$H-NMR (400 MHz, CDCl$_3$)
δ 1.77 (m, 2 H), 2.44-2.50
(m, 6 H), 3.36 (t, J = 5.6 Hz,
2 H), 3.53 (br s, 2 H), 3.72
(t, J = 4.6 Hz, 4 H), 4.64 (s,
2 H), 6.40 (d, J = 3.3 Hz,
1 H), 7.10 (dd, J = 5.1, 1.4 Hz,
1 H), 7.24 (dd, J = 5.1,
3.2 Hz, 1 H), 7.31 (dd,
J = 3.2, 1.4 Hz, 1 H), 7.62 (d,
J = 3.3 Hz, 1 H), 7.90 (dd,
J = 8.0, 2.1 Hz, 1 H), 8.22
(dd, J = 8.0, 0.7 Hz, 1 H),
8.58 (dd, J = 2.1, 0.7 Hz,
1 H), 9.24 (br s, 1 H), 10.04
(br s, 1 H)

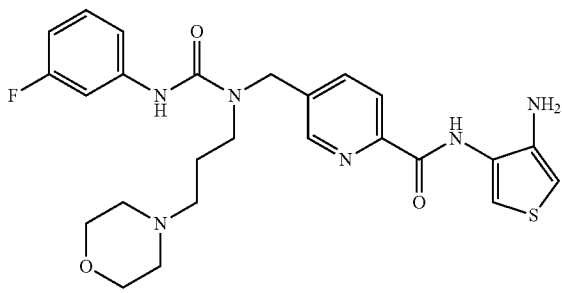

N-(4-Aminothiophen-3-yl)-5-[3-
(3-fluorophenyl)-1-[3-(morpholin-
4-yl)propyl]ureidomethyl]pyridine-
2-carboxylic acid amide
(Compound No. 1-15)

$^1$H-NMR (400 MHz, CDCl$_3$)
δ 1.79 (m, 2 H), 2.44-2.52
(m, 6 H), 3.38 (t, J = 5.6 Hz,
2 H), 3.53 (br s, 2 H), 3.71
(t, J = 4.6 Hz, 4 H), 4.64 (s,
2 H), 6.40 (d, J = 3.4 Hz,
1 H), 6.78 (tdd, J = 8.3, 2.6,
0.8 Hz, 1 H), 7.12 (m, 1 H),
7.26 (m, 1 H), 7.41 (dt,
J = 11.1, 2.3 Hz, 1 H), 7.62 (d,
J = 3.4 Hz, 1 H), 7.90 (dd,
J = 8.1, 2.0 Hz, 1 H), 8.23
(d, J = 8.1 Hz, 1 H), 8.58 (d,
J = 2.0 Hz, 1 H), 9.03 (br s,
1 H), 10.04 (br s, 1 H)

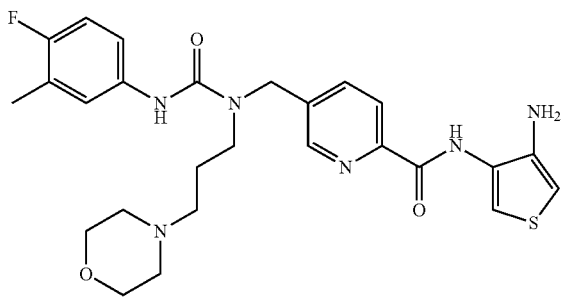

N-(4-Aminothiophen-3-yl)-5-[3-
(4-fluoro-3-methylphenyl)-1-[3-
(morpholin-4-yl)propyl]ureidomethyl]
pyridine-2-carboxylic acid amide
(Compound No. 1-16)

$^1$H-NMR (400 MHz, CDCl$_3$)
δ 1.78 (m, 2 H), 2.27 (d,
J = 2.0 Hz, 3 H), 2.42-2.51 (m,
6 H), 3.38 (t, J = 5.5 Hz,
2 H), 3.54 (br s, 2 H), 3.64
(t, J = 4.5 Hz, 4 H), 4.63 (s,
2 H), 6.40 (d, J = 3.8 Hz,
1 H), 6.95 (t, J = 8.9 Hz,
1 H), 7.13 (m, 1 H), 7.30 (dd,
J = 6.6, 2.7 Hz, 1 H), 7.62
(d, J = 3.8 Hz, 1 H), 7.91
(dd, J = 8.1, 2.1 Hz, 1 H),
8.22 (dd, J = 8.1, 0.7 Hz,
1 H), 8.57 (dd, J = 2.1,
0.7 Hz, 1 H), 9.00 (br s, 1 H),
10.04 (br s, 1 H)

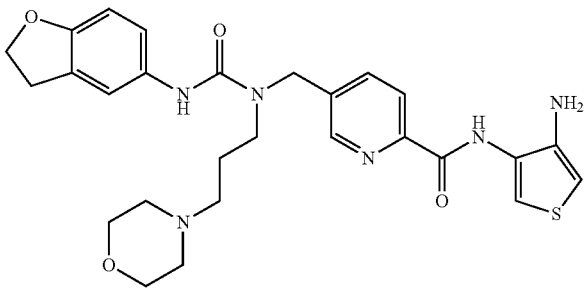

N-(4-Aminothiophen-3-yl)-5-[3-(2,3-dihydro-1-benzofuran-5-yl)-1-[3-(morpholin-4-yl)propyl]ureidomethyl]pyridine-2-carboxylic acid amide (Compound No. 1-17)

$^1$H-NMR (400 MHz, CDCl$_3$) δ 1.77 (m, 2 H), 2.44 (br s, 4 H), 2.48 (t, J = 6.0 Hz, 2 H), 3.21 (t, J = 8.7 Hz, 2 H), 3.37 (t, J = 5.5 Hz, 2 H), 3.54 (br s, 2 H), 3.61 (t, J = 4.5 Hz, 4 H), 4.57 (t, J = 8.7 Hz, 2 H), 4.63 (s, 2 H), 6.40 (d, J = 3.3 Hz, 1 H), 6.72 (d, J = 8.4 Hz, 1 H), 6.95 (dd, J = 8.4, 2.2 Hz, 1 H), 7.34 (d, J = 2.2 Hz, 1 H), 7.61 (d, J = 3.3 Hz, 1 H), 7.92 (dd, J = 8.1, 2.1 Hz, 1 H), 8.22 (dd, J = 8.1, 0.7 Hz, 1 H), 8.58 (dd, J = 2.1, 0.7 Hz, 1 H), 9.00 (br s, 1 H), 10.04 (br s, 1 H)

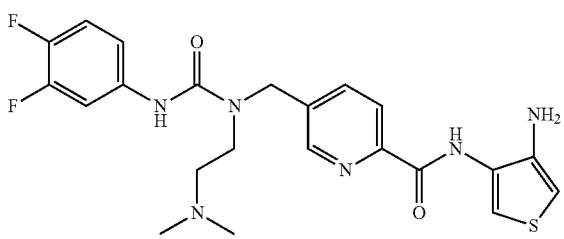

N-(4-Aminothiophen-3-yl)-5-[3-(3,4-difluorophenyl)-1-(2-dimethylaminoethyl)ureidomethyl]pyridine-2-carboxylic acid amide (Compound No. 1-18)

$^1$H-NMR (400 MHz, CDCl$_3$) δ 2.40 (s, 6 H), 2.54 (t, J = 4.2 Hz, 2 H), 3.32 (t, J = 4.2 Hz, 2 H), 3.52 (br s, 2 H), 4.64 (s, 2 H), 6.40 (d, J = 3.4 Hz, 1 H), 6.91 (m, 1 H), 7.04 (m, 1 H), 7.39 (ddd, J = 12.7, 7.2, 2.6 Hz, 1 H), 7.62 (d, J = 3.4 Hz, 1 H), 7.89 (dd, J = 8.0, 2.2 Hz, 1 H), 8.24 (dd, J = 8.0, 0.7 Hz, 1 H), 8.57 (dd, J = 2.2, 0.7 Hz, 1 H), 10.04 (s, 1 H), 11.28 (s, 1 H)

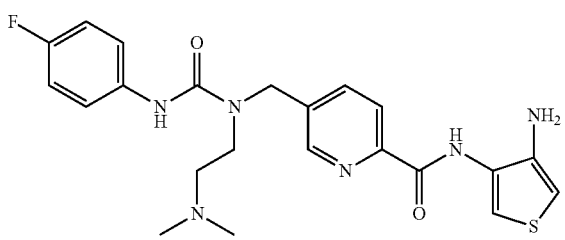

N-(4-Aminothiophen-3-yl)-5-[1-(2-dimethylaminoethyl)-3-(4-fluorophenyl)ureidomethyl]pyridine-2-carboxylic acid amide (Compound No. 1-19)

$^1$H-NMR (400 MHz, CDCl$_3$) δ 2.40 (s, 6 H), 2.53 (t, J = 4.3 Hz, 2 H), 3.34 (t, J = 4.3 Hz, 2 H), 3.53 (br s, 2 H), 4.65 (s, 2 H), 6.40 (d, J = 3.4 Hz, 1 H), 6.98 (t, J = 8.9 Hz, 2 H), 7.30 (dd, J = 8.9, 4.9 Hz, 2 H), 7.62 (d, J = 3.4 Hz, 1 H), 7.90 (dd, J = 8.1, 2.2 Hz, 1 H), 8.24 (dd, J = 8.1, 0.7 Hz, 1 H), 8.58 (dd, J = 2.2, 0.7 Hz, 1 H), 10.04 (s, 1 H), 11.07 (s, 1 H)

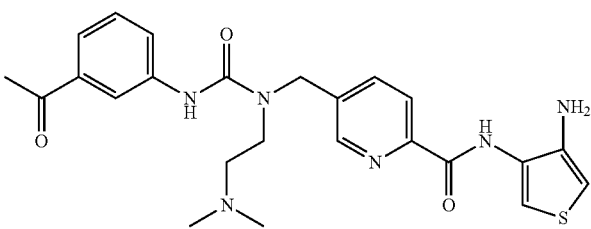

5-[3-(3-Acetylphenyl)-1-(2-dimethylaminoethyl)ureidomethyl]-N-(4-aminothiophen-3-yl)pyridine-2-carboxylic acid amide (Compound No. 1-20)

$^1$H-NMR (400 MHz, CDCl$_3$) δ 2.43 (s, 6 H), 2.56 (t, J = 4.2 Hz, 2 H), 2.61 (s, 3 H), 3.36 (t, J = 4.2 Hz, 2 H), 3.53 (br s, 2 H), 4.67 (s, 2 H), 6.40 (d, J = 3.5 Hz, 1 H), 7.38 (t, J = 7.9 Hz, 1 H), 7.58 (ddd, J = 7.9, 1.5, 1.0 Hz, 1 H), 7.63 (d, J = 3.5 Hz, 1 H), 7.66 (ddd, J = 7.9, 2.2, 1.0 Hz, 1 H), 7.89-7.93 (m, 2 H), 8.25 (dd, J = 8.1, 0.5 Hz, 1 H), 8.59 (dd, J = 2.2, 0.5 Hz, 1 H), 10.05 (s, 1 H), 11.42 (s, 1 H)

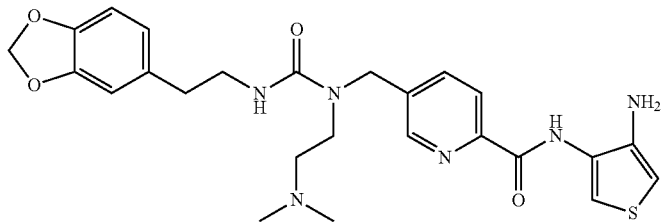

N-(4-Aminothiophen-3-yl)-5-[3-
[2-(benzo[1,3]dioxol-5-yl)ethyl]-
1-(2-dimethylaminoethyl)ureidomethyl]
pyridine-2-carboxylic acid amide
(Compound No. 1-21)

$^1$H-NMR (500 MHz, CDCl$_3$)
δ 2.11 (s, 6 H), 2.33 (t,
J = 4.7 Hz, 2 H), 2.75 (t,
J = 6.8 Hz, 2 H), 3.15 (t,
J = 4.7 Hz, 2 H), 3.46 (q,
J = 6.8 Hz, 2 H), 3.55 (br s,
2 H), 4.58 (s, 2 H), 5.92 (s,
2 H), 6.39 (d, J = 3.5 Hz,
1 H), 6.66 (dd, J = 7.9, 1.6 Hz,
1 H), 6.72 (d, J = 1.6 Hz,
1 H), 6.74 (d, J = 7.9 Hz, 1 H),
7.59 (br s, 1 H), 7.62 (d,
J = 3.5 Hz, 1 H), 7.80 (dd,
J = 7.9, 2.1 Hz, 1 H), 8.21 (dd,
J = 7.9, 0.6 Hz, 1 H), 8.47
(dd, J = 2.1, 0.6 Hz, 1 H),
10.05 (s, 1 H).

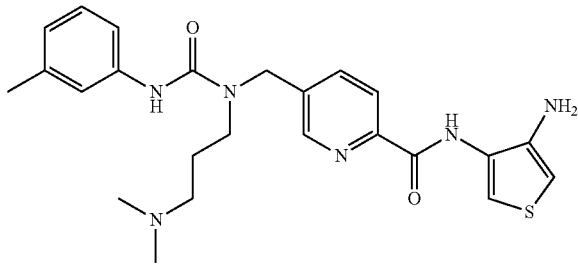

N-(4-Aminothiophen-3-yl)-5-[1-
(3-dimethylaminopropyl)-3-(3-methyl-
phenyl)ureidomethyl]pyridine-
2-carboxylic acid amide
(Compound No. 1-22)

$^1$H-NMR (400 MHz, DMSO-d$_6$)
δ 1.71 (m, 2 H), 2.20 (s, 6 H),
2.26 (s, 3 H), 2.28 (t,
J = 6.3 Hz, 2 H), 3.36 (m, 2 H),
4.62 (s, 2 H), 4.81 (s, 2 H),
6.27 (d, J = 3.7 Hz, 1 H),
6.75 (d, J = 7.8 Hz, 1 H),
7.12 (t, J = 7.8 Hz, 1 H),
7.20 (d, J = 7.8 Hz, 1 H),
7.28 (s, 1 H), 7.65 (d,
J = 3.7 Hz, 1 H), 7.97 (dd,
J = 8.1, 1.8 Hz, 1 H), 8.14 (d,
J = 8.1 Hz, 1 H), 8.67 (d,
J = 1.8 Hz, 1 H), 9.62 (br s,
1 H), 10.19 (br s, 1 H).

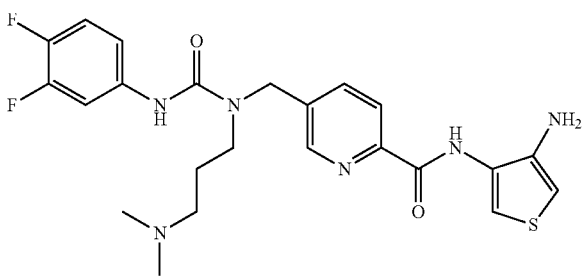

N-(4-Aminothiophen-3-yl)-5-[3-
(3,4-difluorophenyl)-1-(3-dimethyl-
aminopropyl)ureidomethyl]pyridine-
2-carboxylic acid amide
(Compound No. 1-23)

$^1$H-NMR (400 MHz, DMSO-d$_6$)
δ 1.71 (m, 2 H), 2.19 (s, 6 H),
2.27 (t, J = 6.2 Hz, 2 H),
3.36 (m, 2 H), 4.63 (s, 2 H),
4.81 (s, 2 H), 6.27 (d, J = 3.7 Hz,
1 H), 7.09 (m, 1 H),
7.31 (m, 1 H), 7.65 (d,
J = 3.7 Hz, 1 H), 7.68 (m, 1 H),
7.97 (dd, J = 8.1, 1.8 Hz,
1 H), 8.13 (d, J = 8.1 Hz,
1 H), 8.67 (d, J = 1.8 Hz,
1 H), 9.95 (br s, 1 H), 10.19
(s, 1 H).

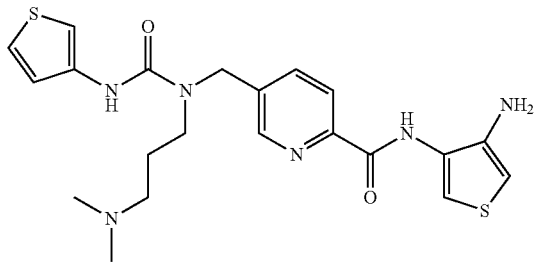

N-(4-Aminothiophen-3-yl)-5-[1-
(3-dimethylaminopropyl)-3-(thiophen-
3-yl)ureidomethyl]pyridine-2-carboxylic
acid amide (Compound No. 1-24)

$^1$H-NMR (400 MHz, DMSO-d$_6$)
δ 1.69 (m, 2 H), 2.19 (s, 6 H),
2.27 (t, J = 6.0 Hz, 2 H),
3.33 (m, 2 H), 4.63 (s, 2 H),
4.81 (s, 2 H), 6.27 (d,
J = 3.5 Hz, 1 H), 7.04 (dd,
J = 5.1, 1.2 Hz, 1 H), 7.28 (dd,
J = 3.3, 1.2 Hz, 1 H), 7.39
(dd, J = 5.1, 3.3 Hz, 1 H),
7.65 (d, J = 3.5 Hz, 1 H),
7.96 (dd, J = 8.1, 1.7 Hz,
1 H), 8.14 (d, J = 8.1 Hz,
1 H), 8.66 (d, J = 1.7 Hz,
1 H), 10.07 (br s, 1 H), 10.19
(s, 1 H).

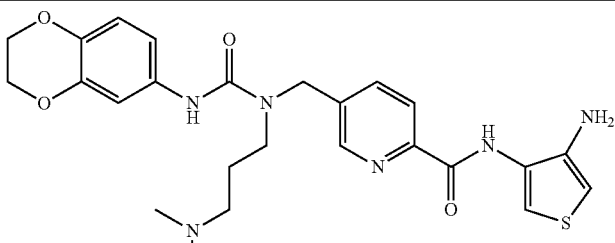

N-(4-Aminothiophen-3-yl)-5-[3-(2,3-dihydrobenzo[1,4]dioxin-6-yl)-1-(3-dimethylaminopropyl)ureidomethyl]pyridine-2-carboxylic acid amide (Compound No. 1-25)

$^1$H-NMR (500 MHz, DMSO-$d_6$) δ 1.68 (m, 2 H), 2.17 (s, 6 H), 2.26 (t, J = 6.3 Hz, 2 H), 3.33 (m, 2 H), 4.16-4.21 (m, 4 H), 4.60 (s, 2 H), 4.81 (br s, 2 H), 6.27 (d, J = 3.5 Hz, 1 H), 6.73 (d, J = 8.7 Hz, 1 H), 6.77 (dd, J = 8.7, 2.4 Hz, 1 H), 7.07 (d, J = 2.4 Hz, 1 H), 7.64 (d, J = 3.5 Hz, 1 H), 7.95 (dd, J = 8.2, 1.9 Hz, 1 H), 8.12 (d, J = 8.2 Hz, 1 H), 8.65 (d, J = 1.9 Hz, 1 H), 9.44 (br s, 1 H), 10.18 (br s, 1 H).

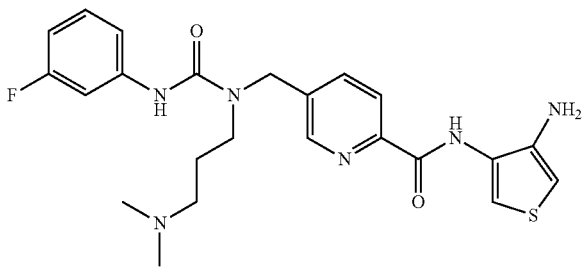

N-(4-Aminothiophen-3-yl)-5-[1-(3-dimethylaminopropyl)-3-(3-fluorophenyl)ureidomethyl]pyridine-2-carboxylic acid amide (Compound No. 1-26)

$^1$H-NMR (400 MHz, DMSO-$d_6$) δ 1.72 (m, 2 H), 2.20 (s, 6 H), 2.28 (t, J = 6.2 Hz, 2 H), 3.36 (t, J = 6.2 Hz, 2 H), 4.63 (s, 2 H), 4.81 (s, 2 H), 6.27 (d, J = 3.6 Hz, 1 H), 6.74 (m, 1 H), 7.08 (d, J = 8.3 Hz, 1 H), 7.28 (m, 1 H), 7.49 (dt, J = 12.5, 2.2 Hz, 1 H), 7.65 (d, J = 3.6 Hz, 1 H), 7.98 (dd, J = 8.1, 2.0 Hz, 1 H), 8.13 (d, J = 8.1 Hz, 1 H), 8.68 (d, J = 2.0 Hz, 1 H), 10.03 (br s, 1 H), 10.19 (br s, 1 H).

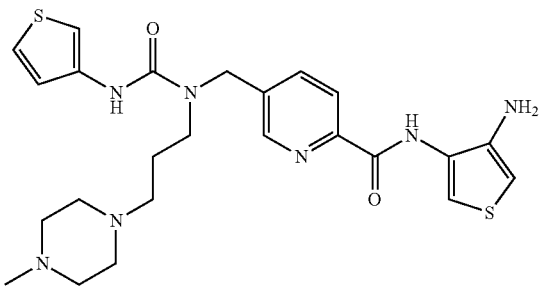

N-(4-Aminothiophen-3-yl)-5-[1-[3-(4-methylpiperazin-1-yl)propyl]-3-(thiophen-3-yl)ureidomethyl]pyridine-2-carboxylic acid amide (Compound No. 1-27)

$^1$H-NMR (400 MHz, CDCl$_3$) δ 1.76 (m, 2 H), 2.29 (s, 3 H), 2.46 (m, 2 H), 2.49 (br s, 8 H), 3.34 (m, 2 H), 3.53 (br s, 2 H), 4.63 (s, 2 H), 6.39 (d, J = 3.4 Hz, 1 H), 7.13 (d, J = 4.3 Hz, 1 H), 7.23 (t, J = 4.3 Hz, 1 H), 7.30 (m, 1 H), 7.62 (d, J = 3.4 Hz, 1 H), 7.90 (d, J = 8.1 Hz, 1 H), 8.21 (d, J = 8.1 Hz, 1 H), 8.56 (s, 1 H), 9.32 (s, 1 H), 10.04 (s, 1 H)

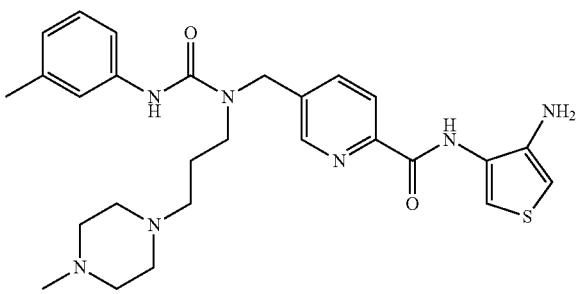

N-(4-Aminothiophen-3-yl)-5-[3-(3-methylphenyl)-1-[3-(4-methylpiperazin-1-yl)propyl]ureidomethyl]pyridine-2-carboxylic acid amide (Compound No. 1-28)

$^1$H-NMR (400 MHz, CDCl$_3$) δ 1.77 (m, 2 H), 2.27 (s, 3 H), 2.35 (s, 3 H), 2.46 (br s, 8 H), 2.47 (t, J = 5.9 Hz, 2 H), 3.37 (t, J = 5.4 Hz, 2 H), 3.53 (br s, 2 H), 4.63 (s, 2 H), 6.38 (d, J = 3.6 Hz, 1 H), 6.90 (d, J = 7.7 Hz, 1 H), 7.20 (t, J = 7.7 Hz, 1 H), 7.26-7.31 (m, 2 H), 7.61 (d, J = 3.6 Hz, 1 H), 7.90 (dd, J = 8.1, 1.7 Hz, 1 H), 8.21 (d, J = 8.1 Hz, 1 H), 8.57 (d, J = 1.7 Hz, 1 H), 8.98 (s, 1 H), 10.04 (s, 1 H)

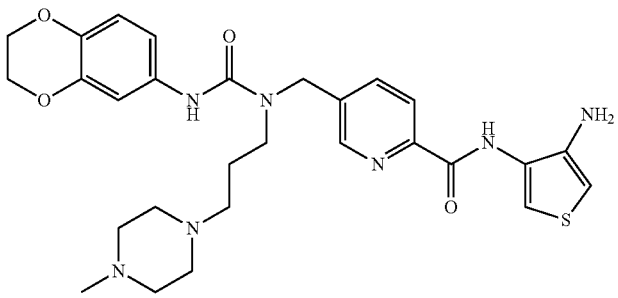

N-(4-Aminothiophen-3-yl)-5-[3-(2,3-dihydrobenzo[1,4]dioxin-6-yl)-1-[3-(4-methylpiperazin-1-yl)propyl]ureidomethyl]pyridine-2-carboxylic acid amide (Compound No. 1-29)

$^1$H-NMR (500 MHz, CDCl$_3$) δ 1.75 (m, 2 H), 2.25 (s, 3 H), 2.41 (br s, 8 H), 2.46 (t, J = 6.0 Hz, 2 H), 3.34 (t, J = 5.3 Hz, 2 H), 3.55 (br s, 2 H), 4.23-4.25 (m, 4 H), 4.60 (s, 2 H), 6.38 (d, J = 3.4 Hz, 1 H), 6.79 (d, J = 8.7 Hz, 1 H), 6.84 (dd, J = 8.7, 2.3 Hz, 1 H), 7.02 (d, J = 2.3 Hz, 1 H), 7.61 (d, J = 3.4 Hz, 1 H), 7.90 (dd, J = 8.1, 2.0 Hz, 1 H), 8.20 (d, J = 8.1 Hz, 1 H), 8.56 (d, J = 2.0 Hz, 1 H), 9.03 (s, 1 H), 10.04 (s, 1 H)

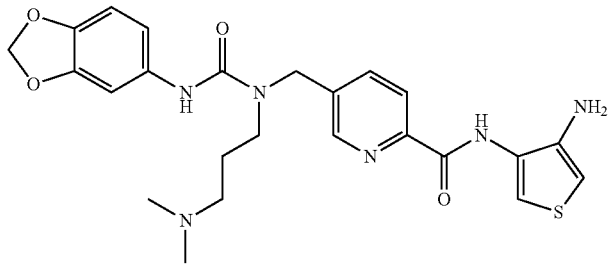

N-(4-Aminothiophen-3-yl)-5-[3-(benzo[1,3]dioxol-5-yl)-1-(3-dimethylaminopropyl)ureidomethyl]pyridine-2-carboxylic acid amide (Compound No. 1-30)

$^1$H-NMR (400 MHz, DMSO-d$_6$) δ 1.69 (m, 2 H), 2.18 (s, 6 H), 2.26 (t, J = 6.3 Hz, 2 H), 3.33 (m, 2 H), 4.61 (s, 2 H), 4.81 (br s, 2 H), 5.95 (s, 2 H), 6.27 (d, J = 3.5 Hz, 1 H), 6.73 (dd, J = 8.4, 2.0 Hz, 1 H), 6.80 (d, J = 8.4 Hz, 1 H), 7.18 (d, J = 2.0 Hz, 1 H), 7.65 (d, J = 3.5 Hz, 1 H), 7.96 (dd, J = 8.1, 2.1 Hz, 1 H), 8.13 (dd, J = 8.1, 0.6 Hz, 1 H), 8.66 (dd, J = 2.1, 0.6 Hz, 1 H), 9.52 (br s, 1 H), 10.19 (br s, 1 H).

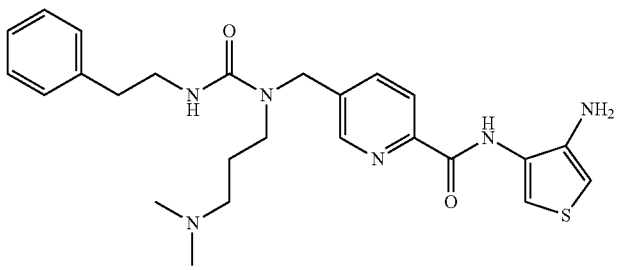

N-(4-Aminothiophen-3-yl)-5-[1-(3-dimethylaminopropyl)-3-phenethyl-ureidomethyl]pyridine-2-carboxylic acid amide (Compound No. 1-31)

$^1$H-NMR (400 MHz, DMSO-d$_6$) δ 1.55 (m, 2 H), 2.05 (s, 6 H), 2.14 (t, J = 6.6 Hz, 2 H), 2.74 (t, J = 7.3 Hz, 2 H), 3.14 (t, J = 6.6 Hz, 2 H), 3.30 (m, 2 H), 4.54 (s, 2 H), 4.81 (br s, 2 H), 6.28 (d, J = 3.7 Hz, 1 H), 7.13 (t, J = 5.5 Hz, 1 H), 7.18-7.22 (m, 3 H), 7.29 (t, J = 7.2 Hz, 2 H), 7.65 (d, J = 3.7 Hz, 1 H), 7.83 (dd, J = 8.1, 2.2 Hz, 1 H), 8.10 (dd, J = 8.1, 0.7 Hz, 1 H), 8.57 (dd, J = 2.2, 0.7 Hz, 1 H), 10.19 (br s, 1 H).

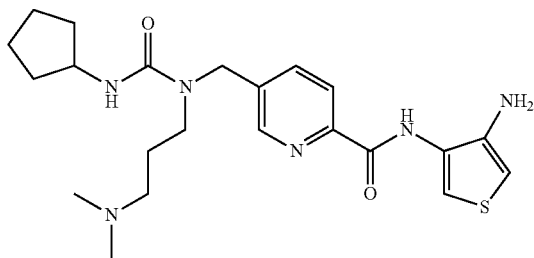

N-(4-Aminothiophen-3-yl)-5-[3-cyclopentyl-1-(3-dimethylaminopropyl)ureidomethyl]pyridine-2-carboxylic acid amide (Compound No. 1-32)

$^1$H-NMR (500 MHz, DMSO-d$_6$) δ 1.35 (m, 2 H), 1.49 (m, 2 H), 1.57 (m, 2 H), 1.62 (m, 2 H), 1.84 (m, 2 H), 2.11 (s, 6 H), 2.17 (t, J = 6.4 Hz, 2 H), 3.17 (t, J = 6.6 Hz, 2 H), 3.91 (m, 1 H), 4.52 (s, 2 H), 4.80 (br s, 2 H), 6.27 (d, J = 3.5 Hz, 1 H), 6.89 (d, J = 6.4 Hz, 1 H), 7.64 (d, J = 3.5 Hz, 1 H), 7.88 (dd, J = 8.2, 1.9 Hz, 1 H), 8.11 (d, J = 8.2 Hz, 1 H), 8.58 (d, J = 1.9 Hz, 1 H), 10.18 (br s, 1 H).

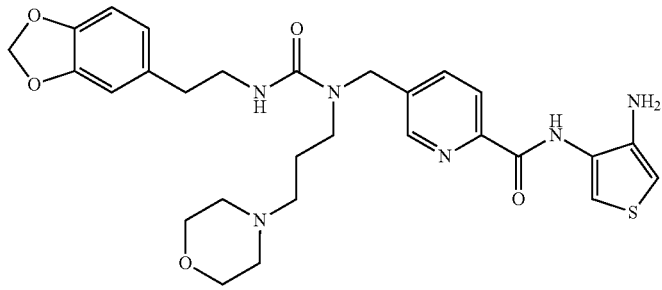

N-(4-Aminothiophen-3-yl)-5-[3-[2-(benzo[1,3]dioxol-5-yl)ethyl]-1-[3-(morpholin-4-yl)propyl]ureido-methyl]pyridine-2-carboxylic acid amide (Compound No. 1-33)

$^1$H-NMR (500 MHz, CDCl$_3$) δ 1.62 (m, 2 H), 2.29-2.36 (m, 6 H), 2.78 (t, J = 6.7 Hz, 2 H), 3.16 (t, J = 5.8 Hz, 2 H), 3.44 (q, J = 6.7 Hz, 2 H), 3.56 (br s, 2 H), 3.60 (br s, 4 H), 4.57 (s, 2 H), 5.92 (s, 2 H), 6.39 (d, J = 3.5 Hz, 1 H), 6.64 (dd, J = 7.9, 1.5 Hz, 1 H), 6.70 (d, J = 1.5 Hz, 1 H), 6.75 (d, J = 7.9 Hz, 1 H), 7.07 (br s, 1 H), 7.62 (d, J = 3.5 Hz, 1 H), 7.79 (dd, J = 7.9, 2.1 Hz, 1 H), 8.22 (dd, J = 7.9, 0.6 Hz, 1 H), 8.46 (dd, J = 2.1, 0.6 Hz, 1 H), 10.05 (s, 1 H)

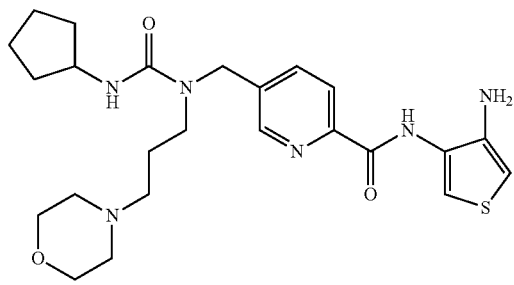

N-(4-Aminothiophen-3-yl)-5-[3-cyclopentyl-1-[3-(morpholin-4-yl)propyl]ureidomethyl]pyridine-2-carboxylic acid amide (Compound No. 1-34)

$^1$H-NMR (400 MHz, CDCl$_3$) δ 1.35 (m, 2 H), 1.56-1.72 (m, 6 H), 2.06 (m, 2 H), 2.37 (t, J = 6.1 Hz, 2 H), 2.44 (t, J = 4.5 Hz, 4 H), 3.21 (t, J = 6.2 Hz, 2 H), 3.54 (br s, 2 H), 3.74 (t, J = 4.5 Hz, 4 H), 4.11 (m, 1 H), 4.57 (s, 2 H), 5.91 (d, J = 6.8 Hz, 1 H), 6.40 (d, J = 3.3 Hz, 1 H), 7.62 (d, J = 3.3 Hz, 1 H), 7.84 (dd, J = 8.0, 2.2 Hz, 1 H), 8.22 (dd, J = 8.0, 0.7 Hz, 1 H), 8.53 (dd, J = 2.2, 0.7 Hz, 1 H), 10.04 (s, 1 H)

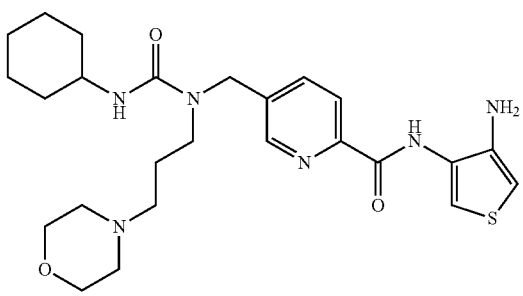

N-(4-Aminothiophen-3-yl)-5-[3-cyclohexyl-1-[3-(morpholin-4-yl)propyl]ureidomethyl]pyridine-2-carboxylic acid amide (Compound No. 1-35)

$^1$H-NMR (500 MHz, CDCl$_3$) δ 1.11 (m, 2 H), 1.37 (m, 2 H), 1.62-1.71 (m, 4 H), 1.75 (d, J = 13.7 Hz, 2 H), 1.99 (d, J = 12.2 Hz, 2 H), 2.36 (t, J = 6.3 Hz, 2 H), 2.44 (br s, 4 H), 3.21 (t, J = 6.1 Hz, 2 H), 3.54 (br s, 2 H), 3.65 (m, 1 H), 3.76 (t, J = 4.7 Hz, 4 H), 4.56 (s, 2 H), 5.86 (d, J = 7.6 Hz, 1 H), 6.40 (d, J = 3.4 Hz, 1 H), 7.61 (d, J = 3.4 Hz, 1 H), 7.84 (dd, J = 8.1, 2.0 Hz, 1 H), 8.21 (d, J = 8.1 Hz, 1 H), 8.52 (d, J = 2.0 Hz, 1 H), 10.03 (s, 1 H)

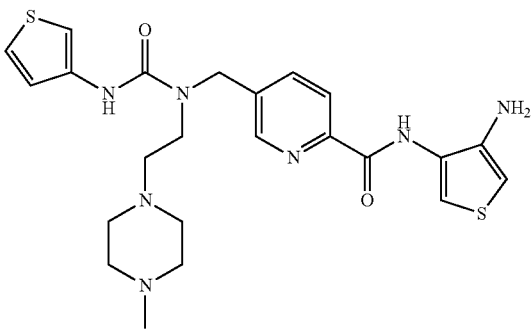

N-(4-Aminothiophen-3-yl)-5-[1-
[2-(4-methylpiperazin-1-yl)ethyl]-
3-(thiophen-3-yl)ureidomethyl]
pyridine-2-carboxylic acid amide
(Compound No. 1-36)

$^1$H-NMR (500 MHz, CDCl$_3$)
δ 2.32 (s, 3 H), 2.52 (br s,
4 H), 2.56 (t, J = 4.3 Hz,
2 H), 2.64 (br s, 4 H), 3.34
(t, J = 4.3 Hz, 2 H), 3.55 (br s,
2 H), 4.64 (s, 2 H), 6.38
(d, J = 3.5 Hz, 1 H), 7.15
(dd, J = 5.1, 1.4 Hz, 1 H),
7.24 (dd, J = 5.1, 3.2 Hz,
1 H), 7.31 (dd, J = 3.2, 1.4 Hz,
1 H), 7.62 (d, J = 3.5 Hz,
1 H), 7.87 (dd, J = 7.9, 1.8 Hz,
1 H), 8.21 (d, J = 7.9 Hz,
1 H), 8.54 (d, J = 1.8 Hz,
1 H), 10.03 (s, 1 H), 10.34
(s, 1 H)

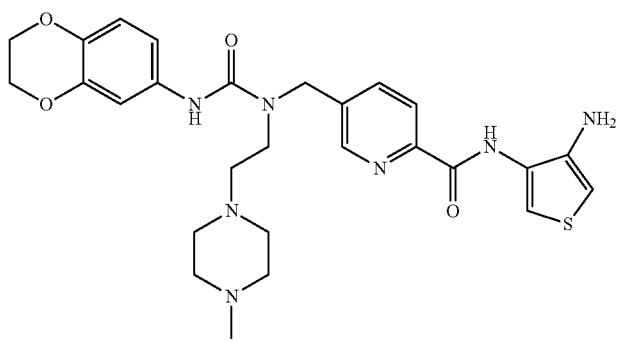

N-(4-Aminothiophen-3-yl)-5-[3-
(2,3-dihydrobenzo[1,4]dioxin-6-yl)-
1-[2-(4-methylpiperazin-1-yl)
ethyl]ureidomethyl]pyridine-2-
carboxylic acid amide
(Compound No. 1-37)

$^1$H-NMR (400 MHz, CDCl$_3$)
δ 2.30 (s, 3 H), 2.51 (br s,
4 H), 2.55 (t, J = 4.3 Hz,
2 H), 2.63 (br s, 4 H), 3.34
(t, J = 4.3 Hz, 2 H), 3.54 (br s,
2 H), 4.21-4.26 (m, 4 H),
4.63 (s, 2 H), 6.39 (d,
J = 3.4 Hz, 1 H), 6.80 (d,
J = 8.5 Hz, 1 H), 6.87 (dd,
J = 8.5, 2.4 Hz, 1 H), 7.03 (d,
J = 2.4 Hz, 1 H), 7.62 (d,
J = 3.4 Hz, 1 H), 7.89 (dd,
J = 7.9, 2.1 Hz, 1 H), 8.22 (d,
J = 7.9 Hz, 1 H), 8.56 (d,
J = 2.1 Hz, 1 H), 9.84 (s, 1 H),
10.04 (s, 1 H)

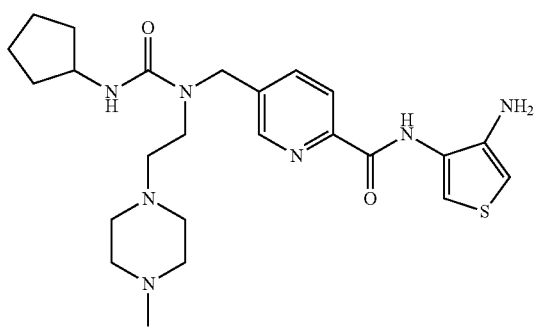

N-(4-Aminothiophen-3-yl)-5-[3-
cyclopentyl-1-[2-(4-methylpiperazin-
1-yl)ethyl]ureidomethyl]pyridine-
2-carboxylic acid amide
(Compound No. 1-38)

$^1$H-NMR (400 MHz, CDCl$_3$)
δ 1.42 (m, 2 H), 1.60 (m, 2 H),
1.70 (m, 2 H), 2.03 (m, 2 H),
2.29 (s, 3 H), 2.43 (br s,
4 H), 2.44 (t, J = 4.5 Hz,
2 H), 2.53 (br s, 4 H), 3.20
(t, J = 4.5 Hz, 2 H), 3.54 (br s,
2 H), 4.10 (m, 1 H), 4.57
(s, 2 H), 6.38 (d, J = 3.7 Hz,
1 H), 7.03 (d, J = 7.2 Hz,
1 H), 7.61 (d, J = 3.7 Hz,
1 H), 7.83 (dd, J = 8.1, 2.2 Hz,
1 H), 8.20 (d, J = 8.1 Hz,
1 H), 8.50 (d, J = 2.2 Hz,
1 H), 10.03 (s, 1 H)

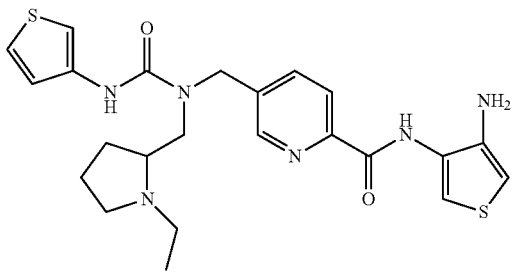

N-(4-Aminothiophen-3-yl)-5-[1-(1-ethylpyrrolidin-2-ylmethyl)-3-(thiophen-3-yl)ureidomethyl]pyridine-2-carboxylic acid amide (Compound No. 1-39)

$^1$H-NMR (400 MHz, CDCl$_3$) δ 1.12 (t, J = 7.2 Hz, 3 H), 1.55 (m, 1 H), 1.75-1.94 (m, 3 H), 2.43-2.55 (m, 2 H), 2.77-2.89 (m, 2 H), 3.18-3.32 (m, 3 H), 3.54 (br s, 2 H), 4.51 (d, J = 15.9 Hz, 1 H), 4.82 (d, J = 15.9 Hz, 1 H), 6.40 (d, J = 3.5 Hz, 1 H), 6.93 (dd, J = 5.1, 1.5 Hz, 1 H), 7.21 (dd, J = 5.1, 3.2 Hz, 1 H), 7.27 (m, 1 H), 7.62 (d, J = 3.5 Hz, 1 H), 7.90 (dd, J = 8.1, 2.2 Hz, 1 H), 8.23 (dd, J = 8.1, 0.6 Hz, 1 H), 8.57 (dd, J = 2.2, 0.6 Hz, 1 H), 10.05 (s, 1 H), 11.77 (s, 1 H)

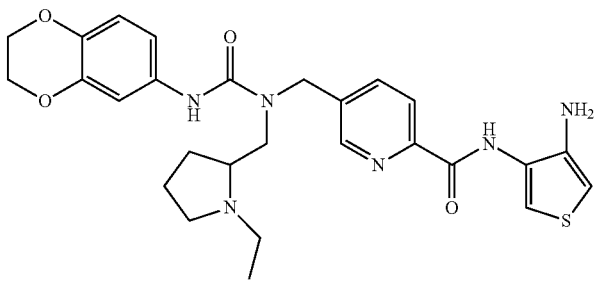

N-(4-Aminothiophen-3-yl)-5-[3-(2,3-dihydrobenzo[1,4]dioxin-6-yl)-1-(1-ethylpyrrolidin-2-ylmethyl)ureidomethyl]pyridine-2-carboxylic acid amide (Compound No. 1-40)

$^1$H-NMR (400 MHz, CDCl$_3$) δ 1.09 (t, J = 7.2 Hz, 3 H), 1.53 (m, 1 H), 1.74-1.96 (m, 3 H), 2.41-2.55 (m, 2 H), 2.76-2.89 (m, 2 H), 3.19-3.35 (m, 3 H), 3.58 (br s, 2 H), 4.20-4.26 (m, 4 H), 4.52 (d, J = 15.6 Hz, 1 H), 4.76 (d, J = 15.6 Hz, 1 H), 6.39 (d, J = 3.4 Hz, 1 H), 6.77 (d, J = 8.8 Hz, 1 H), 6.83 (dd, J = 8.8, 2.3 Hz, 1 H), 6.95 (d, J = 2.3 Hz, 1 H), 7.62 (d, J = 3.4 Hz, 1 H), 7.91 (dd, J = 8.1, 2.2 Hz, 1 H), 8.23 (dd, J = 8.1, 0.6 Hz, 1 H), 8.57 (dd, J = 2.2, 0.6 Hz, 1 H), 10.05 (s, 1 H), 11.17 (s, 1 H)

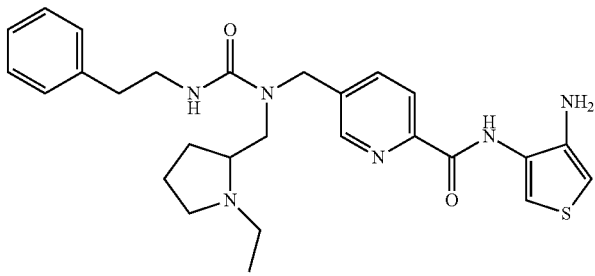

N-(4-Aminothiophen-3-yl)-5-[1-(1-ethylpyrrolidin-2-ylmethyl)-3-phenethylureidomethyl]pyridine-2-carboxylic acid amide (Compound No. 1-41)

$^1$H-NMR (400 MHz, CDCl$_3$) δ 0.93 (t, J = 7.2 Hz, 3 H), 1.39-1.82 (m, 4 H), 2.06-2.26 (m, 2 H), 2.63 (m, 2 H), 2.75-2.91 (m, 3 H), 3.08 (m, 2 H), 3.38 (m, 1 H), 3.52 (br s, 2 H), 3.60 (m, 1 H), 4.43 (d, J = 15.7 Hz, 1 H), 4.72 (d, J = 15.7 Hz, 1 H), 6.40 (d, J = 3.4 Hz, 1 H), 7.19-7.32 (m, 5 H), 7.62 (d, J = 3.4 Hz, 1 H), 7.80 (dd, J = 8.0, 2.0 Hz, 1 H), 8.21 (d, J = 8.0 Hz, 1 H), 8.50 (d, J = 2.0 Hz, 1 H), 8.51 (br s, 1 H), 10.05 (s, 1 H)

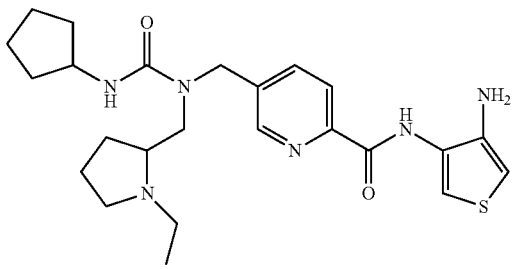

N-(4-Aminothiophen-3-yl)-5-[3-cyclopentyl-1-(1-ethylpyrrolidin-2-ylmethyl)ureidomethyl]pyridine-2-carboxylic acid amide (Compound No. 1-42)

$^1$H-NMR (400 MHz, CDCl$_3$) δ 1.07 (t, J = 7.2 Hz, 3 H), 1.39 (m, 2 H), 1.45-1.87 (m, 8 H), 1.98 (m, 2 H), 2.27-2.44 (m, 2 H), 2.69-2.80 (m, 2 H), 3.06 (m, 1 H), 3.14 (d, J = 5.1 Hz, 2 H), 3.54 (br s, 2 H), 4.05 (m, 1 H), 4.41 (d, J = 15.6 Hz, 1 H), 4.75 (d, J = 15.6 Hz, 1 H), 6.39 (d, J = 3.4 Hz, 1 H), 7.61 (d, J = 3.4 Hz, 1 H), 7.85 (dd, J = 8.0, 2.1 Hz, 1 H), 8.21 (dd, J = 8.0, 0.7 Hz, 1 H), 8.37 (d, J = 5.9 Hz, 1 H), 8.52 (dd, J = 2.1, 0.7 Hz, 1 H), 10.04 (s, 1 H)

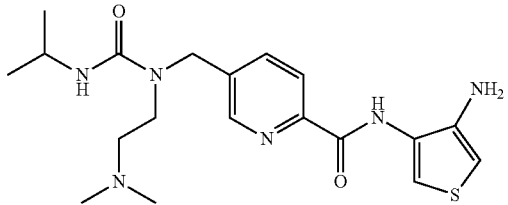

N-(4-Aminothiophen-3-yl)-5-[1-(2-dimethylaminoethyl)-3-isopropyl-ureidomethyl]pyridine-2-carboxylic acid amide (Compound No. 1-43)

$^1$H-NMR (500 MHz, DMSO-d$_6$)
δ 1.06 (d, J = 6.5 Hz, 6 H), 2.15 (s, 6 H), 2.33 (t, J = 5.7 Hz, 2 H), 3.25 (t, J = 5.7 Hz, 2 H), 3.74 (m, 1 H), 4.56 (s, 2 H), 4.80 (br s, 2 H), 6.27 (d, J = 3.7 Hz, 1 H), 7.07 (d, J = 6.7 Hz, 1 H), 7.64 (d, J = 3.7 Hz, 1 H), 7.87 (dd, J = 8.2, 1.9 Hz, 1 H), 8.11 (d, J = 8.2 Hz, 1 H), 8.58 (d, J = 1.9 Hz, 1 H), 10.18 (br s, 1 H).

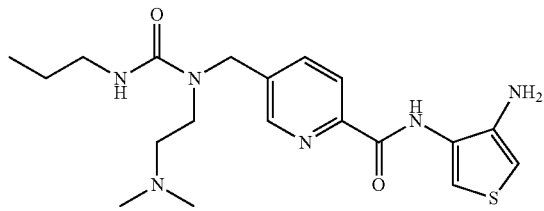

N-(4-Aminothiophen-3-yl)-5-[1-(2-dimethylaminoethyl)-3-propyl-ureidomethyl]pyridine-2-carboxylic acid amide (Compound No. 1-44)

$^1$H-NMR (500 MHz, DMSO-d$_6$)
δ 0.83 (t, J = 7.3 Hz, 3 H), 1.41 (m, 2 H), 2.14 (s, 6 H), 2.33 (t, J = 6.1 Hz, 2 H), 3.00 (m, 2 H), 3.27 (t, J = 6.1 Hz, 2 H), 4.58 (s, 2 H), 4.80 (br s, 2 H), 6.27 (d, J = 3.7 Hz, 1 H), 6.96 (t, J = 5.3 Hz, 1 H), 7.65 (d, J = 3.7 Hz, 1 H), 7.87 (dd, J = 8.1, 1.8 Hz, 1 H), 8.11 (d, J = 8.1 Hz, 1 H), 8.57 (d, J = 1.8 Hz, 1 H), 10.18 (br s, 1 H).

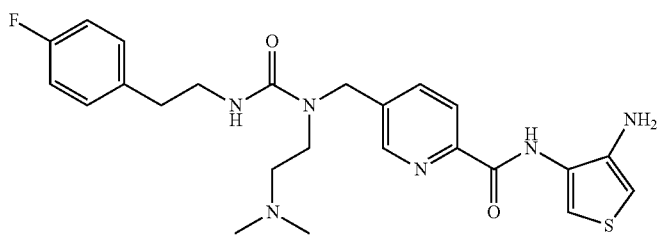

N-(4-Aminothiophen-3-yl)-5-[1-(2-dimethylaminoethyl)-3-(4-fluoro-phenethyl)ureidomethyl]pyridine-2-carboxylic acid amide (Compound No. 1-45)

$^1$H-NMR (500 MHz, DMSO-d$_6$)
δ 2.07 (s, 6 H), 2.27 (m, 2 H), 2.72 (t, J = 7.2 Hz, 2 H), 3.23 (t, J = 6.3 Hz, 2 H), 3.28 (m, 2 H), 4.56 (s, 2 H), 4.80 (br s, 2 H), 6.28 (d, J = 3.5 Hz, 1 H), 6.96 (t, J = 5.2 Hz, 1 H), 7.09 (m, 2 H), 7.21 (m, 2 H), 7.65 (d, J = 3.5 Hz, 1 H), 7.81 (dd, J = 8.0, 1.9 Hz, 1 H), 8.10 (d, J = 8.0 Hz, 1 H), 8.56 (d, J = 1.9 Hz, 1 H), 10.19 (br s, 1 H).

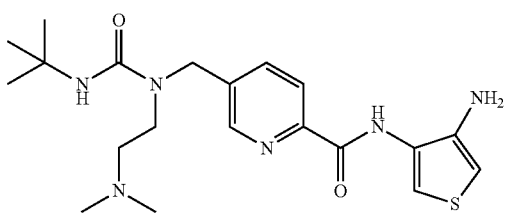

N-(4-Aminothiophen-3-yl)-5-[3-t-butyl-1-(2-dimethylaminoethyl)ureidomethyl]pyridine-2-carboxylic acid amide (Compound No. 1-46)

$^1$H-NMR (400 MHz, DMSO-d$_6$)
δ 1.27 (s, 9 H), 2.17 (s, 6 H), 2.35 (t, J = 5.0 Hz, 2 H), 3.20 (t, J = 5.0 Hz, 2 H), 4.52 (s, 2 H), 4.81 (br s, 2 H), 6.27 (d, J = 3.5 Hz, 1 H), 7.46 (s, 1 H), 7.65 (d, J = 3.5 Hz, 1 H), 7.87 (dd, J = 8.1, 1.8 Hz, 1 H), 8.11 (d, J = 8.1 Hz, 1 H), 8.58 (d, J = 1.8 Hz, 1 H), 10.18 (br s, 1 H).

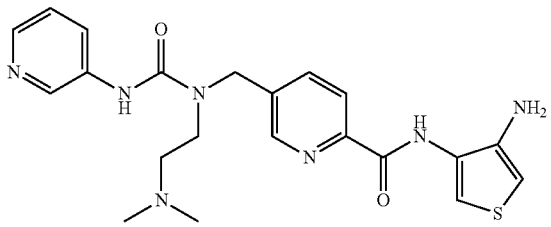

N-(4-Aminothiophen-3-yl)-5-[1-(2-dimethylaminoethyl)-3-(pyridin-3-yl)ureidomethyl]pyridine-2-carboxylic acid amide
(Compound No. 1-47)

$^1$H-NMR (400 MHz, DMSO-$d_6$) δ 2.28 (s, 6 H), 2.51 (m, 2 H), 3.46 (t, J = 5.1 Hz, 2 H), 4.69 (s, 2 H), 4.80 (br s, 2 H), 6.27 (d, J = 3.4 Hz, 1 H), 7.28 (dd, J = 8.3, 4.7 Hz, 1 H), 7.65 (d, J = 3.4 Hz, 1 H), 7.86 (ddd, J = 8.3, 2.6, 1.4 Hz, 1 H), 7.98 (dd, J = 8.2, 1.8 Hz, 1 H), 8.13 (d, J = 8.2 Hz, 1 H), 8.15 (dd, J = 4.7, 1.4 Hz, 1 H), 8.52 (d, J = 2.6 Hz, 1 H), 8.67 (d, J = 1.8 Hz, 1 H), 10.19 (br s, 1 H), 10.54 (br s, 1 H).

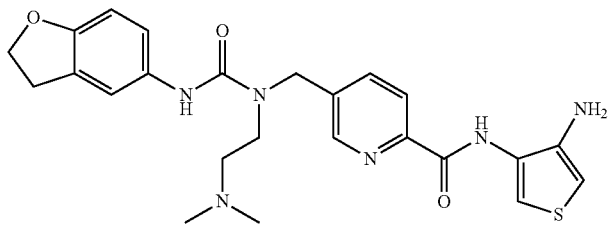

N-(4-Aminothiophen-3-yl)-5-[3-(2,3-dihydro-1-benzofuran-5-yl)-1-(2-dimethylaminoethyl)ureidomethyl]pyridine-2-carboxylic acid amide
(Compound No. 1-48)

$^1$H-NMR (400 MHz, DMSO-$d_6$) δ 2.25 (s, 6 H), 2.46 (t, J = 5.2 Hz, 2 H), 3.13 (t, J = 8.7 Hz, 2 H), 3.40 (t, J = 5.2 Hz, 2 H), 4.47 (t, J = 8.7 Hz, 2 H), 4.65 (s, 2 H), 4.81 (br s, 2 H), 6.27 (d, J = 3.7 Hz, 1 H), 6.63 (d, J = 8.5 Hz, 1 H), 6.97 (dd, J = 8.5, 2.2 Hz, 1 H), 7.30 (d, J = 2.2 Hz, 1 H), 7.65 (d, J = 3.7 Hz, 1 H), 7.96 (dd, J = 8.0, 1.8 Hz, 1 H), 8.13 (d, J = 8.0 Hz, 1 H), 8.65 (d, J = 1.8 Hz, 1 H), 9.79 (br s, 1 H), 10.19 (br s, 1 H).

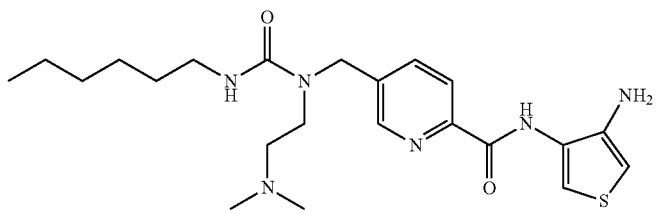

N-(4-Aminothiophen-3-yl)-5-[1-(2-dimethylaminoethyl)-3-hexylureidomethyl]pyridine-2-carboxylic acid amide
(Compound No. 1-49)

$^1$H-NMR (400 MHz, DMSO-$d_6$) δ 0.85 (t, J = 6.8 Hz, 3 H), 1.24 (br s, 6 H), 1.39 (m, 2 H), 2.14 (s, 6 H), 2.33 (m, 2 H), 3.03 (m, 2 H), 3.27 (t, J = 6.4 Hz, 2 H), 4.57 (s, 2 H), 4.81 (br s, 2 H), 6.27 (d, J = 3.5 Hz, 1 H), 6.92 (t, J = 5.5 Hz, 1 H), 7.65 (d, J = 3.5 Hz, 1 H), 7.87 (dd, J = 8.0, 2.2 Hz, 1 H), 8.11 (dd, J = 8.0, 0.7 Hz, 1 H), 8.57 (dd, J = 2.2, 0.7 Hz, 1 H), 10.18 (br s, 1 H).

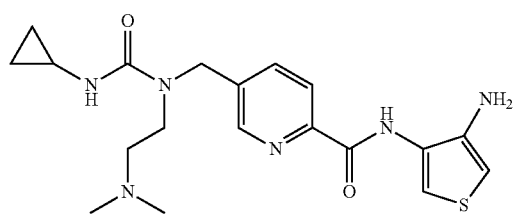

N-(4-Aminothiophen-3-yl)-5-[3-cyclopropyl-1-(2-dimethylaminoethyl)ureidomethyl]pyridine-2-carboxylic acid amide (Compound No. 1-50)

$^1$H-NMR (400 MHz, DMSO-$d_6$) δ 0.32-0.36 (m, 2 H), 0.54-0.58 (m, 2 H), 2.13 (s, 6 H), 2.30-2.33 (m, 3 H), 3.23 (t, J = 5.9 Hz, 2 H), 4.56 (s, 2 H), 4.81 (br s, 2 H), 6.27 (d, J = 3.5 Hz, 1 H), 7.22 (br s, 1 H), 7.65 (d, J = 3.5 Hz, 1 H), 7.86 (dd, J = 8.1, 1.9 Hz, 1 H), 8.11 (d, J = 8.1 Hz, 1 H), 8.57 (d, J = 1.9 Hz, 1 H), 10.18 (br s, 1 H).

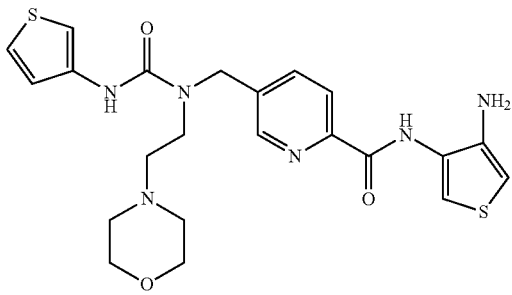

N-(4-Aminothiophen-3-yl)-5-[1-[2-(morpholin-4-yl)ethyl]-3-(thiophen-3-yl)ureidomethyl]pyridine-2-carboxylic acid amide (Compound No. 1-51)

$^1$H-NMR (400 MHz, CDCl$_3$) δ 2.57 (t, J = 4.3 Hz, 2 H), 2.61 (t, J = 4.5 Hz, 4 H), 3.36 (t, J = 4.3 Hz, 2 H), 3.55 (br s, 2 H), 3.78 (t, J = 4.5 Hz, 4 H), 4.67 (s, 2 H), 6.40 (d, J = 3.4 Hz, 1 H), 7.11 (dd, J = 5.1, 1.5 Hz, 1 H), 7.26 (m, 1 H), 7.31 (dd, J = 3.2, 1.5 Hz, 1 H), 7.62 (d, J = 3.4 Hz, 1 H), 7.89 (dd, J = 8.0, 2.0 Hz, 1 H), 8.24 (dd, J = 8.0, 0.6 Hz, 1 H), 8.57 (dd, J = 2.0, 0.6 Hz, 1 H), 10.03 (br s, 1 H), 10.22 (br s, 1 H)

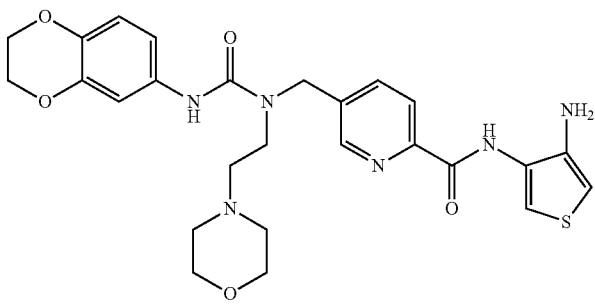

N-(4-Aminothiophen-3-yl)-5-[3-(2,3-dihydrobenzo[1,4]dioxin-6-yl)-1-[2-(morpholin-4-yl)ethyl]ureidomethyl]pyridine-2-carboxylic acid amide (Compound No. 1-52)

$^1$H-NMR (400 MHz, CDCl$_3$) δ 2.56 (t, J = 4.4 Hz, 2 H), 2.60 (t, J = 4.5 Hz, 4 H), 3.36 (t, J = 4.4 Hz, 2 H), 3.57 (br s, 2 H), 3.76 (t, J = 4.5 Hz, 4 H), 4.21-4.28 (m, 4 H), 4.64 (s, 2 H), 6.40 (d, J = 3.4 Hz, 1 H), 6.81 (d, J = 8.7 Hz, 1 H), 6.85 (dd, J = 8.7, 2.4 Hz, 1 H), 6.99 (d, J = 2.4 Hz, 1 H), 7.62 (d, J = 3.4 Hz, 1 H), 7.90 (dd, J = 8.1, 2.0 Hz, 1 H), 8.23 (dd, J = 8.1, 0.7 Hz, 1 H), 8.57 (dd, J = 2.0, 0.7 Hz, 1 H), 9.68 (br s, 1 H), 10.04 (br s, 1 H)

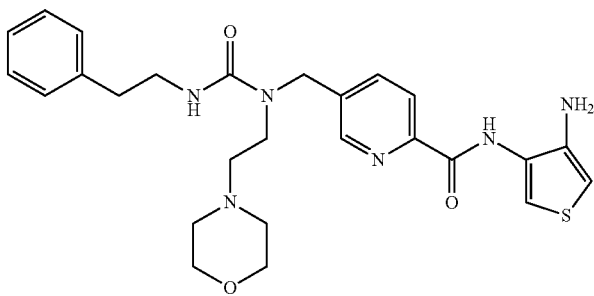

N-(4-Aminothiophen-3-yl)-5-[1-[2-(morpholin-4-yl)ethyl]-3-phenethyl-ureidomethyl]pyridine-2-carboxylic acid amide (Compound No. 1-53)

$^1$H-NMR (400 MHz, CDCl$_3$) δ 2.30 (t, J = 4.5 Hz, 4 H), 2.36 (t, J = 4.8 Hz, 2 H), 2.86 (t, J = 7.0 Hz, 2 H), 3.16 (t, J = 4.8 Hz, 2 H), 3.45 (br s, 4 H), 3.50 (q, J = 7.0 Hz, 2 H), 3.55 (br s, 2 H), 4.59 (s, 2 H), 6.40 (d, J = 3.4 Hz, 1 H), 7.18-7.23 (m, 3 H), 7.25-7.32 (m, 2 H), 7.46 (br s, 1 H), 7.62 (d, J = 3.4 Hz, 1 H), 7.81 (dd, J = 8.1, 2.1 Hz, 1 H), 8.22 (dd, J = 8.1, 0.7 Hz, 1 H), 8.51 (dd, J = 2.1, 0.7 Hz, 1 H), 10.04 (br s, 1 H)

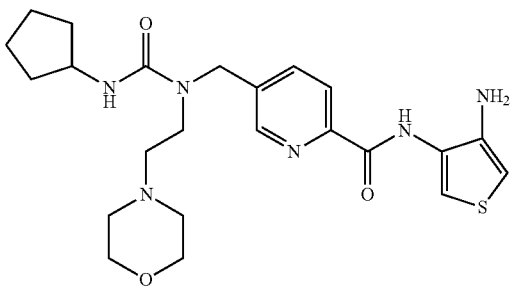

N-(4-Aminothiophen-3-yl)-5-[3-cyclopentyl-1-[2-(morpholin-4-yl)ethyl]ureidomethyl]pyridine-2-carboxylic acid amide
(Compound No. 1-54)

¹H-NMR (400 MHz, CDCl₃) δ 1.40 (m, 2 H), 1.57-1.73 (m, 4 H), 2.05 (m, 2 H), 2.45 (t, J = 4.8 Hz, 2 H), 2.50 (t, J = 4.6 Hz, 4 H), 3.23 (t, J = 4.8 Hz, 2 H), 3.54 (br s, 2 H), 3.71 (t, J = 4.6 Hz, 4 H), 4.11 (m, 1 H), 4.59 (s, 2 H), 6.40 (d, J = 3.4 Hz, 1 H), 6.84 (d, J = 6.8 Hz, 1 H), 7.61 (d, J = 3.4 Hz, 1 H), 7.84 (dd, J = 8.0, 2.1 Hz, 1 H), 8.21 (dd, J = 8.0, 0.6 Hz, 1 H), 8.52 (dd, J = 2.1, 0.6 Hz, 1 H), 10.03 (br s, 1 H)

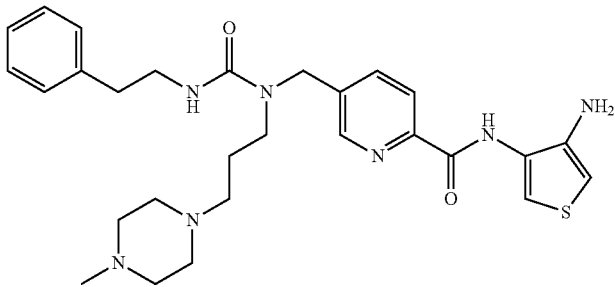

N-(4-Aminothiophen-3-yl)-5-[1-[3-(4-methylpiperazin-1-yl)propyl]-3-phenethylureidomethyl]pyridine-2-carboxylic acid amide
(Compound No. 1-55)

¹H-NMR (400 MHz, CDCl₃) δ 1.60 (m, 2 H), 2.26 (s, 3 H), 2.31 (t, J = 6.0 Hz, 2 H), 2.32 (br s, 8 H), 2.87 (t, J = 6.7 Hz, 2 H), 3.13 (t, J = 5.6 Hz, 2 H), 3.48 (q, J = 6.7 Hz, 2 H), 3.53 (br s, 2 H), 4.56 (s, 2 H), 6.39 (d, J = 3.4 Hz, 1 H), 7.20-7.25 (m, 3 H), 7.27-7.35 (m, 3 H), 7.62 (d, J = 3.4 Hz, 1 H), 7.77 (dd, J = 8.1, 2.2 Hz, 1 H), 8.21 (d, J = 8.1 Hz, 1 H), 8.50 (d, J = 2.2 Hz, 1 H), 10.05 (s, 1 H)

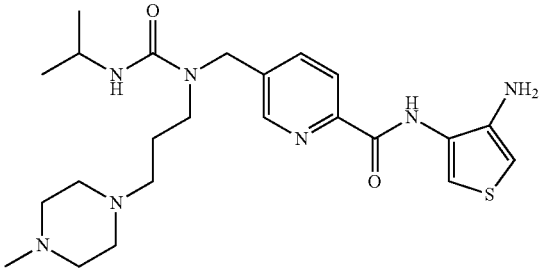

N-(4-Aminothiophen-3-yl)-5-[3-isopropyl-1-[3-(4-methylpiperazin-1-yl)propyl]ureidomethyl]pyridine-2-carboxylic acid amide
(Compound No. 1-56)

¹H-NMR (500 MHz, CDCl₃) δ 1.21 (d, J = 6.4 Hz, 6 H), 1.67 (m, 2 H), 2.31 (s, 3 H), 2.36 (t, J = 6.1 Hz, 2 H), 2.49 (br s, 8 H), 3.19 (t, J = 6.0 Hz, 2 H), 3.57 (br s, 2 H), 4.01 (m, 1 H), 4.55 (s, 2 H), 6.02 (d, J = 8.2 Hz, 1 H), 6.38 (d, J = 3.7 Hz, 1 H), 7.61 (d, J = 3.7 Hz, 1 H), 7.83 (dd, J = 7.9, 1.8 Hz, 1 H), 8.20 (d, J = 7.9 Hz, 1 H), 8.51 (d, J = 1.8 Hz, 1 H), 10.04 (s, 1 H)

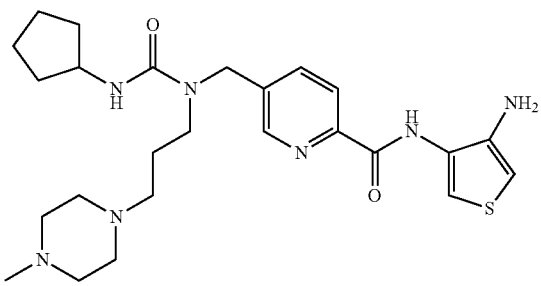

N-(4-Aminothiophen-3-yl)-5-[3-cyclopentyl-1-[3-(4-methylpiperazin-1-yl)propyl]ureidomethyl]pyridine-2-carboxylic acid amide
(Compound No. 1-57)

¹H-NMR (500 MHz, CDCl₃) δ 1.38 (m, 2 H), 1.61 (m, 2 H), 1.64-1.73 (m, 4 H), 2.05 (m, 2 H), 2.30 (s, 3 H), 2.36 (t, J = 6.3 Hz, 2 H), 2.47 (br s, 8 H), 3.19 (t, J = 6.0 Hz, 2 H), 3.54 (br s, 2 H), 4.10 (m, 1 H), 4.56 (s, 2 H), 6.03 (d, J = 7.6 Hz, 1 H), 6.39 (d, J = 3.4 Hz, 1 H), 7.61 (d, J = 3.4 Hz, 1 H), 7.84 (dd, J = 7.9, 1.8 Hz, 1 H), 8.21 (d, J = 7.9 Hz, 1 H), 8.52 (d, J = 1.8 Hz, 1 H), 10.04 (s, 1 H)

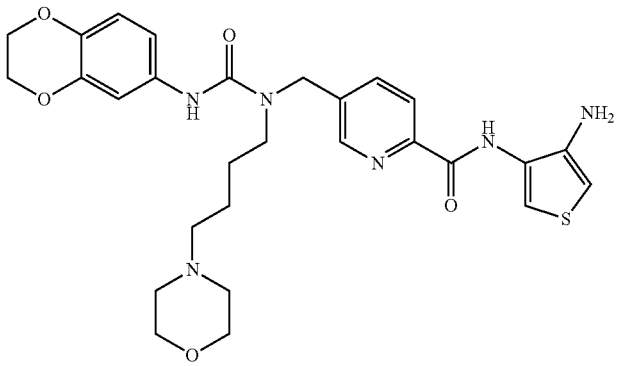

N-(4-Aminothiophen-3-yl)-5-[3-(2,3-dihydrobenzo[1,4]dioxin-6-yl)-1-[4-(morpholin-4-yl)butyl]ureidomethyl]pyridine-2-carboxylic acid amide (Compound No. 1-58)

$^1$H-NMR (400 MHz, CDCl$_3$) δ 1.52 (m, 2 H), 1.66 (m, 2 H), 2.37 (t, J = 7.1 Hz, 2 H), 2.40 (m, 4 H), 3.28 (t, J = 7.9 Hz, 2 H), 3.55 (br s, 2 H), 3.63 (t, J = 4.5 Hz, 4 H), 4.22-4.24 (m, 4 H), 4.65 (s, 2 H), 6.39 (d, J = 3.6 Hz, 1 H), 6.65 (s, 1 H), 6.74 (dd, J = 8.8, 2.4 Hz, 1 H), 6.79 (d, J = 8.8 Hz, 1 H), 6.91 (d, J = 2.4 Hz, 1 H), 7.62 (d, J = 3.6 Hz, 1 H), 7.85 (dd, J = 8.1, 2.0 Hz, 1 H), 8.22 (d, J = 8.1 Hz, 1 H), 8.54 (d, J = 2.0 Hz, 1 H), 10.03 (s, 1 H)

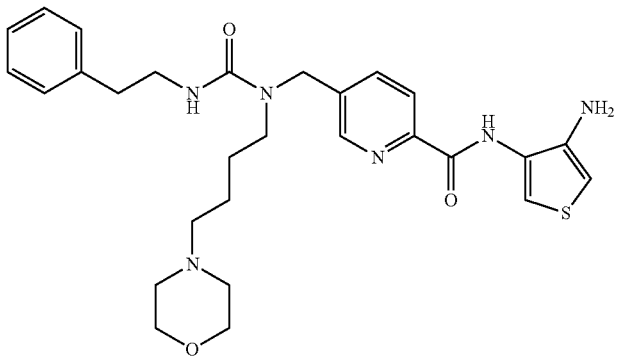

N-(4-Aminothiophen-3-yl)-5-[1-[4-(morpholin-4-yl)butyl]-3-phenethyl-ureidomethyl]pyridine-2-carboxylic acid amide (Compound No. 1-59)

$^1$H-NMR (500 MHz, CDCl$_3$) δ 1.39 (m, 2 H), 1.47 (m, 2 H), 2.24 (t, J = 7.0 Hz, 2 H), 2.33 (m, 4 H), 2.85 (t, J = 6.3 Hz, 2 H), 3.09 (t, J = 7.8 Hz, 2 H), 3.53 (br s, 2 H), 3.54 (q, J = 6.3 Hz, 2 H), 3.65 (t, J = 4.6 Hz, 4 H), 4.57 (s, 2 H), 4.77 (t, J = 6.3 Hz, 1 H), 6.40 (d, J = 3.6 Hz, 1 H), 7.17 (d, J = 7.2 Hz, 2 H), 7.21 (m, 1 H), 7.29 (t, J = 7.2 Hz, 2 H), 7.63 (d, J = 3.6 Hz, 1 H), 7.74 (dd, J = 8.1, 2.0 Hz, 1 H), 8.20 (d, J = 8.1 Hz, 1 H), 8.47 (d, J = 2.0 Hz, 1 H), 10.03 (s, 1 H)

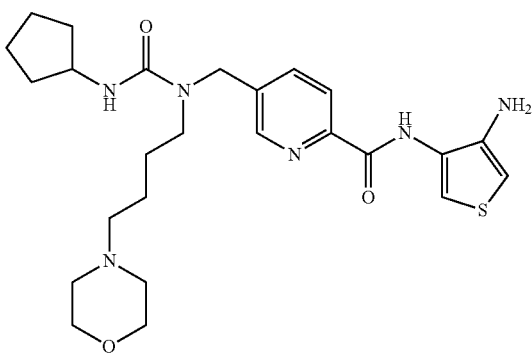

N-(4-Aminothiophen-3-yl)-5-[3-cyclopentyl-1-[4-(morpholin-4-yl)butyl]ureidomethyl]pyridine-2-carboxylic acid amide (Compound No. 1-60)

$^1$H-NMR (400 MHz, CDCl$_3$) δ 1.32 (m, 2 H), 1.46 (m, 2 H), 1.53-1.65 (m, 6 H), 2.00 (m, 2 H), 2.31 (t, J = 7.2 Hz, 2 H), 2.39 (m, 4 H), 3.16 (t, J = 7.6 Hz, 2 H), 3.55 (br s, 2 H), 3.69 (t, J = 4.6 Hz, 4 H), 4.13 (m, 1 H), 4.37 (d, J = 6.8 Hz, 1 H), 4.57 (s, 2 H), 6.38 (d, J = 3.4 Hz, 1 H), 7.61 (d, J = 3.4 Hz, 1 H), 7.78 (dd, J = 7.9, 2.1 Hz, 1 H), 8.20 (d, J = 7.9 Hz, 1 H), 8.49 (d, J = 2.1 Hz, 1 H), 10.02 (s, 1 H)

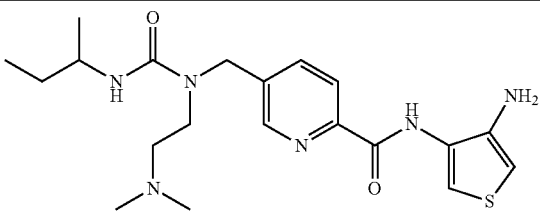

N-(4-Aminothiophen-3-yl)-5-[3-sec-butyl-1-(2-dimethylaminoethyl)ureidomethyl]pyridine-2-carboxylic acid amide (Compound No. 1-61)

$^1$H-NMR (500 MHz, DMSO-d$_6$)
δ 0.83 (t, J = 7.5 Hz, 3 H), 1.03 (d, J = 6.4 Hz, 3 H), 1.40 (m, 2 H), 2.15 (s, 6 H), 2.34 (t, J = 5.7 Hz, 2 H), 3.25 (m, 2 H), 3.58 (m, 1 H), 4.55 (d, J = 16.2 Hz, 1 H), 4.58 (d, J = 16.2 Hz, 1 H), 4.80 (br s, 2 H), 6.27 (d, J = 3.7 Hz, 1 H), 7.00 (d, J = 7.6 Hz, 1 H), 7.64 (d, J = 3.7 Hz, 1 H), 7.87 (dd, J = 8.0, 1.9 Hz, 1 H), 8.11 (d, J = 8.0 Hz, 1 H), 8.58 (d, J = 1.9 Hz, 1 H), 10.18 (br s, 1 H).

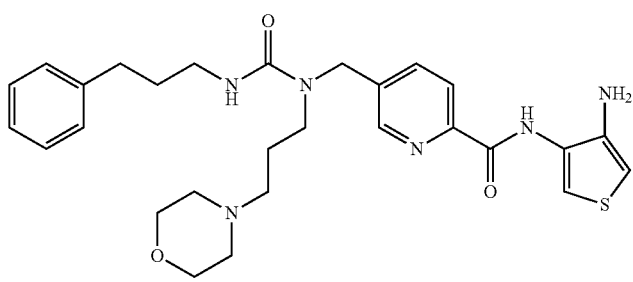

N-(4-Aminothiophen-3-yl)-5-[1-[3-(morpholin-4-yl)propyl]-3-(3-phenylpropyl)ureidomethyl]pyridine-2-carboxylic acid amide (Compound No. 1-62)

$^1$H-NMR (MHz,) δ

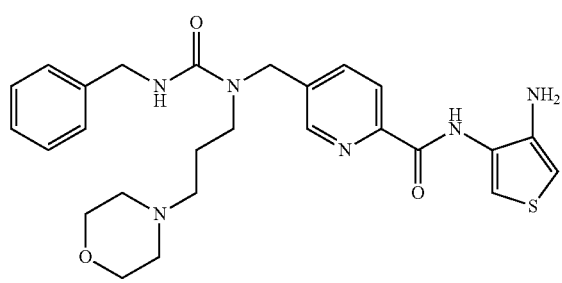

N-(4-Aminothiophen-3-yl)-5-[3-benzyl-1-[3-(morpholin-4-yl)propyl]ureidomethyl]pyridine-2-carboxylic acid amide (Compound No. 1-63)

$^1$H-NMR (400 MHz, CDCl$_3$)
δ 1.67 (m, 2 H), 2.25 (t, J = 4.0 Hz, 4 H), 2.34 (t, J = 6.1 Hz, 2 H), 3.29 (t, J = 5.6 Hz, 2 H), 3.39 (br s, 4 H), 3.54 (s, 2 H), 4.49 (d, J = 5.8 Hz, 2 H), 4.63 (s, 2 H), 6.40 (d, J = 3.4 Hz, 1 H), 7.12-7.28 (m, 2 H), 7.31-7.34 (m, 3 H), 7.57 (t, J = 5.8 Hz, 1 H), 7.62 (d, J = 3.4 Hz, 1 H), 7.87 (dd, J = 8.1, 2.2 Hz, 1 H), 8.23 (dd, J = 8.1, 0.7 Hz, 1 H), 8.56 (dd, J = 2.2, 0.7 Hz, 1 H), 10.04 (s, 1 H).

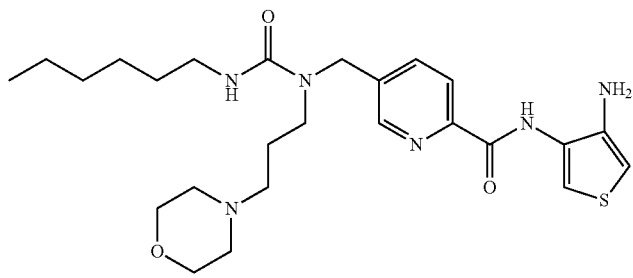

N-(4-Aminothiophen-3-yl)-5-[3-hexyl-1-[3-(morpholin-4-yl)propyl]ureidomethyl]pyridine-2-carboxylic acid amide (Compound No. 1-64)

$^1$H-NMR (400 MHz, CDCl$_3$)
δ δ 0.88 (t, J = 6.8 Hz, 3 H), 1.27-1.34 (m, 6 H), 1.52 (m, 2 H), 1.65 (m, 2 H), 2.38 (t, J = 6.0 Hz, 2 H), 2.44 (br s, 4 H), 3.18-3.24 (m, 4 H), 3.55 (br s, 2 H), 3.73 (t, J = 4.6 Hz, 4 H), 4.57 (s, 2 H), 6.39 (d, J = 3.3 Hz, 1 H), 6.98 (br s, 1 H), 7.61 (d, J = 3.3 Hz, 1 H), 7.83 (dd, J = 8.1, 2.2 Hz, 1 H), 8.21 (dd, J = 8.0, 0.7 Hz, 1 H), 8.52 (dd, J = 2.1, 0.7 Hz, 1 H), 10.03 (s, 1 H)

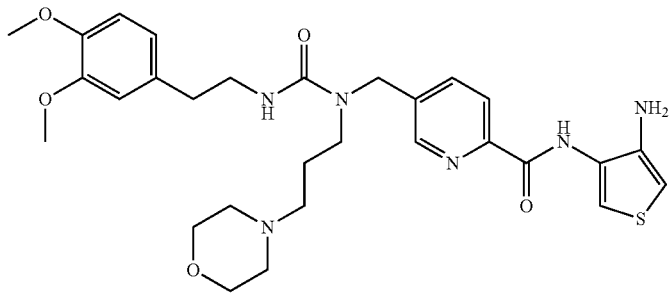

N-(4-Aminothiophen-3-yl)-5-[3-(3,4-dimethoxyphenethyl)-1-[3-(morpholin-4-yl)propyl]ureidomethyl]pyridine-2-carboxylic acid amide
(Compound No. 1-65)

$^1$H-NMR (400 MHz, CDCl$_3$) δ δ 1.62 (m, 2 H), 2.30-2.34 (m, 6 H), 2.81 (t, J = 6.8 Hz, 2 H), 3.16 (t, J = 6.0 Hz, 2 H), 3.46 (m, 2 H), 3.54 (br s, 2 H), 3.60 (br s, 4 H), 3.83 (s, 3 H), 3.84 (s, 3 H), 4.57 (s, 2 H), 6.39 (d, J = 3.7 Hz, 1 H), 6.73 (dd, J = 8.8, 2.2 Hz, 1 H), 6.74 (m, 1 H), 6.80 (d, J = 8.8 Hz, 1 H), 7.09 (s, 1 H), 7.64 (d, J = 3.7 Hz, 1 H), 7.81 (dd, J = 8.0, 2.1 Hz, 1 H), 8.21 (dd, J = 8.0, 0.7 Hz, 1 H), 8.43 (dd, J = 2.1, 0.7 Hz, 1 H), 10.07 (s, 1 H)

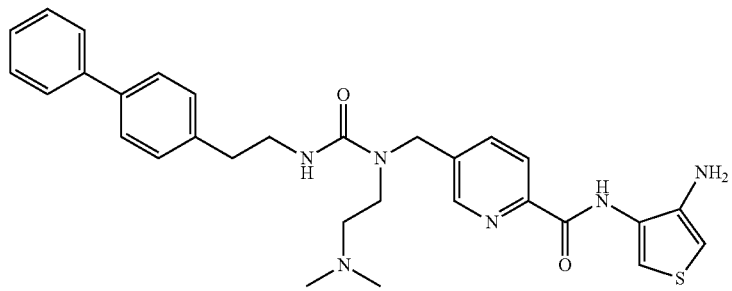

N-(4-Aminothiophen-3-yl)-5-[1-(2-dimethylaminoethyl)-3-(4-phenyl-phenethyl)ureidomethyl]pyridine-2-carboxylic acid amide
(Compound No. 1-66)

$^1$H-NMR (400 MHz, DMSO-d$_6$) δ 2.07 (s, 6 H), 2.28 (t, J = 6.0 Hz, 2 H), 2.78 (t, J = 7.2 Hz, 2 H), 3.26 (t, J = 6.0 Hz, 2 H), 3.32 (m, 2 H), 4.58 (s, 2 H), 4.81 (br s, 2 H), 6.28 (d, J = 3.7 Hz, 1 H), 6.99 (br s, 1 H), 7.27 (d, J = 8.3 Hz, 2 H), 7.33 (t, J = 7.4 Hz, 1 H), 7.43 (t, J = 7.4 Hz, 2 H), 7.57 (d, J = 8.3 Hz, 2 H), 7.61 (m, 2 H), 7.65 (d, J = 3.7 Hz, 1 H), 7.86 (dd, J = 8.0, 2.2 Hz, 1 H), 8.11 (dd, J = 8.0, 0.7 Hz, 1 H), 8.58 (dd, J = 2.2, 0.7 Hz, 1 H), 10.20 (br s, 1 H).

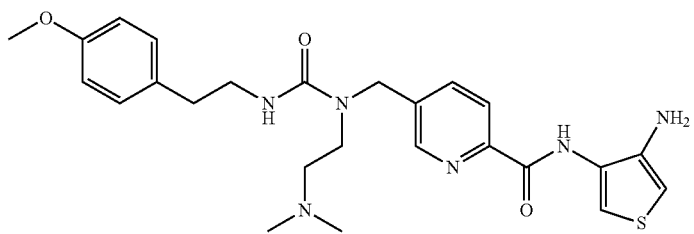

N-(4-Aminothiophen-3-yl)-5-[1-(2-dimethylaminoethyl)-3-(4-methoxy-phenethyl)ureidomethyl]pyridine-2-carboxylic acid amide
(Compound No. 1-67)

$^1$H-NMR (500 MHz, DMSO-d$_6$) δ 2.08 (s, 6 H), 2.27 (t, J = 6.3 Hz, 2 H), 2.66 (t, J = 7.2 Hz, 2 H), 3.22-3.25 (m, 4 H), 3.71 (s, 3 H), 4.56 (s, 2 H), 4.80 (br s, 2 H), 6.27 (d, J = 3.5 Hz, 1 H), 6.83 (d, J = 8.6 Hz, 2 H), 6.92 (t, J = 4.7 Hz, 1 H), 7.09 (d, J = 8.6 Hz, 2 H), 7.65 (d, J = 3.5 Hz, 1 H), 7.81 (dd, J = 8.1, 1.9 Hz, 1 H), 8.10 (d, J = 8.1 Hz, 1 H), 8.56 (d, J = 1.9 Hz, 1 H), 10.19 (br s, 1 H).

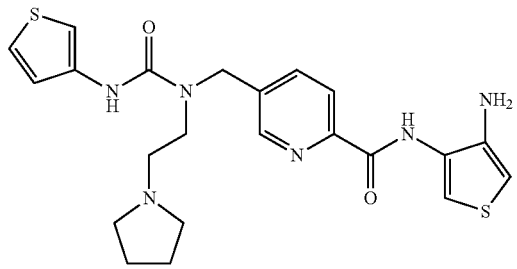

N-(4-Aminothiophen-3-yl)-5-[1-[2-(pyrrolidin-1-yl)ethyl]-3-(thiophen-3-yl)ureidomethyl]pyridine-2-carboxylic acid amide
(Compound No. 1-68)

$^1$H-NMR (500 MHz, CDCl$_3$) δ 1.90 (br s, 4 H), 2.66-2.75 (m, 6 H), 3.35 (t, J = 4.3 Hz, 2 H), 3.51 (br s, 2 H), 4.67 (s, 2 H), 6.40 (d, J = 3.5 Hz, 1 H), 6.92 (dd, J = 5.0, 1.2 Hz, 1 H), 7.21 (dd, J = 5.0, 3.2 Hz, 1 H), 7.28 (dd, J = 3.2, 1.2 Hz, 1 H), 7.62 (d, J = 3.5 Hz, 1 H), 7.89 (dd, J = 8.1, 2.0 Hz, 1 H), 8.23 (d, J = 8.1 Hz, 1 H), 8.57 (d, J = 2.0 Hz, 1 H), 10.04 (s, 1 H), 11.24 (s, 1 H)

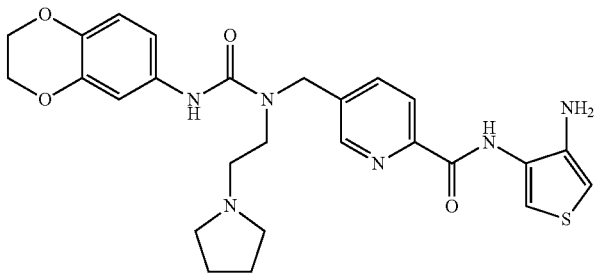

N-(4-Aminothiophen-3-yl)-5-[3-(2,3-dihydrobenzo[1,4]dioxin-6-yl)-1-[2-(pyrrolidin-1-yl)ethyl]ureidomethyl]pyridine-2-carboxylic acid amide (Compound No. 1-69)

$^1$H-NMR (500 MHz, CDCl$_3$) δ 1.89 (br s, 4 H), 2.65-2.74 (m, 6 H), 3.34 (t, J = 4.3 Hz, 2 H), 3.53 (br s, 2 H), 4.20-4.26 (m, 4 H), 4.64 (s, 2 H), 6.39 (d, J = 3.4 Hz, 1 H), 6.77 (d, J = 8.6 Hz, 1 H), 6.80 (dd, J = 8.6, 2.2 Hz, 1 H), 6.93 (d, J = 2.2 Hz, 1 H), 7.62 (d, J = 3.4 Hz, 1 H), 7.90 (dd, J = 7.9, 1.8 Hz, 1 H), 8.23 (d, J = 7.9 Hz, 1 H), 8.57 (d, J = 1.8 Hz, 1 H), 10.04 (s, 1 H), 10.60 (s, 1 H)

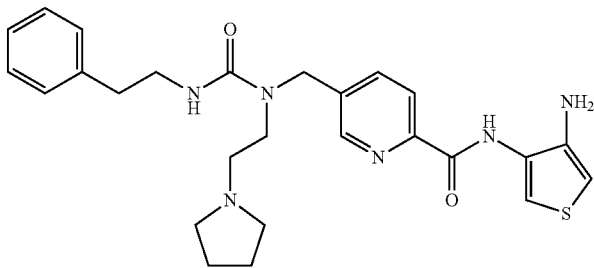

N-(4-Aminothiophen-3-yl)-5-[3-phenethyl-1-[2-(pyrrolidin-1-yl)ethyl]ureidomethyl]pyridine-2-carboxylic acid amide (Compound No. 1-70)

$^1$H-NMR (400 MHz, CDCl$_3$) δ 1.66 (m, 4 H), 2.42 (br s, 4 H), 2.53 (t, J = 5.1 Hz, 2 H), 2.83 (t, J = 7.3 Hz, 2 H), 3.18 (t, J = 5.1 Hz, 2 H), 3.37 (br s, 2 H), 3.46 (q, J = 7.3 Hz, 2 H), 4.58 (s, 2 H), 6.39 (d, J = 3.5 Hz, 1 H), 7.19-7.24 (m, 3 H), 7.29 (m, 2 H), 7.62 (d, J = 3.5 Hz, 1 H), 7.76 (br s, 1 H), 7.79 (dd, J = 8.0, 2.2 Hz, 1 H), 8.20 (dd, J = 8.0, 0.7 Hz, 1 H), 8.49 (dd, J = 2.2, 0.7 Hz, 1 H), 10.05 (s, 1 H)

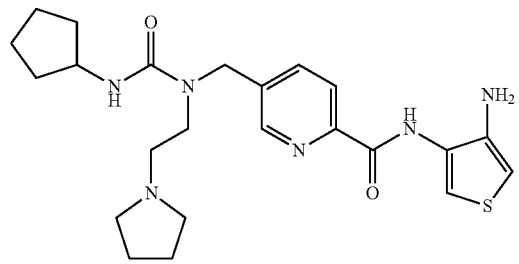

N-(4-Aminothiophen-3-yl)-5-[3-cyclopentyl-1-[2-(pyrrolidin-1-yl)ethyl]ureidomethyl]pyridine-2-carboxylic acid amide (Compound No. 1-71)

$^1$H-NMR (500 MHz, CDCl$_3$) δ 1.34 (m, 2 H), 1.54-1.69 (m, 4 H), 1.79 (m, 4 H), 2.00 (m, 2 H), 2.54-2.62 (m, 6 H), 3.21 (t, J = 4.6 Hz, 2 H), 3.54 (br s, 2 H), 4.07 (m, 1 H), 4.59 (s, 2 H), 6.39 (d, J = 3.5 Hz, 1 H), 7.61 (d, J = 3.5 Hz, 1 H), 7.78 (d, J = 5.5 Hz, 1 H), 7.84 (dd, J = 8.0, 2.1 Hz, 1 H), 8.21 (dd, J = 8.0, 0.6 Hz, 1 H), 8.52 (dd, J = 2.1, 0.6 Hz, 1 H), 10.04 (s, 1 H)

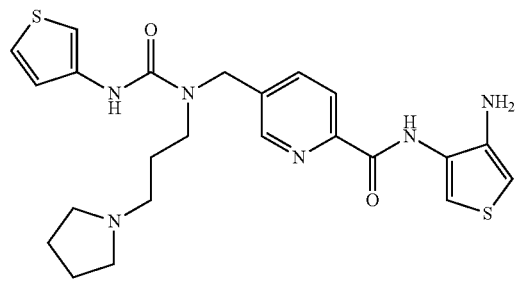

N-(4-Aminothiophen-3-yl)-5-[1-[3-(pyrrolidin-1-yl)propyl]-3-(thiophen-3-yl)ureidomethyl]pyridine-2-carboxylic acid amide (Compound No. 1-72)

$^1$H-NMR (500 MHz, CDCl$_3$) δ 1.72 (m, 2 H), 1.88 (m, 4 H), 2.51-2.60 (m, 6 H), 3.39 (t, J = 5.6 Hz, 2 H), 3.52 (br s, 2 H), 4.63 (s, 2 H), 6.39 (d, J = 3.5 Hz, 1 H), 6.96 (dd, J = 5.1, 1.3 Hz, 1 H), 7.20 (dd, J = 5.1, 3.3 Hz, 1 H), 7.31 (dd, J = 3.3, 1.3 Hz, 1 H), 7.61 (d, J = 3.5 Hz, 1 H), 7.90 (dd, J = 8.1, 2.3 Hz, 1 H), 8.22 (dd, J = 8.1, 0.7 Hz, 1 H), 8.58 (dd, J = 2.3, 0.7 Hz, 1 H), 10.04 (s, 1 H), 10.25 (s, 1 H)

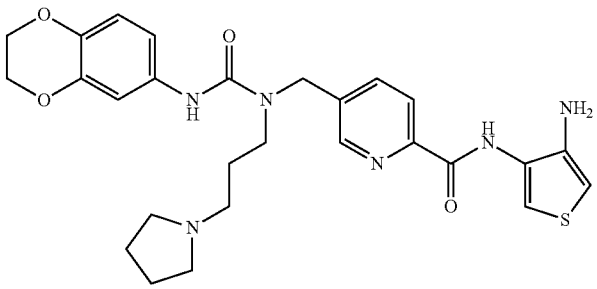

N-(4-Aminothiophen-3-yl)-5-[3-(2,3-dihydrobenzo[1,4]dioxin-6-yl)-1-[3-(pyrrolidin-1-yl)propyl]ureidomethyl]pyridine-2-carboxylic acid amide (Compound No. 1-73)

$^1$H-NMR (400 MHz, CDCl$_3$)
δ 1.72 (m, 2 H), 1.84 (m, 4 H), 2.48-2.60 (m, 6 H), 3.39 (t, J = 5.5 Hz, 2 H), 3.54 (br s, 2 H), 4.20-4.26 (m, 4 H), 4.61 (s, 2 H), 6.39 (d, J = 3.4 Hz, 1 H), 6.77 (d, J = 8.7 Hz, 1 H), 6.86 (dd, J = 8.7, 2.3 Hz, 1 H), 7.00 (d, J = 2.3 Hz, 1 H), 7.61 (d, J = 3.4 Hz, 1 H), 7.91 (dd, J = 8.1, 2.2 Hz, 1 H), 8.21 (dd, J = 8.1, 0.7 Hz, 1 H), 8.58 (dd, J = 2.2, 0.7 Hz, 1 H), 9.73 (s, 1 H), 10.05 (s, 1 H)

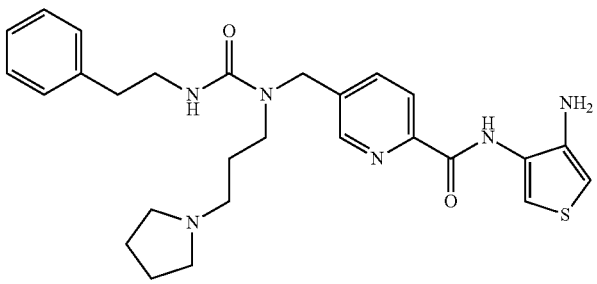

N-(4-Aminothiophen-3-yl)-5-[3-phenethyl-1-[3-(pyrrolidin-1-yl)propyl]ureidomethyl]pyridine-2-carboxylic acid amide (Compound No. 1-74)

$^1$H-NMR (500 MHz, CDCl$_3$)
δ 1.60 (br s, 2 H), 1.70 (br s, 4 H), 2.41 (br s, 6 H), 2.83 (t, J = 6.8 Hz, 2 H), 3.20 (br s, 2 H), 3.45 (q, J = 6.8 Hz, 2 H), 3.53 (br s, 2 H), 4.56 (s, 2 H), 6.40 (d, J = 3.7 Hz, 1 H), 7.19-7.23 (m, 3 H), 7.26-7.31 (m, 2 H), 7.62 (d, J = 3.7 Hz, 1 H), 7.78 (d, J = 7.9 Hz, 1 H), 7.87 (br s, 1 H), 8.21 (d, J = 7.9 Hz, 1 H), 8.50 (s, 1 H), 10.05 (s, 1 H)

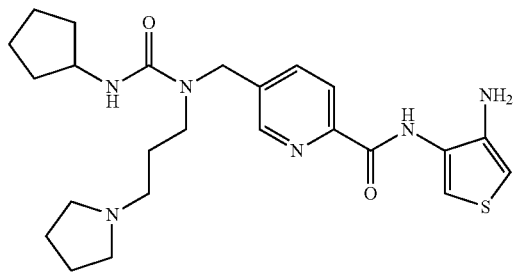

N-(4-Aminothiophen-3-yl)-5-[3-cyclopentyl-1-[3-(pyrrolidin-1-yl)propyl]ureidomethyl]pyridine-2-carboxylic acid amide (Compound No. 1-75)

$^1$H-NMR (500 MHz, CDCl$_3$)
δ 1.31 (m, 2 H), 1.54-1.71 (m, 6 H), 1.80 (br s, 4 H), 2.05 (m, 2 H), 2.44 (t, J = 5.8 Hz, 2 H), 2.49 (br s, 4 H), 3.24 (t, J = 5.8 Hz, 2 H), 3.53 (br s, 2 H), 4.03 (m, 1 H), 4.55 (s, 2 H), 6.39 (d, J = 3.4 Hz, 1 H), 7.06 (d, J = 6.1 Hz, 1 H), 7.61 (d, J = 3.4 Hz, 1 H), 7.85 (dd, J = 7.9, 2.0 Hz, 1 H), 8.21 (d, J = 7.9 Hz, 1 H), 8.53 (d, J = 2.0 Hz, 1 H), 10.04 (s, 1 H)

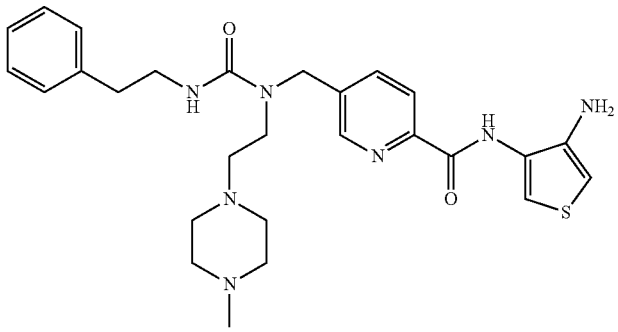

N-(4-Aminothiophen-3-yl)-5-[1-
[2-(4-methylpiperazin-1-yl)ethyl]-
3-phenethylureidomethyl]pyridine-
2-carboxylic acid amide
(Compound No. 1-76)

$^1$H-NMR (400 MHz, CDCl$_3$)
δ 2.21 (br s, 4 H), 2.24 (s,
3 H), 2.39 (t, J = 4.5 Hz,
2 H), 2.40 (br s, 4 H), 2.88
(t, J = 6.5 Hz, 2 H), 3.16 (t,
J = 4.5 Hz, 2 H), 3.49 (q,
J = 6.5 Hz, 2 H), 3.57 (br s,
2 H), 4.59 (s, 2 H), 6.40 (d,
J = 3.6 Hz, 1 H), 7.20-7.24
(m, 3 H), 7.30 (t, J = 7.3 Hz,
2 H), 7.63 (d, J = 3.6 Hz,
1 H), 7.73 (br s, 1 H), 7.80
(dd, J = 8.1, 2.2 Hz, 1 H),
8.22 (d, J = 8.1 Hz, 1 H),
8.50 (d, J = 2.2 Hz, 1 H),
10.05 (s, 1 H)

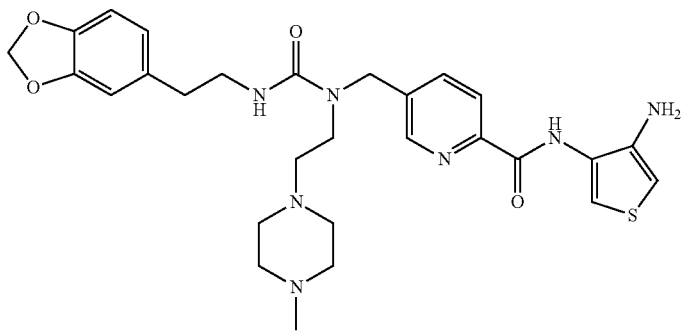

N-(4-Aminothiophen-3-yl)-5-[2-
[3-(benzo[1,3]dioxol-5-yl)]ethyl-
1-[2-(4-methylpiperazin-1-yl)ethyl]-
ureidomethyl]pyridine-2-carboxylic
acid amide (Compound No. 1-77)

$^1$H-NMR (500 MHz, CDCl$_3$)
δ 2.24 (s, 3 H), 2.28 (br s,
4 H), 2.40 (t, J = 4.6 Hz,
2 H), 2.42 (br s, 4 H), 2.78
(t, J = 6.7 Hz, 2 H), 3.17 (t,
J = 4.6 Hz, 2 H), 3.43 (q,
J = 6.7 Hz, 2 H), 3.56 (br s,
2 H), 4.58 (s, 2 H), 5.92 (s,
2 H), 6.39 (d, J = 3.4 Hz,
1 H), 6.65 (dd, J = 7.9, 1.5 Hz,
1 H), 6.71 (d, J = 1.5 Hz,
1 H), 6.74 (d, J = 7.9 Hz,
1 H), 7.62 (d, J = 3.4 Hz,
1 H), 7.65 (br s, 1 H), 7.80
(dd, J = 7.9, 2.1 Hz, 1 H),
8.21 (d, J = 7.9 Hz, 1 H),
8.47 (d, J = 2.1 Hz, 1 H),
10.04 (s, 1 H)

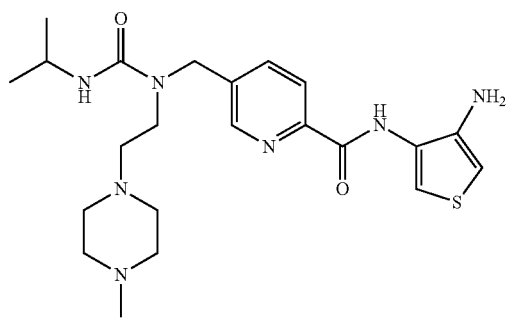

N-(4-Aminothiophen-3-yl)-5-[3-
isopropyl-1-[2-(4-methylpiperazin-
1-yl)ethyl]ureidomethyl]pyridine-
2-carboxylic acid amide
(Compound No. 1-78)

$^1$H-NMR (400 MHz, CDCl$_3$)
δ 1.23 (d, J = 6.6 Hz, 6 H),
2.31 (s, 3 H), 2.45 (t,
J = 4.6 Hz, 2 H), 2.47 (br s,
4 H), 2.55 (br s, 4 H), 3.21 (t,
J = 4.6 Hz, 2 H), 3.56 (br s,
2 H), 4.00 (m, 1 H), 4.59 (s,
2 H), 6.40 (d, J = 3.4 Hz,
1 H), 7.04 (d, J = 7.3 Hz,
1 H), 7.62 (d, J = 3.4 Hz,
1 H), 7.84 (dd, J = 8.1,
2.2 Hz, 1 H), 8.22 (d,
J = 8.1 Hz, 1 H), 8.52 (d,
J = 2.2 Hz, 1 H), 10.04
(s, 1 H)

-continued

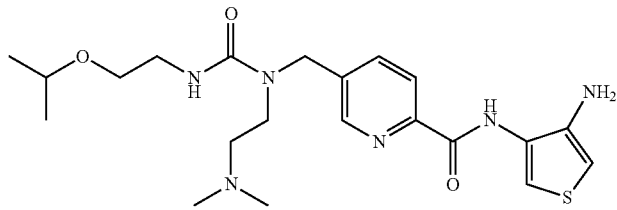

N-(4-Aminothiophen-3-yl)-5-[1-(2-dimethylaminoethyl)-3-(2-isopropyl-oxyethyl)ureidomethyl]pyridine-2-carboxylic acid amide (Compound No. 1-79)

$^1$H-NMR (500 MHz, DMSO-d$_6$)
δ 1.07 (d, J = 6.1 Hz, 6 H), 2.14 (s, 6 H), 2.33 (t, J = 6.1 Hz, 2 H), 3.17 (m, 2 H), 3.27 (t, J = 6.1 Hz, 2 H), 3.37 (t, J = 6.0 Hz, 2 H), 3.53 (m, 1 H), 4.58 (s, 2 H), 4.79 (br s, 2 H), 6.28 (d, J = 3.7 Hz, 1 H), 6.99 (t, J = 5.2 Hz, 1 H), 7.64 (d, J = 3.7 Hz, 1 H), 7.88 (dd, J = 8.0, 1.9 Hz, 1 H), 8.10 (d, J = 8.1 Hz, 1 H), 8.58 (d, J = 1.9 Hz, 1 H), 10.18 (br s, 1 H).

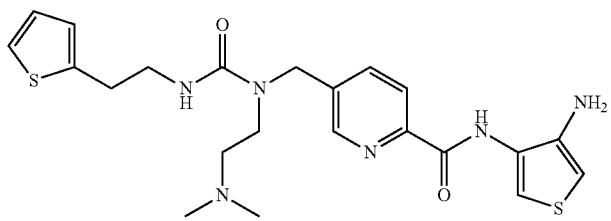

N-(4-Aminothiophen-3-yl)-5-[1-(2-dimethylaminoethyl)-3-[2-(thiophen-2-yl)ethyl]ureidomethyl]pyridine-2-carboxylic acid amide (Compound No. 1-80)

$^1$H-NMR (500 MHz, DMSO-d$_6$)
δ 2.11 (s, 6 H), 2.32 (t, J = 6.2 Hz, 2 H), 2.95 (t, J = 7.0 Hz, 2 H), 3.26 (t, J = 6.2 Hz, 2 H), 3.30 (m, 2 H), 4.58 (s, 2 H), 4.80 (br s, 2 H), 6.28 (d, J = 3.4 Hz, 1 H), 6.86 (m, 1 H), 6.95 (m, 1 H), 7.10 (t, J = 5.2 Hz, 1 H), 7.33 (dd, J = 5.2, 1.2 Hz, 1 H), 7.65 (d, J = 3.4 Hz, 1 H), 7.85 (dd, J = 8.1, 1.1 Hz, 1 H), 8.10 (d, J = 8.1 Hz, 1 H), 8.57 (d, J = 1.1 Hz, 1 H), 10.19 (br s, 1 H).

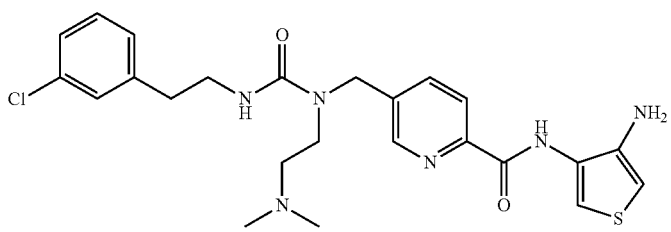

N-(4-Aminothiophen-3-yl)-5-[3-(3-chlorophenethyl)-1-(2-dimethyl-aminoethyl)ureidomethyl]pyridine-2-carboxylic acid amide (Compound No. 1-81)

$^1$H-NMR (400 MHz, DMSO-d$_6$)
δ 2.07 (s, 6 H), 2.26 (t, J = 6.2 Hz, 2 H), 2.76 (t, J = 6.8 Hz, 2 H), 3.22 (t, J = 6.2 Hz, 2 H), 3.30 (m, 2 H), 4.56 (s, 2 H), 4.81 (br s, 2 H), 6.28 (d, J = 3.5 Hz, 1 H), 6.98 (t, J = 5.2 Hz, 1 H), 7.16 (dt, J = 7.3, 1.3 Hz, 1 H), 7.24-7.33 (m, 3 H), 7.65 (d, J = 3.5 Hz, 1 H), 7.80 (dd, J = 8.1, 2.1 Hz, 1 H), 8.09 (dd, J = 8.1, 0.7 Hz, 1 H), 8.55 (dd, J = 2.1, 0.7 Hz, 1 H), 10.19 (br s, 1 H).

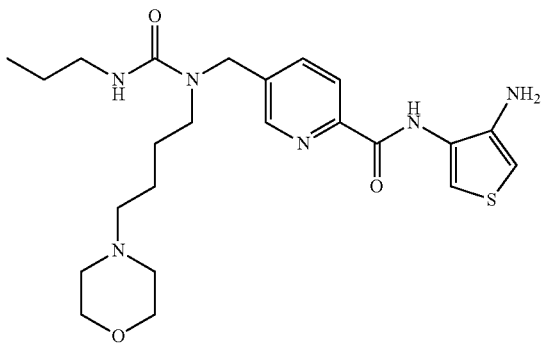

N-(4-Aminothiophen-3-yl)-5-[1-[4-(morpholin-4-yl)butyl]-3-propyl-ureidomethyl]pyridine-2-carboxylic acid amide (Compound No. 1-82)

$^1$H-NMR (400 MHz, CDCl$_3$)
δ 0.91 (t, J = 7.3 Hz, 3 H), 1.48 (m, 2 H), 1.50-1.63 (m, 4 H), 2.34 (t, J = 6.8 Hz, 2 H), 2.41 (m, 4 H), 3.17 (t, J = 7.7 Hz, 2 H), 3.24 (q, J = 6.3 Hz, 2 H), 3.56 (br s, 2 H), 3.70 (t, J = 4.5 Hz, 4 H), 4.60 (s, 2 H), 4.82 (t, J = 6.3 Hz, 1 H), 6.39 (d, J = 3.6 Hz, 1 H), 7.62 (d, J = 3.6 Hz, 1 H), 7.80 (dd, J = 7.9, 1.8 Hz, 1 H), 8.21 (d, J = 7.9 Hz, 1 H), 8.50 (d, J = 1.8 Hz, 1 H), 10.03 (s, 1 H)

| | |
|---|---|
| 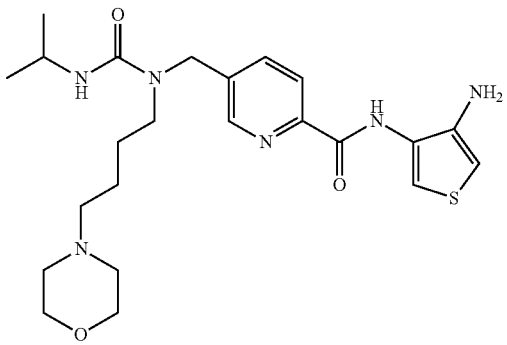<br>N-(4-Aminothiophen-3-yl)-5-[3-isopropyl-1-[4-(morpholin-4-yl)butyl]ureidomethyl]pyridine-2-carboxylic acid amide (Compound No. 1-83) | $^1$H-NMR (400 MHz, CDCl$_3$) δ 1.17 (d, J = 6.1 Hz, 6 H), 1.48 (m, 2 H), 1.58 (m, 2 H), 2.33 (t, J = 6.8 Hz, 2 H), 2.41 (m, 4 H), 3.17 (t, J = 7.3 Hz, 2 H), 3.55 (br s, 2 H), 3.71 (m, 4 H), 4.02 (m, 1 H), 4.26 (d, J = 7.3 Hz, 1 H), 4.59 (s, 2 H), 6.40 (d, J = 2.4 Hz, 1 H), 7.62 (d, J = 2.4 Hz, 1 H), 7.79 (d, J = 8.1 Hz,1 H), 8.22 (d, J = 8.1 Hz, 1 H), 8.50 (s, 1 H), 10.03 (s, 1 H) |
| 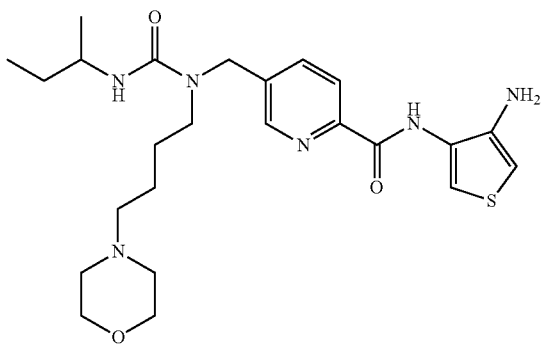<br>N-(4-Aminothiophen-3-yl)-5-[3-sec-butyl-1-[4-(morpholin-4-yl)butyl]ureidomethyl]pyridine-2-carboxylic acid amide (Compound No. 1-84) | $^1$H-NMR (500 MHz, CDCl$_3$) δ 0.90 (t, J = 7.5 Hz, 3 H), 1.14 (d, J = 6.4 Hz, 3 H), 1.43-1.51 (m, 4 H), 1.59 (m, 2 H), 2.33 (t, J = 7.0 Hz, 2 H), 2.40 (m, 4 H), 3.18 (m, 2 H), 3.56 (br s, 2 H), 3.70 (t, J = 4.6 Hz, 4 H), 3.85 (m, 1 H), 4.24 (d, J = 7.9 Hz, 1 H), 4.57 (d, J = 16.5 Hz, 1 H), 4.61 (d, J = 16.5 Hz, 1 H), 6.39 (d, J = 3.4 Hz, 1 H), 7.62 (d, J = 3.4 Hz, 1 H), 7.79 (dd, J = 7.9, 2.1 Hz, 1 H), 8.22 (d, J = 7.9 Hz, 1 H), 8.50 (d, J = 2.1 Hz, 1 H), 10.03 (s, 1 H) |
| 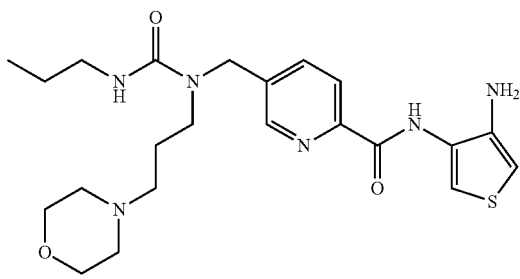<br>N-(4-Aminothiophen-3-yl)-5-[1-[3-(morpholin-4-yl)propyl-3-propyl]ureidomethyl]pyridine-2-carboxylic acid amide (Compound No. 1-85) | $^1$H-NMR (400 MHz, CDCl$_3$) δ δ 0.94 (t, J = 7.3 Hz, 3 H), 1.54 (m, 2 H), 1.66 (m, 2 H), 2.38 (t, J = 6.1 Hz, 2 H), 2.44 (br s, 4 H), 3.17-3.24 (m, 4 H), 3.53 (s, 2 H), 3.73 (t, J = 4.6 Hz, 4 H), 4.57 (s, 2 H), 6.39 (d, J = 3.7 Hz, 1 H), 7.03 (t, J = 5.6 Hz, 1 H), 7.61 (d, J = 3.7 Hz, 1 H), 7.84 (dd, J = 8.1, 2.2 Hz, 1 H), 8.21 (dd, J = 8.1, 0.7 Hz, 1 H), 8.52 (dd, J = 2.1, 0.7 Hz, 1 H), 10.03 (s, 1 H) |

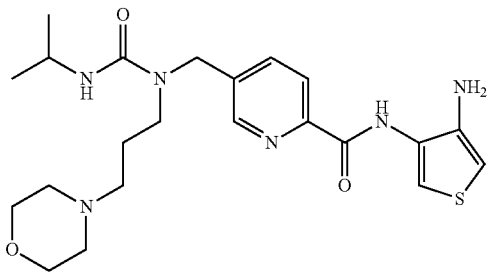

N-(4-Aminothiophen-3-yl)-5-[3-isopropyl-1-[3-(morpholin-4-yl)propyl]ureidomethyl]pyridine-2-carboxylic acid amide (Compound No. 1-86)

$^1$H-NMR (500 MHz, CDCl$_3$)
δ 1.20 (d, J = 6.7 Hz, 6 H), 1.68 (m, 2 H), 2.36 (t, J = 6.3 Hz, 2 H), 2.44 (br s, 4 H), 3.20 (t, J = 6.1 Hz, 2 H), 3.53 (s, 2 H), 3.75 (t, J = 4.7 Hz, 4 H), 4.02 (m, 1 H), 4.57 (s, 2 H), 5.87 (d, J = 7.9 Hz, 1 H), 6.40 (d, J = 3.6 Hz, 1 H), 7.61 (d, J = 3.6 Hz, 1 H), 7.84 (dd, J = 8.0, 1.9 Hz, 1 H), 8.22 (d, J = 8.0 Hz, 1 H), 8.53 (d, J = 1.9 Hz, 1 H), 10.03 (s, 1 H)

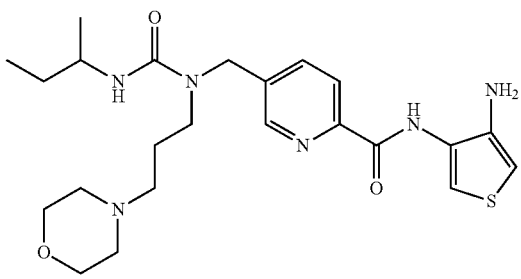

N-(4-Aminothiophen-3-yl)-5-[3-sec-butyl-1-[3-(morpholin-4-yl)propyl]ureidomethyl]pyridine-2-carboxylic acid amide (Compound No. 1-87)

$^1$H-NMR (400 MHz, CDCl$_3$)
δ 0.94 (t, J = 7.4 Hz, 3 H), 1.17 (d, J = 6.6 Hz, 3 H), 1.50 (m, 2 H), 1.68 (m, 2 H), 2.34 (m, 1 H), 2.40 (m, 1 H), 2.44 (m, 4 H), 3.18 (m, 1 H), 3.24 (m, 1 H), 3.53 (s, 2 H), 3.74 (t, J = 4.0 Hz, 4 H), 3.81 (m, 1 H), 4.53 (d, J = 15.9 Hz, 1 H), 4.62 (d, J = 15.9 Hz, 1 H), 5.83 (d, J = 8.8 Hz, 1 H), 6.40 (d, J = 3.6 Hz, 1 H), 7.61 (d, J = 3.6 Hz, 1 H), 7.84 (dd, J = 7.9, 2.2 Hz, 1 H), 8.22 (dd, J = 7.9, 0.7 Hz, 1 H), 8.52 (dd, J = 2.2, 0.7 Hz, 1 H), 10.03 (s, 1 H)

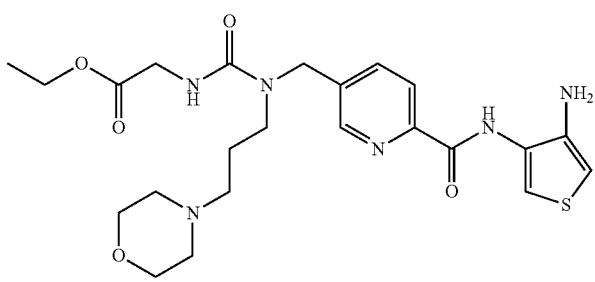

N-(4-Aminothiophen-3-yl)-5-[3-ethoxycarbonylmethyl-1-[3-(morpholin-4-yl)propyl]ureidomethyl]pyridine-2-carboxylic acid amide (Compound No. 1-88)

$^1$H-NMR (400 MHz, CDCl$_3$)
δ 1.29 (t, J = 7.1 Hz, 3 H), 1.70 (m, 2 H), 2.47 (t, J = 5.9 Hz, 2 H), 2.48 (br s, 4 H), 3.30 (t, J = 5.6 Hz, 2 H), 3.53 (s, 2 H), 3.68 (br s, 4 H), 3.94 (t, J = 4.6 Hz, 2 H), 4.21 (q, J = 7.1 Hz, 2 H), 4.59 (s, 2 H), 6.39 (d, J = 3.4 Hz, 1 H), 7.61 (d, J = 3.4 Hz, 1 H), 7.85 (dd, J = 7.9, 2.0 Hz, 1 H), 7.94 (br s, 1 H), 8.21 (dd, J = 7.9, 0.7 Hz, 1 H), 8.53 (dd, J = 2.0, 0.7 Hz, 1 H), 10.03 (s, 1 H)

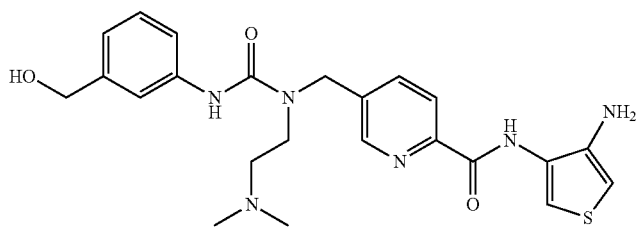

N-(4-Aminothiophen-3-yl)-5-[1-(2-dimethylaminoethyl)-3-(3-hydroxymethylphenyl)ureidomethyl]pyridine-2-carboxylic acid amide (Compound No. 1-89)

$^1$H-NMR (500 MHz, DMSO-d$_6$)
δ 2.27 (s, 6 H), 2.48 (m, 2 H), 3.43 (t, J = 5.2 Hz, 2 H), 4.44 (d, J = 5.8 Hz, 2 H), 4.67 (s, 2 H), 4.80 (s, 2 H), 5.13 (t, J = 5.8 Hz, 1 H), 6.27 (d, J = 3.7 Hz, 1 H), 6.87 (d, J = 7.8 Hz, 1 H), 7.18 (t, J = 7.8 Hz, 1 H), 7.23 (d, J = 7.8 Hz, 1 H), 7.37 (s, 1 H), 7.66 (d, J = 3.7 Hz, 1 H), 7.97 (dd, J = 7.9, 2.1 Hz, 1 H), 8.13 (d, J = 7.9, 0.6 Hz, 1 H), 8.67 (dd, J = 2.1, 0.6 Hz, 1 H), 10.19 (br s, 2 H).

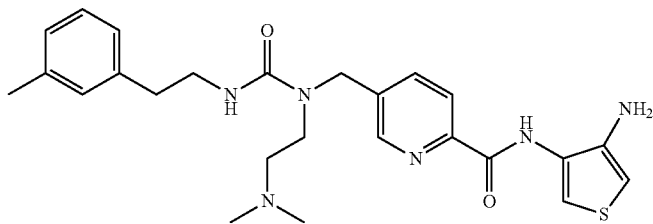

N-(4-Aminothiophen-3-yl)-5-[1-(2-dimethylaminoethyl)-3-(3-methyl-phenethyl)ureidomethyl]pyridine-2-carboxylic acid amide (Compound No. 1-90)

¹H-NMR (400 MHz, DMSO-d₆) δ 2.07 (s, 6 H), 2.26-2.29 (m, 5 H), 2.69 (t, J = 7.1 Hz, 2 H), 3.23 (t, J = 6.5 Hz, 2 H), 3.28 (m, 2 H), 4.57 (s, 2 H), 4.80 (br s, 2 H), 6.28 (d, J = 3.7 Hz, 1 H), 6.97-7.01 (m, 4 H), 7.16 (t, J = 7.7 Hz, 1 H), 7.65 (d, J = 3.7 Hz, 1 H), 7.82 (dd, J = 8.1, 1.8 Hz, 1 H), 8.09 (d, J = 8.1 Hz, 1 H), 8.56 (d, J = 1.8 Hz, 1 H), 10.19 (br s, 1 H).

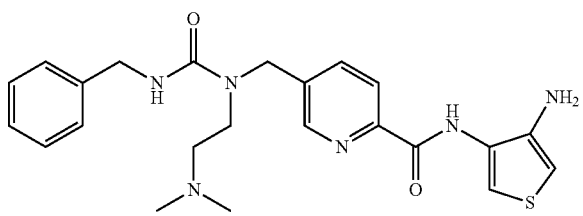

N-(4-Aminothiophen-3-yl)-5-[3-benzyl-1-(2-dimethylaminoethyl)ureidomethyl]pyridine-2-carboxylic acid amide (Compound No. 1-91)

¹H-NMR (400 MHz, DMSO-d₆) δ 2.17 (s, 6 H), 2.51 (m, 2 H), 2.98 (m, 2 H), 3.07 (m, 2 H), 4.59 (s, 2 H), 4.80 (br s, 2 H), 6.27 (d, J = 3.7 Hz, 1 H), 6.95 (br s, 1 H), 7.15-7.20 (m, 3 H), 7.27 (t, J = 7.6 Hz, 2 H), 7.64 (d, J = 3.7 Hz, 1 H), 7.88 (dd, J = 8.1, 2.2 Hz, 1 H), 8.11 (dd, J = 8.1, 0.5 Hz, 1 H), 8.58 (dd, J = 2.2, 0.5 Hz, 1 H), 10.18 (br s, 1 H).

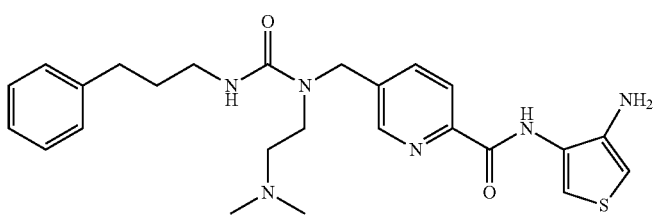

N-(4-Aminothiophen-3-yl)-5-[1-(2-dimethylaminoethyl)-3-(3-phenyl-propyl)ureidomethyl]pyridine-2-carboxylic acid amide (Compound No. 1-92)

¹H-NMR (400 MHz, DMSO-d₆) δ 2.17 (s, 6 H), 2.51 (m, 2 H), 2.98 (m, 2 H), 3.07 (m, 2 H), 4.59 (s, 2 H), 4.80 (br s, 2 H), 6.27 (d, J = 3.7 Hz, 1 H), 6.95 (br s, 1 H), 7.15-7.20 (m, 3 H), 7.27 (t, J = 7.6 Hz, 2 H), 7.64 (d, J = 3.7 Hz, 1 H), 7.88 (dd, J = 8.1, 2.2 Hz, 1 H), 8.11 (dd, J = 8.1, 0.5 Hz, 1 H), 8.58 (dd, J = 2.2, 0.5 Hz, 1 H), 10.18 (br s, 1 H).

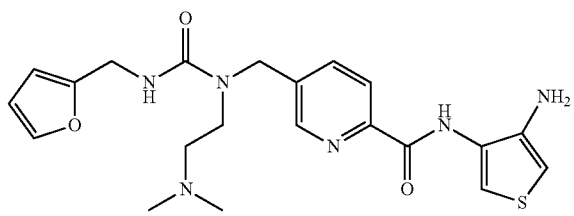

N-(4-Aminothiophen-3-yl)-5-[1-(2-dimethylaminoethyl)-3-(furan-2-ylmethyl)ureidomethyl]pyridine-2-carboxylic acid amide (Compound No. 1-93)

¹H-NMR (500 MHz, DMSO-d₆) δ 2.10 (s, 6 H), 2.33 (t, J = 6.0 Hz, 2 H), 3.29 (t, J = 6.0 Hz, 2 H), 4.24 (d, J = 5.2 Hz, 2 H), 4.60 (s, 2 H), 4.80 (br s, 2 H), 6.17 (dd, J = 3.1, 0.9 Hz, 1 H), 6.28 (d, J = 3.5 Hz, 1 H), 6.38 (dd, J = 3.1, 1.8 Hz, 1 H), 7.56 (dd, J = 1.8, 0.9 Hz, 1 H), 7.61 (br s, 1 H), 7.65 (d, J = 3.5 Hz, 1 H), 7.88 (dd, J = 8.1, 2.0 Hz, 1 H), 8.11 (d, J = 8.1 Hz, 1 H), 8.59 (d, J = 2.0 Hz, 1 H), 10.18 (br s, 1 H).

| | |
|---|---|
| 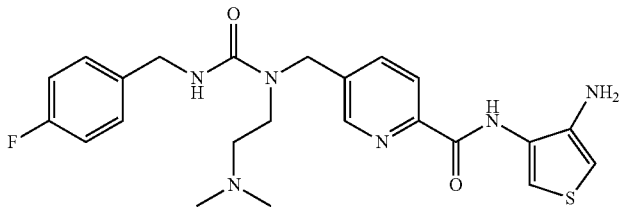<br>N-(4-Aminothiophen-3-yl)-5-[1-(2-dimethylaminoethyl)-3-(4-fluoro-benzyl)ureidomethyl]pyridine-2-carboxylic acid amide<br>(Compound No. 1-94) | $^1$H-NMR (400 MHz, DMSO-d$_6$)<br>δ 2.10 (s, 6 H), 2.34 (t, J = 6.1 Hz, 2 H), 3.30 (m, 2 H), 4.23 (d, J = 5.4 Hz, 2 H), 4.61 (s, 2 H), 4.81 (br s, 2 H), 6.28 (d, J = 3.7 Hz, 1 H), 7.13 (t, J = 8.9 Hz, 2 H), 7.28 (m, 2 H), 7.51 (t, J = 5.4 Hz, 1 H), 7.65 (d, J = 3.7 Hz, 1 H), 7.88 (dd, J = 7.9, 2.0 Hz, 1 H), 8.11 (d, J = 7.9 Hz, 1 H), 8.59 (d, J = 2.0 Hz, 1 H), 10.18 (br s, 1 H). |
| 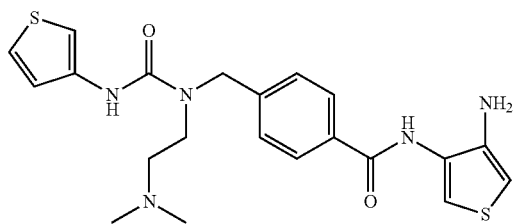<br>N-(4-Aminothiophen-3-yl)-4-[1-(2-dimethylaminoethyl)-3-(thiophen-3-yl)ureidomethyl]benzamide<br>(Compound No. 1-95) | $^1$H-NMR (400 MHz, CDCl$_3$)<br>δ 2.37 (s, 6 H), 2.48 (t, J = 4.3 Hz, 2 H), 3.31 (t, J = 4.3 Hz, 2 H), 3.39 (br s, 2 H), 4.64 (s, 2 H), 6.47 (d, J = 3.4 Hz, 1 H), 6.88 (dd, J = 5.1, 1.4 Hz, 1 H), 7.20 (dd, J = 5.1, 3.2 Hz, 1 H), 7.31 (dd, J = 3.2, 1.4 Hz, 1 H), 7.42 (d, J = 8.3 Hz, 2 H), 7.56 (d, J = 3.4 Hz, 1 H), 7.84 (d, J = 8.3 Hz, 2 H), 8.21 (s, 1 H), 11.37 (br s, 1 H) |
| 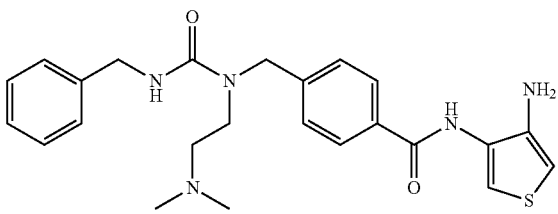<br>N-(4-Aminothiophen-3-yl)-4-[3-benzyl-1-(2-dimethylaminoethyl)ureidomethyl]benzamide<br>(Compound No. 1-96) | $^1$H-NMR (400 MHz, CDCl$_3$)<br>δ 2.04 (s, 6 H), 2.34 (t, J = 4.6 Hz, 2 H), 3.22 (t, J = 4.6 Hz, 2 H), 3.47 (br s, 2 H), 4.38 (d, J = 4.9 Hz, 2 H), 4.58 (s, 2 H), 6.46 (d, J = 3.4 Hz, 1 H), 7.26 (m, 1 H), 7.30-7.35 (m, 4 H), 7.38 (d, J = 8.4 Hz, 2 H), 7.55 (d, J = 3.4 Hz, 1 H), 7.84 (d, J = 8.4 Hz, 2 H), 8.26 (br s, 2 H) |
| 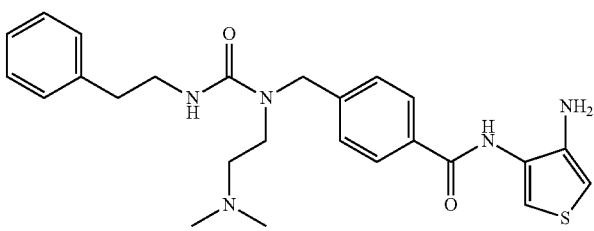<br>N-(4-Aminothiophen-3-yl)-4-[1-(2-dimethylaminoethyl)-3-phenethyl-ureidomethyl]benzamide<br>(Compound No. 1-97) | $^1$H-NMR (400 MHz, CDCl$_3$)<br>δ 2.05 (s, 6 H), 2.28 (t, J = 4.9 Hz, 2 H), 2.83 (t, J = 6.7 Hz, 2 H), 3.15 (t, J = 4.9 Hz, 2 H), 3.41 (br s, 2 H), 3.52 (q, J = 6.7 Hz, 2 H), 4.55 (s, 2 H), 6.47 (d, J = 3.5 Hz, 1 H), 7.17-7.24 (m, 3 H), 7.25-7.32 (m, 2 H), 7.35 (d, J = 8.2 Hz, 2 H), 7.43 (br s, 1 H), 7.56 (d, J = 3.5 Hz, 1 H), 7.83 (d, J = 8.2 Hz, 2 H), 8.21 (s, 1 H) |
| 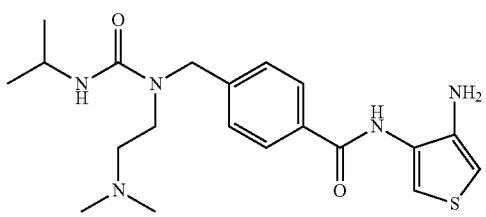<br>N-(4-Aminothiophen-3-yl)-4-[1-(2-dimethylaminoethyl)-3-isopropyl-ureidomethyl]benzamide<br>(Compound No. 1-98) | $^1$H-NMR (400 MHz, CDCl$_3$)<br>δ 1.14 (d, J = 6.3 Hz, 6 H), 2.24 (s, 6 H), 2.37 (t, J = 4.6 Hz, 2 H), 3.19 (t, J = 4.6 Hz, 2 H), 3.50 (br s, 2 H), 3.90 (m, 1 H), 4.55 (s, 2 H), 6.46 (d, J = 3.5 Hz, 1 H), 7.37 (d, J = 8.3 Hz, 2 H), 7.55 (d, J = 3.5 Hz, 1 H), 7.65 (br s, 1 H), 7.84 (d, J = 8.3 Hz, 2 H), 8.24 (br s, 1 H) |

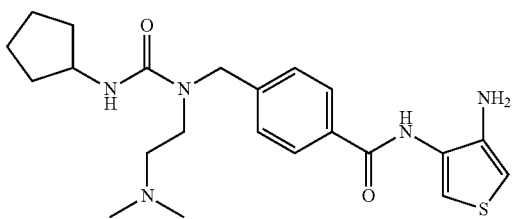

N-(4-Aminothiophen-3-yl)-4-[3-cyclopentyl-1-(2-dimethylaminoethyl)ureidomethyl]benzamide
(Compound No. 1-99)

¹H-NMR (400 MHz, CDCl₃) δ 1.38 (m, 2 H), 1.53-1.68 (m, 4 H), 1.95 (m, 2 H), 2.24 (s, 6 H), 2.36 (t, J = 4.5 Hz, 2 H), 3.18 (t, J = 4.5 Hz, 2 H), 3.48 (br s, 2 H), 4.08 (m, 1 H), 4.55 (s, 2 H), 6.46 (d, J = 3.4 Hz, 1 H), 7.37 (d, J = 8.3 Hz, 2 H), 7.55 (d, J = 3.4 Hz, 1 H), 7.79 (br s, 1 H), 7.84 (d, J = 8.3 Hz, 2 H), 8.25 (br s, 1 H)

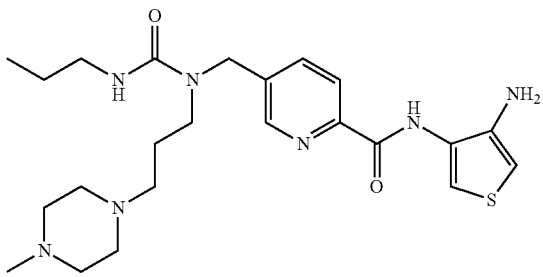

N-(4-Aminothiophen-3-yl)-5-[1-[3-(4-methylpiperazin-1-yl)propyl]-3-propylureidomethyl]pyridine-2-carboxylic acid amide
(Compound No. 1-100)

¹H-NMR (400 MHz, CDCl₃) δ 0.94 (t, J = 7.4 Hz, 3 H), 1.56 (m, 2 H), 1.65 (m, 2 H), 2.31 (s, 3 H), 2.37 (t, J = 6.0 Hz, 2 H), 2.47 (br s, 8 H), 3.18-3.23 (m, 4 H), 3.55 (br s, 2 H), 4.56 (s, 2 H), 6.39 (d, J = 3.6 Hz, 1 H), 7.19 (m, 1 H), 7.61 (d, J = 3.6 Hz, 1 H), 7.83 (dd, J = 7.9, 2.1 Hz, 1 H), 8.20 (d, J = 7.9 Hz, 1 H), 8.51 (d, J = 2.1 Hz, 1 H), 10.03 (s, 1 H)

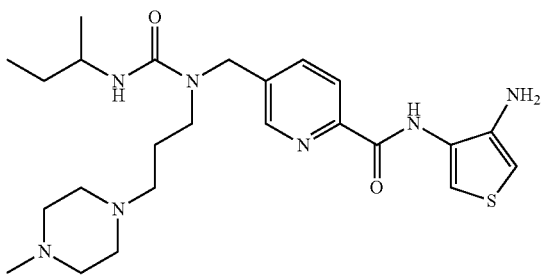

N-(4-Aminothiophen-3-yl)-5-[3-sec-butyl-1-[3-(4-methylpiperazin-1-yl)propyl]ureidomethyl]pyridine-2-carboxylic acid amide
(Compound No. 1-101)

¹H-NMR (500 MHz, CDCl₃) δ 0.94 (t, J = 7.5 Hz, 3 H), 1.18 (d, J = 6.7 Hz, 3 H), 1.42-1.59 (m, 2 H), 1.67 (m, 2 H), 2.31 (s, 3 H), 2.34 (m, 1 H), 2.39 (m, 1 H), 2.48 (br s, 8 H), 3.17 (m, 1 H), 3.23 (m, 1 H), 3.55 (br s, 2 H), 3.80 (m, 1 H), 4.52 (d, J = 15.9 Hz, 1 H), 4.61 (d, 15.9 Hz, 1 H), 5.94 (d, J = 8.2 Hz, 1 H), 6.39 (d, J = 3.6 Hz, 1 H), 7.61 (d, J = 3.6 Hz, 1 H), 7.83 (dd, J = 8.1, 2.0 Hz, 1 H), 8.21 (d, J = 8.1 Hz, 1 H), 8.52 (d, J = 2.0 Hz, 1 H), 10.03 (s, 1 H)

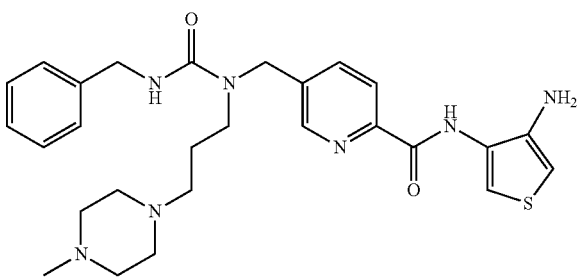

N-(4-Aminothiophen-3-yl)-5-[3-benzyl-1-[3-(4-methylpiperazin-1-yl)propyl]ureidomethyl]pyridine-2-carboxylic acid amide
(Compound No. 1-102)

¹H-NMR (400 MHz, CDCl₃) δ 1.67 (m, 2 H), 2.09 (s, 3 H), 2.31 (br s, 8 H), 2.35 (t, J = 5.7 Hz, 2 H), 3.29 (m, 2 H), 3.55 (br s, 2 H), 4.50 (d, J = 5.6 Hz, 2 H), 4.62 (s, 2 H), 6.39 (d, J = 3.3 Hz, 1 H), 7.25 (m, 1 H), 7.30-7.35 (m, 4 H), 7.62 (d, J = 3.3 Hz, 1 H), 7.79 (m, 1 H), 7.87 (d, J = 8.1 Hz, 1 H), 3.22 (d, J = 8.1 Hz, 1 H), 8.56 (s, 1 H), 10.05 (s, 1 H)

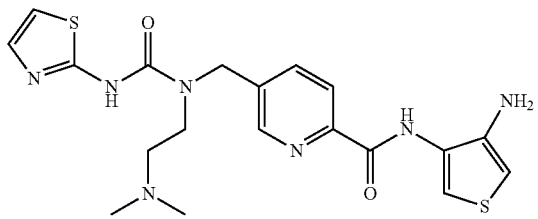

N-(4-Aminothiophen-3-yl)-5-[1-
(2-dimethylaminoethyl)-3-(thiazol-
2-yl)ureidomethyl]pyridine-2-
carboxylic acid amide
(Compound No. 1-103)

¹H-NMR (400 MHz, DMSO-d₆)
δ 2.28 (s, 6 H), 2.50 (m, 2 H),
3.49 (t, J = 4.8 Hz, 2 H),
4.72 (s, 2 H), 4.80 (br s,
2 H), 6.27 (d, J = 3.5 Hz,
1 H), 7.00 (d, J = 3.7 Hz,
1 H), 7.32 (d, J = 3.7 Hz,
1 H), 7.65 (d, J = 3.5 Hz,
1 H), 7.96 (dd, J = 8.1,
2.1 Hz, 1 H), 8.13 (d,
J = 8.1 Hz, 1 H), 8.66 (d,
J = 2.1 Hz, 1 H), 10.19
(br s, 1 H).

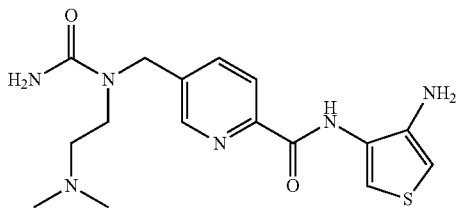

N-(4-Aminothiophen-3-yl)-5-[1-
(2-dimethylaminoethyl)ureidomethyl]
pyridine-2-carboxylic acid amide
(Compound No. 1-104)

¹H-NMR (400 MHz, DMSO-d₆)
δ 2.12 (s, 6 H), 2.32 (t,
J = 6.5 Hz, 2 H), 3.26 (t,
J = 6.5 Hz, 2 H), 4.57 (s,
2 H), 4.80 (br s, 2 H), 6.11
(s, 2 H), 6.27 (d, J = 3.7 Hz,
1 H), 7.65 (d, J = 3.7 Hz,
1 H), 7.89 (dd, J = 8.0,
1.9 Hz, 1 H), 8.12 (d,
J = 8.0 Hz, 1 H), 8.58
(d, J = 1.9 Hz, 1 H),
10.18 (br s, 1 H).

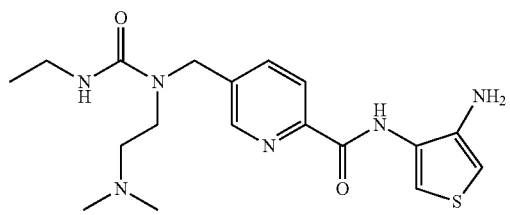

N-(4-Aminothiophen-3-yl)-5-[1-
(2-dimethylaminoethyl)-3-ethyl-
ureidomethyl]pyridine-2-
carboxylic acid amide
(Compound No. 1-105)

¹H-NMR (400 MHz, DMSO-d₆)
δ 1.02 (t, J = 7.1 Hz, 3 H),
2.13 (s, 6 H), 2.32 (t,
J = 6.2 Hz, 2 H), 3.07 (m,
2 H), 3.26 (t, J = 6.2 Hz,
2 H), 4.57 (s, 2 H), 4.81
(br s, 2 H), 6.27 (d, J = 3.5 Hz,
1 H), 6.93 (t, J = 4.8 Hz,
1 H), 7.65 (d, J = 3.5 Hz,
1 H), 7.87 (dd, J = 8.1,
2.0 Hz, 1 H), 8.11 (dd,
J = 8.1, 0.5 Hz, 1 H), 8.57
(dd, J = 2.0, 0.5 Hz, 1 H),
10.18 (br s, 1 H).

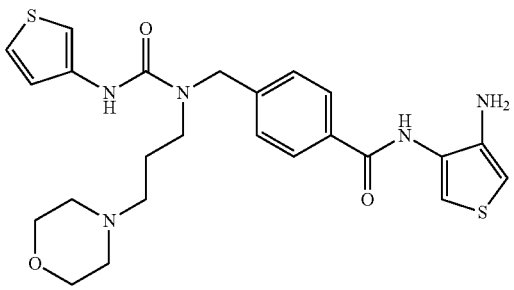

N-(4-Aminothiophen-3-yl)-4-[1-[3-
(morpholin-4-yl)propyl]-3-(thiophen-
3-yl)ureidomethyl]benzamide
(Compound No. 1-106)

¹H-NMR (400 MHz, CDCl₃)
δ 1.74 (m, 2 H), 2.41-2.50
(m, 6 H), 3.36 (t, J = 5.7 Hz,
2 H), 3.53 (br s, 2 H), 3.72
(t, J = 4.6 Hz, 4 H), 4.63 (s,
2 H), 6.48 (d, J = 3.4 Hz,
1 H), 7.10 (dd, J = 5.1, 1.3 Hz,
1 H), 7.23 (dd, J = 5.1,
3.3 Hz, 1 H), 7.32 (dd,
J = 3.3, 1.3 Hz, 1 H), 7.44 (d,
J = 8.3 Hz, 2 H), 7.56 (d,
J = 3.4 Hz, 1 H), 7.84 (d,
J = 8.3 Hz, 2 H), 8.16 (s, 1 H),
9.10 (s, 1 H)

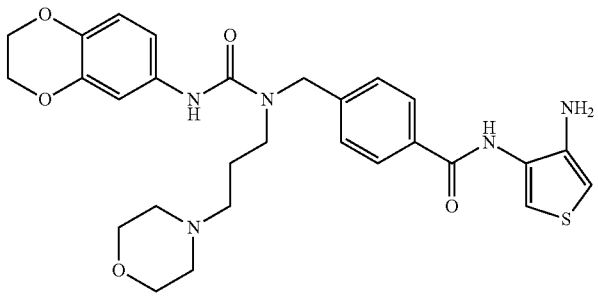

N-(4-Aminothiophen-3-yl)-4-[3-(2,3-dihydrobenzo[1,4]dioxin-6-yl)-1-[3-(morpholin-4-yl)propyl]ureidomethyl]benzamide (Compound No. 1-107)

$^1$H-NMR (400 MHz, CDCl$_3$) δ 1.72 (m, 2 H), 2.40-2.48 (m, 6 H), 3.35 (t, J = 5.6 Hz, 2 H), 3.48 (br s, 2 H), 3.65 (t, J = 4.6 Hz, 4 H), 4.21-4.26 (m, 4 H), 4.60 (s, 2 H), 6.45 (d, J = 3.4 Hz, 1 H), 6.79 (d, J = 8.7 Hz, 1 H), 6.82 (dd, J = 8.7, 2.4 Hz, 1 H), 6.99 (d, J = 2.4 Hz, 1 H), 7.42 (d, J = 8.3 Hz, 2 H), 7.55 (d, J = 3.4 Hz, 1 H), 7.82 (d, J = 8.3 Hz, 2 H), 8.22 (s, 1 H), 8.78 (s, 1 H)

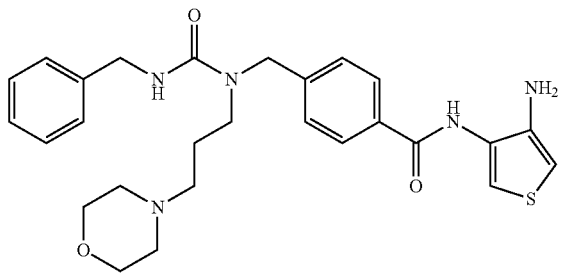

N-(4-Aminothiophen-3-yl)-4-[3-benzyl-1-[3-(morpholin-4-yl)propyl]ureidomethyl]benzamide (Compound No. 1-108)

$^1$H-NMR (500 MHz, CDCl$_3$) δ 1.64 (m, 2 H), 2.25 (br s, 4 H), 2.32 (t, J = 6.0 Hz, 2 H), 3.29 (t, J = 5.8 Hz, 2 H), 3.41 (br s, 6 H), 4.49 (d, J = 5.8 Hz, 2 H), 4.62 (s, 2 H), 6.48 (d, J = 3.7 Hz, 1 H), 7.31-7.34 (m, 5 H), 7.40 (br s, 1 H), 7.42 (d, J = 8.2 Hz, 2 H), 7.56 (d, J = 3.7 Hz, 1 H), 7.85 (d, J = 8.2 Hz, 2 H), 8.18 (s, 1 H)

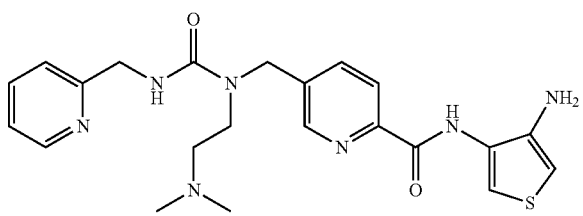

N-(4-Aminothiophen-3-yl)-5-[1-(2-dimethylaminoethyl)-3-(pyridin-2-ylmethyl)ureidomethyl]pyridine-2-carboxylic acid amide (Compound No. 1-109)

$^1$H-NMR (400 MHz, DMSO-d$_6$) δ 2.20 (s, 6 H), 2.50 (m, 2 H), 3.39 (t, J = 6.1 Hz, 2 H), 4.36 (d, J = 5.5 Hz, 2 H), 4.65 (s, 2 H), 4.81 (br s, 2 H), 6.28 (d, J = 3.5 Hz, 1 H), 7.22-7.26 (m, 2 H), 7.56 (t, J = 5.5 Hz, 1 H), 7.65 (d, J = 3.5 Hz, 1 H), 7.74 (td, J = 7.6, 1.8 Hz, 1 H), 7.93 (dd, J = 8.0, 2.2 Hz, 1 H), 8.13 (dd, J = 8.0, 0.6 Hz, 1 H), 8.49 (ddd, J = 4.9, 1.8, 1.0 Hz, 1 H), 8.62 (dd, J = 2.2, 0.6 Hz, 1 H), 10.19 (br s, 1 H).

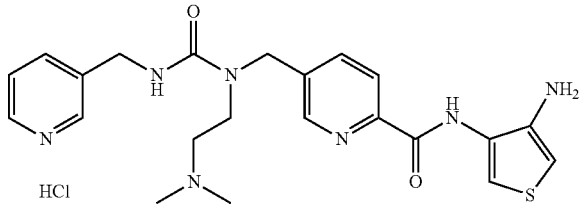

N-(4-Aminothiophen-3-yl)-5-[1-(2-dimethylaminoethyl)-3-(pyridin-3-ylmethyl)ureidomethyl]pyridine-2-carboxylic acid amide hydrochloride (Compound No. 1-110)

$^1$H-NMR (500 MHz, DMSO-d$_6$) δ 2.78 (d, J = 4.6 Hz, 6 H), 3.27 (m, 2 H), 3.69 (t, J = 7.0 Hz, 2 H), 4.45 (d, J = 5.5 Hz, 2H), 4.71 (s, 2 H), 7.55 (d, J = 3.7 Hz, 1 H), 7.83 (d, J = 3.7 Hz, 1 H), 7.91-7.95 (m, 2 H), 8.02 (dd, J = 7.9, 5.7 Hz, 1 H), 8.15 (d, J = 8.2 Hz, 1 H), 8.49 (d, J = 7.9 Hz, 1 H), 8.65 (d, J = 1.8 Hz, 1 H), 8.81 (d, J = 5.7 Hz, 1 H), 8.87 (br s, 1 H), 10.62 (br s, 1 H), 10.67 (br s, 1 H).

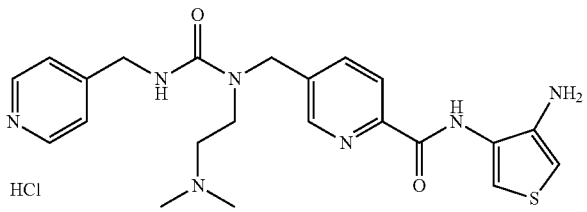

N-(4-Aminothiophen-3-yl)-5-[1-(2-dimethylaminoethyl)-3-(pyridin-4-ylmethyl)ureidomethyl]pyridine-2-carboxylic acid amide hydrochloride (Compound No. 1-111)

$^1$H-NMR (500 MHz, DMSO-d$_6$) δ 2.79 (d, J = 4.9 Hz, 6 H), 3.29 (m, 2 H), 3.71 (t, J = 7.0 Hz, 2 H), 4.52 (d, J = 5.5 Hz, 2 H), 4.74 (s, 2 H), 7.47 (br s, 1 H), 7.82 (d, J = 3.7 Hz, 1 H), 7.93-7.98 (m, 4 H), 8.18 (d, J = 7.9 Hz, 1 H), 8.67 (d, J = 2.1 Hz, 1 H), 8.85 (d, J = 6.7 Hz, 2 H), 10.57 (br s, 1 H), 10.67 (br s, 1 H).

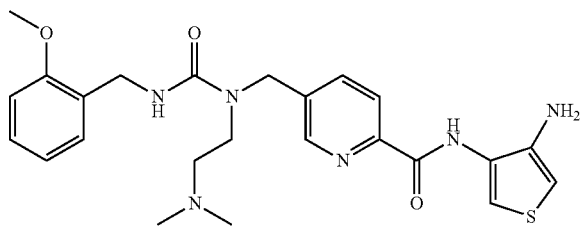

N-(4-Aminothiophen-3-yl)-5-[1-(2-dimethylaminoethyl)-3-(2-methoxybenzyl)ureidomethyl]pyridine-2-carboxylic acid amide (Compound No. 1-112)

$^1$H-NMR (500 MHz, DMSO-d$_6$) δ 2.10 (s, 6 H), 2.36 (t, J = 6.0 Hz, 2 H), 3.33 (t, J = 6.0 Hz, 2 H), 3.79 (s, 3 H), 4.23 (d, J = 5.5 Hz, 2 H), 4.62 (s, 2 H), 4.80 (br s, 2 H), 6.28 (d, J = 3.4 Hz, 1 H), 6.89 (t, J = 7.7 Hz, 1 H), 6.95 (d, J = 7.7 Hz, 1 H), 7.13 (d, J = 7.7 Hz, 1 H), 7.21 (t, J = 7.7 Hz, 1 H), 7.35 (br s, 1 H), 7.65 (d, J = 3.4 Hz, 1 H), 7.90 (dd, J = 8.0, 1.9 Hz, 1 H), 8.11 (d, J = 8.0 Hz, 1 H), 8.60 (d, J = 1.9 Hz, 1 H), 10.19 (br s, 1 H).

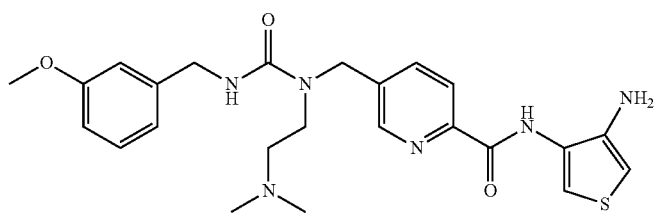

N-(4-Aminothiophen-3-yl)-5-[1-(2-dimethylaminoethyl)-3-(3-methoxybenzyl)ureidomethyl]pyridine-2-carboxylic acid amide (Compound No. 1-113)

$^1$H-NMR (500 MHz, DMSO-d$_6$) δ 2.11 (s, 6 H), 2.36 (t, J = 6.2 Hz, 2 H), 3.34 (t, J = 6.2 Hz, 2 H), 3.72 (s, 3 H), 4.24 (d, J = 5.5 Hz, 2 H), 4.62 (s, 2 H), 4.80 (br s, 2 H), 6.28 (d, J = 3.5 Hz, 1 H), 6.76-6.82 (m, 3 H), 7.21 (t, J = 7.8 Hz, 1 H), 7.46 (t, J = 5.5 Hz, 1 H), 7.65 (d, J = 3.5 Hz, 1 H), 7.89 (dd, J = 8.1, 1.8 Hz, 1 H), 8.10 (d, J = 8.1 Hz, 1 H), 8.60 (d, J = 1.8 Hz, 1 H), 10.18 (br s, 1 H).

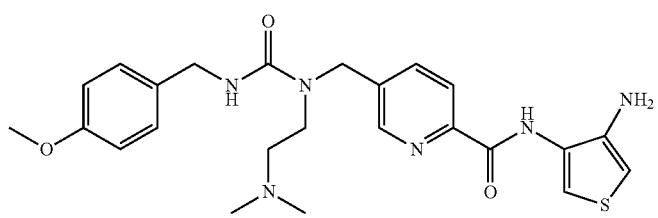

N-(4-Aminothiophen-3-yl)-5-[1-(2-dimethylaminoethyl)-3-(4-methoxybenzyl)ureidomethyl]pyridine-2-carboxylic acid amide (Compound No. 1-114)

$^1$H-NMR (500 MHz, DMSO-d$_6$) δ 2.10 (s, 6 H), 2.35 (t, J = 6.1 Hz, 2 H), 3.31 (t, J = 6.1 Hz, 2 H), 3.72 (s, 3 H), 4.18 (d, J = 5.3 Hz, 2 H), 4.61 (s, 2 H), 4.80 (br s, 2 H), 6.28 (d, J = 3.5 Hz, 1 H), 6.86 (d, J = 8.9 Hz, 2 H), 7.16 (d, J = 8.9 Hz, 2 H), 7.45 (t, J = 5.3 Hz, 1 H), 7.65 (d, J = 3.5 Hz, 1 H), 7.88 (dd, J = 8.1, 2.0 Hz, 1 H), 8.11 (d, J = 8.1 Hz, 1 H), 8.58 (d, J = 2.0 Hz, 1 H), 10.18 (br s, 1 H).

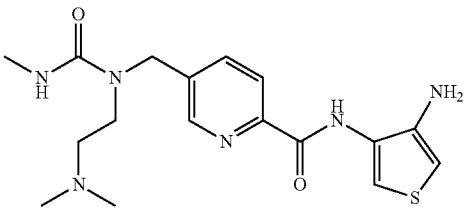

N-(4-Aminothiophen-3-yl)-5-[1-(2-dimethylaminoethyl)-3-methyl-ureidomethyl]pyridine-2-carboxylic acid amide (Compound No. 1-115)

$^1$H-NMR (500 MHz, DMSO-d$_6$) δ 2.15 (s, 6 H), 2.35 (t, J = 6.1 Hz, 2 H), 2.59 (d, J = 4.3 Hz, 3 H), 3.28 (t, J = 6.1 Hz, 2 H), 4.58 (s, 2 H), 4.80 (br s, 2 H), 6.27 (d, J = 3.7 Hz, 1 H), 6.67 (m, 1 H), 7.64 (d, J = 3.7 Hz, 1 H), 7.87 (dd, J = 7.9, 2.1 Hz, 1 H), 8.11 (d, J = 7.9 Hz, 1 H), 8.57 (d, J = 2.1 Hz, 1 H), 10.18 (br s, 1 H).

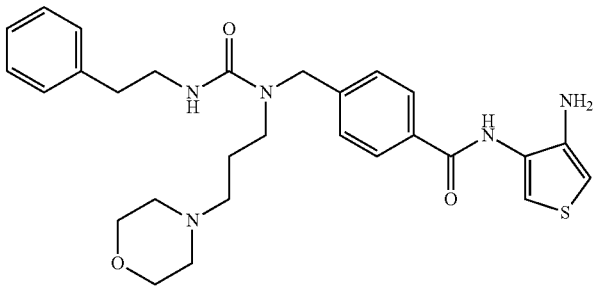

N-(4-Aminothiophen-3-yl)-4-[1-[3-(morpholin-4-yl)propyl]-3-phenethyl-ureidomethyl]benzamide (Compound No. 1-116)

$^1$H-NMR (400 MHz, CDCl$_3$) δ 1.55 (m, 2 H), 2.22-2.32 (m, 6 H), 2.86 (t, J = 6.7 Hz, 2 H), 3.16 (t, J = 5.7 Hz, 2 H), 3.39 (br s, 2 H), 3.48 (q, J = 6.7 Hz, 2 H), 3.53 (br s, 4 H), 4.56 (s, 2 H), 6.48 (d, J = 3.4 Hz, 1 H), 6.92 (br s, 1 H), 7.18-7.24 (m, 3 H), 7.30 (t, J = 7.2 Hz, 2 H), 7.36 (d, J = 8.2 Hz, 2 H), 7.56 (d, J = 3.4 Hz, 1 H), 7.84 (d, J = 8.2 Hz, 2 H), 8.18 (br s, 1 H)

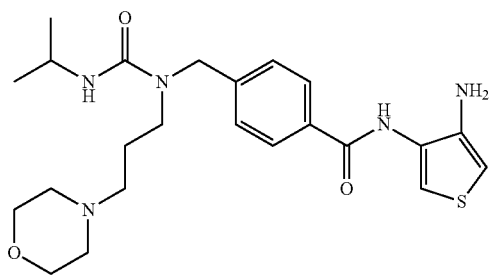

N-(4-Aminothiophen-3-yl)-4-[3-isopropyl-1-[3-(morpholin-4-yl)propyl]ureidomethyl]benzamide (Compound No. 1-117)

$^1$H-NMR (400 MHz, CDCl$_3$) δ 1.18 (d, J = 6.6 Hz, 6 H), 1.66 (m, 2 H), 2.35 (t, J = 6.1 Hz, 2 H), 2.44 (br s, 4 H), 3.23 (t, J = 6.3 Hz, 2 H), 3.41 (br s, 2 H), 3.75 (t, J = 4.5 Hz, 4 H), 4.02 (m, 1 H), 4.54 (s, 2 H), 5.61 (d, J = 7.3 Hz, 1 H), 6.48 (d, J = 3.5 Hz, 1 H), 7.38 (d, J = 8.3 Hz, 2 H), 7.56 (d, J = 3.5 Hz, 1 H), 7.84 (d, J = 8.3 Hz, 2 H), 8.19 (br s, 1 H)

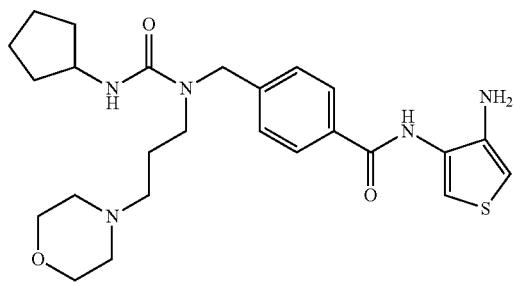

N-(4-Aminothiophen-3-yl)-4-[3-cyclopentyl-1-[3-(morpholin-4-yl)propyl]ureidomethyl]benzamide (Compound No. 1-118)

$^1$H-NMR (400 MHz, CDCl$_3$) δ 1.33 (m, 2 H), 1.50-1.73 (m, 6 H), 2.04 (m, 2 H), 2.35 (t, J = 6.3 Hz, 2 H), 2.43 (br s, 4 H), 3.23 (t, J = 6.2 Hz, 2 H), 3.41 (br s, 2 H), 3.73 (t, J = 4.5 Hz, 4 H), 4.11 (m, 1 H), 4.54 (s, 2 H), 5.63 (d, J = 6.6 Hz, 1 H), 6.47 (d, J = 3.4 Hz, 1 H), 7.38 (d, J = 8.3 Hz, 2 H), 7.56 (d, J = 3.4 Hz, 1 H), 7.84 (d, J = 8.3 Hz, 2 H), 8.20 (br s, 1 H)

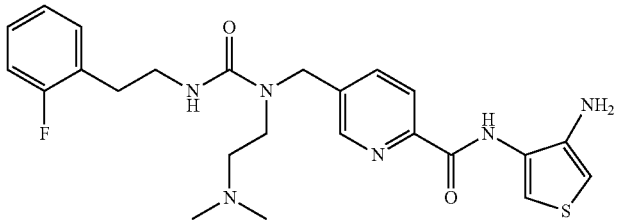

N-(4-Aminothiophen-3-yl)-5-[1-
(2-dimethylaminoethyl)-3-(2-fluoro-
phenethyl)ureidomethyl]pyridine-
2-carboxylic acid amide
(Compound No. 1-119)

$^1$H-NMR (400 MHz, DMSO-d$_6$)
δ 2.07 (s, 6 H), 2.27 (t,
J = 6.3 Hz, 2 H), 2.78 (t,
J = 7.1 Hz, 2 H), 3.23 (t,
J = 6.3 Hz, 2 H), 3.29 (m,
2 H), 4.56 (s, 2 H), 4.81
(br s, 2 H), 6.28 (d,
J = 3.4 Hz, 1 H),
7.02 (t, J = 5.4 Hz, 1 H),
7.10-7.16 (m, 2 H),
7.24-7.29 (m, 2 H), 7.65 (d,
J = 3.4 Hz, 1 H), 7.81 (dd,
J = 8.0, 2.0 Hz, 1 H), 8.09
(d, J = 8.0 Hz, 1 H), 8.55 (d,
J = 2.0 Hz, 1 H), 10.19 (br s,
1 H).

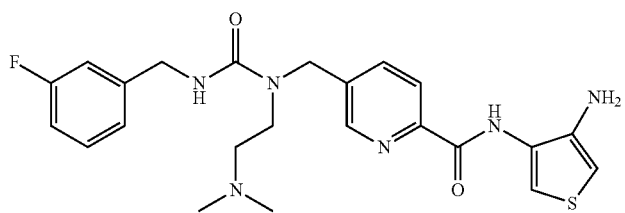

N-(4-Aminothiophen-3-yl)-5-[1-
(2-dimethylaminoethyl)-3-(3-fluoro-
benzyl)ureidomethyl]pyridine-
2-carboxylic acid amide
(Compound No. 1-120)

$^1$H-NMR (400 MHz, DMSO-d$_6$)
δ 2.11 (s, 6 H), 2.36 (t,
J = 6.3 Hz, 2 H), 3.35 (t,
J = 6.3 Hz, 2 H), 4.27 (d,
J = 5.5 Hz, 2 H), 4.62 (s, 2 H),
4.80 (br s, 2 H), 6.28 (d,
J = 3.7 Hz, 1 H), 7.01-7.09
(m, 3 H), 7.34 (m, 1 H), 7.51 (t,
J = 5.5 Hz, 1 H), 7.65 (d,
J = 3.7 Hz, 1 H), 7.89 (dd,
J = 8.0, 2.1 Hz, 1 H), 8.11 (dd,
J = 8.0, 0.6 Hz, 1 H), 8.59 (dd,
J = 2.1, 0.6 Hz, 1 H), 10.18
(br s, 1 H).

Example 2

N-(4-Aminothiophen-3-yl)-4-[1-(2-dimethylaminoethyl)-3-(indan-5-yl)ureidomethyl]benzamide (Compound No. 2-1)

A solution of 4-[1-(2-dimethylaminoethyl)-3-(indan-5-yl)ureidomethyl]benzoic acid (Reference Compound No. 11-1, 77 mg, 0.20 mmol), 3,4-diaminothiophene dihydrochloride (45 mg, 0.24 mmol), N,N-diisopropylethylamine (77 µL, 0.44 mmol) and HATU (90 mg, 0.24 mmol) in DMF (2.0 mL) was stirred at room temperature overnight. Water (30 mL) was added to the reaction solution, and then the whole was extracted with ethyl acetate (30 mL) three times. The organic layer was washed with water (30 mL) and brine (30 mL), dried over anhydrous magnesium sulfate, and then the solvent was evaporated under reduced pressure. The obtained residue was purified by silica gel (NH-modified silica gel) column chromatography (chloroform-methanol) to give 55 mg of the title compound as a brown amorphous product. (Yield 58%)

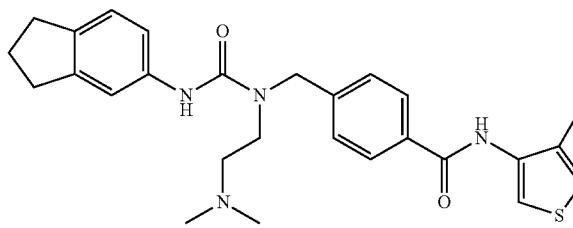

$^1$H-NMR (400 MHz, DMSO-d$_6$)
δ 1.99(m, 2H), 2.27(s, 6H),
2.50(m, 2H), 2.79(m, 4H),
3.38(m, 2H), 4.61(s, 2H),
4.87(s, 2H), 6.13(d, J =
3.7 Hz, 1H), 7.05(dd, J =
8.1, 1.8 Hz, 1H), 7.08(d,
J = 8.1 Hz, 1H), 7.31(br s,
1H), 7.43(d, J = 8.2 Hz,
2H), 7.50(d, J = 3.7 Hz,
1H), 7.91(d, J = 8.2 Hz,
2H), 9.64(br s, 1H), 9.91
(br s, 1H)

By using Reference Compound No. 1-2 and commercially available compounds, the following Compound No. 2-2 was obtained by a method similar to that of Compound No. 2-1.

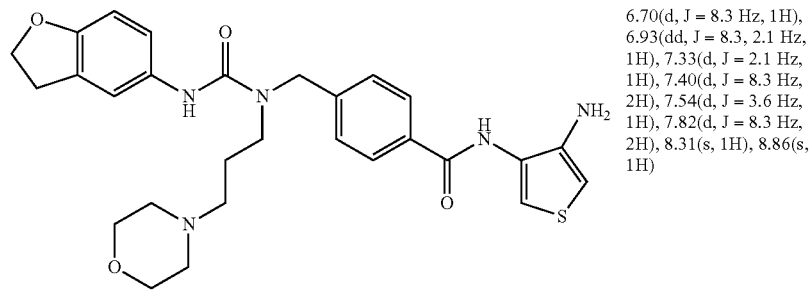

6.70(d, J = 8.3 Hz, 1H), 6.93(dd, J = 8.3, 2.1 Hz, 1H), 7.33(d, J = 2.1 Hz, 1H), 7.40(d, J = 8.3 Hz, 2H), 7.54(d, J = 3.6 Hz, 1H), 7.82(d, J = 8.3 Hz, 2H), 8.31(s, 1H), 8.86(s, 1H)

N-(4-Aminothiophen-3-yl)-4-[3-(2,3-dihydro-1-benzofuran-5-yl)-1-[3-morpholin-4-yl)propyl]ureidomethyl]benzamide (Compound No.2-2)

Preparation Examples

Hereinafter, typical preparation examples of the present compound will be shown.

1) Tablet (in 150 mg)

| | |
|---|---|
| The Present compound | 1 mg |
| Lactose | 100 mg |
| Cornstarch | 40 mg |
| Calcium carboxymethyl cellulose | 4.5 mg |
| Hydroxypropyl cellulose | 4 mg |
| Magnesium stearate | 0.5 mg |

A tablet of the above-mentioned formulation is coated using 3 mg of a coating agent (for example, a conventional coating agent such as hydroxypropylmethyl cellulose, macrogol or a silicone resin), whereby a desired tablet can be obtained. In addition, a desired tablet can be obtained by appropriately changing the kinds and/or amounts of the present compound and additives.

2) Capsule (in 150 mg)

| | |
|---|---|
| The Present compound | 5 mg |
| Lactose | 135 mg |
| Calcium carboxymethyl cellulose | 4.5 mg |
| Hydroxypropyl cellulose | 4 mg |
| Magnesium stearate | 1.5 mg |

A desired capsule can be obtained by appropriately changing the kinds and/or amounts of the present compound and additives.

3) Eye Drop (in 100 mL)

| | |
|---|---|
| The Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kinds and/or amounts of the present compound and additives.

[Pharmacological Test]

1. Test for Evaluation of HDAC Inhibitory Activity

Using HDAC Fluorimetric Assay/Drug Discovery Kit (manufactured by Biomol), HDAC inhibitory activity of the present compounds was measured according to the protocol included with the kit. The kit contains Buffer, HeLa nuclear extract (includes HDAC), Substrate, Developer and Trichostatin A (an HDAC inhibitor).

(Preparation of Test Compound Solution)

A test compound was dissolved in dimethyl sulfoxide (hereinafter referred to as "DMSO"), whereby a 2 mg/mL solution was prepared. Then, the resulting solution was diluted with Buffer containing 5% DMSO, whereby a 150 μM test compound solution was prepared.

(Test Method and Measurement Method)

1) To a 384-well culture plate, the test compound solution was added in an amount of 2 μl, per well.

2) HeLa nuclear extract was diluted 30-fold with Buffer. The resulting solution was added in an amount of 3 μl, per well, and then incubation was performed at 37° C. for 2 hours.

3) Substrate was diluted 500-fold with Buffer. The resulting solution was added in an amount of 5 μl, per well (the final concentration of the test compound was 30 μM), and then incubation was performed at 37° C. for 10 minutes.

4) Developer was diluted 20-fold with Buffer and Trichostatin A (2 μM) was added to it. The resulting solution was added in an amount of 10 μl, per well, and then incubation was performed at room temperature for 15 minutes.

5) The fluorescence intensity of each well was measured using multilabel counter ARVO (manufactured by Wallac) with excitation at 360 nm and emission at 460 nm.

6) A control data was obtained from the same experiment except that Buffer containing 5% DMSO was added instead of the test compound solution as the above-mentioned procedure from 1) to 5).

7) A blank data was obtained from the same experiment except that Buffer containing 5% DMSO was added instead of the test compound solution and that Buffer was added instead of Hela nuclear extract as the above-mentioned procedure from 1) to 5).

(Calculation Equation for Enzyme Inhibitory Rate)

Enzyme inhibitory rate (%) was calculated using the following equation.

(Enzyme Inhibitory Rate(%))=100×[1−{(Fluorescence Intensity of Test Compound Solution)−(Florescence Intensity of Blank)}/{(Florescence Intensity of Control)−(Florescence Intensity of Blank)}]

(Test Results)

As an example of the test results, the enzyme inhibitory rate of the respective test compound (Compound No. 1-1, Compound No. 1-7, Compound No. 1-8, Compound No. 1-18, Compound No. 1-24, Compound No. 1-34, Compound No. 1-43, Compound No. 1-56, Compound No. 1-59, Compound No. 1-71, Compound No. 1-77, Compound No. 1-82, Compound No. 1-88, Compound No. 1-103, Compound No. 1-104, Compound No. 2-2) are shown in Table I.

TABLE I

| Test Compound | Enzyme Inhibitory Rate (%) |
|---|---|
| Compound No. 1-1 | 97 |
| Compound No. 1-7 | 100 |
| Compound No. 1-8 | 96 |
| Compound No. 1-18 | 97 |
| Compound No. 1-24 | 100 |
| Compound No. 1-34 | 97 |
| Compound No. 1-43 | 100 |
| Compound No. 1-56 | 97 |
| Compound No. 1-59 | 97 |
| Compound No. 1-71 | 100 |
| Compound No. 1-77 | 100 |
| Compound No. 1-82 | 96 |
| Compound No. 1-88 | 95 |
| Compound No. 1-103 | 97 |
| Compound No. 1-104 | 97 |
| Compound No. 2-2 | 93 |

If the enzyme inhibitory rate was more than 100%, the value is shown to be 100% in Table I.

2. Test for Evaluation of Effect of Morphological Change on Trabecular Meshwork Cells As a method for evaluating a cellular morphological change, an evaluation system using the cell shape index (hereinafter referred to as "CSI") as an index has been reported in The Journal of Clinical Investigation, 103, 1141-1150 (1999). Therefore, according to the method described in the above document, an effect of morphological change of the present compounds on trabecular meshwork cells was evaluated.

(Used Cells)

A human trabecular meshwork cell line (hereinafter referred to as "TM-1 cells") reported in Investigative Ophthalmology & Visual Science, 43, 151-161 (2002) was used.

(Preparation of Reagents)

Culture medium 1: A reagent was prepared by adding fetal bovine serum (10%), L-glutamine (2 mM), amphotericin B (2.5 µg/mL), and gentamicin (25 µg/mL) to Dulbecco's Modified Eagle Medium (hereinafter referred to as "D-MEM").

Culture medium 2: A reagent was prepared by adding fetal bovine serum (3%), L-glutamine (2 mM), amphotericin B (2.5 µg/mL), and gentamicin (25 µg/mL) were added to D-MEM.

Cell staining liquid: A mixed liquid of Calcein-AM (16 µM) and Hoechst 33342 (40 µM) was prepared by diluting a Calcein-AM solution (cytoplasmic staining reagent, manufactured by Dojindo Laboratories) and a Hoechst 33342 solution (nuclear staining reagent, manufactured by Dojindo Laboratories) with D-MEM containing L-glutamine (2 mM), amphotericin B (2.5 µg/mL), and gentamicin (25 µg/mL).

(Preparation of Cells)

TM-1 cells subcultured at 37° C. in a 8% carbon dioxide gas atmosphere were treated with a trypsin/EDTA solution (0.05% trypsin and 0.53 mM tetrasodium ethylenediaminetetraacetate) at 24 hours before performing a drug treatment mentioned below and seeded on a 96-well culture plate. The culture medium 1 was used for the subculture of the cells. The culture medium 2 was used for the cell culture after seeding the cells on the plate.

(Preparation of Test Compound Solution)

A test compound was dissolved in DMSO, whereby a 5 mM solution was prepared. Then, the resulting solution was diluted with the culture medium 2, whereby a 200 µM test compound solution was prepared.

(Preparation of Positive Control Compound Solution)

It has been reported that Y-27632 which is a Rho kinase inhibitor induces a morphological change in trabecular meshwork cells in Investigative Ophthalmology & Visual Science, 42, 137-144 (2001). Therefore, Y-27632 (produced according to the method described in WO 90/05723) was used as a positive control, and dissolved in DMSO in the same manner as the test compound, whereby a 5 mM solution was prepared, and then, the resulting solution was diluted with the culture medium 2, whereby a 200 µM positive control compound solution was prepared.

(Test Method and Measurement Method)

1) To a 96-well culture plate, a solution of TM-1 cells adjusted to a cell density of $1.6 \times 10^4$ cells/mL was added in an amount of 95 µl, ($1.5 \times 10^4$ cells) per well.

2) Incubation was performed at 37° C. in a 8% carbon dioxide gas atmosphere for 24 hours.

3) The test compound solution or positive control compound solution was added in an amount of 5 µl, per well (the final concentration of the test compound or positive control compound was 10 µM). As a control, the culture medium 2 containing DMSO (4%) was added in an amount of 5 µL per well.

4) Incubation was performed at 37° C. in a 8% carbon dioxide gas atmosphere for 24 hours.

5) The cell staining liquid was added in an amount of 10 µL per well.

6) Incubation was performed at 37° C. in a 8% carbon dioxide gas atmosphere for 1 hour to stain the cells.

7) A 37% formaldehyde solution was added in an amount of 10 µL per well.

8) Incubation was performed at room temperature for 1 hour to fix the cells.

9) Washing with phosphate-buffered saline was performed.

10) Using Array Scan Vti HCS reader (manufactured by Cellomics), images of stained cells magnified with a 20-fold objective lens were captured in 80 fields (10 fields×8 wells) per test compound addition group.

11) CSI was calculated for each cell and an average value was obtained for each test compound addition group.

(Calculation Equation for CSI)

CSI was calculated using the following equation.

$$CSI = 4\pi \times (\text{Cell Area})/(\text{Cell Perimeter})^2$$

(Test Results)

As an example of the test results, the CSI values of the respective test compound (Compound No. 1-1, Compound No. 1-7, Compound No. 1-8, Compound No. 1-18, Compound No. 1-24, Compound No. 1-34, Compound No. 1-43, Compound No. 1-56, Compound No. 1-59, Compound No. 1-71, Compound No. 1-77, Compound No. 1-82, Compound No. 1-88, Compound No. 1-103, Compound No. 1-104, Compound No. 2-2, Y-27632) are shown in Table II.

TABLE II

| Test Compound | CSI |
| --- | --- |
| Control | 0.694 |
| Compound No. 1-1 | 0.527 |
| Compound No. 1-7 | 0.523 |
| Compound No. 1-8 | 0.548 |
| Compound No. 1-18 | 0.519 |
| Compound No. 1-24 | 0.509 |
| Compound No. 1-34 | 0.516 |
| Compound No. 1-43 | 0.522 |
| Compound No. 1-56 | 0.422 |
| Compound No. 1-59 | 0.500 |
| Compound No. 1-71 | 0.481 |
| Compound No. 1-77 | 0.515 |
| Compound No. 1-82 | 0.507 |
| Compound No. 1-88 | 0.539 |
| Compound No. 1-103 | 0.496 |
| Compound No. 1-104 | 0.505 |
| Compound No. 2-2 | 0.555 |
| Y-27632 | 0.627 |

3. Test for Evaluation of Intraocular Pressure-Lowering Effect

In order to evaluate an intraocular pressure-lowering effect of the present compounds, a test for evaluation of intraocular pressure-lowering effect of intracameral administration of a drug using male Japanese White rabbits was performed.

(Preparation of Test Compound Administration Liquid)

A test compound was dissolved in physiological saline containing 0.5% DMSO, whereby a 1 mM test compound administration liquid was prepared.

(Test Method and Measurement Method)

One drop of 0.4% oxybuprocaine hydrochloride eye drop was instilled into both eyes of each male Japanese White rabbit to achieve local anesthesia, and thereafter, the intraocular pressure was measured using an applanation tonometer. Then, by using a syringe fitted with a 30-gauge needle, the test compound administration liquid (20 µL) was intracamerally administered to one eye. As a control, 20 µL of the vehicle (physiological saline containing 0.5% DMSO) for the test compound was intracamerally administered. After the lapse of a certain period of time from the administration of the test compound or vehicle, one drop of 0.4% oxybuprocaine hydrochloride eye drop was instilled into the administered eye to achieve local anesthesia, and thereafter, the intraocular pressure was measured using an applanation tonometer.

(Calculation Equation for Intraocular Pressure Reduction Rate)

The intraocular pressure-lowering effect of each test compound was evaluated by calculating an intraocular pressure reduction rate. The intraocular pressure reduction rate (%) was calculated using the following equation.

(Intraocular Pressure Reduction Rate(%))=100×{(Average Value of Intraocular Pressure of Control Group)−(Average Value of Intraocular Pressure of Each Test Compound Administration Group)}/ (Average Value of Intraocular Pressure of Control Group)

(Test Results and Discussion)

As an example of the test results, the intraocular pressure reduction rates of the respective test compound administration groups at 9 hours after administering the respective test compounds (Compound 1-43 and Compound 1-82) are shown in Table III (one group consisting of 6 cases).

TABLE III

| Test Compound | Intraocular Pressure Reduction Rate (%) |
| --- | --- |
| Compound No. 1-43 | 7 |
| Compound No. 1-82 | 25 |

As shown in Table I, the present compounds have an excellent HDAC inhibitory activity and are expected to be useful as a preventive and/or therapeutic agent for diseases which an HDAC inhibitor is considered to be useful in treating, for example cancer, autoimmune diseases, inflammatory diseases, neurodegenerative diseases, infectious disease, hematopoietic disorders, fibrosis, cardiovascular disorders, diseases associated with angiogenesis. Additionally, as shown in Table II, the present compounds have an excellent effect of cellular morphological change on trabecular meshwork cells equal to or greater than that of Y-27632 used as the positive control (lower CSI indicates greater morphological changes in Table II). Further, as shown in Table III, the present compounds have an excellent intraocular pressure-lowering effect also in the test using actual animal models. Accordingly, the present compounds can be used as an intraocular pressure-lowering agent and are expected to be useful as a preventive and/or therapeutic agent for diseases associated with aqueous humor circulation and/or intraocular pressure, particularly as a preventive and/or therapeutic agent for glaucoma, ocular hypertension, and the like.

The invention claimed is:

1. A compound represented by the following formula (1) or a salt thereof:

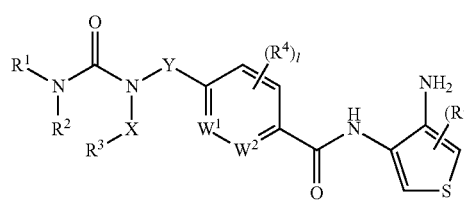

wherein $R^1$ and $R^2$ are the same or different and represent a hydrogen atom, a lower alkyl group which may have a substituent, a lower alkenyl group which may have a substituent, a lower alkynyl group which may have a substituent or a group represented by the following formula (2):

(2)

$R^3$ represents a hydroxy group, a lower alkoxy group which may have a substituent, a lower cycloalkyloxy group which may have a substituent, an aryloxy group which may have a substituent, a carboxy group, a lower alkoxycarbonyl group which may have a substituent, —$NR^aR^b$ or a group represented by the following formula (3):

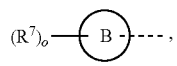
(3)

$R^4$ and $R^5$ are the same or different and represent a halogen atom, a lower alkyl group, a hydroxy group, or a lower alkoxy group;

$R^6$ represents a halogen atom, a lower alkyl group which may have a substituent, an aryl group which may have a substituent, a heterocyclic group which may have a substituent, a hydroxy group, a lower alkoxy group which may have a substituent, a mercapto group, a lower alkylthio group which may have a substituent, a lower alkylcarbonyl group which may have a substituent, an amino group, a nitro group or a cyano group;

$R^7$ represents a lower alkyl group which may have a substituent, a hydroxy group or a lower alkoxy group which may have a substituent;

$R^a$ and $R^b$ are the same or different and represent a hydrogen atom or a lower alkyl group which may have a substituent;

the ring A represents a cyclic hydrocarbon or a heterocyclic ring;

the ring B represents a heterocyclic ring having one or plural heteroatoms selected from the group consisting of a nitrogen atom and an oxygen atom in the ring;

X represents a lower alkylene group which may have a substituent;

Y represents a lower alkylene group which may have a substituent;

Z represents a single bond or a lower alkylene group which may have a substituent;

$W^1$-$W^2$ W represents N—CH or CH—N; and l, m, n and o are the same or different and represent 0, 1, 2 or 3.

2. The compound or a salt thereof according to claim 1, wherein, in the formula (1), $R^1$ and $R^2$ are the same or different and represent a hydrogen atom, a lower alkyl group, a lower alkyl group having a lower alkoxy group as a substituent, a lower alkyl group having a lower alkoxycarbonyl group as a substituent, a lower alkenyl group, a lower alkynyl group or a group represented by the following formula (2):

(2)

$R^3$ represents a hydroxy group, a lower alkoxy group, a lower cycloalkyloxy group, an aryloxy group, a carboxy group, a lower alkoxycarbonyl group, —$NR^aR^b$, or a group represented by the following formula (3);

(3)

$R^6$ represents a halogen atom, a lower alkyl group, a lower alkyl group having a hydroxy group as a substituent, a lower alkyl group having a lower alkoxy group as a substituent, an aryl group, a heterocyclic group, a hydroxy group, a lower alkoxy group, a mercapto group, a lower alkylthio group, a lower alkylcarbonyl group, an amino group, a nitro group or a cyano group;

$R^7$ represents a lower alkyl group or a lower alkoxy group;

$R^a$ and $R^b$ are the same or different and represent a hydrogen atom or a lower alkyl group;

the ring A represents a cyclic hydrocarbon or a heterocyclic ring;

the ring B represents a heterocyclic ring having one or plural heteroatoms selected from the group consisting of a nitrogen atom and an oxygen atom in the ring;

X and Y represent a lower alkylene group;

Z represents a single bond or a lower alkylene group;

n represents CH—N;

l and m represent 0; and n and o are the same or different and represent 0, 1, 2 or 3.

3. The compound or a salt thereof according to claim 1 or 2, wherein, in the formula (1), $R^1$ represents a hydrogen atom, a lower alkyl group, a lower alkyl group having a lower alkoxy group as a substituent, a lower alkyl group having a lower alkoxycarbonyl group as a substituent or a group represented by the following formula (2):

(2)

$R^2$ represents a hydrogen atom;

$R^3$ represents —$NR^aR^b$ or a group represented by the following formula (3):

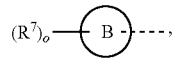
(3)

$R^6$ represents a halogen atom, a lower alkyl group, a lower alkyl group having a hydroxyl group as a substituent, an aryl group, a lower alkoxy group or a lower alkylcarbonyl group;

R⁷ represents a lower alkyl group;
R$^a$ and R$^b$ represent a lower alkyl group;
the ring A represents a cyclic hydrocarbon or a heterocyclic ring;
the ring B represents a heterocyclic ring having one or plural heteroatoms selected from the group consisting of a nitrogen atom and an oxygen atom in the ring;
X and Y represent a lower alkylene group;
Z represents a single bond or a lower alkylene group;
$W^1$-$W^2$ represents CH—N;
l and m represent 0;
n represents 0, 1 or 2; and
o represents 0 or 1.

4. The compound or a salt thereof according to claim 1 or 2, wherein, in the formula (1), the ring A represents cyclopentane, cyclohexane, benzene, indan, thiophene, furan, benzo[1,3]dioxole, 2,3-dihydro-1-benzofuran, thiazole, 2,3-dihydrobenzo[1,4]dioxine or pyridine.

5. The compound or a salt thereof according to claim 3, wherein, in the formula (1), the ring A represents cyclopentane, cyclohexane, benzene, indan, thiophene, furan, benzo[1,3]dioxole, 2,3-dihydro-1-benzofuran, thiazole, 2,3-dihydrobenzo[1,4]dioxine or pyridine.

6. The compound or a salt thereof according to claim 1 or 2, wherein, in the formula (1), the ring B represents pyrrolidine, piperazine or morpholine.

7. The compound or a salt thereof according to claim 3, wherein, in the formula (1), the ring B represents pyrrolidine, piperazine or morpholine.

8. A compound or a salt thereof selected from the group consisting of

N-(4-aminothiophen-3-yl)-5-[3-(2,3-dihydrobenzo[1,4]dioxin-6-yl)-1-(2-dimethylaminoethyl)ureidomethyl]pyridine-2-carboxylic acid amide, N-(4-aminothiophen-3-yl)-5-[1-(2-dimethylaminoethyl)-3-(thiophen-3-yl)ureidomethyl]pyridine-2-carboxylic acid amide, N-(4-aminothiophen-3-yl)-5-[1-(2-dimethylaminoethyl)-3-phenethylureidomethyl]pyridine-2-carboxylic acid amide, N-(4-aminothiophen-3-yl)-5-[1-(3-dimethylaminopropyl)-3-(thiophen-3-yl)ureidomethyl]pyridine-2-carboxylic acid amide, N-(4-aminothiophen-3-yl)-5-[3-cyclopentyl-1-[3-(morpholin-4-yl)propyl]ureidomethyl]pyridine-2-carboxylic acid amide, N-(4-aminothiopen-3-yl)-5-[1-(2-dimethylaminoethyl)-3-isopropylureidomethyl]pyridine-2-carboxylic acid amide, N-(4-aminothiophen-3-yl)-5-[3-isopropyl-1-[3-(4-methylpiperazin-1-yl)propyl]ureidomethyl]pyridine-2-carboxylic acid amide, N-(4-aminothiophen-3-yl)-5-[1-[4-(morpholin-4-yl)butyl]-3-phenethylureidomethyl]pyridine-2-carboxylic acid amide, N-(4-aminothiophen-3-yl)-5-[3-cyclopentyl-1-[2-(pyrrolidin-1-yl)ethyl]ureidomethyl]pyridine-2-carboxylic acid amide, N-(4-aminothiophen-3-yl)-5-[2-[3-(benzo[1,3]dioxol-5-yl)]ethyl-1-[2-(4-methylpiperazin-1-yl)ethyl]ureidomethyl]pyridine-2-carboxylic acid amide, N-(4-aminothiophen-3-yl)-5-[1-[4-(morpholin-4-yl)butyl]-3-propylureidomethyl]pyridine-2-carboxylic acid amide, N-(4-aminothiophen-3-yl)-5-[3-ethoxycarbonylmethyl-1-[3-(morpholin-4-yl)propyl]ureidomethyl]pyridine-2-carboxylic acid amide, N-(4-aminothiophen-3-yl)-5-[1-(2-dimethylaminoethyl)-3-(thiazol-2-yl)ureidomethyl]pyridine-2-carboxylic acid amide, and N-(4-aminothiophen-3-yl)-5-[1-(2-dimethylaminoethyl)ureidomethyl]pyridine-2-carboxylic acid amide.

9. A pharmaceutical composition comprising (i) a pharmaceutically effective amount of at least one compound selected from the group consisting of the compound and a salt thereof according to any one of claim 1, 2 or 8 and (ii) a pharmaceutical carrier.

10. A histone deacetylase inhibitor comprising a pharmaceutically effective amount of at least one compound selected from the group consisting of the compound and a salt thereof according to any one of claim 1, 2 or 8 as an active ingredient and a pharmaceutical carrier.

11. An intraocular pressure-lowering agent comprising a pharmaceutically effective amount of at least one compound selected from the group consisting of the compound and a salt thereof according to any one of claim 1, 2 or 8 as an active ingredient and a pharmaceutical carrier.

12. A therapeutic agent for glaucoma or ocular hypertension comprising a pharmaceutically effective amount of at least one compound selected from the group consisting of the compound and a salt thereof according to any one of claim 1, 2 or 8 as an active ingredient and a pharmaceutical carrier.

13. A method for lowering an intraocular pressure comprising administering to a patient in need thereof a pharmaceutically effective amount of at least one compound selected from the group consisting of the compound and a salt thereof according to any one of claim 1, 2 or 8.

14. A method for treating glaucoma or ocular hypertension comprising administering to a patient in need thereof a pharmaceutically effective amount of at least one compound selected from the group consisting of the compound and a salt thereof according to any one of claim 1, 2 or 8.

* * * * *